US012703727B2

(12) United States Patent
Paszek et al.

(10) Patent No.: US 12,703,727 B2
(45) Date of Patent: Aug. 11, 2026

(54) RECOMBINANT MUCINS, AND COMPOSITIONS AND METHODS FOR USING THE SAME

(71) Applicant: Cornell University, Ithaca, NY (US)

(72) Inventors: Matthew Paszek, Lansing, NY (US); Heidi Reesink, Lansing, NY (US); Carolyn Shurer, Houston, TX (US); Hao Pan, Ithaca, NY (US)

(73) Assignee: Cornell University, Ithaca, NY (US)

(*) Notice: Subject to any disclaimer, the term of this patent is extended or adjusted under 35 U.S.C. 154(b) by 1252 days.

(21) Appl. No.: 17/422,740

(22) PCT Filed: Jan. 15, 2020

(86) PCT No.: PCT/US2020/013743

§ 371 (c)(1),
(2) Date: Jul. 13, 2021

(87) PCT Pub. No.: WO2020/150390

PCT Pub. Date: Jul. 23, 2020

(65) Prior Publication Data

US 2022/0127319 A1 Apr. 28, 2022

Related U.S. Application Data

(60) Provisional application No. 62/792,660, filed on Jan. 15, 2019.

(51) Int. Cl.

| | |
|---|---|
| ***C07K 14/47*** | (2006.01) |
| ***A61K 38/00*** | (2006.01) |
| *A61L 12/14* | (2006.01) |
| *A61L 101/46* | (2006.01) |
| *A61P 19/02* | (2006.01) |

(52) U.S. Cl.

CPC .......... *C07K 14/4727* (2013.01); *A61K 38/00* (2013.01); *A61L 12/14* (2013.01); *A61L 2101/46* (2020.08); *A61P 19/02* (2018.01); *C07K 14/4725* (2013.01); *C07K 2319/02* (2013.01); *C07K 2319/03* (2013.01)

(58) Field of Classification Search

CPC ............ C07K 2319/03; C07K 2319/02; C07K 14/14725; C07K 14/4727; A61K 38/00; A61L 2101/46; A61L 12/14; A61P 19/02

See application file for complete search history.

(56) References Cited

U.S. PATENT DOCUMENTS

| | | | |
|---|---|---|---|
| 10,723,773 B2 | 7/2020 | Schmidt et al. | |
| 2006/0173171 A1* | 8/2006 | Bamdad | G01N 33/57484 424/143.1 |
| 2008/0286211 A1 | 11/2008 | Barker | |
| 2010/0074935 A1 | 3/2010 | Flannery et al. | |
| 2010/0151514 A1 | 6/2010 | Ushida et al. | |
| 2013/0196930 A1 | 8/2013 | Flannery et al. | |
| 2014/0010861 A1 | 1/2014 | Bancel et al. | |
| 2014/0187474 A1 | 7/2014 | Sonnenburg | |
| 2015/0010606 A1 | 1/2015 | Roller et al. | |
| 2015/0343019 A1 | 12/2015 | Flannery et al. | |
| 2016/0280767 A1 | 9/2016 | Beri et al. | |
| 2017/0198263 A1 | 7/2017 | Dias et al. | |
| 2017/0305980 A1 | 10/2017 | O'Brien et al. | |
| 2018/0125926 A1 | 5/2018 | Williams et al. | |
| 2018/0353571 A1 | 12/2018 | Jay et al. | |

FOREIGN PATENT DOCUMENTS

| | | | |
|---|---|---|---|
| CN | 1867350 | A | 11/2006 |
| CN | 102924584 | A | 2/2013 |
| CN | 109055426 | A | 12/2018 |
| CN | 113905753 | A | 1/2022 |
| JP | 2007502122 | A | 2/2007 |
| JP | 2011519949 | A | 7/2011 |
| JP | 2011520812 | A | 7/2011 |
| JP | 2018505867 | A | 3/2018 |
| JP | 2018515534 | A | 6/2018 |
| WO | 2005016130 | A2 | 2/2005 |
| WO | 2009137602 | A1 | 11/2009 |
| WO | 2009137603 | A1 | 11/2009 |
| WO | 2011019963 | A2 | 2/2011 |
| WO | 2016187508 | A2 | 11/2016 |
| WO | 2017165674 | A1 | 9/2017 |
| WO | 2018006005 | A1 | 1/2018 |

OTHER PUBLICATIONS

Gendler et al., JBC, vol. 263, No. 26, 1988 (Year: 1988).*
Engelmann (Glycobiology vol. 15 No. 11 pp. 1111-1124, 2005) (Year: 2005).*
Link (Journal of Biotechnology 110 (2004) 51-62) (Year: 2004).*
Jager et al (BMC Biotechnology 2013, 13:52) (Year: 2013).*
Uniprot Accession No. A0A2J8V8A7, SubName: Full=PRG4 isoform 6 {ECO:000313 | EMBL:PNJ53749.1}, Mar. 28, 2018, 2 pages. https://www.uniprot.org/uniprot/A0A2J8V8A7.txt.
Rhee, D.K., et al., The secreted glycoprotein lubricin protects cartilage surfaces and inhibits synovial cell overgrowth, The Journal of Clinical Investigation, Mar. 1, 2005, vol. 115, Issue 3, pp. 622-631.
Shurer, C.R., et al., Stable recombinant production of codon-scrambled lubricin and mucin in human cells, Biotechnology and Bioengineering, Jan. 26, 2019, vol. 116, Issue 6, pp. 1292-1303.
Ai, M., et al., Anti-Lubricin Monoclonal Antibodies Created Using Lubricin-Knockout Mice Immunodetect Lubricin in Several Species and in Patients with Healthy and Diseased Joints, PLOS One, Feb. 2, 2015, vol. 10, Issue 2, p. e0116237 (17 pages).
Uniprotkb, Accession No. A0A2J8V8A7, "PRG4 isoform 6 {ECO:0000313|EMBL:PNJ53749.1}", Mar. 28, 2018, https://rest.uniprot.org/unisave/A0A2J8V8A7?format=txt&versions=1.

(Continued)

*Primary Examiner* — Brian Gangle
*Assistant Examiner* — Andrea K McCollum
(74) *Attorney, Agent, or Firm* — Hodgson Russ LLP

(57) ABSTRACT

Provided are compositions and methods related to improved mucins, methods of making the improved mucins, and cells and cell cultures that express glycosylated mucins. The compositions and methods provide improved cell cultures, and improved methods of producing co-expressed proteins that are distinct from the mucins.

14 Claims, 41 Drawing Sheets

Specification includes a Sequence Listing.

(56) References Cited

OTHER PUBLICATIONS

Uniprot, "*Equus caballus* (Horse),F6VTD3," Jun. 27, 2011, https://rest.uniprot.org/unisave/F6VTD3?format=txt&versions=1.
Flannery et al., "Articular Cartilage Superficial Zone Protein (SZP) Is Homologous to Megakaryocyte Stimulating Factor Precursor and Is a Multifunctional Proteoglycan with Potential Growth-Promoting, Cytoprotective, and Lubricating Properties in Cartilage Metabolism," Biochemical and Biophysical Research Communications, 1999, pp. 535-541, vol. 254, No. 3.
Uniprotkb, "Q92954.PRG4_Human," EMBL DataBase, Mar. 28, 2018.
Shurer et al., "Stable recombinant production of codon-scrambled lubricin and mucin in human cells," Biotechnology and Bioengineering, 2019, pp. 1292-1303.
Definition of codon from https://www.cancer.gov/publications/dictionaries/genetics-dictionary/def/codon, pp. 1-3. Accessed Sep. 13, 2024. (Year: 2024).
Yampolsky et al., "The Exchangeability of Amino Acids in Proteins," Genetics, 2005, 170: 1459-1472. (Year: 2005).

* cited by examiner

Part I Figures

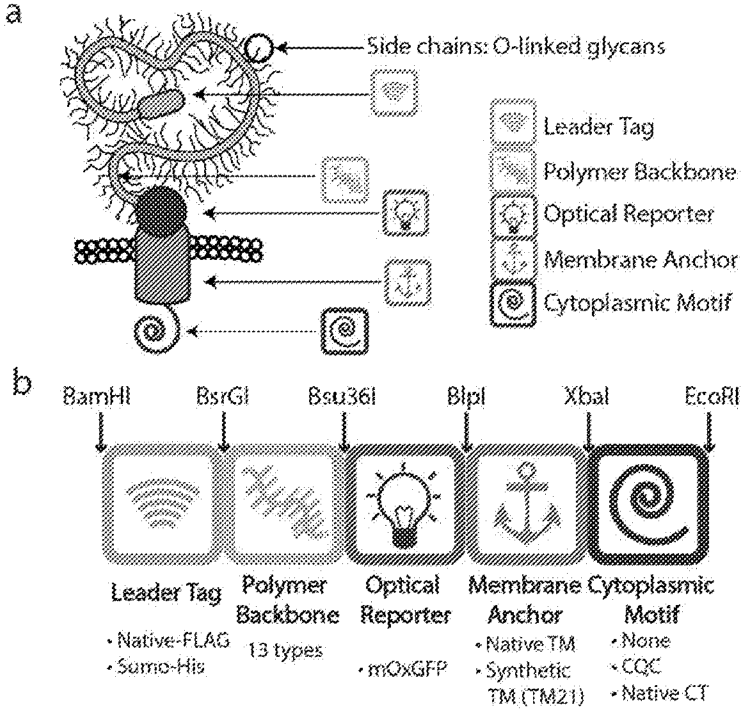

c

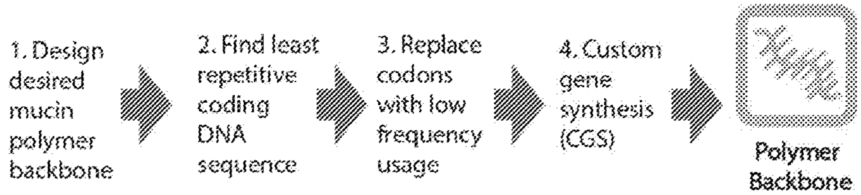

d

Condon-scrambled Polymer Backbones (13 total)

| Name | Sequence | # Repeats | %S/T |
|---|---|---|---|
| Wild-type Muc1 | PDTRPAPGSTAPPAHGVTSA | x0, x10, x21, x42 | 25.0 |
| Muc1 single mutant (Muc1_S) | PDTRPAPGATAPPAHGVTSA | x21 | 20.0 |
| Muc1 double mutant (Muc1_D) | PDTRPAPGATAPPAHGVTAA | x21 | 15.0 |
| Muc1 triple mutant (Muc1_T) | PDARPAPGATAPPAHGVTAA | x21 | 10.0 |
| Synthetic 1 (Syn1) | DAATPAP | x40, x80 | 14.2 |
| Synthetic 2 (Syn2) | DAATPAPP | x40, x80 | 12.5 |
| Synthetic 3 (Syn3) | PPASTSAPG | x40 | 33.3 |
| Lubricin consensus (Syn4) | KEPAPTTP | x20 | 25.0 |

Figure 1 a

Condon-scrambled Muc1 GFP (Muc1_# GFP)

Native-FLAG Muc1_# mOxGFP Native TM 0, 10, 21, 42 repeats of PDTRPAPGSTAPPAHGVTSA c Condon-scrambled Muc1 TM21 (Muc1_#)

Native-FLAG Muc1_# TM21

10, 21, 42 repeats of PDTRPAPGSTAPPAHGVTSA d

| Muc1_# | Backbone MW (kDa) |
|---|---|
| Muc1_42 | 95.0 |
| Muc1_21 | 55.8 |
| Muc1_10 | 35.2 |

b

O-Glycans (PNA) MUC1 TR GFP Nuclei

Muc1_42 GFP

Muc1_21 GFP

Muc1_10 GFP

Muc1_0 GFP

Mock

10 μm e

Muc1_42 Muc1_21 Muc1_10 Mock kDa 191 97 64 51 39

O-Glycans (PNA)

MUC1 TR

β-actin 39 28 f

Mock Muc1_10

Muc1_21 Muc1_42

Part II Figures

Part III Figures

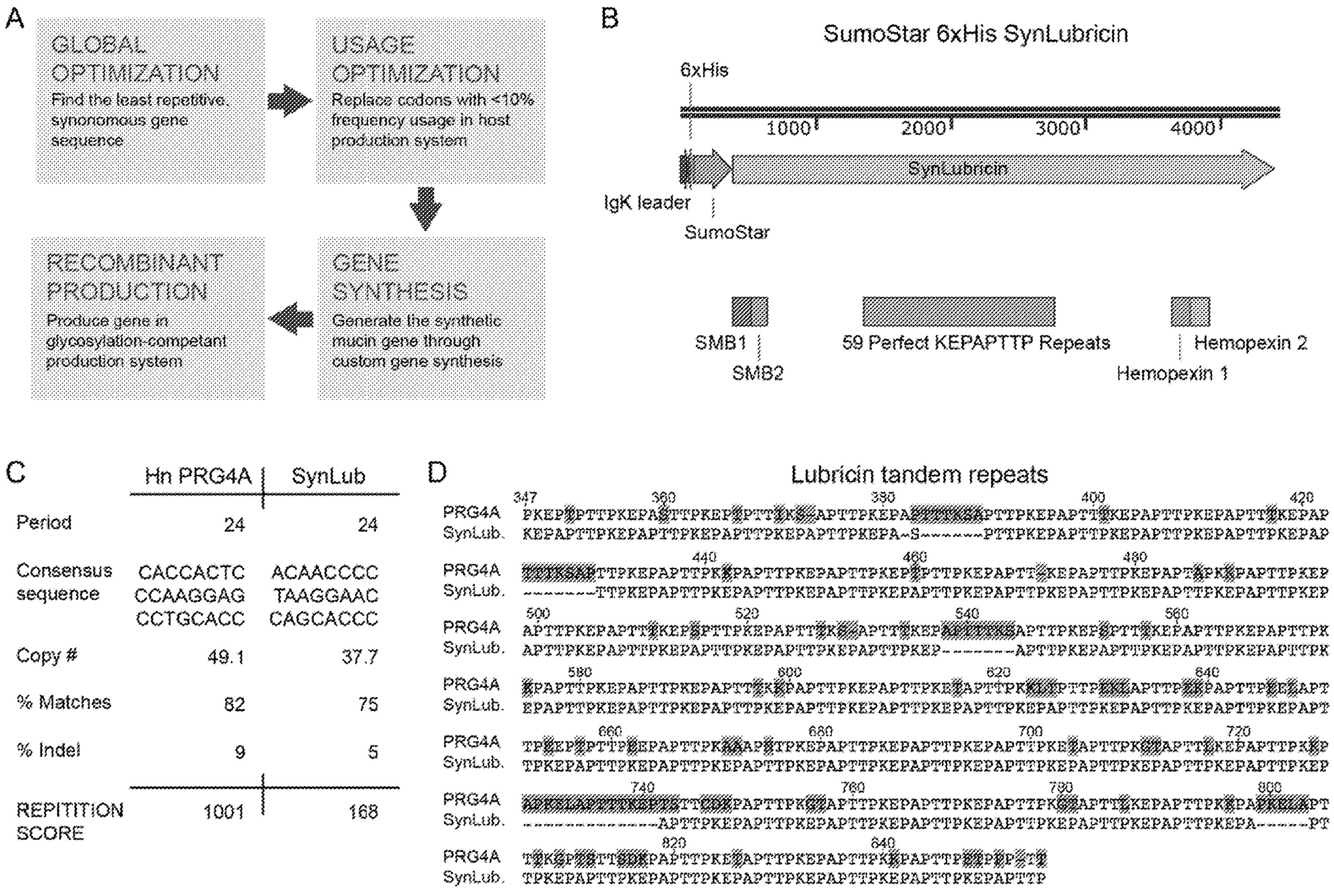

GLOBAL OPTIMIZATION
Find the least repetitive, synonomous gene sequence

USAGE OPTIMIZATION
Replace codons with <10% frequency usage in host production system GENE SYNTHESIS
Generate the synthetic mucin gene through custom gene synthesis RECOMBINANT PRODUCTION
Produce gene in glycosylation-competant production system

B

SumoStar 6xHis SynLubricin

6xHis
1000 2000 3000 4000
SynLubricin
IgK leader
SumoStar
SMB1
SMB2
59 Perfect KEPAPTTP Repeats
Hemopexin 2
Hemopexin 1

C

| | Hn PRG4A | SynLub |
|---|---|---|
| Period | 24 | 24 |
| Consensus sequence | CACCACTC CCAAGGAG CCTGCACC | ACAACCCC TAAGGAAC CAGCACCC |
| Copy # | 49.1 | 37.7 |
| % Matches | 82 | 75 |
| % Indel | 9 | 5 |
| REPITITION SCORE | 1001 | 168 |

D

Lubricin tandem repeats

```
         347          360                 380                 400                 420
PRG4A    PKEPTPTTPKEPATTTPKEPTPTTTKS-APTTPKEPATTTTKSAPTTPKEPAPTTTKEPAPTTPKEPAPTTTKEPAP
SynLub.  KEPAPTTPKEPAPTTPKEPAPTTPKEPAPTTPKEPA-S------PTTPKEPAPTTPKEPAPTTPKEPAPTTPKEPAP

                     440                 460                 480
PRG4A    TTTKSAPTTPKEPAPTTPKEPAPTTPKEPAPTTPKEPTPTTPKEPAPTTTKEPAPTTPKEPAPTAPKEPAPTTPKEP
SynLub.  -------TTPKEPAPTTPKEPAPTTPKEPAPTTPKEPAPTTPKEPAPTTPKEPAPTTPKEPAPTTPKEPAPTTPKEP

         500                 520                 540                 560
PRG4A    APTTPKEPAPTTTKEPTPTTPKEPAPTTTKS-APTTTKEPAPTTTKSAPTTPKEPTPTTTKEPAPTTPKEPAPTTPK
SynLub.  APTTPKEPAPTTPKEPAPTTPKEPAPTTPKEPAPTTPKEP--------APTTPKEPAPTTPKEPAPTTPKEPAPTTPK

            580                 600                 620                 640
PRG4A    EPAPTTPKEPAPTTPKEPAPTTTKKPAPTTPKEPAPTTPKETAPTTPKKLTPTTPEKEAPTTPEKPAPTTPEEAPT
SynLub.  EPAPTTPKEPAPTTPKEPAPTTPKEPAPTTPKEPAPTTPKEPAPTTPKEPAPTTPKEPAPTTPKEPAPTTPKEPAPT

                660                 680                 700                 720
PRG4A    TPEEPEPTTPEEPAPTTPKAAAPKTPKEPAPTTPKEPAPTTPKEPAPTTPKETAPTTPKGTAPTTTKEPAPTTPKKP
SynLub.  TPKEPAPTTPKEPAPTTPKEPAPTTPKEPAPTTPKEPAPTTPKEPAPTTPKEPAPTTPKEPAPTTPKEPAPTTPKEP

                     740                 760                 780                 800
PRG4A    APKSLAPTTTKEPTSTTCDKPAPTTPKGTAPTTPKEPAPTTPKEPAPTTPKGTAPTTTKEPAPTTPKKPAPKELAPT
SynLub.  --------------APTTPKEPAPTTPKEPAPTTPKEPAPTTPKEPAPTTPKEPAPTTPKEPA------PT

                     820                 840
PRG4A    TTKKPTTTTEDKPAPTTPKETAPTTPKEPAPTTPKKPAPTTPTTPTPETT
SynLub.  TPKEPAPTTPKEPAPTTPKEPAPTTPKEPAPTTPKEPAPTTPKEPAPTTP
```

Part IV Figures

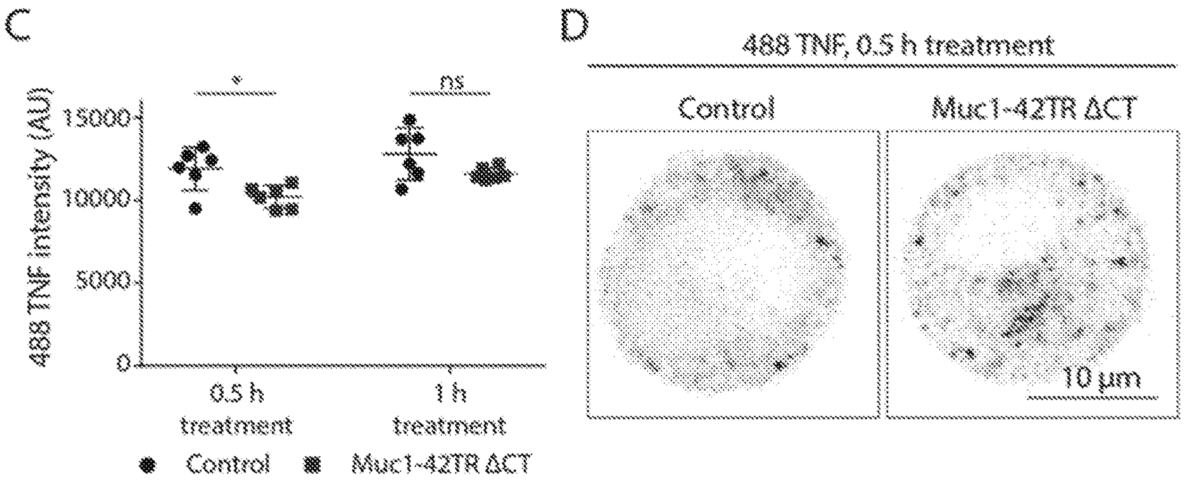
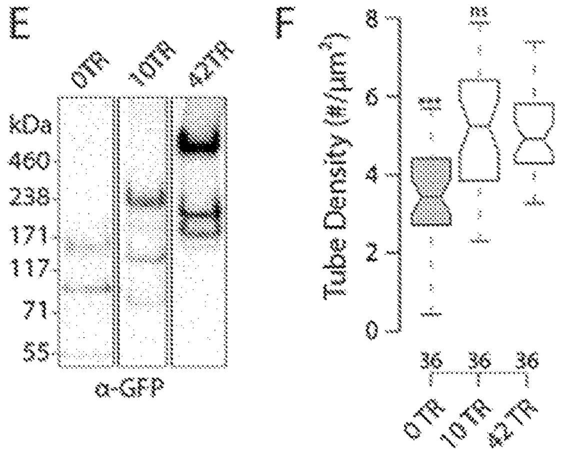
Figure 35 (continued)

| Cell population | Integrated density | # Molecules | # Cells loaded |
|---|---|---|---|
| a | 345 | 1.85e10 | 2.94e4 |
| b | 1128 | 1.41e11 | 3.75e4 |
| c | 2364 | 5.00e11 | 3.76e4 |
| d | 4840 | 1.71e12 | 3.75e4 |
| e | 4456 | 1.48e12 | 7.22e3 |

RECOMBINANT MUCINS, AND COMPOSITIONS AND METHODS FOR USING THE SAME

CROSS REFERENCE TO RELATED APPLICATIONS

This application claims priority to U.S. provisional patent application No. 62/792,660, filed Jan. 15, 2019, the entire disclosure of which is incorporated herein by reference.

STATEMENT REGARDING FEDERALLY SPONSORED RESEARCH

This invention was made with government support under AR068469, GM119133, and CA210184 awarded by the National Institutes of Health. The government has certain rights in the invention.

FIELD OF THE DISCLOSURE

The disclosure provided improved glycoproteins, and compositions and methods related to the same.

BACKGROUND OF THE DISCLOSURE

Protein therapeutic agents represent a large and rapidly growing portion of the pharmaceutical market. Current biologics enable the treatment of a wide variety of human diseases, including cancer, autoimmune disorders, arthritis and infectious diseases. The commercial success of biologics has been a major impetus for the development of improved manufacturing technologies that reliably produce the biological agents on a large scale.

The majority of all recombinant protein pharmaceuticals are produced in mammalian cells at present. Mammalian cells are preferred over prokaryotic organisms for production of protein therapeutics because eukaryote-specific post-translational modifications are often required for protein functionality and appropriate pharmacokinetics. As an example, monoclonal antibodies, a major class of protein therapeutics, must be post-translationally modified with sugar structures called glycans in a post-translational modification process called glycosylation. Without glycosylation, therapeutic antibodies typically have poor stability and pharmacokinetics in vivo.

Today, the majority of all recombinant protein pharmaceuticals are produced in the mammalian Chinese Hamster Ovary (CHO) cell line. However, a significant drawback CHO cells for bio-manufacturing is their capacity to generate glycans that are not native to humans. These glycans can produce deleterious immune responses and have been implicated in therapeutic resistance, which remains a significant concern for physicians and patients. The risk of patient immune responses from CHO-derived products has motivated a deeper consideration of the use of human cell lines for manufacturing recombinant protein therapies.

Suspension adapted human embryonic kidney 293 cells (293-F) have become the most popular host cell line for the production of biological therapeutics with human glycosylation patterns. The 293-F cell system has several desirable features for recombinant protein production, including a fast proliferation rate, a high level of protein production, and ease of transient transfection. Recently, the United States Food and Drug Administration (FDA) has approved several therapeutic agents produced in 293-F cells. However, compared to CHO-cell systems, 293-F cells can exhibit a higher propensity to form large aggregates in suspension, limiting their yield and reliability for bio-manufacturing. While special medium formulations have been developed to reduce cell clumping, aggregation continues to be a challenge for mammalian suspension cell culture, especially at the high cell densities required for fast, high-yield protein production. Exogenous addition of anti-clumping agents also introduces additional molecules that must be purified away from secreted protein products. An alternative strategy would be to genetically engineer production cells to have reduced adhesion, but few approaches have been developed at the current time. Thus there is an ongoing, unmet need for alternative compositions and methods for protein production, and for improved glycoproteins that are suitable for use in a number of diverse applications. The present disclosure is pertinent to this need.

SUMMARY OF THE DISCLOSURE

The disclosure provides modified mammalian cells that express modified polypeptides that act as mucins, and mammalian cell cultures that comprise such cells. In embodiments, the cells comprise recombinant polypeptides expressed from recombinant polynucleotides introduced into the cells.

In embodiments, the polypeptides comprise a transmembrane anchor and a segment external to the cells. The segment external to the cells includes repeated amino acid sequences. In embodiments, the repeated amino acid sequences are selected from: KEPAPTTP (SEQ ID NO:1); DAATPAP (SEQ ID NO:2); DAATPAPP (SEQ ID NO: 3); PPASTSAPG (SEQ ID NO:4); PDTRPAPGATAPPAHGVTSA (SEQ ID NO:5); PDTRPAPGATAPPAHGVTAA (SEQ ID NO:6); PDARPAPGATAPPAHGVTAA (SEQ ID NO:7); PDTRPAPGSTAPPAHGVTSA (SEQ ID NO:8), and combinations thereof. The repeated amino acid sequence may be repeated contiguously 10-120 times. In certain embodiments, the repeated amino acid sequence is repeated contiguously 21, 40, 42, 59 or 80 times.

In embodiments, the cells are modified mammalian cells. In embodiments, the cells are modified human cells, which may be human embryonic kidney cells, which in certain embodiments include human 293-F cells. In embodiments, the modified human cells that express modified mucins are adapted to growth in a suspension culture. In embodiments, the modified cells in the suspension culture exhibit less aggregation relative to a suitable control value. A non-limiting example of a suitable control value is a value obtained from a suspended cell culture comprising cells that do not express the recombinant polypeptide comprising the repeated amino acid sequences. The modified cells may be present in a suspension cell culture that is present in a suspended cell bioreactor.

In certain embodiments, the modified cells express a second, distinct polypeptide. This is achieved by further modifying the cells such that they comprise an introduced polynucleotide encoding a distinct polypeptide that is different from the polypeptide comprising the repeated amino acid sequences.

In embodiments, the polypeptides expressed by the modified cells exhibit O-glycans on the segment external to the cells. This segment can comprise one or a combination of Core 2 O-glycan, GlcNAcβ1-6(Galβ1-3)GalNAc and/or the Core 2 derivatives of GlcNAcβ1-6(Galβ1-3)GalNAc at an abundance of at least 5% relative to all Core 1, Core 2, Core 3, Core 4, Core 5, Core 6, Core 7, and Core 8 O-glycans.

In an embodiment, the polypeptides expressed by the cells as described above include a transmembrane anchor that comprises a cytoplasmic recycling motif.

Isolated polynucleotides that encode the polypeptides of this disclosure are included, as are expression vectors comprising such polynucleotides. In embodiments, the polynucleotides are incorporated into the modified cells such that they are integrated into a chromosome of the cells, which may be achieved by random integration.

The disclosure includes a method of making cells that express the described polypeptides. This approach comprises introducing an isolated/recombinant polynucleotide that encodes a described polypeptide into the cells such that the polypeptide is expressed.

Also included is a method for producing a desired polypeptide or another agent, which may be distinct from the polypeptide comprising the repeated sequences. The method comprises expressing the desired polypeptide or producing another agent in modified mammalian cells that express a modified mucin polypeptide described herein. The method may further comprise separating the desired polypeptide or the other agent from the cells.

BRIEF DESCRIPTION OF THE FIGURES

The figures and tables of this disclosure are divided into four Parts (Part I, Part II, Part III, and Part IV), as described below.

Part I Figures

FIG. 1: Combinatorial Genetic Encoded Library for Sequence-Specific Mucins. (a) Schematic diagram of the combinatorial sequence-specific mucins. (b) Schematic shows the swappable bio-bricks and flanking restriction sites for complete mucin construction. (c) Work flow for the design and fabrication of cDNAs for the mucin tandem-repeat backbones. (d) Summary of codon-scrambled mucin backbones in the library. The Wild-type Muc1 sequence is SEQ ID NO:8. The Muc1 single mutant (Muc1_S) is SEQ ID NO:5. The Muc1 double mutant (Muc1_D) is SEQ ID NO:6. The Muc1 triple mutant (Muc1_T) is SEQ ID NO:7. The Synthetic 1 (Syn1) is DAATPAP is SEQ ID NO:2. The Synthetic 2 (Syn2) is SEQ ID NO:3. The Synthetic 3 (Syn3) is SEQ ID NO:4. The Lubricin consensus sequence (Syn4) is SEQ ID NO:1.

Part II Figures

Figure 12:
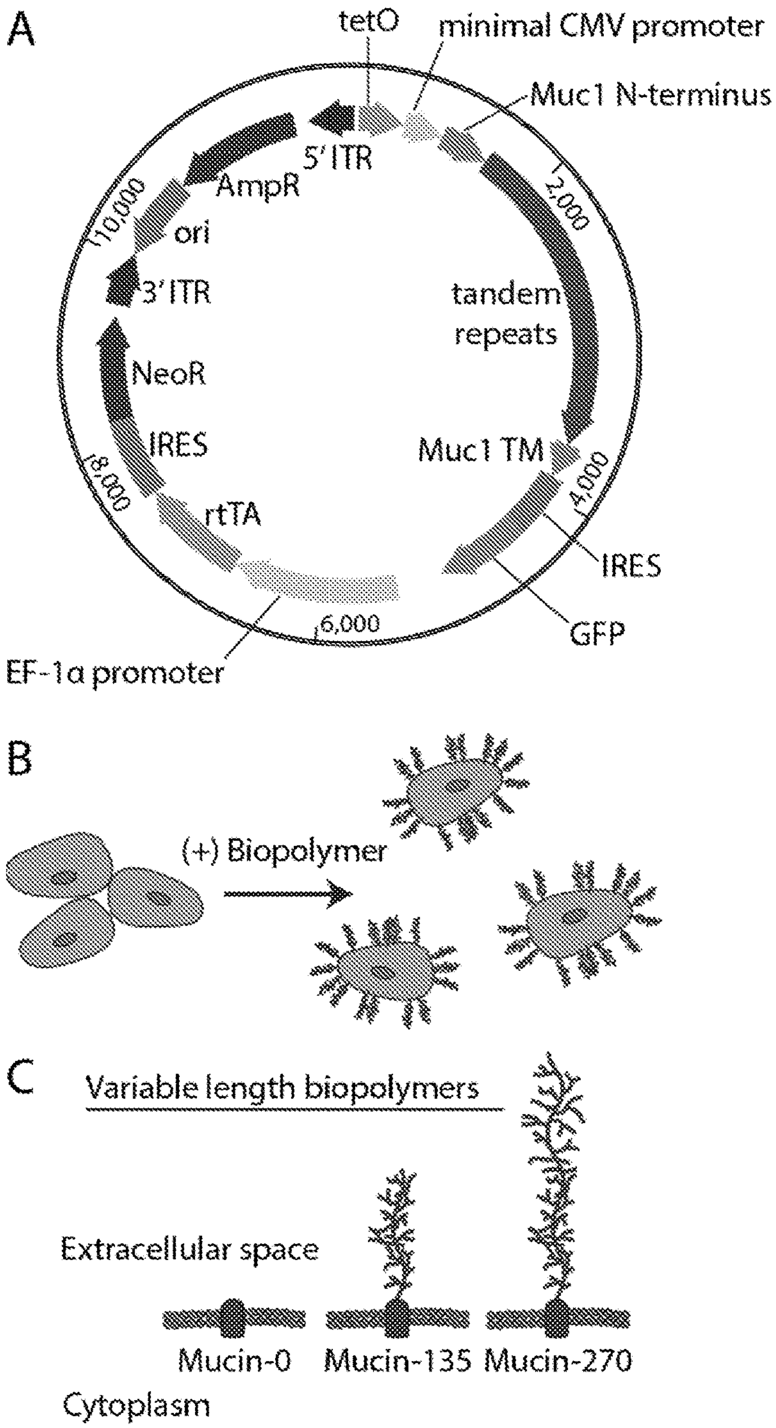

FIG. 12: Engineering Biopolymer-Coated Cell Lines. A transposon-based method was used to stably integrate the DNA encoding the engineered biopolymers under a doxycycline inducible promoter. A, Schematic representation of the all-in-one vector used for producing biopolymer-coated cell lines showing key elements. For incorporation into the cellular genome, the vector includes a tetracycline responsive element (tetO), a minimal CMV promoter, the Muc1 signal sequence (Muc1 N-terminus), the tandem repeats of the biopolymer (0, 21, or 42 repeats of PDTRPAPGSTAPPAHGVTSA (SEQ ID NO:8), the transmembrane domain of Muc1 (Muc1 TM), the bicistronic green fluorescent protein reporter (IRES GFP), a EF-1α promoter, the reverse tetracycline transactivator (rtTA), and a second bicistronic neomycin resistance cassette (IRES NeoR). These elements were all flanked by 5' and 3' inverted terminal repeat sequences (ITRs) required for transposon-mediated incorporation into the genome. For vector replication and production in bacteria, there was also an ampicillin resistance cassette (AmpR) and an origin of replication (ori). B, Schematic representation of membrane bound biopolymers expressed by the cells and localized to the cells surface. C, Schematic of the relative size of the extracellular domain of the engineered biopolymers designated Mucin-0, Mucin-135, and Mucin-270 for their respective length in nm. The predicted molecular weight of these proteins was 42 kDa, 81 kDa, and 120 kDa, respectively.

Figure 13:
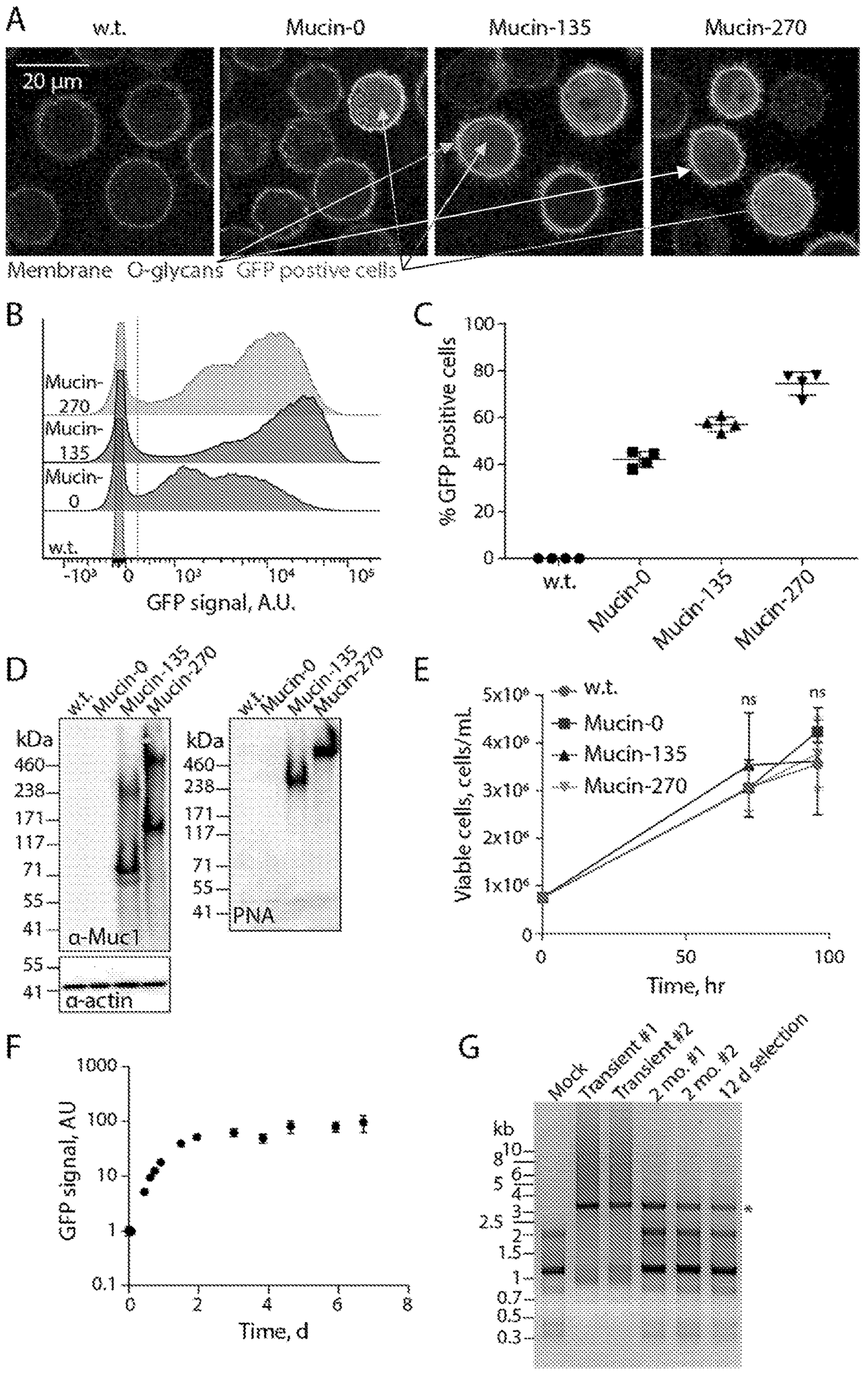

FIG. 13: Validation of Biopolymer Coatings. Expression and cell-surface localization of biopolymer coatings was validated for the new, engineered 293-F cell lines. A, Representative confocal microscopy images of stable suspension adapted human embryonic kidney 293 (293-F) cell lines—wild type (w.t.), or stably expressing the Mucin-0, Mucin-135, or Mucin-270 biopolymer. Images show the cell membrane (shown in blue, CF633 Wheat Germ Agglutinin, WGA), O-glycans covalently attached to the Mucin-135 and Mucin-270 biopolymers (shown in red, CF568 Peanut Agglutinin, PNA), and green-fluorescent protein (shown in green, GFP) which is co-expressed on the plasmid with the Mucin-0, Mucin-135 and Mucin-270 biopolymer. B, Representative flow cytometry histograms showing the polydisperse population of biopolymer expressing cell lines compared to w.t. cells, y-axis is scaled to show the population distribution of GFP positive cells. >50,000 cells per histogram. C, Quantification of the percent of cells which are GFP positive for each cell line. Cells with GFP signal above the gray line in FIG. 2B were considered GFP positive. Mean and S.D. are shown, >50,000 cells per sample, n=4. D, Representative immunoblot (left) and lectin blot (right) of whole cell lysates for each generated stable cell line compared to w.t. cells, n=3. E, Viable cell concentration determined by hemocytometer counting with trypan blue exclusion, n=3. F, GFP signal of Mucin-270 cells after induction of expression at t=0 hr, measured by flow cytometry, n=3, >15,000 cells per sample. G, Agarose gel showing polymerase chain reaction (PCR) product of Mucin-270 gene from DNA extracted from non-transfected cells (Mock), w.t. cells transiently transfected (Transient), or cells with the Mucin-270 gene incorporated in the genome and cultured for 2 months (2 mo.) or 12 days (12 d) after gentamycin selection. Star indicates the predicted molecular weight of Mucin-270 PCR product. #1 and #2 are biological replicates. Mean and S.D. shown, ns—not significant.

Figure 14:
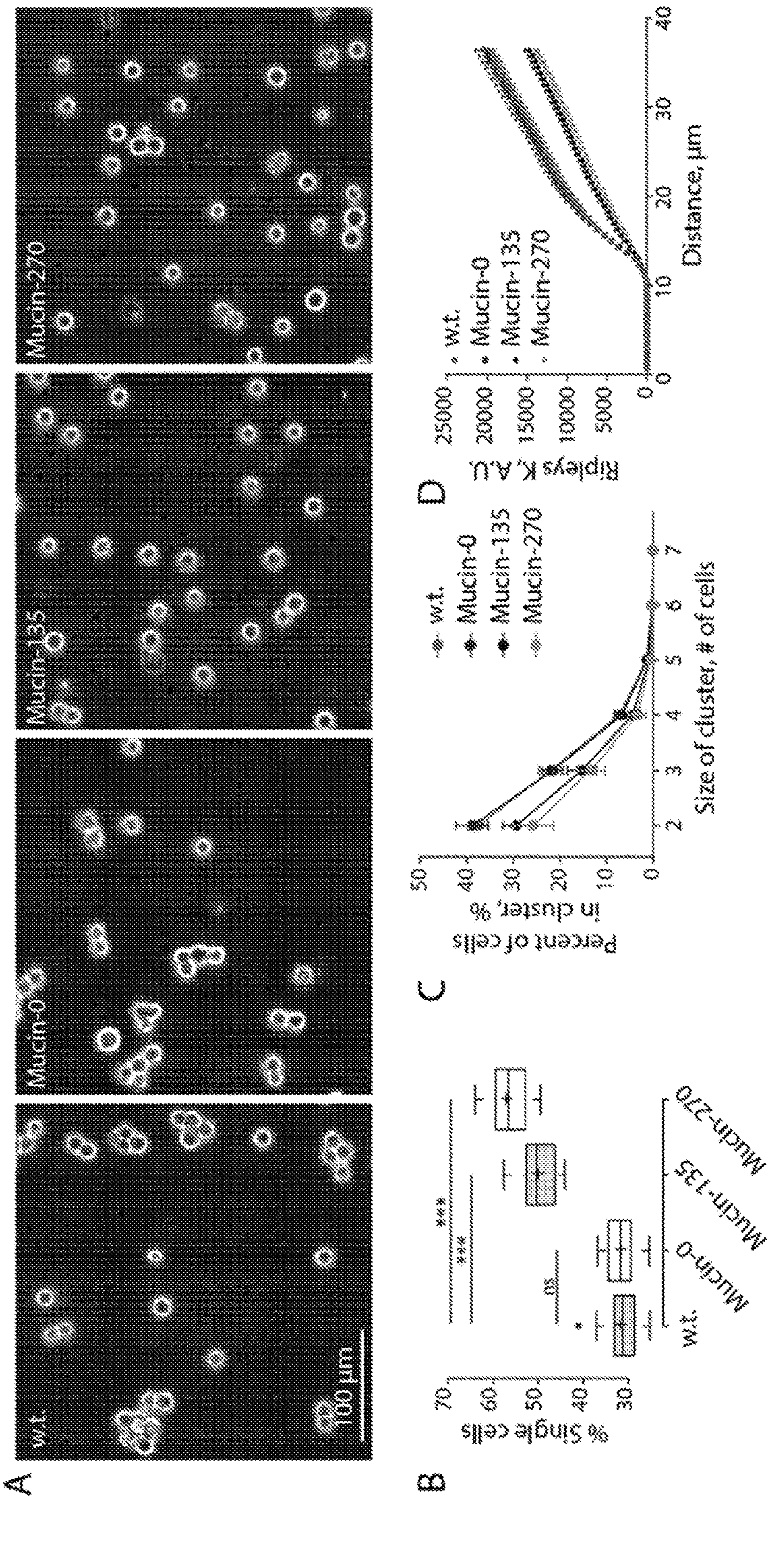

FIG. 14: Biopolymer Coatings Reduced Cell Aggregation. Genetically-encoded biopolymer coatings of Mucin-135 and Mucin-270 size reduce cell aggregation in suspension cell culture. A, Representative phase contrast images for w.t. and biopolymer cell lines. Images were for cells grown at a concentration of $3.8\pm0.7\times10^6$ cells/mL at 72 hr post-induction. B, Quantification of the fraction of cells in various cluster sizes from phase contrast images such as those shown in FIG. 3A, 3 biological replicate samples, 2 technical replicate samples, 3 images analyzed per sample, samples (further discussion of replicates in Materials and Methods section). Center lines show the medians; box limits indicate the 25th and 75th percentiles as determined by R software; whiskers extend 1.5 times the interquartile range from the 25th and 75th percentiles, outliers are represented by dots; crosses represent sample means. C, Quantification of the fraction of cells which are in clusters of various sizes from phase contrast images such as those shown in FIG. 3A. Mean and S.D. are shown. D, Ripleys K function versus distance calculated for the cell distribution acquired from phase contrast images such as those shown in FIG. 3A. Mean and S.E.M. are shown, replicates described in FIG. 3B. ns—not significant; *p<0.05; p<0.01; *p<0.005.

Figure 15:
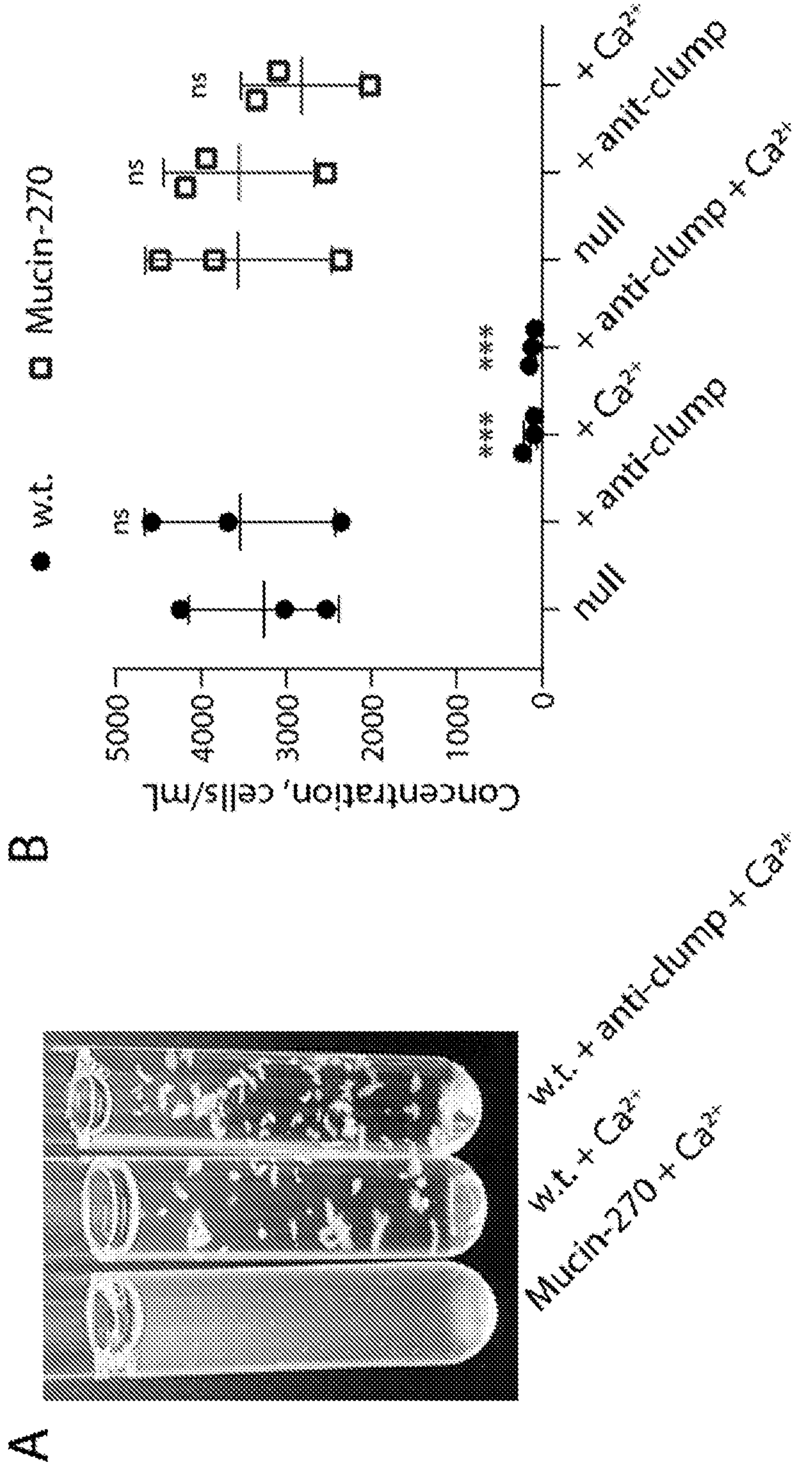

FIG. 15: Mucin-270 Reduced Aggregation in High Calcium Culture Media. The Mucin-270 cell line out-performs commercial anti-clumping solution in highly aggregating conditions. A, Image of Mucin-270 and w.t. cultures grown in media with 2 mM $CaCl_2$ (+$Ca^{2+}$). Mucin-270 expression significantly decreases cell aggregation, even compared to commercially available anti-clumping reagent (+anti-clump). B, Quantification of the concentration of w.t. or Mucin-270-expressing cells in suspension for control cultures with no treatment (null), with the addition of commercial anti-clumping reagent (+anti-clump), with the addition of 2 mM $CaCl_2$ (+$Ca^{2+}$), or with both anti-clumping reagent and 2 mM $CaCl_2$ (+anti-clump+$Ca^{2+}$). Statistical comparison is to null condition for each cell line. Mean and S.D. are shown, n=3. ns—not significant; *p<0.05; p<0.01; *p<0.005.

Figure 16:
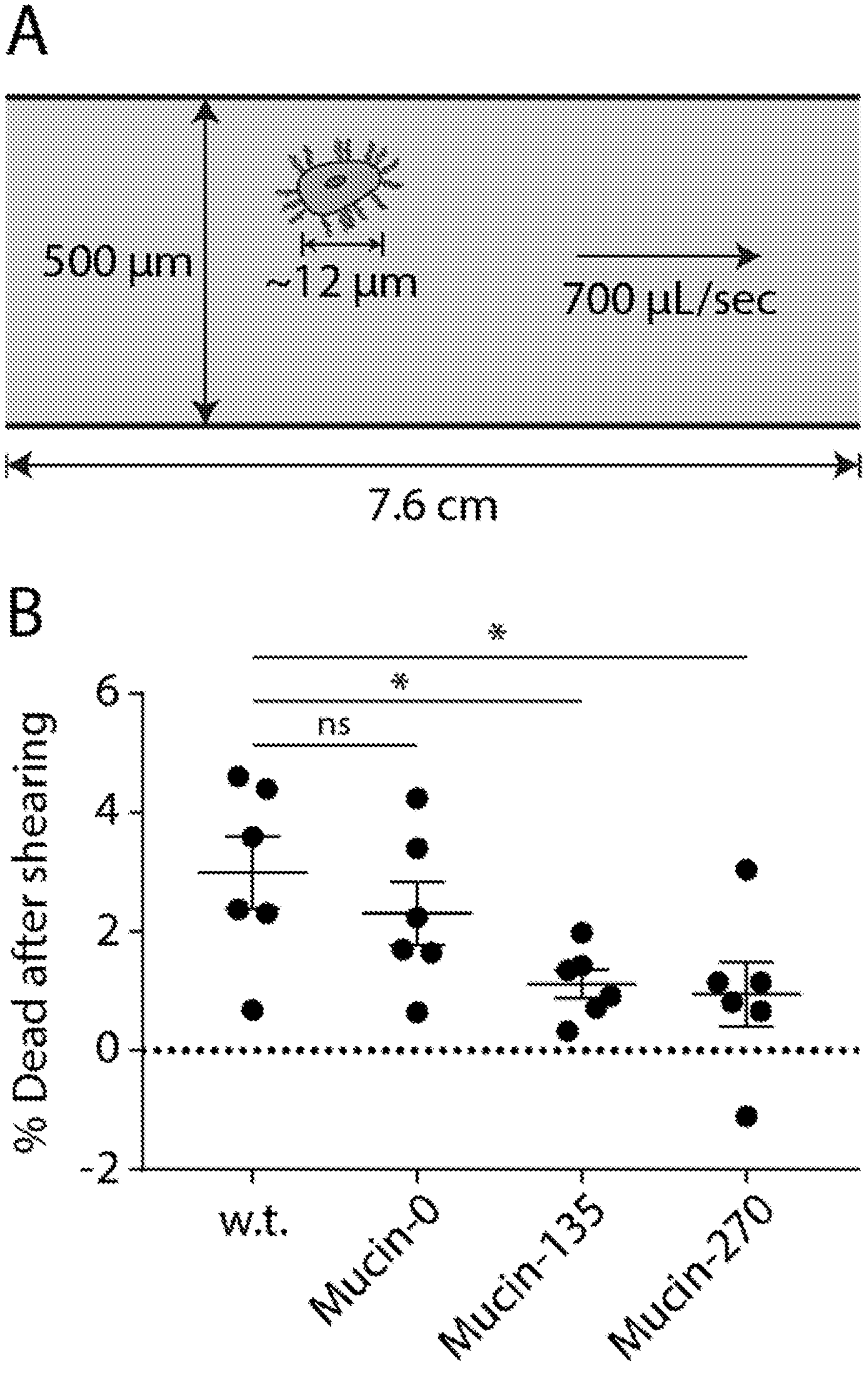

FIG. 16: Biopolymer Coating Enhanced Resistance to Shear Stresses. Expression of the stably incorporated biopolymers protects cells from shear stresses. A, Schematic representation of the experimental setup for shearing cells. Briefly, cells were sheared by flowing through a 500 μm Teflon tube under a constant applied force of 1 kg in gravity before being analyzed by flow cytometry with a live/dead cell stain. B, Quantification of the fraction of dead cells after shearing the cells for the w.t. and biopolymer cell lines, Mean and S.E.M. are shown, >50,000 cells measured for each population, n=6. ns—not significant; *p<0.05; p<0.01; *p<0.005.

Figure 17:
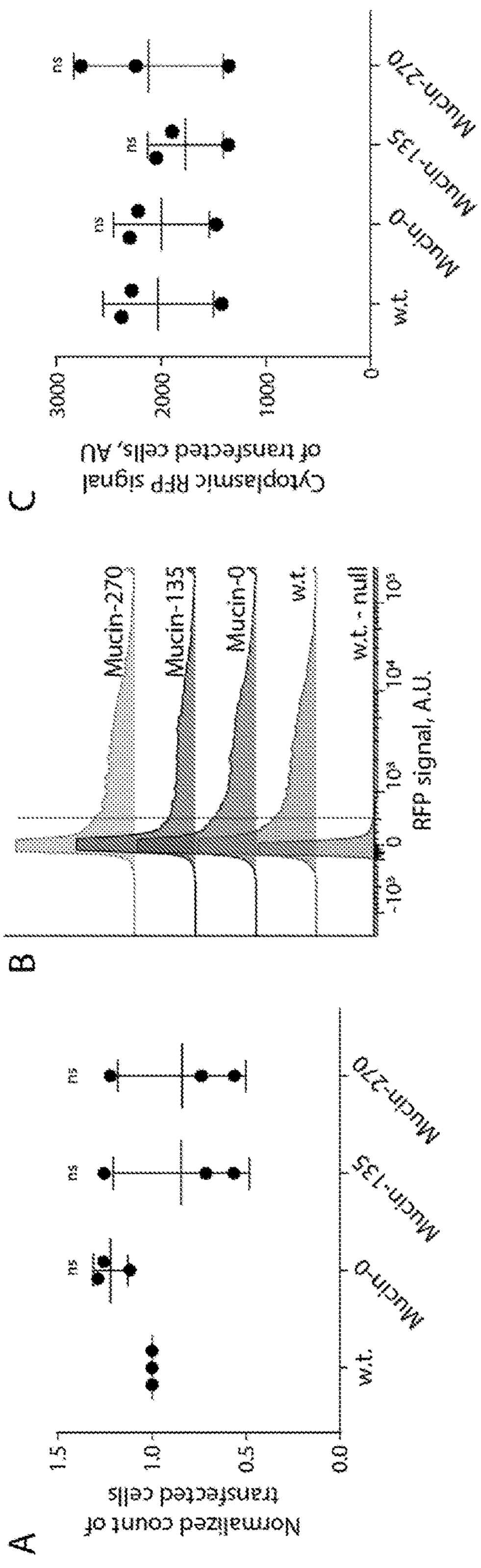

FIG. 17: Biopolymer Coated Cells can be Transfected. Transfection was determined for the biopolymer coated cell lines by transfection with a cytoplasmic red-fluorescent protein (RFP). A, Quantification of the number of cells for w.t. and biopolymer coated cells transiently transfected with cytoplasmic RFP. The count of transfected cells was normalized to the count of w.t. cells transfected per experiment to account for variable transfection efficiency between replicate transfections. >50,000 cells measured for each population, n=3. B, Representative flow cytometry histogram showing the distribution of expression among transfected cell populations. The peak to the left of the gray line, centered around zero, represented the non-transfected population for each cell line which is further validated by the overlapping histogram of non-transfected w.t. cells (w.t.—null). C, Quantification of the geometric mean of RFP for positively transfected cells from B. Mean and S.D. shown, ns—not significant; *p<0.05; p<0.01; *p<0.005.

Figure 18:
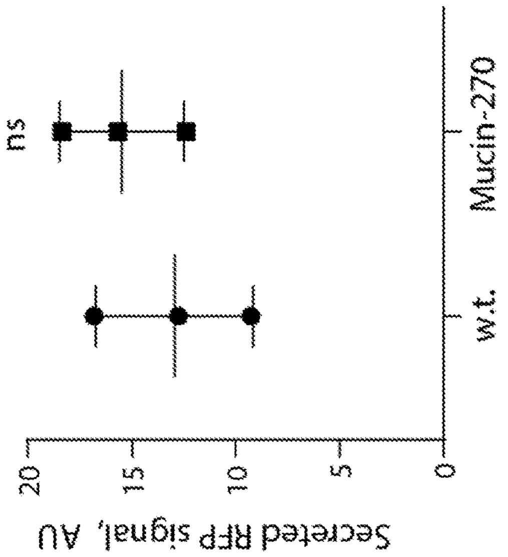

FIG. 18: Mucin-270 cells Produced Comparable Levels of Recombinant Protein Expression. Quantification of secreted, recombinant RFP from media supernatant of w.t. or Mucin-270-expressing cultures transiently transfected with secreted RFP, n=3. Mean and S.D. shown, ns—not significant; *p<0.05; p<0.01; *p<0.005.

Figure 19:
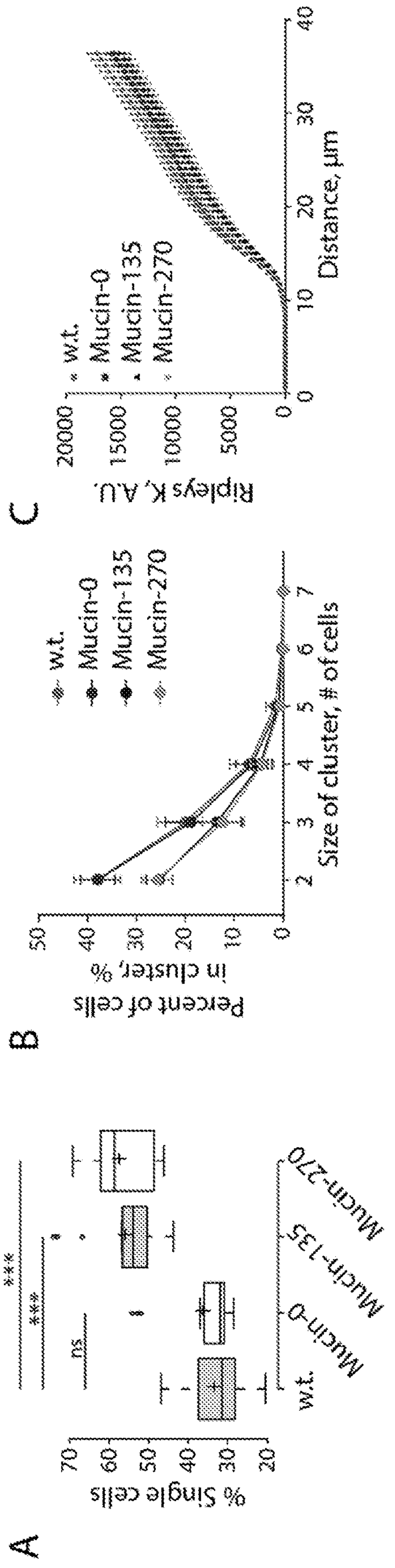

FIG. 19: Additional data to accompany FIG. 14 acquired 24 hr prior. A, Quantification of the fraction of cells in various cluster sizes from phase contrast images such as those shown in FIG. 3A. Cells are grown at $3.2\pm0.7\times10^6$ cells/mL for 48 hr for all panels. Center lines show the medians; box limits indicate the 25th and 75th percentiles as determined by R software; whiskers extend 1.5 times the interquartile range from the 25th and 75th percentiles, outliers are represented by dots; crosses represent sample means. B, Quantification of the fraction of cells which are in clusters of various sizes from phase contrast images such as those shown in FIG. 3A. Mean and S.D. are shown. C, Ripley's K function versus distance calculated for the cell distribution acquired from phase contrast images such as those shown in FIG. 3A. Mean and S.E.M. are shown, replicates described in FIG. 3B, n=3. ns—not significant; *p<0.05; p<0.01; *p<0.005.

Part III Figures

Figure 20:
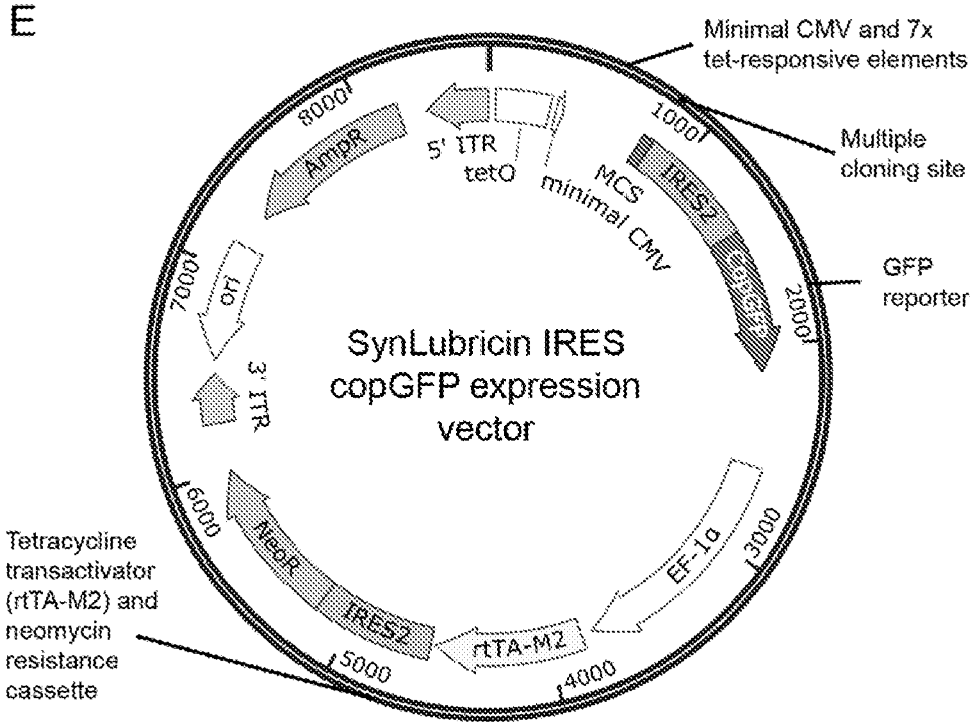

FIG. 20: Design and synthesis of synonymous lubricin (SynLubricin). A) Overview of the design and production strategy for synthetic, codon-scrambled mucins. DNA sequences for the desired protein product were optimized through a global optimization to minimize repetitive DNA sequences by codon scrambling, followed by a second optimization that reassigned codons with infrequent usage in the host cell system. B) SynLubricin was constructed of 59 perfect repeats of KEPAPTTP (SEQ ID NO:1) flanked by the native human N- and C-termini of PRG4. An IgK signal sequence and SumoStar tag was fused to SynLubricin for secretion and purification. SynLubricin also retains the two somatomedin B domains (SMB 1 and 2) and the two Hemopexin domains of the native protein. C) Calculated repetition score for the nucleotides encoding the tandem repeats of human PRG4 isoform A (PRG4A) and SynLubricin. D) Alignment of amino acid sequence of human PRG4 and SynLubricin. The PRG4A sequence in the alignment is amino acids 347-853 of SEQ ID NO:66. The SynLub sequence in the alignment is amino acids 347-818 of SEQ ID NO:68. E) Vector map illustrating the tetracycline-inducible promoter, multiple cloning site (MCS) for cDNA of interest, bicistronic GFP reporter (IRES2 CopGFP), and second expression cassette for the rtTA-M2 tetracycline transactivator and neomycin-resistance gene.

Figure 21:
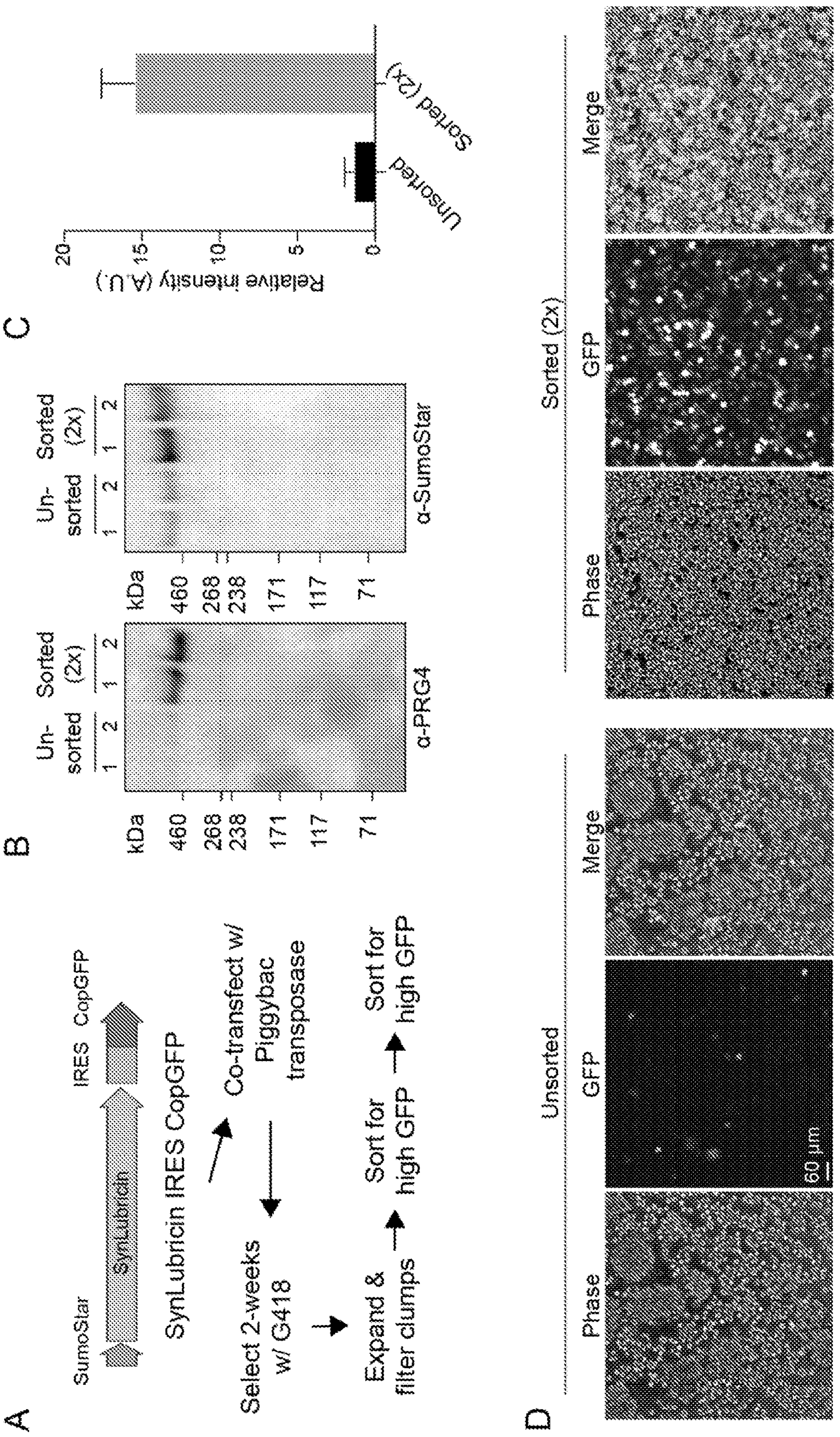

FIG. 21: Sorting strategy to isolate stable polyclonal cell populations that produce high levels of SynLubricin. A) Strategy for isolation of stable cell populations expressing high levels of SynLubricin. B) Western blots of 293-F media supernatant showing relative SynLubricin production in unsorted and twice-sorted (2×) cell populations; 1 and 2 indicate samples from two independent experiments; probed with anti-PRG4 (MABT401) and SUMO antibodies. C) Quantification of the relative intensity of signal from anti-PRG4 Western blots in B. D) Phase-contrast and fluorescence micrographs of unsorted and twice-sorted 293-F cells expressing SynLubricin.

Figure 22:
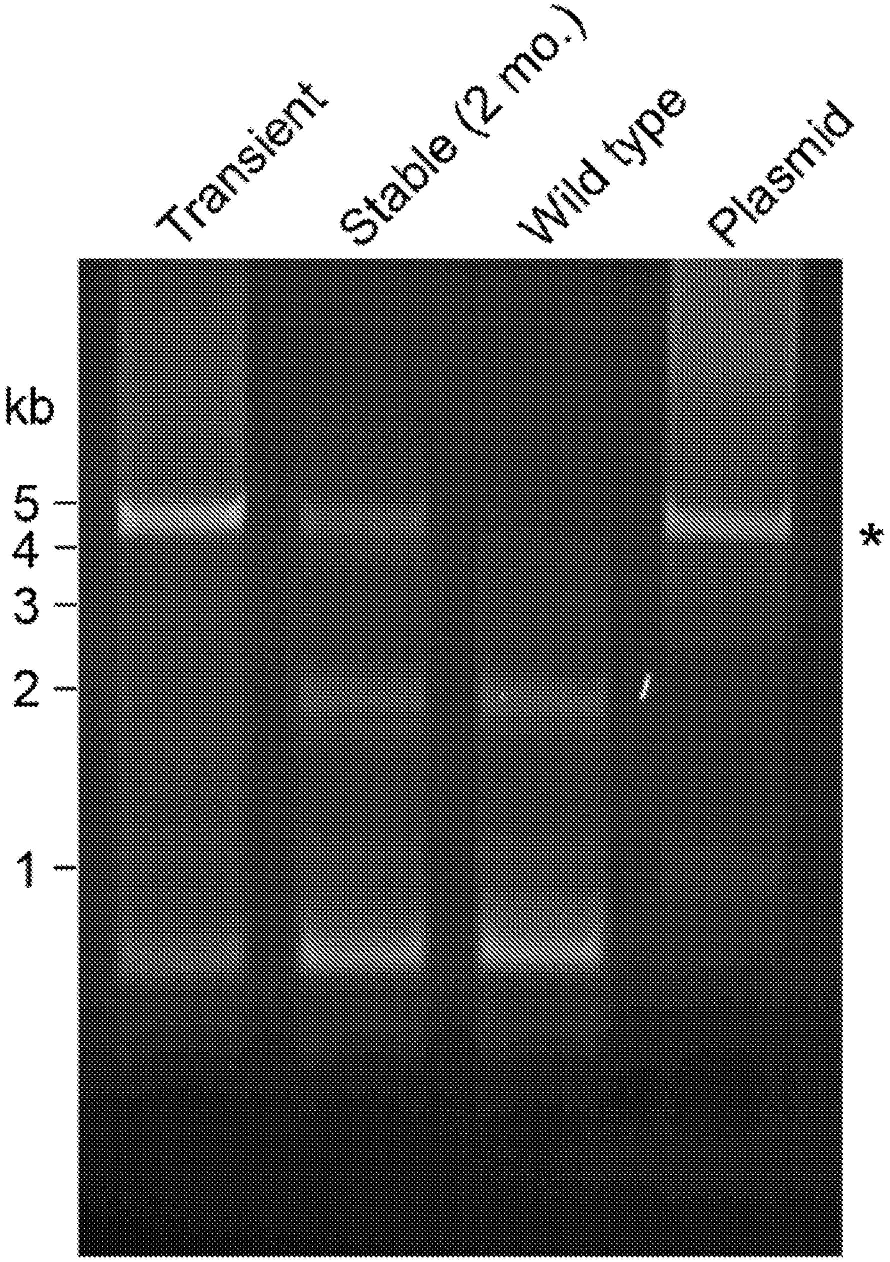

FIG. 22: Integrated SynLubricin cDNA is stable in the cellular genome. PCR amplification of SynLubricin coding region in genomic DNA extracts of wild-type and stably integrated 293-F cells cultured continuously for 2 months. As positive controls, PCR amplifications of SynLubricin plasmid and DNA extract from SynLubricin transiently transfected 293-F cells (Transient) are shown. The expected size of full-length SynLubricin is indicated by the star.

Figure 23:
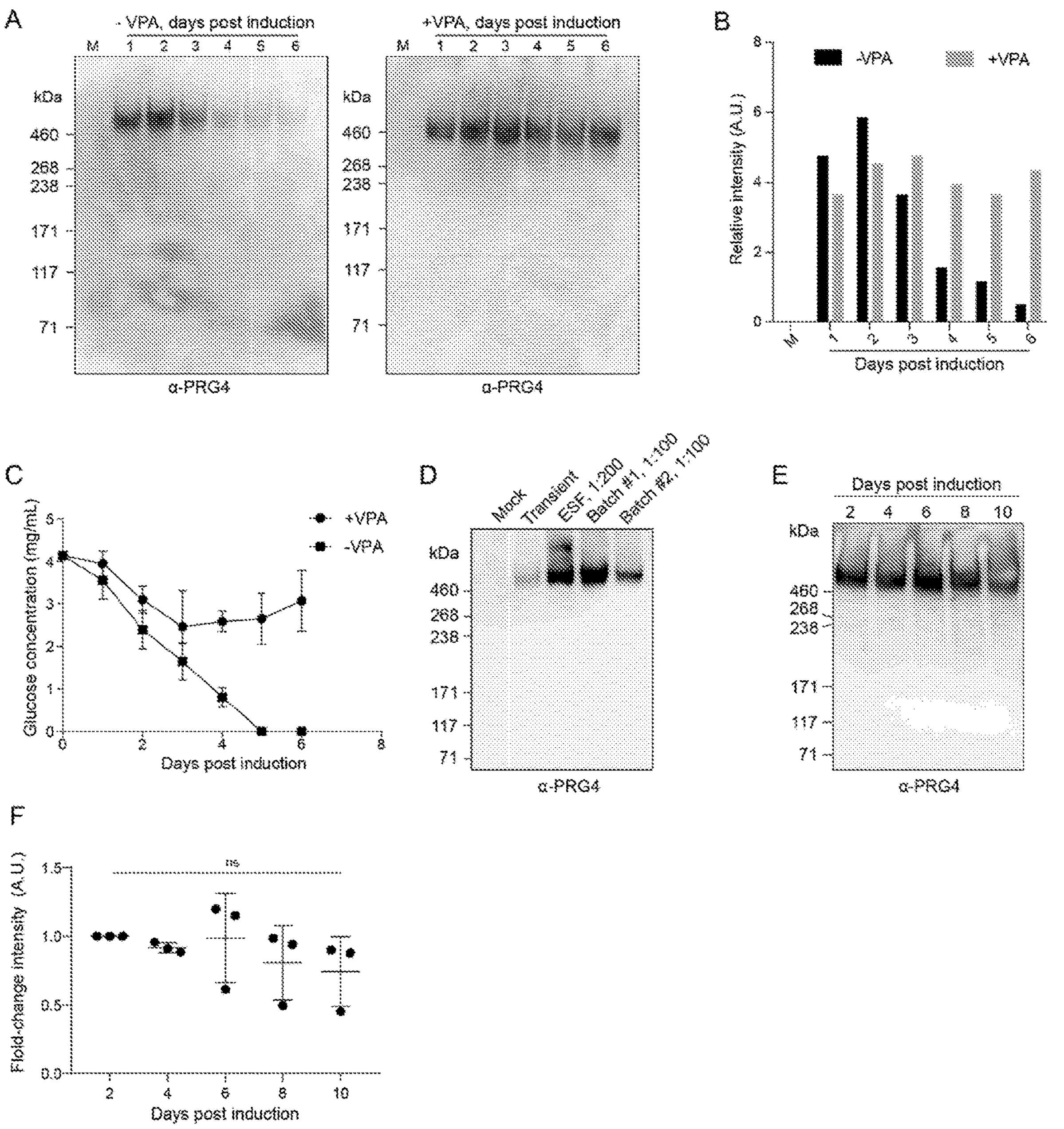

FIG. 23: Optimization of SynLubricin production. A) Western blots showing relative production of SynLubricin over time in media of control cells and sorted 293-F cells induced with 1 μg/mL doxycycline for the indicated number of days in the absence or presence of the histone deacetylase inhibitor valproic acid (VPA; 3.5 mM). B) Quantification of the relative intensity of signal for the blots shown in A. C) Time course for glucose consumption in sorted 293-F cells induced at day 0 with 1 μg/mL doxycycline with or without 3.5 mM VPA. Mean and S.D. shown, n=3. D) Western blot showing lubricin in the media harvested from non-producing control cells (Mock), cells transiently transfected with SynLubricin cDNA (Transient), and two successive 1-L batch cultures of sorted 293-F cells induced for three days with 1 μg/mL doxycycline and 3.5 mM VPA (Batch #1 and Batch #2); equine synovial fluid (ESF) was loaded as a control. E) Representative Western blot of SynLubricin produced from stably expressing 293-F cells collected at indicated time points after 1 μg/mL doxycycline induction on day 0. F) Quantification of Western blot replicates represented in B, n=3, ns—not significant.

Figure 24:
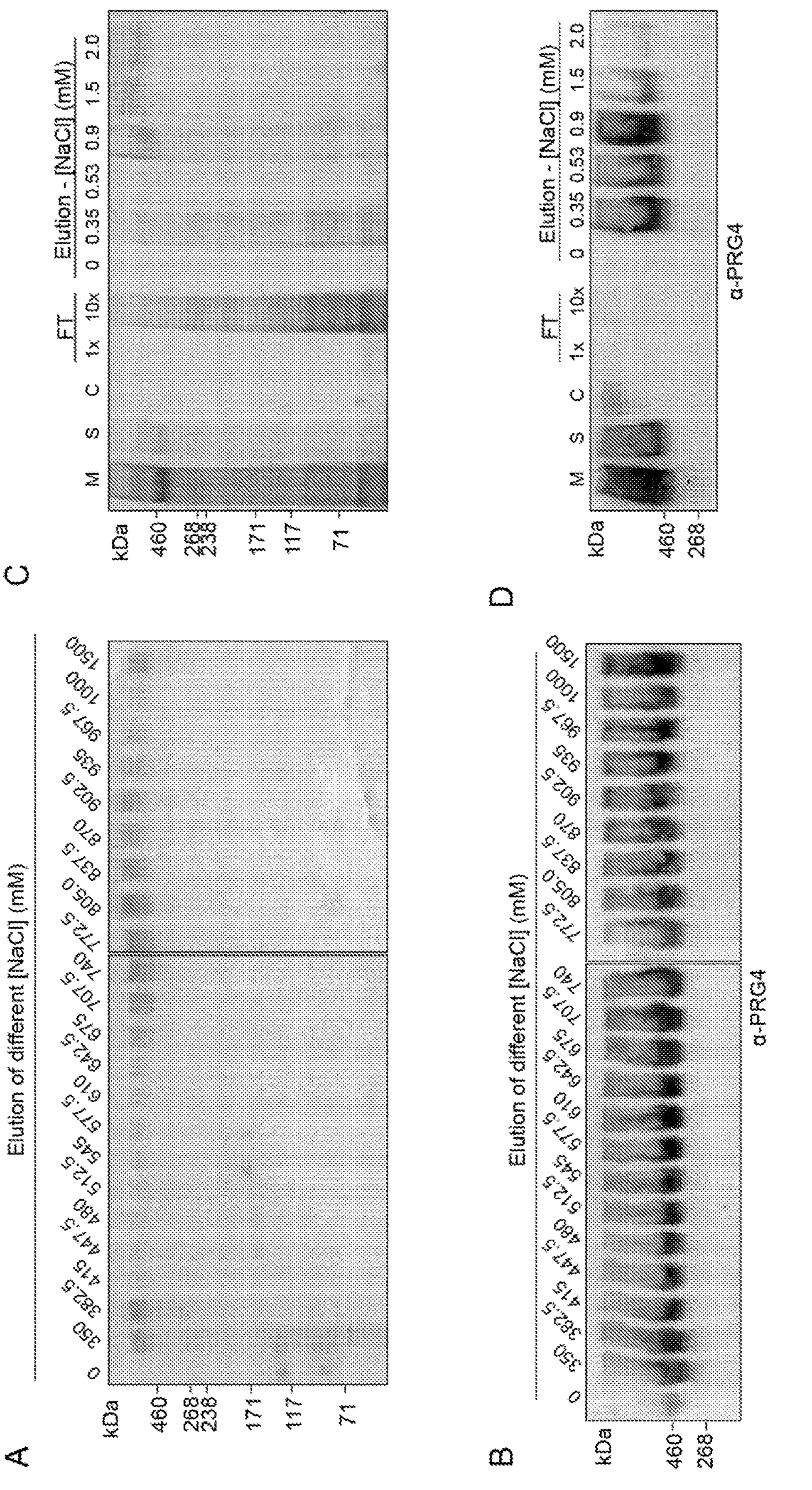

FIG. 24: Purification of SynLubricin by anionic exchange chromatography. A) Sliver stain and B) Western blot showed SynLubrcin eluted continuously from Q Sepharose® resin over a broad range of NaCl concentrations (concentrations indicated above lanes in mM). C) Sliver stain and D) Western blot showing harvested SynLubricin media supernatant (M), 10-fold diluted SynLubricin media supernatant (S), wild-type 293-F conditioned media (C), flow through (FT-1×), 10-fold concentrated flow through (FT-10×), and eluted fractions at indicated salt concentration (shown above lanes in mM).

Figure 25:
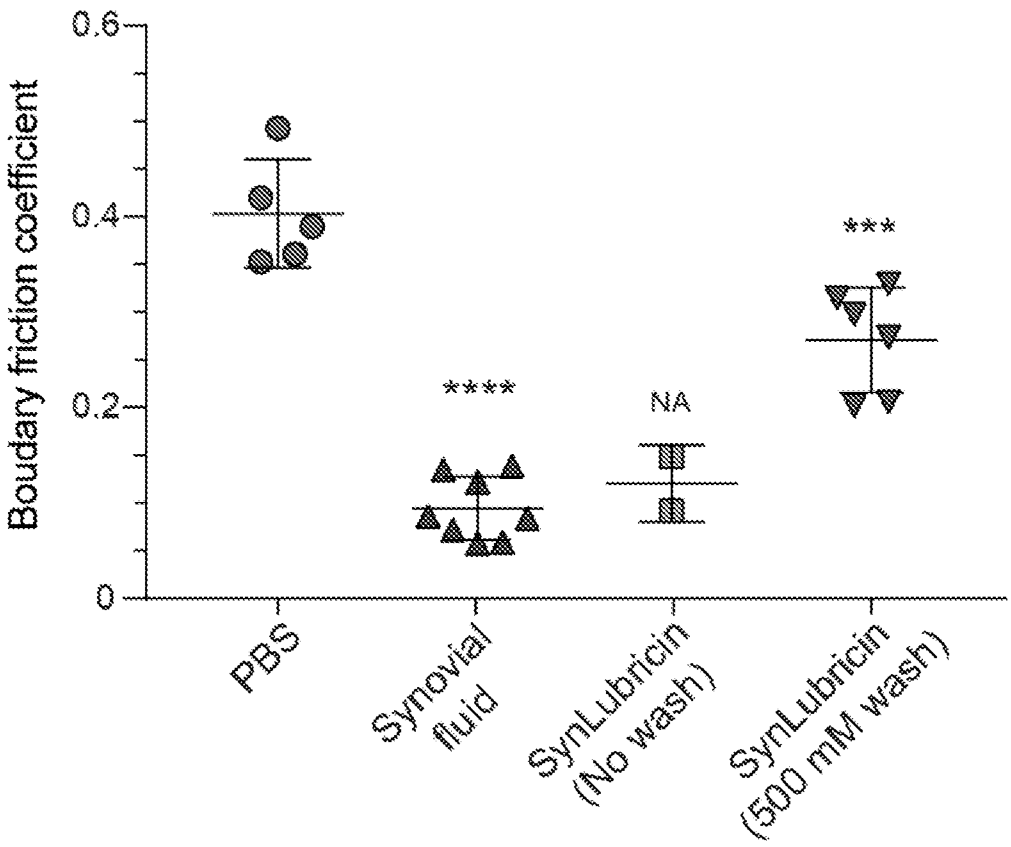

FIG. 25: Lubrication of cartilage explants shows functionality of SynLubricin. Friction coefficients of NaCl-extracted cartilage explants bathed in saline (PBS), bovine synovial fluid, or SynLubricin. Prior to lubrication analysis, the SynLubricin was purified with DEAE Sepharose, eluting either without washing or after a stringent 500 mM NaCl wash. Mean and S.D. are shown with independent measurements indicated. *$p<0.001$, **$p<0.0001$; NA: statistical testing is not applicable due to sample size.

Figure 26:
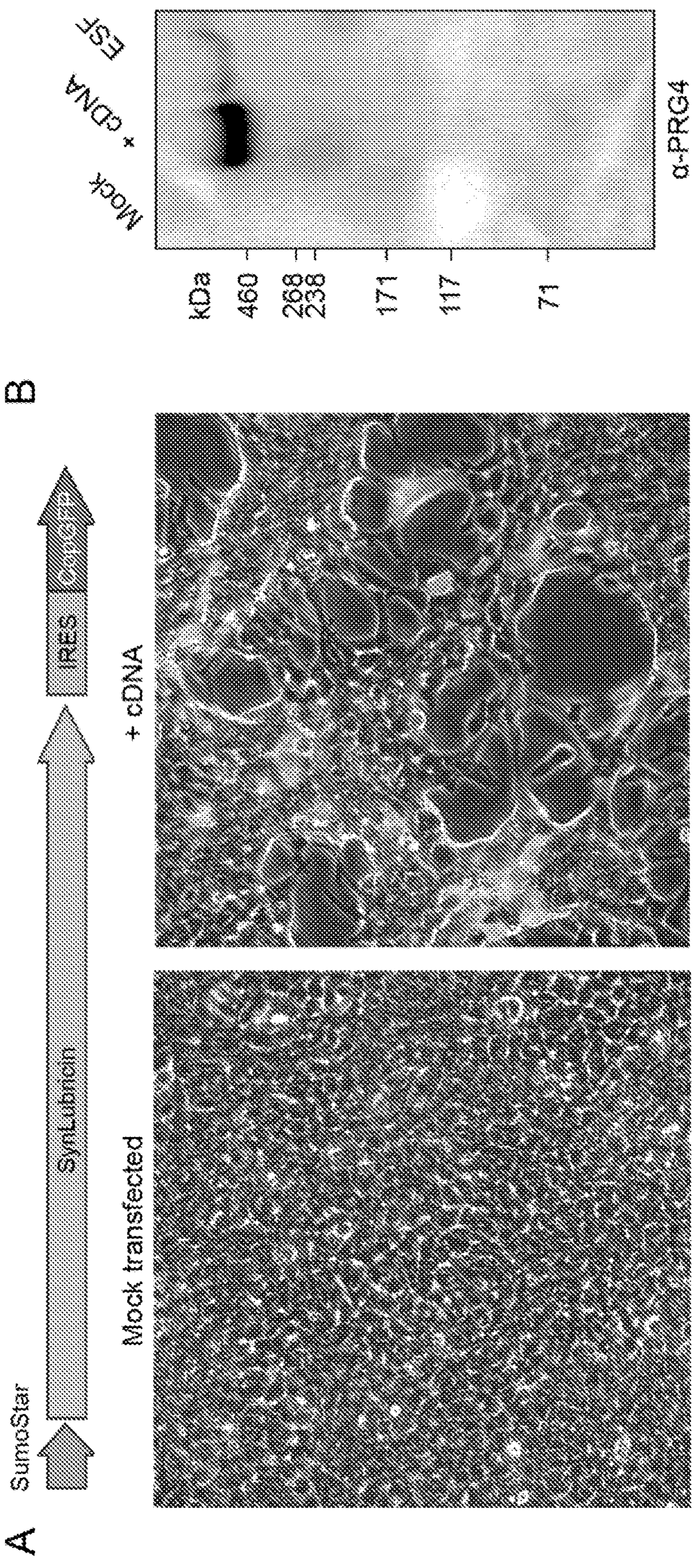

FIG. 26: Transient expression of SynLubricin altered adherent cell morphology. A) Morphology of 293-T cells mock transfected or transfected with cDNA for bicistronic SynLubricin IRES copGFP. Images shown are a merged overlay of phase contrast and fluorescence micrographs. Note the inhibition of cell-cell adhesion near cells expressing high levels of the copGFP reporter. B) Western blot of equine synovial fluid (ESF) and media supernatant from mock-transfected and SynLubricin-transfected cells probed with MABT401 antibody against PRG4 tandem repeats.

Figure 27:
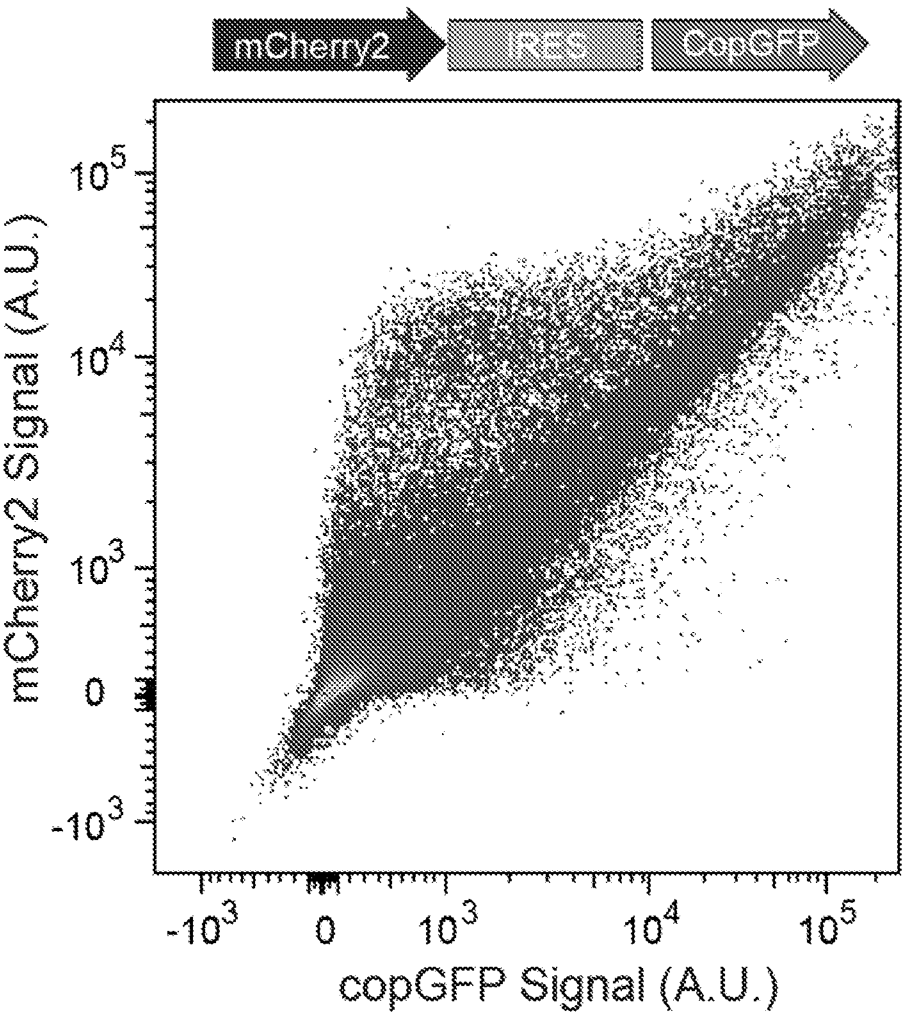

FIG. 27: Validation of new transposon-based gene delivery vector. Flow cytometry results showing correlation of levels of mCherry2 and the copGFP reporter.

Figure 28:
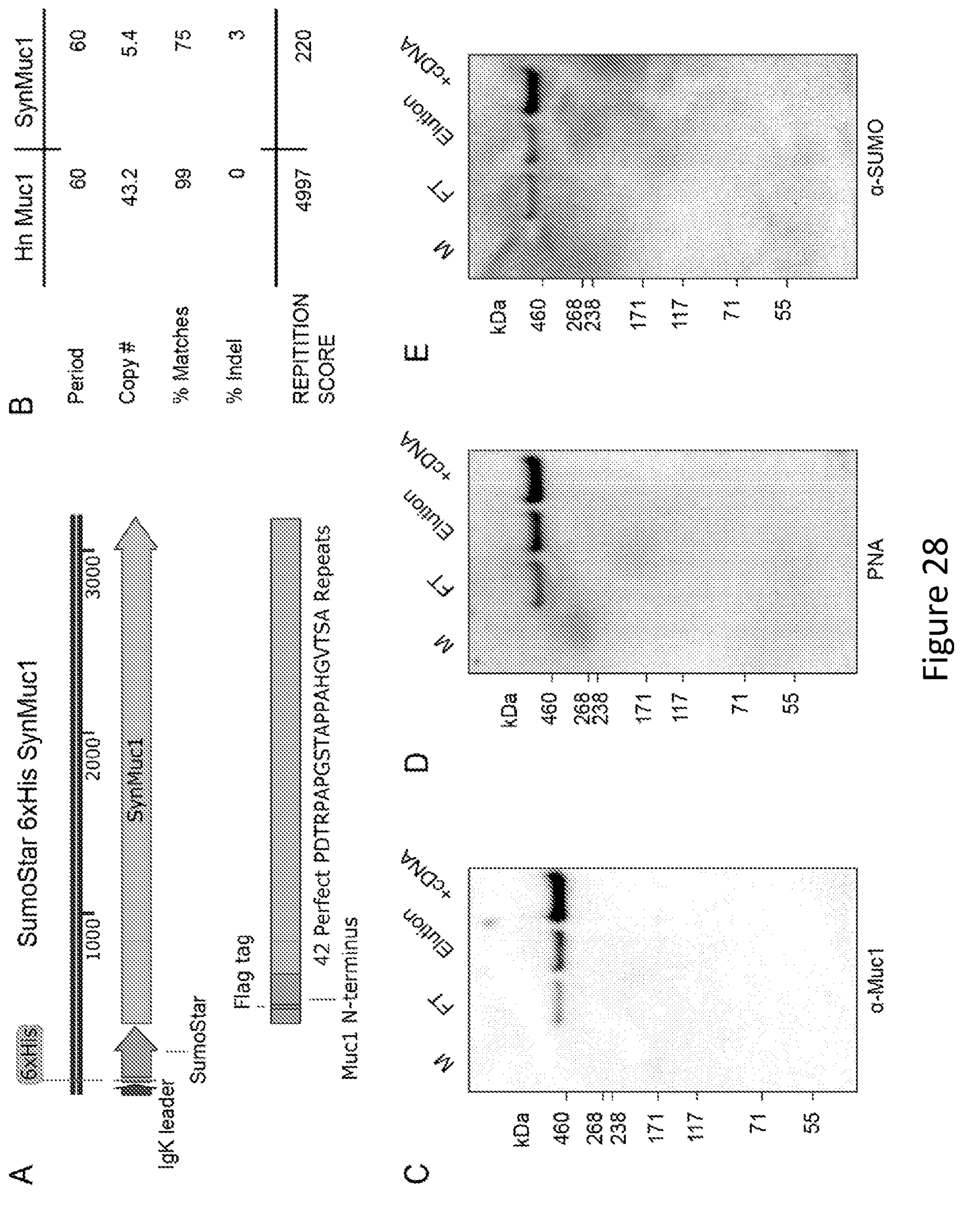

FIG. 28: Application of the codon-scrambling strategy for Muc1. The sequence shown on FIG. 28 is PDTRPAPGSTAPPAHGVTSA (unmodified Muc1 repeat) (SEQ ID NO:8). A) Schematic of SynMuc1 with codon-scrambled tandem repeats. B) Calculated repetition score for the nucleotides encoding the tandem repeats of human Muc1 and SynMuc1. C) Western blot of media supernatant from 293-F cells transfected with SynMuc1 cDNA (+cDNA) or non-transfected cells (M), Ni-NTA resin flow through from His-affinity purification (FT), and eluted protein (Elution) probed with a Muc1 antibody. D) PNA-lectin blot of C. E) Western blot of C, probed with a SUMO antibody.

Figure 29:
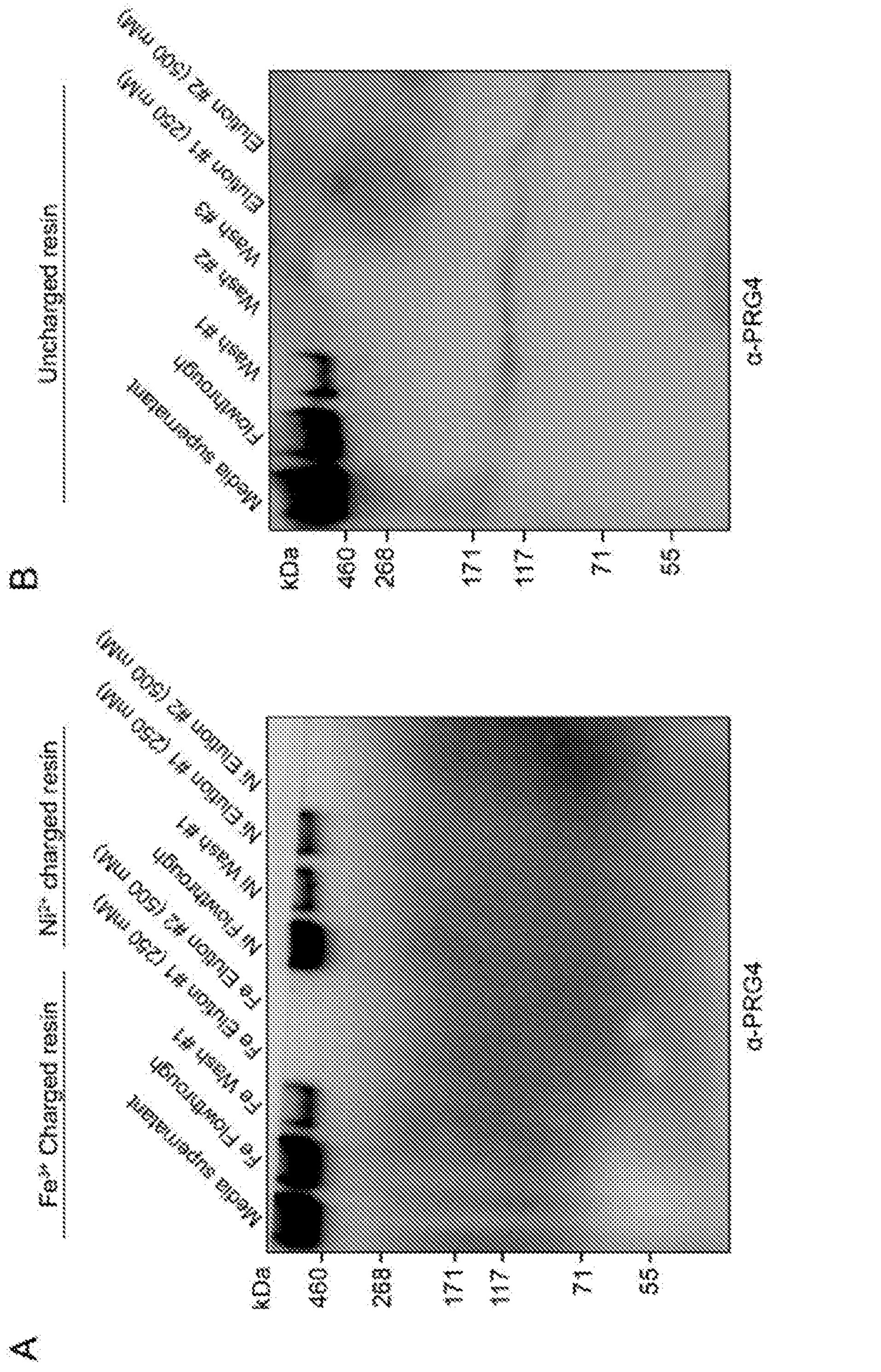

FIG. 29: SynLubricin has low affinity for immobilized-metal-affinity-chromatography (IMAC) resin. A) Western blot of media supernatant and the IMAC purification flow throughs, washes, and eluted fractions from $Fe^{3+}$ and $Ni^{2+}$ loaded nitrotriacetic acid (NTA) resins. Elutions were performed at the indicated NaCl concentration. No non-specific binding of sialic acids to multivalent $Fe^{3+}$ was observed. B) Western blot of flow through, wash, and eluted fractions from uncharged NTA resin.

Part IV Figures

Figure 30:
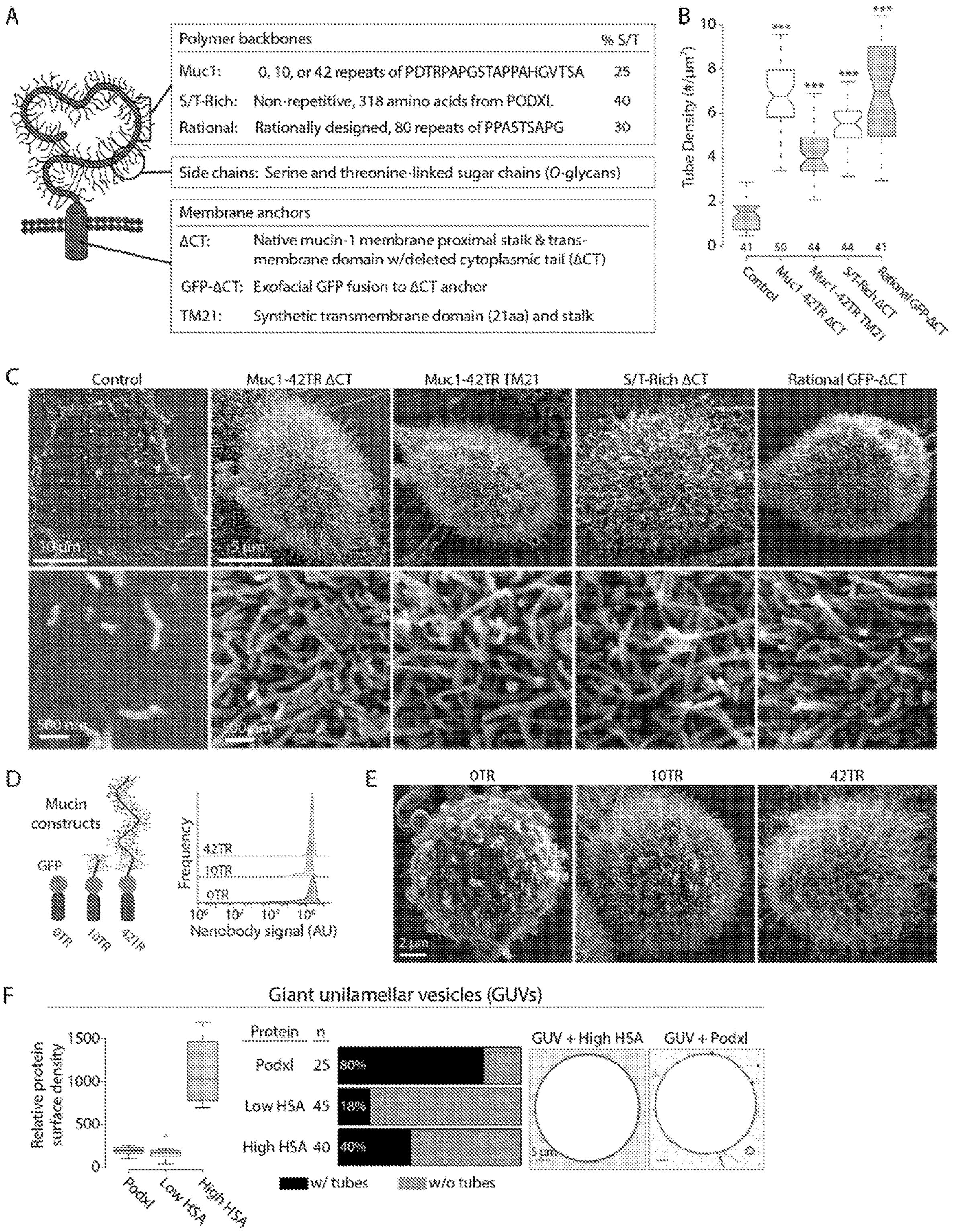

FIG. 30: Glycocalyx polymers induce membrane projections. (A) Schematic and table illustrating the genetically encoded biopolymers that were constructed and used throughout this work. The gene library encoded native and synthetic mucins comprised of a central polypeptide core, sugar side chains linked to serine (S) and threonine (T) residues, and a transmembrane anchor. (B) Quantification of membrane tube density in epithelial cells, showing mucin polymers induce dramatic tubularization compared to wild-type (Control) cells. Number of cells analyzed is shown on the x-axis for each condition. Box notches here and elsewhere indicate 95% confidence intervals. (C) Scanning electron microscopy (SEM) images showing membrane morphologies of cells expressing the indicated biopolymer. (D) (left) Cartoons of Muc1 GFP-ΔCT polymers of varying length, as indicated by the number of tandem repeats (TR). (right) Flow cytometry data showing similar cell-surface expression levels of indicated mucins using a GFP-binding nanobody, n=3, >40,000 cells per population. (E) Representative SEM images of cells described in (D). (F) (left) Quantification of relative protein surface density on giant unilamellar vesicles (GUVs) with membrane-anchored Podocalyxin (Podxl) at low density, human serum albumin (HSA) at low density (Low HSA), or HSA at high density (High HSA), n=10-20. All GUVs were formulated with 10 mole % Ni-NTA-lipid for protein anchorage. (center) Quantification of the fraction of GUVs with or without tubes; n is the number of GUVs analyzed for each protein. (right) Representative confocal images of GUVs. ***$p<0.001$ (post-hoc student's two tailed t test).

Figure 31:
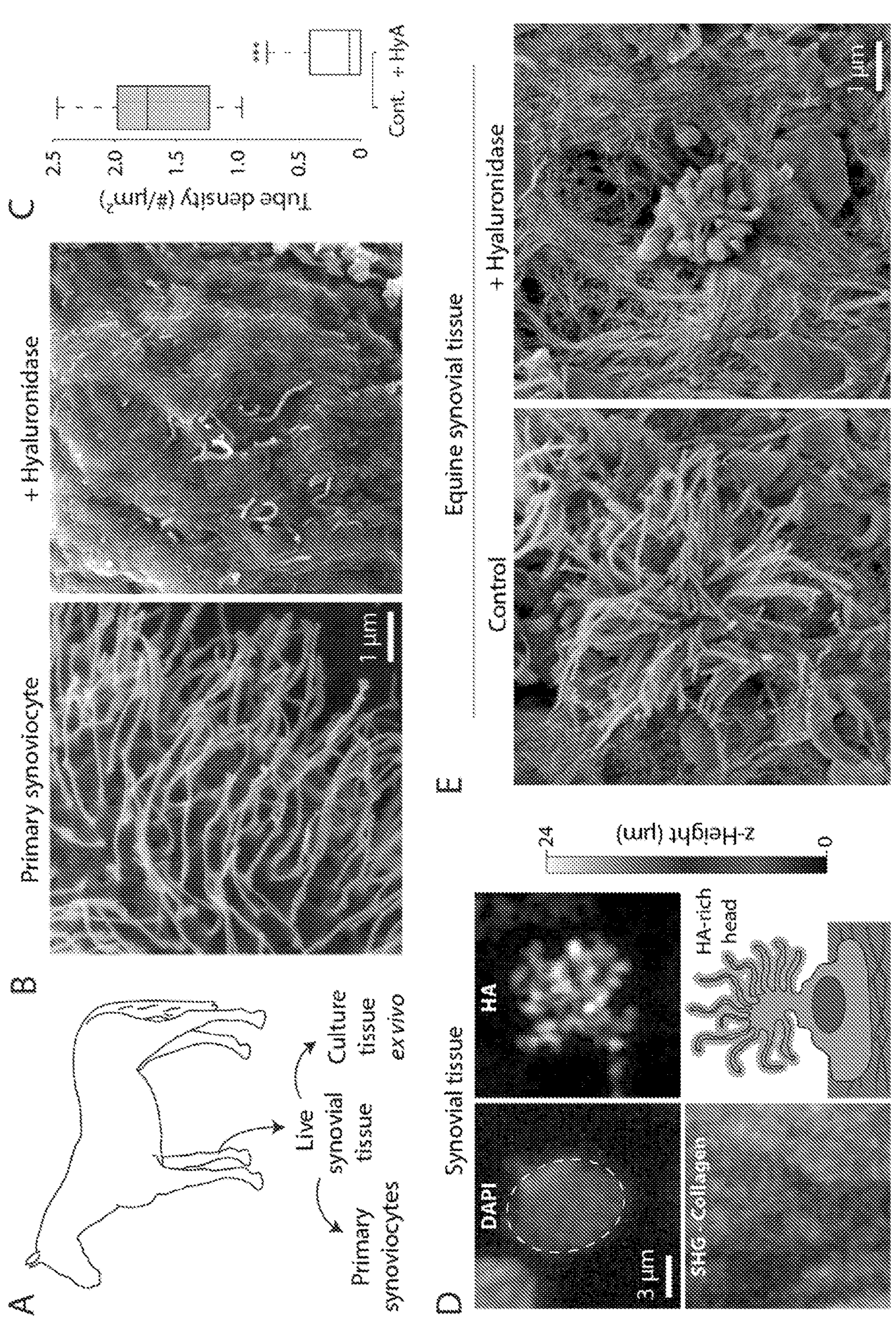

FIG. 31: Membrane morphology of tissue synoviocytes is regulated by the glycocalyx. (A) Experimental workflow for resected equine synovial tissues. (B) Representative SEM images of hyaluronic acid synthase 3 (HAS3) expressing primary synoviocytes showing retraction of membrane tubules following 30 minutes of hyaluronidase (HyA) treatment to digest hyaluronic acid (HA). (C) Quantification showing tubule density was dependent on the presence of HA. (D) Images of freshly resected synovial tissue showing the nucleus (DAPI), surface-anchored HA (hyaluronic acid binding protein, HABP) of a representative synoviocyte, and the tissue collagen (second harmonic generation, SHG). Depth along the z-axis is coded according to the color bar. Note the HA-enriched membrane extensions protruding from the synovial tissue surface. Lower right panel shows a cartoon representation of the observed tissue synoviocyte. (E) Membrane tubules are visible, by SEM, on synoviocytes in freshly excised equine synovial tissue. The synoviocyte head is pseudo-colored in orange protruding from the synovial tissue. HyA treatment to digest HA resulted in the rapid retraction of synoviocyte tubules (right). ***$p<0.001$ (post-hoc student's two-tailed t test).

Figure 32:
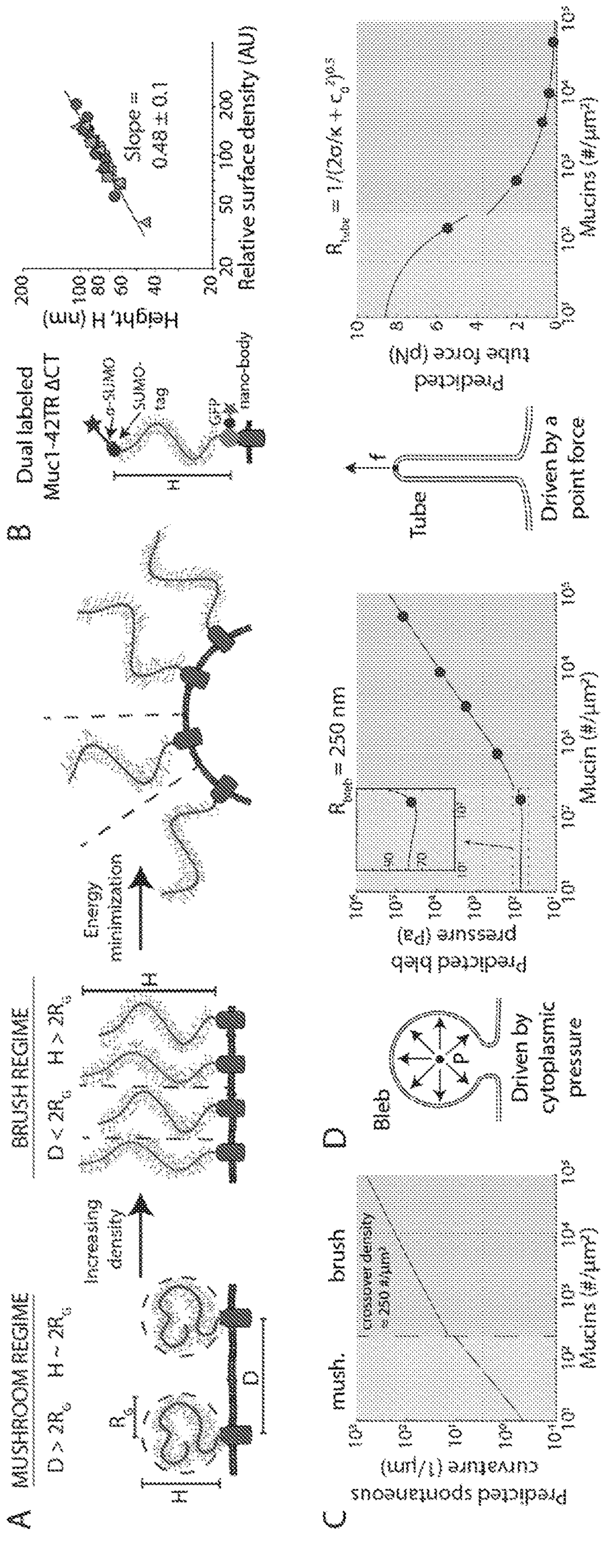

FIG. 32: Polymer brush model of the glycocalyx and generation of preferred membrane shapes (A) Polymer model of membrane bending illustrating proposed spontaneous membrane curvature induced by the cellular glycocalyx. Low density polymers are non-interacting and adopt a compact structure in the "mushroom" regime. In the "brush" regime, polymers overlap (the average distance between polymers, D, is less than the twice the radius of gyration, $R_G$) and extend to avoid each other, increasing the height of the polymer brush (H). Entropic pressures are the basis for membrane curvature generation by polymer mushrooms and brushes. (B) Muc1 construct with SUMO and GFP tags flanking the polymer domain for visualization of polymer extension with expansion microscopy (ExM). Polymer extension versus polymer fluorescence intensity, a proportional measure of surface density, showing the indicated scaling relation. Dots, squares, and triangles indicate measurements from three samples. The red line shows a linear regression through all data points. (C) Theoretical prediction of spontaneous curvature generation by Muc1 polymer mushrooms and polymer brushes. Blue: estimated mushroom regime (mush.); pink: estimated brush regime (brush). The computational model here considers mucins of length 270 nm having monomeric segments of length 15 nm (Kuhn length). These parameters were based on experimental characterization of native Muc1-42TR and selected for comparison to experiments below. (D) (left) Theoretical prediction of required pressure (Pa) as a function of mucin concentration for blebs of radii=250 nm. The insert shows a pressure minimum near the mushroom-brush transition. (right) Theoretical prediction of the required point force (pN) as a function of mucin concentration for maintaining membrane tubules.

Figure 33:
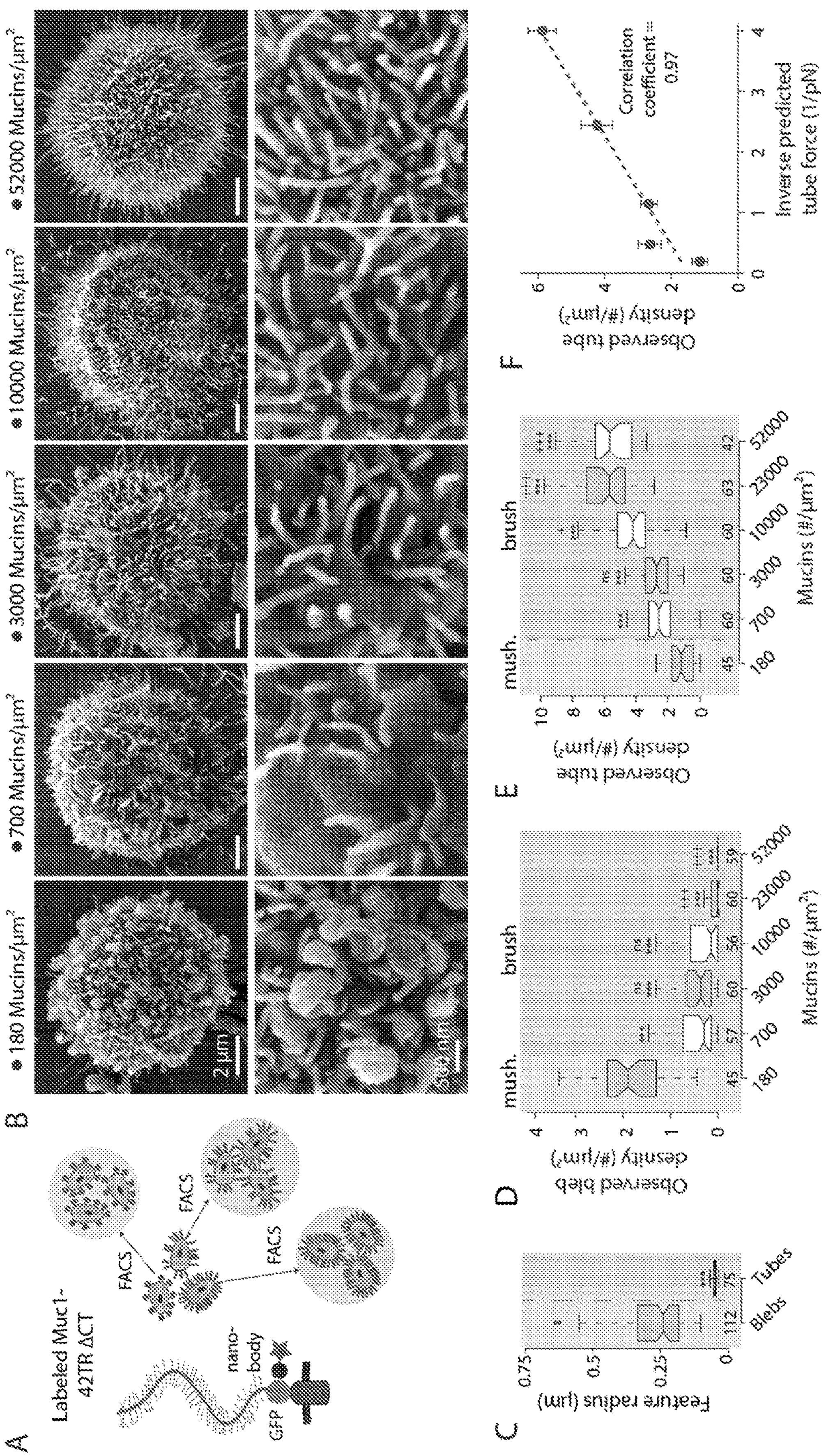

FIG. 33: Preferred membrane shape depends on cell-surface biopolymer concentrations. (A) Strategy for sorting cells into populations with varying levels of cell surface mucin (Muc1-42TR-GFP ΔCT) using fluorescence-activated cell sorting (FACS). (B) Representative SEM images showing the transition of membrane morphological features of sorted cell populations with the indicated mucin surface density. Mucin densities were chosen to match the indicated points on the theoretical graphs (FIG. 3D). (C) Average radius of bleb structures measured in the mushroom regime and tube structures measured in the brush regime. (D) Observed density of membrane blebs on sorted cell populations having the indicated average mucin surface density. Significance was determined between mushroom regime and brush regime (*) or between the lowest brush regime density and all other brush mucin densities (+). (E) Observed density of membrane tubes on sorted cell populations having the indicated average mucin surface density. Symbols defined in (D). (F) Inverse predicted force from (FIG. 3D, right) versus the observed tube density from (E) exhibits a linear relationship and Pearson correlation coefficient of 0.97. Number of measurements shown on the x-axis of boxplots. Error bars indicate 95% confidence intervals. ns—not significant; */+$p<0.05$; /++$p<0.01$; */+++ $p<0.001$ (post-hoc student's two-tailed t test).

Figure 34:
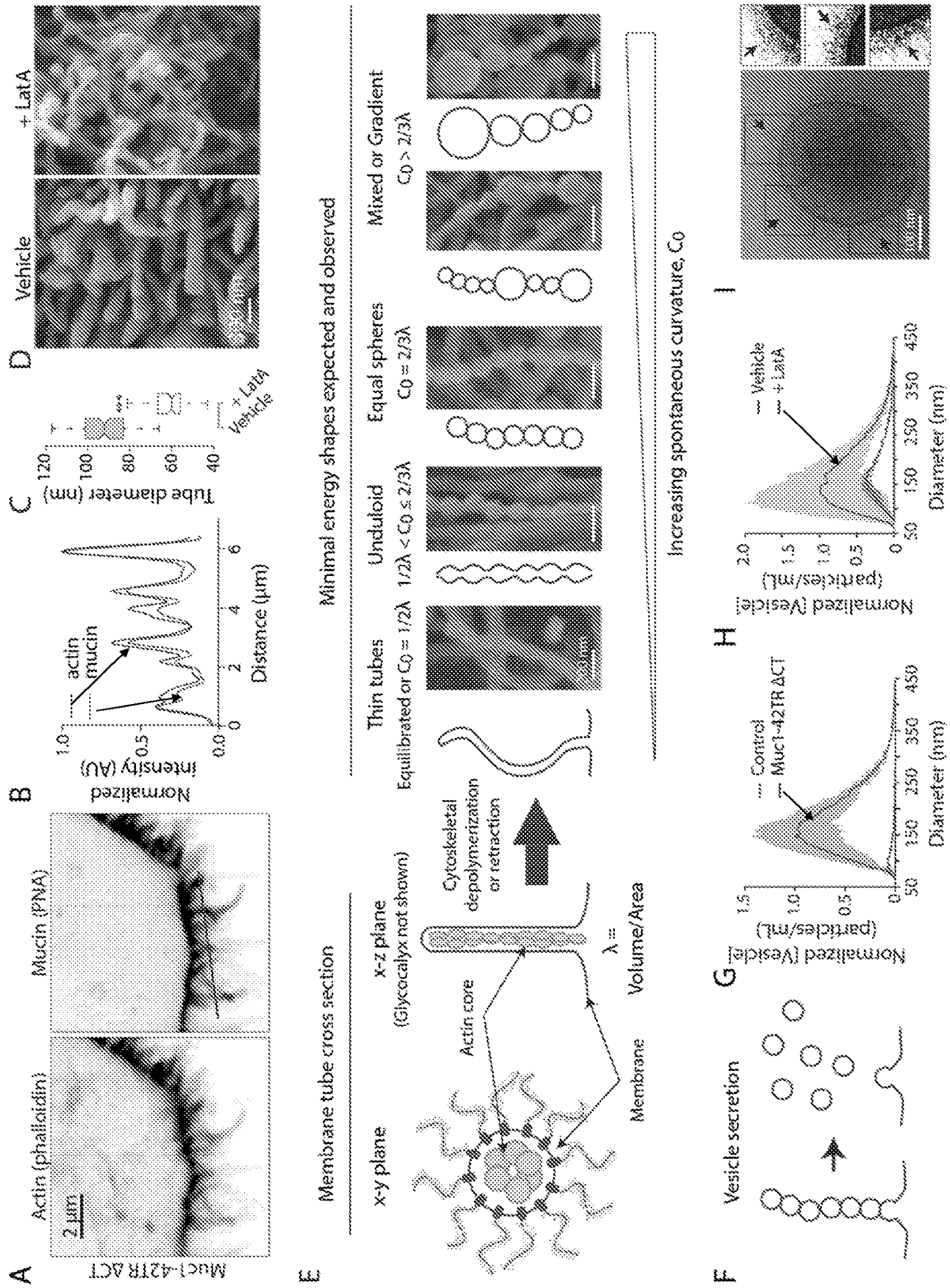

FIG. 34: Glycocalyx-mediated membrane instabilities and extracellular vesicle biogenesis. (A) Representative confocal microscopy images of epithelial cells expressing Muc1-42TR ΔCT and stained with PNA (peanut agglutinin) for mucins and phalloidin for actin, n=3. (B) Fluorescent intensity line trace from (A) (PNA image, red line). Values are normalized for their respective maximum intensities for phalloidin and PNA stains. (C) Average diameter of tubules in Muc1-42TR ΔCT expressing cells following treatment with DMSO (Vehicle) or with 10 μM Latrunculin-A (+LatA) to disrupt actin assembly. (D) Representative SEM images of tubules in vehicle treated or LatA treated cells expressing Muc1-42TR ΔCT. (E) (left) Cartoon schematic of a proposed model in which the actin core resists the spontaneous membrane curvature driven by the glycocalyx brush. Upon actin depolymerization, membrane tubules are destabilized and predicted to relax into (right) various pearled structures and/or thin tubes that represent minimal energy surfaces. Schematic drawings of these predictions are shown alongside representative pseudo-colored SEM images of cells expressing Muc1-42TR ΔCT. (F) Cartoon schematic of proposed mechanism where pearling and vesiculated membrane instabilities (left) are disrupted and lead to microvesicle shedding (right). (G) Representative histogram showing the average concentration and size distribution of extracellular vesicles for wild-type (Control) and Muc1-42TR ΔCT expressing cells and (H) showing Muc1-42TR ΔCT cells treated with DMSO (Vehicle) or Latrunculin A (+LatA). Particle concentration is normalized to the max peak for each graph. Shaded area shows 95% confidence interval, n=5, 5, 4, 7, respectively. (I) Representative cryogenic transmission electron microscopy (cryo-TEM) image of a vesicle collected from cells expressing Muc1-42TR ΔCT. Red boxes indicate pseudo-colored regions of interest shown on the right. ***$p<0.001$ (post hoc two-tailed student's t test).

Figure 35:
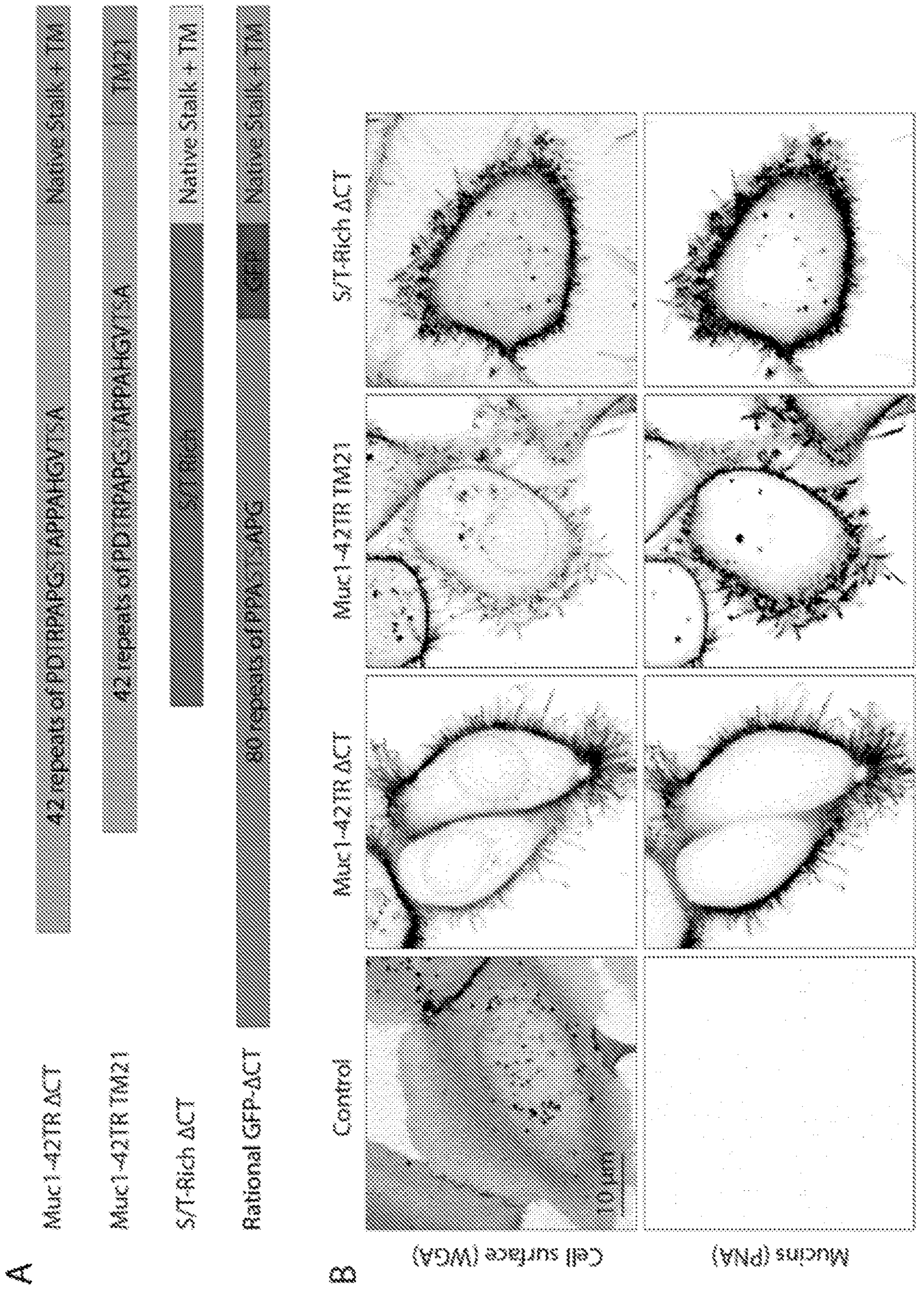

FIG. 35: Validation of genetically encoded mucins. (A) Cartoon representations of the genetically-encoded glycoproteins. Mucin-1 (Muc1) contains 42 repeats of PDTRPAPGSTAPPAHGVTSA (SEQ ID NO:8) and Podocalyxin (S/T-Rich) has a serine- and threonine-rich region for O-glycosylation. The engineered glycoproteins lack the native cytoplasmic tail signaling domain (ΔCT) while retaining the native transmembrane domain (TM) or exchanged with a synthetic 21-amino-acid transmembrane anchor (TM21). The rationally designed mucin (Rational GFP-ΔCT) contains 80 repeats of PPASTSAPG (SEQ ID NO:4) fused to a fluorescent marker (GFP) and the native stalk and TM without the native cytoplasmic tail signaling domain (ΔCT). (B) Representative confocal microscopy images showing membrane tubularization induced by various engineered glycoproteins compared to wild-type (Control) cells. The cell surface is visualized with lectin WGA (wheat germ agglutinin). Mucin staining with lectin PNA (peanut agglutinin) confirms glycoprotein O-glycosylation and surface localization on MCF10A cells, n=3. (C) Quantification of endocytosis of Alexa Fluor 488 labeled transferrin (488 TNF) after 0.5 or 1 h of treatment. Quantification performed with flow cytometry, median signal reported with background subtraction, >10,000 cells per population, n=6, error bars are S.D. (D) Representative confocal microscopy images of endocytosed 488 TNF after 0.5 h of treatment. (E) Western blot showing polymer sizes expressed in epithelial cells, analyzed with an antibody against the green fluorescent protein (GFP) tag, n=2. (F) Quantification of tube density for the indicated mucin size. Number of cells analyzed is shown on the x-axis for each condition. Box notches indicate 95% confidence intervals. Statistical comparison is to 42TR. ns—not significant, *p<0.05, p<0.01, *p<0.001 (post-hoc student's two-tailed t test).

Figure 36:
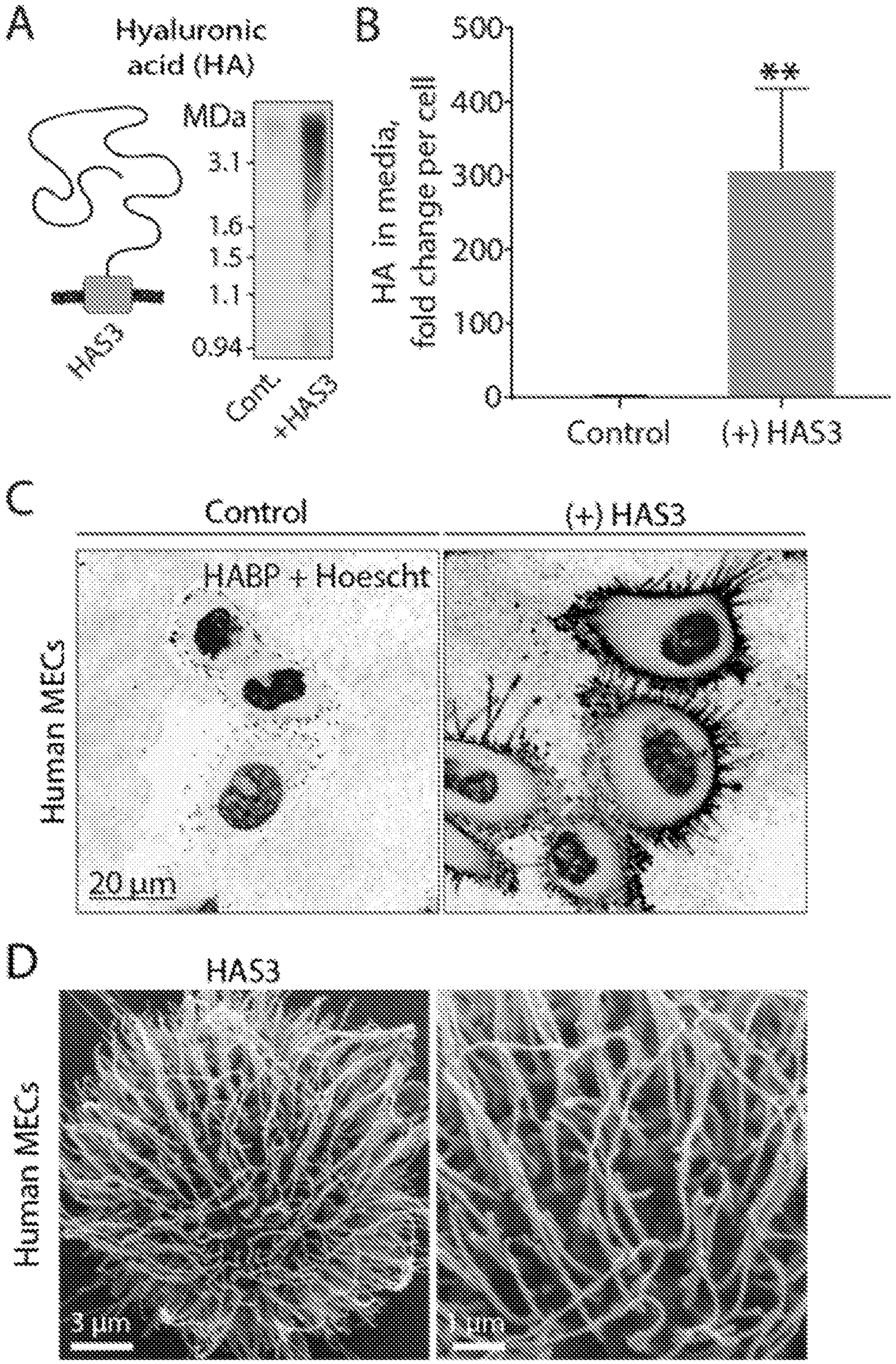

FIG. 36: Hyaluronic acid localizes on the cell surface and induces cell-surface projections. (A) (left) Cartoon of hyaluronic acid (HA) extruded by the transmembrane protein hyaluronic acid synthase 3 (HAS3). (right) Blot of HA in lysates of wild-type (Cont.) and hyaluronic acid synthase 3 (HAS3) expressing human mammary epithelial cells (MECs, MCF10A). Note that the expressed HA is a giant linear polymer in the MDa range. (B) ELISA quantification of HA secreted by MECs into their media, normalized to the number of cells in the sample and the HA secretion of Control cells, n=3. (C) Representative confocal microscopy images of human MECs, either wild-type (Control) or stably expressing HAS3. Cells are stained with Hoescht (nucleus) and Alexa Fluor 568 hyaluronic acid binding protein (HABP). (D) Representative SEM images showing highly elongated membrane tubules in HAS3-expressing human MECs (left) and a zoomed in region on the same cell (right). **p<0.01 (post-hoc student's two-tailed t test).

Figure 37:
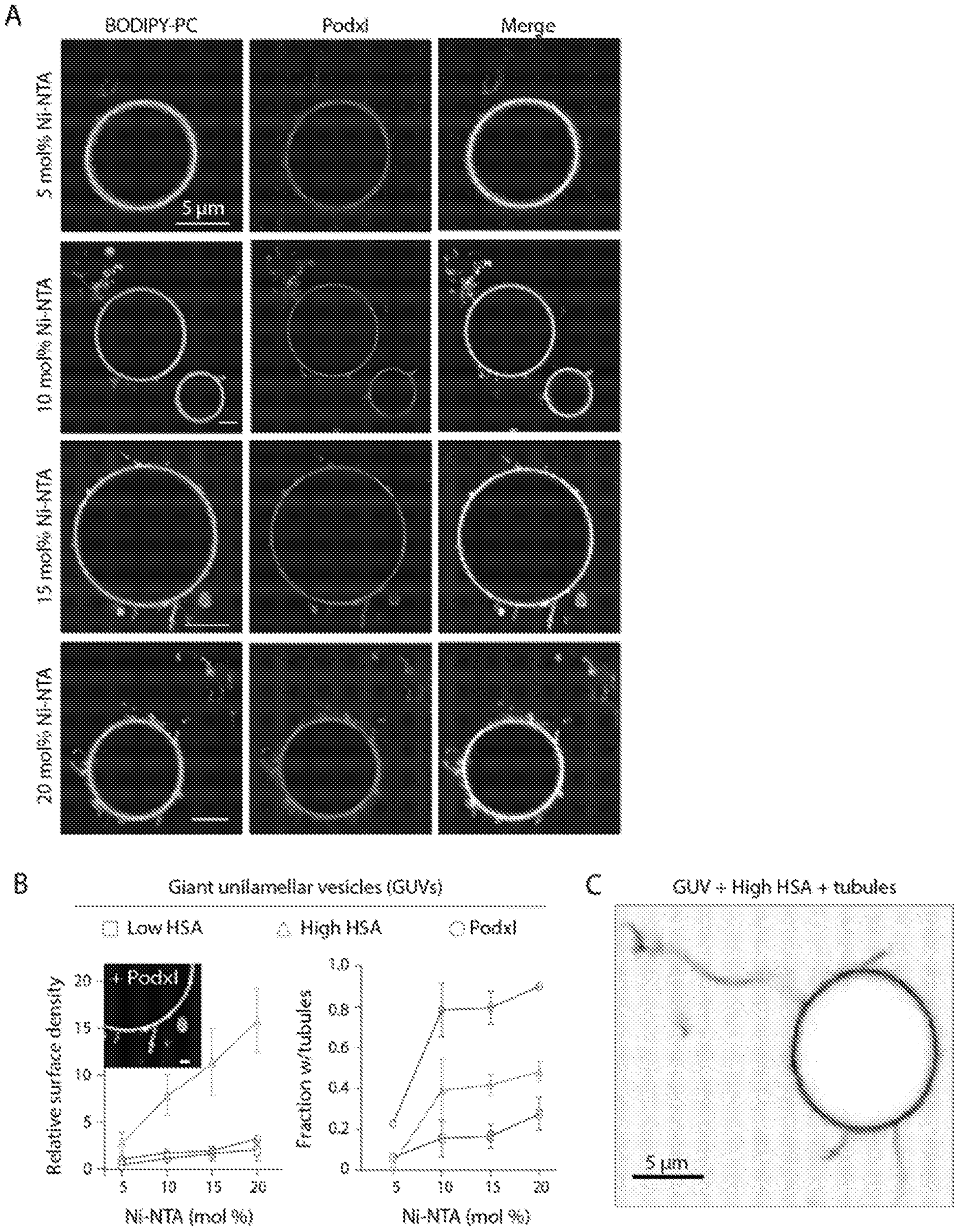

FIG. 37: Mucins cause tubularization of model lipid membranes.

(A) Representative confocal images of DOPC giant unilamellar vesicles (GUVs) labeled with Bodipy-PC with an increasing fraction of Ni-NTA lipids. Recombinant Alexa Fluor 568-labeled Podocalyxin (Podxl) associates with the GUV via a polyhistidine tag. Scale bar is 5 μm in each BODIPY-PC image. (B) (left) Quantification of fluorescent intensity (relative surface density) of Alexa Fluor 568-labeled human serum albumin (HSA) or Podxl on GUVs at different Ni-NTA lipid levels, n=10-20. A similar HSA surface density to the mucin surface density (Low HSA) and a several-fold higher HSA surface density (High HSA) were used to control for protein crowding effects. (right) Quantification of the fraction of GUVs with tubes at different Ni-NTA lipid levels for each recombinant protein—Low HSA, High HSA, and Podxl, error bars are standard deviation, n=20-90 GUVs over 1-3 experiments. (C) Representative confocal image of Alexa Fluor 568-HSA for a GUV with High HSA forming tubules.

Figure 38:
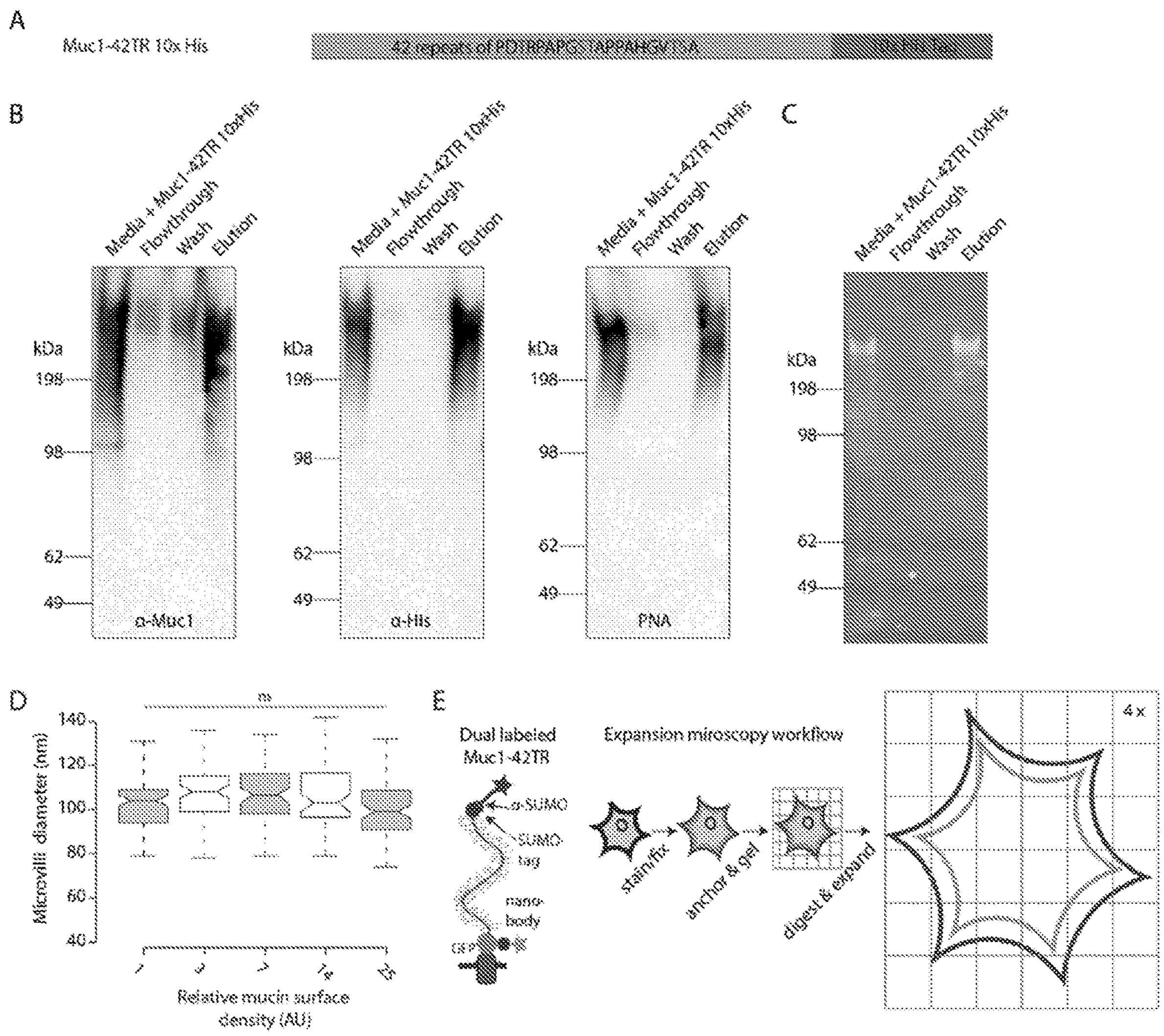

FIG. 38: Supporting information for physical characterization of individual mucins and mucin ensembles. (A) Cartoon representation of the recombinant Muc1 42 tandem repeat (Muc1-42TR) polymer fused to a 10×-histidine tag. (B) Western blot validation of recombinant Muc1-42TR production (Media+Muc1-42TR 10×His), Ni-NTA resin binding of the protein (Flowthrough), wash of non-specific proteins (Wash), and purified recombinant Muc1-42TR polymer (Elution). Samples are probed with anti-Muc1 and anti-His antibodies as well as PNA (peanut agglutinin) to bind O-linked glycans. (C) SYPRO Ruby protein gel stain for samples described in B. (D) Quantification of epithelial microvilli diameter for the indicated relative mucin surface densities. Box notches indicate 95% confidence intervals. (E) (left) Mucin construct (Muc1-42TR) with SUMO and GFP tags flanking the polymer domain for visualization of polymer extension with expansion microscopy (ExM). (right) ExM sample workflow. First, samples are stained and fixed. Then the proteins are chemically linked (anchored) to monomers which polymerize to form a gel. Proteins are then digested, and the gel is expanded to four times the original size. ns—not significant.

Figure 39:
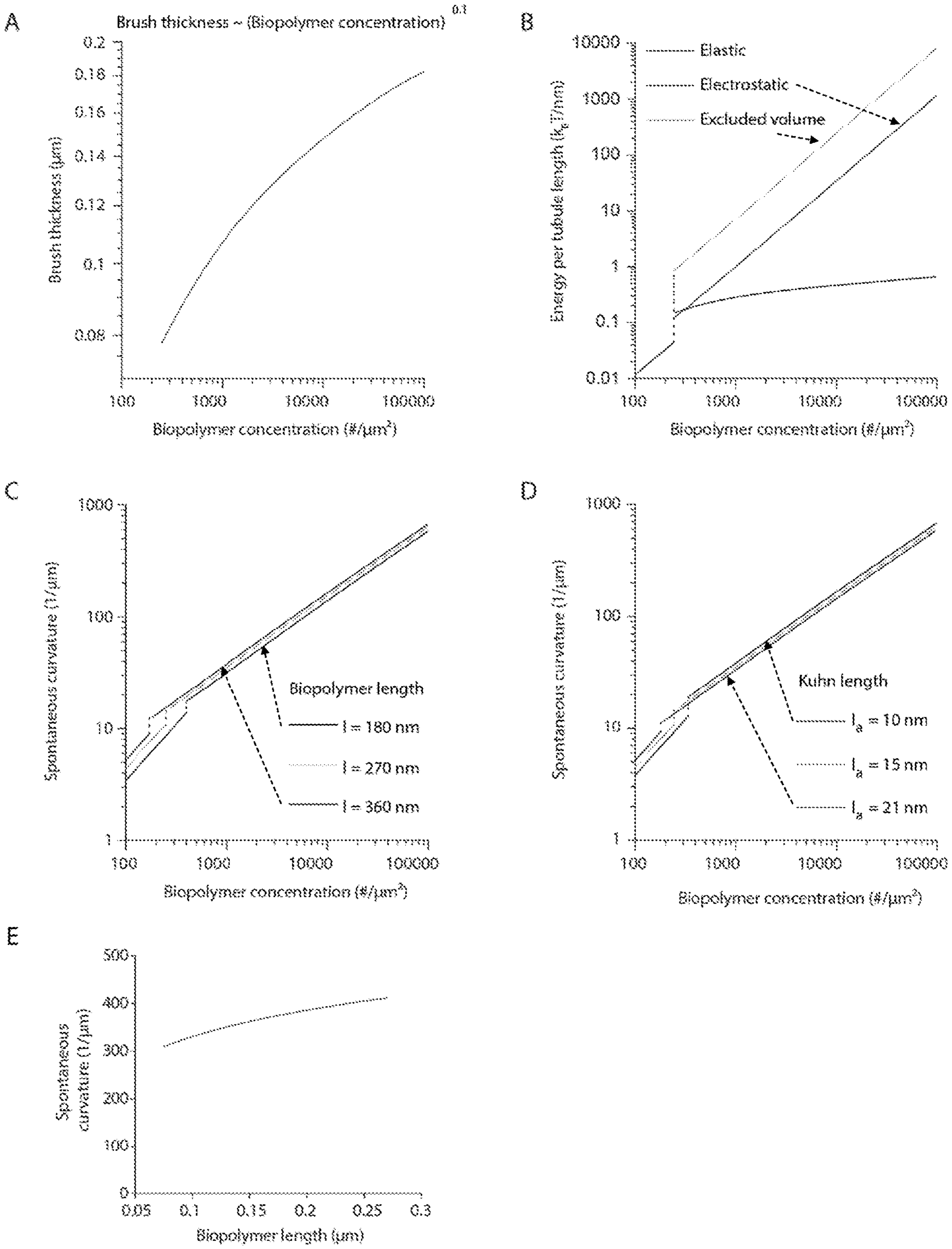

FIG. 39: Additional polymer brush theory predictions for curvature generation by intermolecular interactions in the glycocalyx. (A) Graph for the predicted brush thickness as a function of biopolymer surface density in the brush regime. Brush thickness scales approximately as a power law with biopolymer concentration. (B) Plot showing energetic contributions as functions of the biopolymer density. In the mushroom regime, polymers have only elastic energy, while in an extended brush, excluded volume and electrostatic interactions contribute to biopolymer free energy. (C) Plot depicting variation of spontaneous curvature generated with biopolymer density and molecular length. (D) Graph displaying trend of spontaneous curvature as a function of biopolymer density and Kuhn length. Kuhn length, equal to twice the persistence length, is directly proportional to polymer bending stiffness, and is referred to as the length of a monomeric segment in the manuscript. Plots in (A-D) are in log-log format. Plots in (A) and (B) use biopolymer length, l=270 nm, and monomeric segment length, $l_a$=15 nm. Plot (C) employs polymer monomer segment size of 15 nm, and (D) uses biopolymer length of 270 nm. (E) Predicted dependence of spontaneous curvature on biopolymer length at high density. This graph uses polymers of $l_a$=15 nm packed at a density of 50000 #/μm$^2$.

Figure 40:
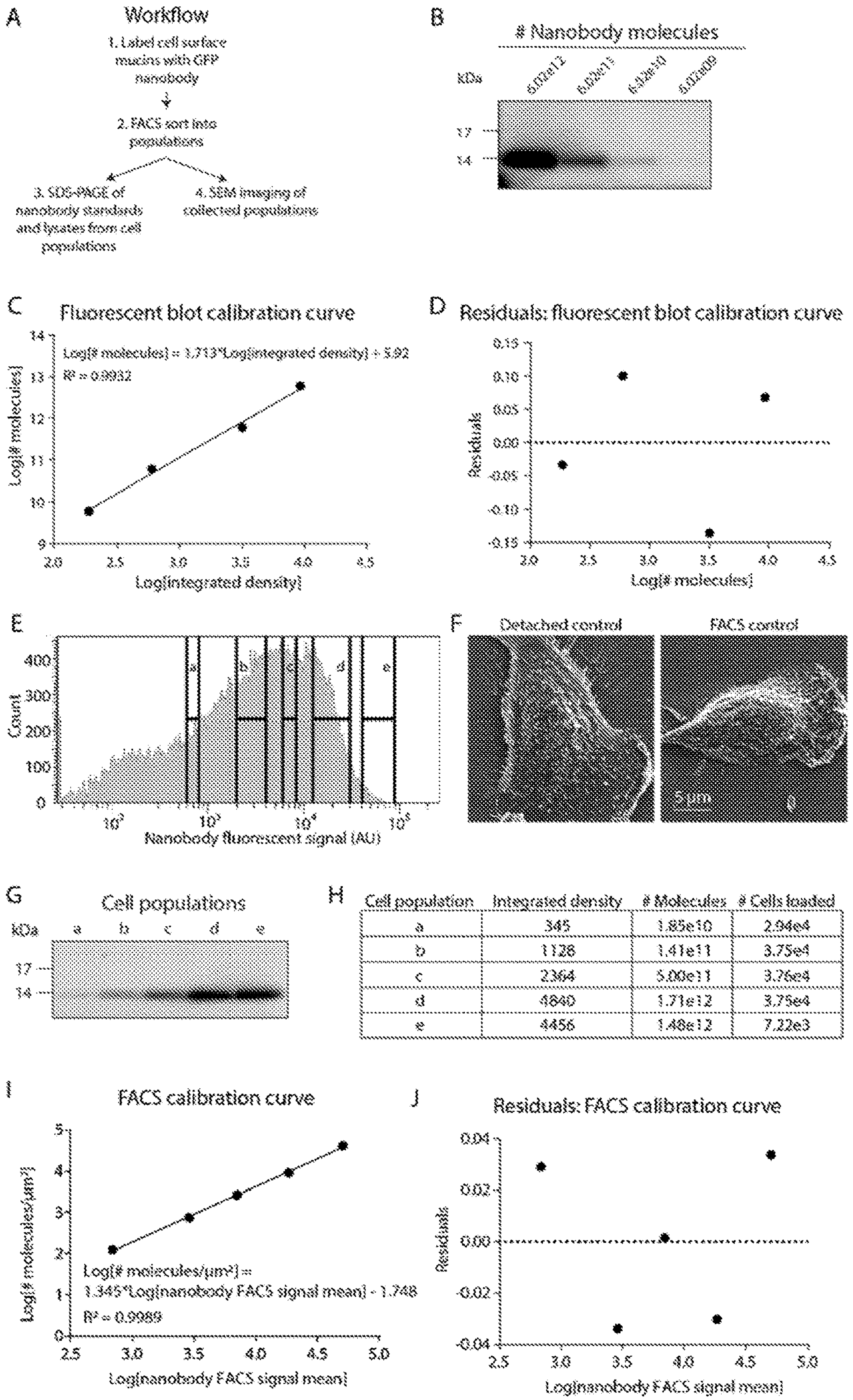

FIG. 40: Fluorescence-activated sorting and quantification of Muc1 surface densities. (A) Extended workflow for quantitative experiments at different Muc1 surface densities. (B) SDS-Page calibration of Alexa Fluor 647 labeled nanobody. (C) Calibration curve between the log value for integrated density of fluorescence signal from nanobody dilution series (shown in (B)) versus the log value of the number of molecule loaded. A linear regression fit and $R^2$ value are shown. (D) Residuals for the linear regression fit shown in (C). (E) Fluorescence-activated cell sorting (FACS) histogram showing the nanobody fluorescence signal and the populations 'a' through 'e' collected for these experiments. (F) Representative scanning electron microscopy (SEM) images of wild type cells which were non-enzymatically detached from the substrate then re-adhered (detached control) for SEM imaging and cells which were non-enzymatically detached from the substrate, collected through the FACS, then re-adhered (FACS control). These images demonstrate that the method of FACS collection did not influence the membrane shapes observed with Muc1-42TR ΔCT expression (shown in FIG. 2F). (G) SDS-Page analysis of fluorescent nanobody signal in each cell population, a-e, after collection and lysis of the cells. (H) Table describing the integrated density signal from the fluorescence image shown in (G), the calculated number of molecules based on the calibration curve in (C), and the number of cells loaded in the protein gel, (G), based on the number of cells collected with FACS for each population, (E). (I) Calibration curve between the log of the nanobody mean signal from the FACS versus the number of molecules calculated for each population. The number of molecules per sample was normalized by the number of cells loaded and the approximate area per cell. Linear regression fit and $R^2$ values shown. (J) Residuals for linear regression fit shown in (I).

Figure 5:
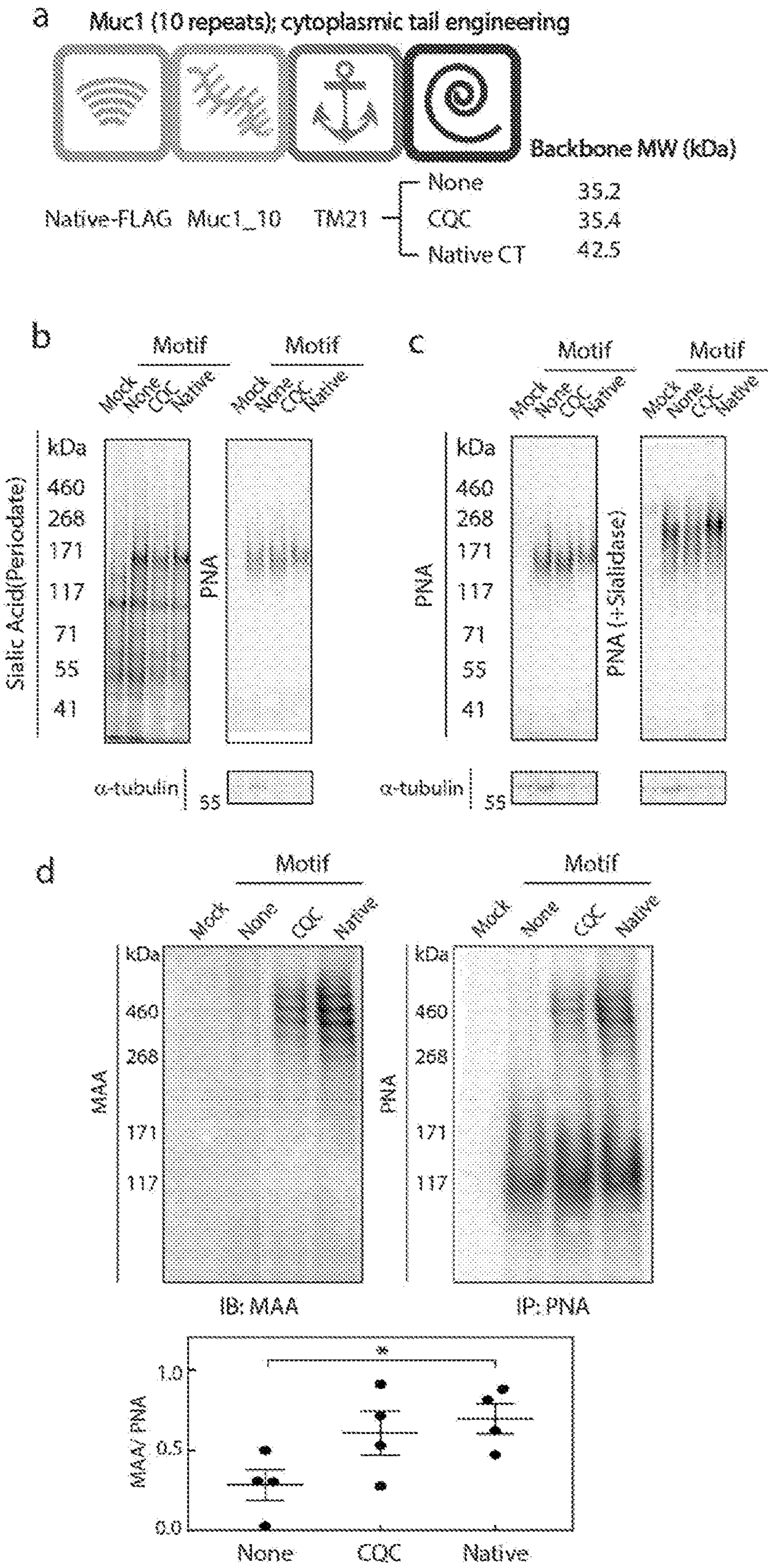
FIG. 5: Tuning Mucin Glycosylation through Cytoplasmic Tail Engineering. (a) Components and features of cell-surface mucins with synthetic 21-amino-acid transmembrane anchors (TM21) and engineered cytoplasmic motifs; native CT refers to a native cytoplasmic tail adapted from Muc1. (b) Lectin blot analysis of the indicated mucin isoforms from transiently transfected HEK293T cells to detect sialylated O-glycans by periodate oxidation and Core-I structures by PNA; blots are representative of three independent experiments. (c) PNA-lectin blot analysis of the indicated mucin isoforms before and after sialidase treatment; blots are representative of three independent experiments. (d) Top: Representative MAA and PNA lectin blot analysis (from four independent experiments) of the indicated mucin isoforms immunoprecipitated from transiently transfected HEK293T cells. Bottom: Ratiometric intensity of sialic acid to Core 1 glycan signal (MAA:PNA); data presented as the mean and SEM from four independent experiments. *P<0.05
Figure 41:
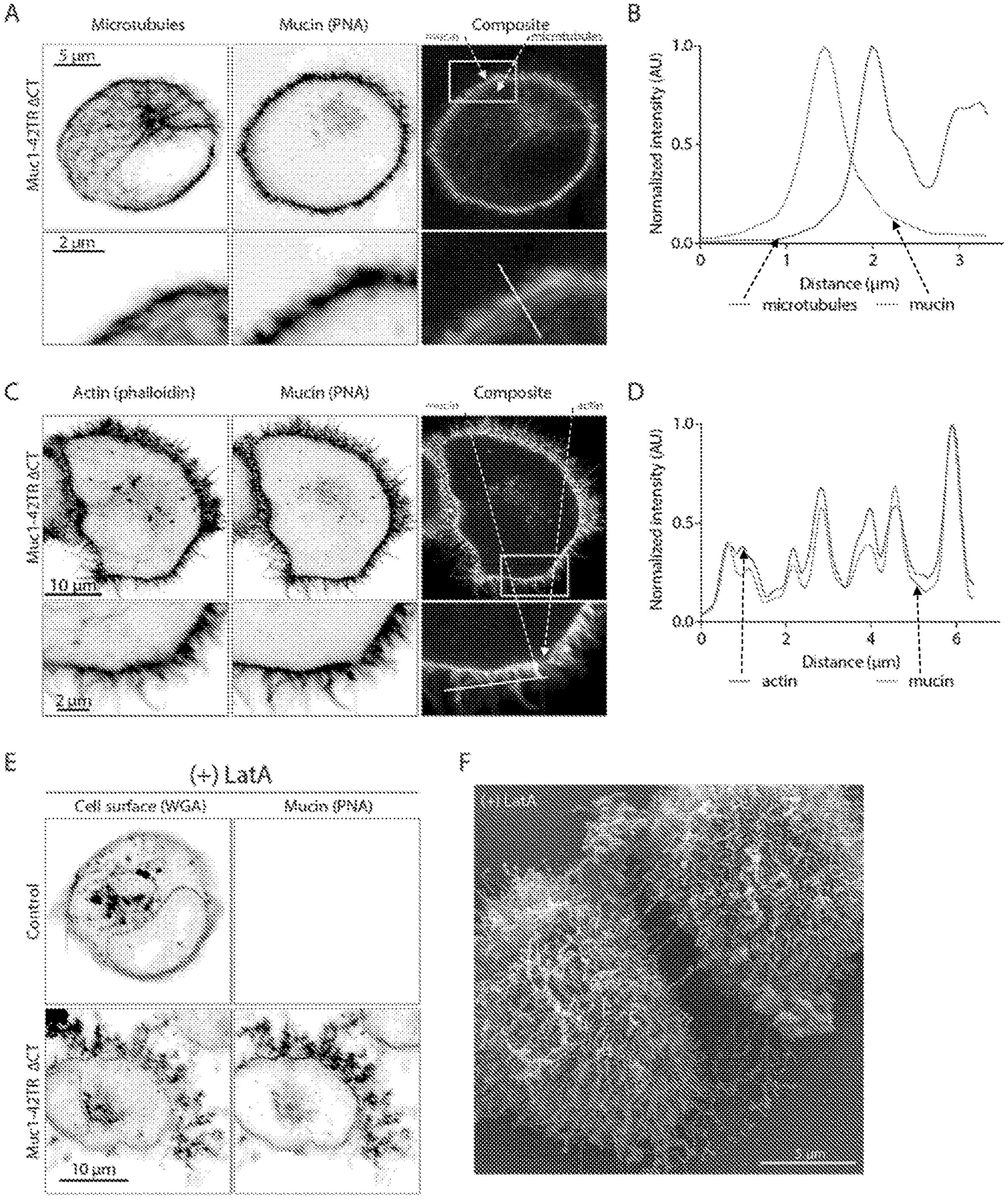

FIG. 41: Tubular membrane shapes contain filamentous actin cores and resemble microvilli. (A) Representative confocal microscopy images of epithelial cells expressing Muc1-42TR ΔCT showing indirect microtubule staining with anti-microtubule and Alexa Fluor 568-labeled secondary antibodies. Mucins are labeled with Alexa Fluor 647 PNA (peanut agglutinin). The bottom row shows the region of interest from the composite image (yellow box), n=3. (B) Fluorescent intensity line trace from (A) (bottom row, yellow line). Values are normalized for their respective maximum intensities. (C) Representative confocal microscopy images of epithelial cells expressing Muc1-42TR ΔCT showing actin staining with Alexa Fluor 568 phalloidin. Mucins are labeled with Alexa Fluor 647 PNA. The bottom row shows the region of interest from the composite image (yellow box), n=3. This data repeats and elaborates on (FIG. 5A, B). (D) Fluorescent intensity line trace from (C) (bottom row, yellow line). Values are normalized for their respective maximum intensities. (E) Representative confocal microscopy images of the midplane of wild type (Control) or Muc1-42TR ΔCT cells which have been treated with 10 μM Latrunculin-A (LatA) for 1 h, n=3. (F) Representative SEM image of LatA treated Muc1-42TR ΔCT cells.

DETAILED DESCRIPTION

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The disclosure includes every amino acid sequence described herein, and every polynucleotide sequence that encodes the amino acid sequences, including but not limited to cDNA sequences, and mRNA sequences. Complementary sequences, and reverse complementary sequences are also included. Expression vectors comprising such nucleotide sequences are encompassed by the disclosure.

The disclosure relates generally to improved glycoproteins, compositions comprising the proteins for use in diverse applications, and methods of making and using the glycoproteins. In embodiments, the glycoproteins are mucins and/or lubricins.

The disclosure includes cells and cell cultures that express the proteins described herein. In certain embodiments, the disclosure includes cell cultures that are improved for producing any of a variety of proteins due to reduced clumping, aggregation, etc. of the cells. In embodiments, the disclosure relates to reducing clumping, including but not limited to extreme clumping. “Extreme clumping” as used herein refers to the association of multiple cells (≥3 to hundreds of cells) into irregular masses or aggregates. Cell clumping/aggregation can be measured by direct observation of large cell aggregates observed by eye or microscopically as compared to single cells. For especially large aggregates, cells can be stained with a nuclear stain (e.g., DAPI) and lysed to determine how many cells are comprised the cell aggregate. An alternative method for quantitating the propensity of cells to clump involves the addition of calcium to precipitate cells, followed by turbidometric measurements. In embodiments, cells described in this disclosure exhibit less aggregation relative to a control. Any suitable control or reference value can be used. In embodiments, modified cells of this disclosure exhibit less aggregation compared to cells without the same modifications (e.g., unmodified cells), wherein the modified cells and unmodified cells are cultured in high calcium conditions, such as a higher than typical cell concentrations of $CaCl_2$). One non-limiting embodiment of a high calcium concentration is 2 mM $CaCl_2$). In embodiments, less aggregation can comprise fewer cell aggregates relative to a control control value. In embodiments, a cell aggregate comprises a group of more than than three cells in contact with one another.

In embodiments, cell cultures that have been engineered to express modified mucins and/or lubricins as described herein are also modified to recombinantly express at least one other protein. Thus, the disclosure provides for cells expressing a modified mucin and/or lubricin, the cells further expressing at least a second recombinant protein, wherein expression of the second recombinant protein is improved relative to a reference. An improvement in expression can comprise, for example, expression of more protein, secretion of more protein, recovery of more protein, and other parameters that will be apparent to those skilled in the art.

In embodiments, the cells that express proteins of this disclosure are eukaryotic cells. In certain embodiments, the cells are eukaryotic cells, including but not limited to insect and mammalian cells. In embodiments, the mammalian cells are not Chinese hamster ovary (CHO) cells, although in certain instances CHO cells may be used. In embodiments, the cells are mammalian epithelial cells. In embodiments, the cells are human cells, and thus are better suited for producing, for example, human biologics, than non-human mammalian cells. In embodiments, the cells are human 293 cells. In embodiments, 293 cells are derived from 293 cells and stably express the SV40 large T antigen. In embodiments, the cells are human 293 cells adapted for growth in suspension cultures (293 suspension cells). In embodiments, the cells are human 293-F cells, which are commercially available from a variety of vendors.

In certain approaches, such as therapeutic approaches, the present disclosure includes modifying heterologous, or cells obtained from an individual, to express one or more of the glycoproteins described herein. Thus, in embodiments, human or non-human cells can be modified to, for example, correct a defect in a mucin or mucin-like protein, or the production thereof. In embodiments, cells modified according to this disclosure are totipotent, pluripotent, oligopotent stem, or multipotent stem cells. In embodiments, the cells are hematopoetic cells. In embodiments, the cells are chondrocytes. In embodiments, the cells are mesenchymal stem cells or marrow stromal cells. In embodiments, the cells are synovial cells. In embodiments, the cells are chondrogenic precursor cells. In embodiments, the cells endogenously produce cartilage-specific gene products, such as type II collagen and/or cartilage-specific chondroitin sulfate proteoglycan (CSPG). In embodiments, the cells are epithelial cells, or precursors thereof, or are goblet cells. In embodiments, the cells are immune cells, and include but are not necessarily limited to T cells, such as CD4+ and CD8+ T cells, and dendritic cells. Cells can be modified according to any established technique, including but not limited to use of viral expression vectors, or by chromosome editing, such as by any suitable CRISPR-based gene editing approach. Modified cells can be administered to an individual in need thereof. In embodiments, transgenic non-human animals that have been created to express one or more of the modified proteins of this disclosure can be produced and used to study a wide range of biological functions, disorders and conditions.

As discussed above, in certain embodiments cells modified according to this disclosure to improve protein production can be used to increase expression of any particular protein, without limitation. In this regard, a modified mucin and/or lubricin protein described herein may be referred to as a “first” polypeptide, and a desired protein that is produced by the cells may be referred to as a “second” polypeptide. The second polypeptide thus may be distinct from the first polypeptide. The terms “first” and “second” are used for convenience, are not meant to indicate importance, or limit the disclosure to co-production of only two distinct polypeptides, but production of only two distinct polypeptides is also included within the scope of the disclosure.

Representative second polypeptides include, for example, biologic agents that are or have a protein component, and thus include antibodies or fragments or derivatives thereof, protein or peptide vaccines, enzymes, structural proteins, and the like. In embodiments, the protein is any protein that can be suitable for use as a pharmaceutical/biologic agent, a nutraceutical, a dietary or other food supplement, a food additive, a filler, a binder, or for any other use or purpose.

In embodiments, a modified cell as described herein is used to produce a viral particle. In embodiments, the viral particles are pathogenic. In embodiments, the viral particles are not pathogenic. In embodiments, the viral particles are attenuated viruses. In embodiments, the viral particles comprise a virus like particle (VLP). In embodiments, one or more than one viral protein can be produced. In embodiments, viral ribonucleoprotein (vRNP) complexes can be produced. In embodiments, viral particles produced using the compositions and methods described herein comprise viral proteins and a cell-derived envelope. In embodiments, second, or more than second polypeptides, comprise lentiviruses and lentiviral particles, including but not limited to pseudoviral particles. In embodiments, the second of further polypeptides comprise one or more recombinant adeno-associated virus (rAAV) proteins. Such proteins include the well-known rep, cap and adeno-helper components. The rep component comprises four overlapping genes encoding Rep proteins required for the AAV life cycle (Rep78, Rep68, Rep52 and Rep40). The cap component comprises overlapping nucleotide sequences of capsid proteins VP1, VP2 and VP3, which interact together to form a capsid of an icosahedral symmetry. Adeno Helper function proteins may also be produced.

In embodiments, the second polypeptide comprises an agent with binds to a target with specificity. In embodiments, the second polypeptide comprises an intact immunoglobulin, or fragments of immunoglobulins, including but not necessarily limited to antigen-binding (Fab) fragments, Fab' fragments, $(Fab')_2$ fragments, Fd (N-terminal part of the heavy chain) fragments, Fv fragments, dAb fragments, single domain fragments or single monomeric variable antibody domains, isolated CDR regions, single-chain variable fragment (scFv), and the like. In embodiments, the second polypeptide comprises a T cell receptor (TCR), such as a TCR $\alpha$ and/or $\beta$ chain. In embodiments, the second polypeptide comprises a binding moiety of a bi-specific or tri-specific antibody. In embodiments, the second polypeptide comprises a chimeric antigen receptor (CAR), which can be expressed on immune cells such as T cells (CAR T cells).

In embodiments, the compositions and methods of this disclosure also include using the modified cells as described herein to produce a secreted membrane vesicle. The type of vesicle is not particularly limited, and includes any membrane-bound vesicles secreted by cells, representative examples of which include exosomes, microvesicles, apoptotic bodies, and other extra-vesicular bodies, such as ectosomes.

In embodiments, the disclosure includes expression, including increased expression, of a distinct protein, such as the aforementioned second polypeptide. In embodiments, the distinct protein (e.g., the non-mucin or non mucin-like protein) can be expressed from a separate gene, or mRNA, or can be encoded and expressed from the same mRNA, such as a bicistronic mRNA that may include any suitable feature, such as an internal ribosome entry sequence (an IRES).

In embodiments, any glycoprotein described herein can be present in a fusion protein. Fusion proteins are produced recombinantly and contain in a single, contiguous polypeptide, segments of distinct proteins. In embodiments, a fusion protein described herein comprises a glycoprotein or segment thereof, and a second protein or segment that is not particularly limited. In embodiments, the second protein produced a detectable signal, and thus includes, for example, fluorescent proteins.

It will be also be recognized from the description and figures of this disclosure that cells, including human cells, which express the described mucins and display them on their surface, are transfection competent. Thus, the described mucin coating does not impede transfection. This is in contrast to currently available anti-clumping agents (e.g., agents designed to inhibit cell aggregation), which are known to inhibit transfection. Further, as will also be apparent from the description and figures of this disclosure, modified cells comprising the described mucins are able to produce and secrete high levels of recombinant protein, such as a representative red fluorescent protein, as further described herein. In embodiments, a high levels of protein comprises 1-10 g/L of protein, inclusive, and including all ranges of numbers there between, and further including all expressions of ranges of weight and volumes, including, for example, milligrams and micrograms, and micrograms and microliters.

In certain embodiments, the compositions and methods of this disclosure involve recombinantly produced proteins that have repeated amino acid sequences, such as tandem repeat sequences. In embodiments, the tandem repeat sequences are either modified relative to their naturally occurring sequences, or are the same as their naturally occurring sequences, but the number of repeats may have been altered, relative to the number of repeats in a naturally occurring protein. Combinations of distinct repeats may be included in the polypeptides described herein.

In embodiments, the disclosure comprises introducing an expression vector described herein that encodes one or more proteins described herein, which may be a codon-optimized expression vector, into a suitable cell/cell culture, allowing expression of the protein(s), and recovering the protein(s) from the cells. In embodiments, cells in a cell culture are modified to express at least protein described herein using any suitable expression vector.

The expression vector may be integrated into a chromosome of the cells, or may be maintained permanently or transiently as an epigenetic element. The expression vector may be configured to express the protein(s) in a constituent or inducible manner. In one non-limiting embodiment, a transposon based expression vector can be used, or a lentiviral expression system can be used. In a non-limiting embodiment, a lentiviral system can be excluded as a tool to express the proteins described herein. In embodiments, any protein described herein may, or may not include, a signal sequence. In embodiments, a polynucleotide, such as a cDNA encoding one or more of the proteins described herein, is randomly integrated into one or more chromosomes to produce the modified cells. In embodiments, a randomized transposition of a cDNA into the genome is used.

In embodiments, codon-optimized expression vectors comprise a threshold number of altered codons, wherein the altered codons do not change the amino acid encoded by the particular codons. Thus, optimized codons may contain, for example, changes in wobble bases. In embodiments, at least one codon is altered, and from one codon to all of the codons that encode each amino acid in the particular protein may be altered. In embodiments, the codon optimized cDNAs reduce cDNA sequence repetitiveness to improve stability of the nucleotide sequence during DNA processing, including but not necessarily limited to slippage during replication, transcription, reverse transcription and other nucleotide processing operations on repetitive nucleotide sequences which often result in deletions or amplifications of cDNAs and mRNAs. In embodiments, codons with less than a predetermined threshold of frequency of usage in the pertinent cell type are replaced with codons that have a higher frequency of usage. For example, in one embodiment codons that have less than or equal to 10% usage frequency in human cells can be replaced.

In embodiments, the mucin/lubricin protein, or a protein for which improved production may be desired, can be modified for recovery using any suitable approach, including but not limited to including one or more purification tags, including but not limited to a His-tag. In an embodiment, a His-tag is a linear sequence of n histidine residues where n is typically 6-10. His-tags achieve purification by binding specifically to nickel or cobalt ions, which may be for example, attached to a substrate, such as any suitable beads. The His-tag, or any other suitable purification tag, may be placed at the N-terminus of the protein, at the C-terminus of the protein, or interior to the protein. In embodiments, a FLAG-tag, or FLAG octapeptide, or FLAG epitope, is may be included in proteins of this disclosure. Suitable FLAG sequences are known in the art. In embodiments, a Small ubiquitin-related modifier (SUMO) tag, such as a His-SUMO tag can be included. In embodiments, protease cleavage sites can be included, such as for protein identification, separation, purification, etc. The proteins can be purified to any desired degree of purity.

In non-limiting embodiments, the tandem repeats that are included in proteins of this disclosure comprise any one or any combination of the following amino acid segments: KEPAPTTP (SEQ ID NO:1) (lubricin-like repeat); KEPAPTP (SEQ ID NO:9) (modified lubricin-like repeat); KEPAPTTTP (SEQ ID NO:10) (modified lubricin-like repeat); DAATPAP (SEQ ID NO:2) (synthetic mucin repeat); DAATPAPP (SEQ ID NO:3) (synthetic mucin repeat); PPASTSAPG (SEQ ID NO:4) (synthetic mucin repeat); PDTRPAPGSTAPPAHGVTSA (SEQ ID NO:8) (Muc1 repeat); PDTRPAPGATAPPAHGVTSA (SEQ ID NO:5) (Modified Muc1 repeat); PDTRPAPGATAPPAHGVTAA (SEQ ID NO:6) (Modified Muc1 repeat); and PDARPAPGATAPPAHGVTAA (SEQ ID NO:7) (Modified Muc1 repeat).

In embodiments, from 2-120 repeats are included in a protein of this disclosure. In non-limiting embodiments 10, 21, 40, 42, 59 or 80 repeats are included. In embodiments, any amino acid sequence described herein can be a segment of a longer tandem repeat, and thus may have additional amino acid sequences on its N- or C-terminus. In embodiments, the amino acid sequence of a tandem repeat described herein comprises or consists of from 7-80 amino acids. In embodiments, a tandem repeat described herein exhibits an estimated length of approximately 135 nm, or 270 nm. In non-limiting embodiments, a protein of this disclosure comprises at least one amino acid modification, and/or is expressed from a codon-optimized expression vector, and has an apparent molecular weights of approximately 470, 210, or 170 kDa. In embodiments, the repeats are perfect repeats, meaning the identical sequence is repeated in the protein, which differs from certain tandem repeats that occur naturally.

In embodiments, the disclosure includes all cDNA and amino acid sequences disclosed in Parts I-IV of the Examples, and variants thereof as described herein. From time to time, such representative sequences are referred to for convenience as "biobricks." In non-limiting embodiments, the disclosure provides polypeptides, such as glycoproteins, and codon-optimized expression vectors encoding the glycoproteins, that are described herein as SynMuc1 and SynLubricin, as well as Muc_42, Muc_21, Muc_10, Muc1_0, Muc1_21D, Muc_215, Muc1_21T, Syn1_40, Syn1_80, Syn2_40, Syn2_80, Syn3_40. As used herein, mucin-135 and mucin-270 are the same mucin as as Muc_21 and Muc_42, respectively.

Polypeptides comprising amino acid sequences that are at least 90% identical to the amino acid sequence of these sequences are included. In embodiments, the proteins comprise mutations, relative to an endogenous protein. An "endogenous" protein is a protein that is normally encoded by an unmodified gene. Likewise, an endogenous gene or other polynucleotide comprises a DNA sequence that is unmodified, such as by recombinant, gene editing, or other approaches. Mutations, as further described below, can include amino acid insertions, deletions, and changes, and may also include additional repeated sequences, or fewer repeated sequences, relative to an endogenous sequence.

In embodiments, tandem repeat amino acid sequences are introduced into a glycoprotein at its N-terminus, its C-terminus, or both the N-terminus and C-terminus.

In embodiments, a recombinantly produced protein described herein comprises variants that have tandem repeats of any one or combination of the tandem repeat sequences described herein, wherein the variants comprise modifications of such sequences. Expression vectors encoding the variants are included. In embodiments, the modifications comprise amino acid segments that have between 90.0-99.9% amino acid identity, inclusive, and including all ranges of numbers there between to the first decimal point, with contiguous amino acid and polynucleotide sequences expressly described herein. In embodiments, tandem repeats comprised by recombinantly produced proteins of this disclosure have 90, 95, 97, 98, 99 or 99.5% amino acid sequence identity to the amino acid sequences described herein, across their full length(s). In embodiments, amino acid substitutions, such as alanine substitutions, are used create Muc1-like variants, and can be used in any other protein described herein, with tandem repeats with altered frequencies of S/T glycosylation sites that can comprise a percentage of S/T sites in mucin backbones from, for example, at least 10%, and up to 33%, or more. In embodiments, an amino acid such as alanine can be substituted for S/T in one, two, or three, four, or five, or more glycosylation sites.

A recombinant protein is a protein expressed from a polynucleotide that has been introduced to a cell that did not comprise a coding sequence for that protein prior to introducing the polynucleotide. The same applies to recombinant cDNA sequences.

As is known in the art, to determine the percent identity of two nucleotide or amino acid sequences, the sequences are aligned for optimal comparison purposes (e.g., gaps may be introduced). The nucleotides or amino acids at corresponding nucleotide or amino acid positions are then compared. When a position in the first sequence is occupied by the same nucleotide or amino acid as the corresponding position in the second sequence, then the molecules are identical at that position. The percent identity between the two sequences is a function of the number of identical positions shared by the sequences (i.e., % identity=# of identical positions/total # of positions×100).

In certain embodiments, the tandem repeat variants described herein comprise a change of 1, 2, 3, 4, or 5 amino acids. In embodiments, an amino acid can be deleted, added, or changed. In embodiments, an amino acid that is changed is a serine, a threonine, or a combination of serine and threonine residues are changed. In embodiments, about 1-50% of serine and/or threonine residues are changed. In embodiments, a serine or threonine residue present in a native protein sequence is changed to an alanine, or to another amino acid. In embodiments, a protein of this disclosure comprises fewer, or no amino acids that are present in a native (non-modified and/or endogenous protein). In embodiments, a native protein comprises one or any combination of asparagine, aspartic acid, glycine, isoleucine, leucine, and/or serine, which can be engineered recombinantly out of representative proteins of this disclosure.

In embodiments, amino acid changes introduced into proteins of this disclosure result in changed glycosylation patterns. Thus, in embodiments, the disclosure provides for production of recombinant proteins with controllable glycosylation patterns. In embodiments, the number of O-linked oligosaccharides present on a protein of this disclosure is modified. In embodiments, the glycosylation pattern is changed relative to a control, such as a protein in which a corresponding glycosylation site is not changed. In embodiments, one or more properties of the proteins, and or cells that express the proteins, is changed. In embodiments, the stoichiometry of oligosaccharides to protein/amino acids is changed in, for example, a glycoprotein of this disclosure. In embodiments, a protein of this disclosure comprises a percentage by weight of glycosidic residues that is different from a suitable control. In embodiments, cells modified according to this disclosure have one or more characteristics, which may be improved relative to a control, or not diminished relative to a control, such as turbidity, viability during or after exposure to a shear stress, such as a shear stress that arises during mixing the cells in, for example, a bioreactor.

In embodiments, a recombinantly produced protein as described herein comprises a change relative to a control, such as an unmodified protein, in the Core 1 O-glycan structure, Galβ1-3GalNac, and/or the amount of Core 1 derivatives of Galβ1-3GalNAc, and/or the amount of terminally substituted sialic acids therein, or a change in GalNAc (N-acetylgalactosamine) monosaccharide glycosylation. In embodiments, a protein described herein can comprise the Core 2 O-glycan, GlcNAcβ1-6(Galβ1-3)GalNAc and/or the Core 2 derivatives of GlcNAcβ1-6(Galβ1-3)GalNAc, which comprise at least 5 percent of all Core 1, Core 2, Core 3, Core 4, Core 5, Core 6, Core 7, and Cor e8 O-glycan structures. In embodiments, such a protein is produced by human cells that are cultured as further described herein, including but not necessarily limited to a suspension culture.

Figure 3:
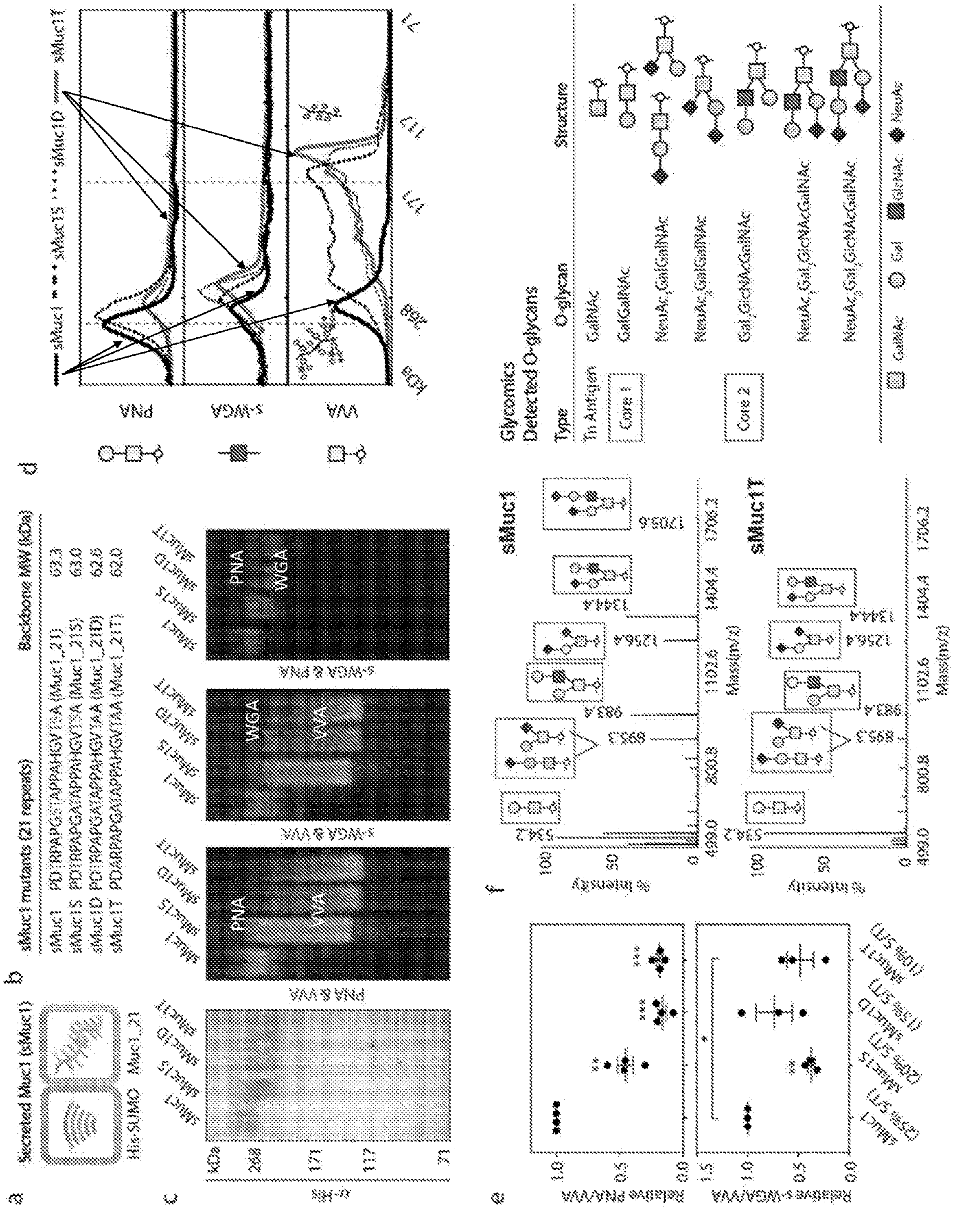
FIG. 3: Engineering the Frequency of Glycosylation Sites in the Muc1 Polymer Backbone Tunes O-glycan Maturation. (a) Components and features of secreted Muc1 and engineered variants each with 21 tandem repeats. (b) Tandem repeat sequences of secreted mucin mutants and the molecular weight of the polypeptide backbones. Single, double, and triple glycosylation mutants (sMuc1S, sMuc1D, and sMuc1T) have one, two or three, serine/threonine (S/T) to alanine substitutions per repeat, respectively. The sequences under sMuc1 mutants (21 repeats) are from top down: SEQ ID NO:8, SEQ ID NO:5, SEQ ID NO:6 and SEQ ID NO:7. (c) Representative Western blot analysis of affinity-purified recombinant secreted mucins from FreeStyle™ 293-F cell culture media probed with anti-SUMOstar antibody and PNA, s-WGA and VVA lectins (of three independent experiments). The lectin blot was co-stained in multiple colors with PNA-Alexa Fluor 568, s-WGA-FITC, and biotinylated VVA (Secondary: NeutrAvidin-Dylight 650). (d) Representative fluorescence intensity electrophoretograms of the blots in (c). (e) Ratiometric intensity analysis of PNA to VVA signal (upper) and s-WGA to VVA signal (lower) for the indicated mucins and their corresponding frequency of S/T glycosylation sites in the polymer backbone. Ratiometric fluorescence intensity was quantified along each lane and normalized to signal from the secreted mucin with wild-type Muc1 tandem repeats (sMuc1); data presented as the mean and SEM from at least three independent experiments. *$P<0.05$ $P<0.01$ *$P<0.001$ (f) Left: MALDI-TOF mass spectra registered for samples of permethylated glycan alditols from secreted mucins with wild-type Muc1 tandem repeats (sMuc1) and triple mutant (sMuc1T) from HEK293T cell culture media. The ion signals were annotated with respect to the relative masses of molecular ions (m/z) detected as sodium adducts and by assignment of the respective core structure (red for Core 1 and black for Core 2). Right: Schematic presentation of O-linked glycans detected on the secreted mucins.

In this regard, FIG. 3*f* provides a representative relative abundance of core O-glycan structures. The relative abundance is based on the frequency of the glycans (i.e numbers) and is given by the spectral intensity on the MALDI-MS mass chromatogram for O-glycans released from glycoprotein by beta-elimination. Relative abundance of O-glycans as summarized in FIG. 3 is as follows: GalNAc monosaccharide 86.3%; Core 1 8.2%; representative example being GalNAc-Gal; Core 2 5.3%. Core III and IV, V, VI, VII, VIII were not detected. If present, they were present at very low levels that are below the detection limit of MALDI-MS.

In embodiments, proteins of this disclosure may be in the form of monomers, dimers, multimers, and combinations thereof. In embodiments, monomer/dimer ratios, proportions, and/or concentrations are changed, relative to suitable controls.

In embodiments, segments of proteins described herein can be separated by any suitable linking amino acids. In embodiments, linker can comprise from 1-20 amino acids, inclusive, and including all integers and ranges of integers there between. In general, linkers are comprised of a glycine, serine, or serine and glycine. In embodiments, linking amino acids do not intereven tandem repeats. In embodiments, no linker is included in a polypeptide of this disclosure.

In embodiments, any one or combination of proteins described herein can be associated with a cell membrane. In embodiments, the disclosure thus provides biopolymers with tunable sizes, O-glycan side-chain spacing, and distinct glycan types for glycocalyx editing.

In embodiments, secreted forms of glycosylation mutants are provided.

In embodiments, the disclosure provides proteins, and DNA sequences encoding the proteins, that have a polymer backbone, and at least one of the following elements, non-limiting examples of which are provided herein: a leader tag; an optical reporter, such as any fluorescent protein, a transmembrane domain; and a cytoplasmic motif. Any one or any combination of these elements can be excluded from the constructs presented herein. In embodiments, cell surface mucins include a cytoplasmic recycling motif on a transmembrane domain, which can alter glycosyolation and/or sialylation of the proteins, and further illustrated herein by the description and figures. In embodiments, the cytoplasmic recycling motif comprises or consists of the amino acid sequence CQC. Cytoplasmic recycling and motifs that facilitate the same are known in the art. Such motifs facilitate trafficking through the trans Golgi network (TGN), endosome, and/or from the endosome back to the plasma membrane. (See, for example, a review in Pandey KN. Front Biosci (Landmark Ed). 2009; 14:5339-5360. 2009 Jun. 1. doi:10.2741/3599, and specifically for the CQC motif, Kinlough, et al., Apr. 28, 2006, The Journal of Biological Chemistry 281, 12112-12122).

In embodiments, a polypeptide of this disclosure may have one or more modified amino acids that are, for example, conjugated to another moiety. In embodiments, a polypeptide of this disclosure is conjugated to at least one azido group such that they can be readily conjugated to other moieties, such as using click chemistry. In embodiments, a polypeptide of this disclosure is cyclized, or stapled.

In embodiments, a tandem repeat sequence described herein is incorporated into any glycoprotein. In embodiments, the glycoprotein is any mucin or lubricin protein. In embodiments, the mucin is any of MUC1, MUC2, MUC3A, MUC3B, MUC4, MUC5AC, MUC5B, MUC6, MUC7, MUC8, MUC12, MUC13, MUC15, MUC16, MUC17, MUC19, MUC20, and PODXL, the amino acid sequences of which are known in the art. In embodiments, the glycoprotein is Proteoglycan 4, also referred to in the art as lubricin, which comprises a protein that in humans is encoded by the PRG4 gene. In non-limiting the disclosure provides a modified mucin termed SynMuc1, as described further below. In another non-limiting embodiment, a modified lubricin is provided as SynLubricin, as further described below.

In an embodiment, production of protein is increased using cells modified herein, wherein the cells are present in a cell culture container, including but not limited to any cell culture dish, and bioreactors. In embodiments, modified cells according to this disclosure are used in bioreactors to produce any desired protein, or combination thereof. In non-limiting embodiments, the bioreactor comprises a suspended cell bioreactor. In embodiments, bioreactors have a volume of from 1-25,000 liters, inclusive, and including all numbers and ranges of numbers there between. In embodiments, the bioreactor is has a volume of at least 100 liters, or at least 1,000 liters.

In embodiments, cDNA libraries are provided. In embodiments, the disclosure comprises providing a cDNA library as described herein, and selecting one or a combination of the cDNAs described or modifying cells by introducing the cDNA and/or an expression vector encoding the cDNA into a cell. Selection can be based upon an intended or actual use for the cells, such as for use in protein production, based on any particular protein and cell expression system. Kits encoding the proteins are also included.

In embodiments, one or more proteins described herein can be combined with other agent(s), such as biodegradable polymer(s), nanoparticlespectin, alginate, cross-linked derivatives of poly(acrylic acid), polyvinyl alcohol, polyvinyl pyrollidone, polysaccharides, hydroxypropyl methylcellulose, carboxymethylcellulose, lectins, rheology modifiers, plasticizers, chondroitin, glucosamine, and/or any hyaluronic acid.

For use in prophylaxis and/or therapy of diseases wherein, for example, anti-adhesive agents may be of benefit, compositions described herein can be administered in a conventional dosage form prepared by mixing with a standard pharmaceutically acceptable carrier according to known techniques. Some examples of pharmaceutically acceptable carriers can be found in: *Remington: The Science and Practice of Pharmacy* (2005) 21st Edition, Philadelphia, PA Lippincott Williams & Wilkins, the disclosure of which is incorporated herein by reference. In embodiments, pharmaceutical and other compositions comprising the proteins described herein can be provided as liquids, tablets, powders, sprays, ointments, hydrogels, and aerosols.

In embodiments, pharmaceutical compositions comprising one or more proteins of this disclosure can be administered to an individual using any suitable route, including but not necessarily limited to topically, orally and parenterally, and as further described below. For example, the proteins can be administered intravenously, by direct injection into synovial joints or other synovial structures (tendon sheaths, bursae), intraperitoneally, by direct injection into the pericardial sac, by direct injection into the pleural cavity, subdermally, subcutaneously, or by direct application to skin, mucous membranes, or the eye.

In embodiments, the disclosure comprises methods, compositions, and devices for treating an ocular disease, disorder or condition in a mammal. In embodiments, proteins produced by cells as described herein are used for treatment of eye disease or condition using any method or device known to those of ordinary skill in the art. In embodiments, compositions comprising the proteins are used for intracameral, intravitreous, subconjunctival, sub-Tenon's, subretinal, or topical application to the corneal surface. The proteins may be delivered directly to the eye (for example: topical ocular drops or ointments; slow release devices in the cul-de-sac or implanted adjacent to the sclera or within the eye) using techniques well known by those skilled in the art. It is further contemplated that the proteins described herein may be formulated in intraocular insert or implant devices.

In embodiments, a pharmaceutical comprising one or more proteins described herein is used to treat an eye disorder that comprises one or more diseases or injury to the retina, including age-related macular degeneration (AMD), retinitis pigmentosa (RP), and diabetic retinopathy (DR). In an embodiment, the individual has dry, atrophic (nonexudative) age-related macular degeneration, defined as progressive age-related degeneration of the macular associated with retinal pigment epithelial changes including atrophy and drusen, which is a common cause of vision loss in adults for which therapy is limited. In embodiments, the disorder comprises one or more diseases or injury to the cornea. In embodiments, the individual has glaucoma, which may include primary, secondary and/or congenital glaucoma.

In embodiments, proteins of this disclosure can be provided in the form of eye drops. In embodiments, the eye drops comprise any one or more of steroids, antihistamines, sympathomimetics, beta receptor blockers, parasympathomimetics, parasympatholytics, prostaglandins, nonsteroidal anti-inflammatory drugs (NSAIDs), antibiotics, antifungal, or topical anesthetics. In certain embodiments, the eye drops are for use with any dry eye condition. In embodiments, the eye drops are for use in lubrication of eyes, including but not necessarily for a contact lens wearer. In embodiments, the compositions are provided as lubricating eye drops. In embodiments, the lubricating eye drops comprise artificial tears. In embodiments, the eye drops may be free of medications, and thus function only as lubricating/tear-replacement compositions. In other embodiments, the eye drops may be for treatment of ocular allergic reactions, and thus my also comprise antihistamines, and/or vasoconstriction agents.

In embodiments, compositions comprising proteins described herein can be used in conjunction with contact lenses. In embodiments, the proteins are used in a contact lens solution. Thus, proteins described herein can be mixed with any suitable contact lens solution components, which include but are not necessarily limited to saline, mild abrasives, surfactants, anti-fungal and anti-bacterial agents, which include but are not limited to conventional amicrobial agents, or hydrogen peroxide or boric acid, and preservatives, such as ascorbic acid or edetate disodium. Contact lenses provided in a solution comprising one or more proteins described herein are included within the scope of this disclosure.

In embodiments, compositions comprising proteins described here can be directed to a mucosal lining. The mucosal lining, includes, for example, the upper and lower respiratory tract, eye, buccal cavity, nose, rectum, vagina, urogenital tract, periodontal pocket, intestines and colon. In certain embodiments, the compositions can be used for oral inhalations. In embodiments, the oral inhalation comprises nasal applications, and thus may include nasal sprays, nasal drops, and nasal ointments. In embodiments, oral inhalation may comprise bronchial sprays and inhalers. In embodiments, the proteins may be used to access mucosa through use of throat lozenges, chewing gum, mouthwashes or gargles, suppositories, or tampons.

In embodiments, compositions comprising proteins described herein are used as surgical anti-adhesives (intraperitoneal lubricants to lubricate viscera and prevent post-op intestinal and visceral adhesions during intra-abdominal surgical procedures/manipulations; intrapleural lubricants to lubricate lungs and prevent postoperative pleural adhesions during intra-thoracic surgical procedures/manipulations; intrapericardial lubricants to lubricate the cardiac surface and prevent post-op pericardial adhesions during cardiac surgical procedures/manipulations). As a post-operative synovial fluid replacement following any arthroscopic, tenoscopic, or bursoscopic procedure to maintain lubrication and prevent adhesions or pannus formation.

In embodiments, an article of manufacture may be coated and/or impregnated with a composition comprising any of the proteins described herein. In embodiments, the article of manufacture is coated on any porous or non-porous surface. In embodiments, the article comprises a medical device, including but not necessarily limited to a surgical device, a dental or orthopedic device, sutures, catheters, an intubation device, an anesthesia delivery device, a dressing, bandage, etc. In embodiments, proteins described herein are used to coat cell culture devices, including, but not necessarily limited to, cell culture plates, multiwell plates, bioreactors, and any other surface, wherein an anti-adhesive property is desirable.

In another aspect the disclosure includes a supplement product, such as a nutraceutical product, a dietary supplement, a food ingredient, etc., The supplement product can be provided in the form of, for example, a liquid, capsules, tablets, softgels, powders, and the lie.

In embodiments, a pharmaceutical and/or nutraceutical product comprising one or more proteins described herein is provided in a container, such as any suitable closed or sealable container which may be sterile. In embodiments, the product comprises printed material. The printed material can be provided as a product insert, label, or as a component of packaging. The printed material provides an indication that composition comprising the polypeptides is to be used for treating any disease, disorder, or condition as described herein, or for producing an anti-adhesive effect for any purpose. In one embodiment, polypeptides described herein are used as a supplement for treating a condition of joints, including, but not necessarily limited to joint pain, arthritis, including, but not necessarily limited to, osteoarthritis, rheumatoid arthritis, injuries to joints, menisci or cartilage, such as sports injuries, or in conjunction with joint/ligament repair surgeries. Thus, administering compositions described herein for the purposes of improving the health or well-being of an individual, are included within the disclosure. In embodiments, compositions of this disclosure can be injected directly into a joint and/or synovial fluid. In embodiments, compositions of this disclosure can be also be used for injection directly into the tendon, tendon sheath, ligament or bursa following a tendon, ligament or bursal injury, trauma or infection.

The disclosure may be better understood by reference to the following non-limiting Examples, which are provided as exemplary of the disclosure, divided into four Parts. The following examples are presented in order to more fully illustrate the embodiments of the disclosure and should in no way be construed, however, as limiting the broad scope of the disclosure. The reference listings of this disclosure is not an indication that any particular cited reference is material to patentability.

Examples

Part I

This Part I of the disclosure provides non-limiting and representative examples of sequence-specific mucins with controllable glycosylation patterns, and data and discussion of the same.

In particular, this Part I relates to the understanding that, prior to the present disclosure, few design guidelines existed for encoding customized mucin glycoproteins with tunable glycosylation patterns. Part I accordingly provides a library of swappable DNA bricks for mucin leader tags, membrane anchors, cytoplasmic motifs, and optical reporters, as well as codon-optimized native mucin repeats and new, rationally designed domains for synthetic mucins. Of the more than 400 possible cDNA combinations, this Part I provides a library of over 50 mucins, each with unique chemical, structural, and optical properties. The library is applied to develop general guidelines for the design and engineering of mucins, which form a part of this disclosure. Surprisingly, it was discovered that the extension of the immature α-GalNAc Tn-antigen to Core 1 and Core 2 glycan structures strongly depends on the frequency of O-glycosylation sites along the mucin backbone. As will be apparent to those skilled in the art from this disclosure, sialyation of glycan structures is readily tuned through recycling motifs on the mucin cytoplasmic tail. It is also demonstrated that the overall length of the mucin polypeptide backbone can have unexpected effects on glycosylation. Without intending to be bound by any particular theory, it is expected that that the mucin parts inventory presented here, along with the described design guidelines for making new mucins, can be broadly applied for glycocalyx research and mucin-based biotechnologies.

Introduction to Part I

Cell-surface mucins are a family of membrane-anchored biopolymers that are defined by their unstructured polypeptide backbone with a high density of sugar side chains (1). While historically viewed as simple structural molecules that protect the cellular surface and resist pathological cell deposition(2), cell-surface mucins are now recognized to have more sophisticated roles in regulating cellular life. In the cellular glycocalyx, mucin ensembles present bio-active glycan epitopes that mediate adhesion and communication between cells and with their external world. For instance, mucin sialic acids can modulate immune cell function through ligation of SIGLEC receptors on natural killer cells and other cell types in the microenvironment(3). Mucins can also physically regulate the spatiotemporal dynamics of receptor activation and signaling responses(4). Dense crowding of mucins in the glycocalyx is proposed to control the diffusion and activation of receptors on the cell surface, and to have a sieving effect that controls the passage of soluble factors from the microenvironment to the cell surface(5).

A key feature of mucins is that their molecular architecture can change dynamically through modulation of the types and frequencies of glycan side chains that are appended along the polypeptide backbone. For instance, the charge, size, and arrangement of glycans are proposed to control the extension and rigidity of the mucin backbone(6, 7). Glycosylation often changes dramatically with cell-state transitions, including differentiation and transformation(8, 9). As such, both the chemical and physical character of mucins is intimately coupled to cellular state, contributing to the diverse modulatory roles that mucins can play in cellular adhesion, communication, and signaling. However, how precise backbone sequences and glycosylation patterns contribute to the function of individual mucins and the collective behaviors of mucins in the glycocalyx is largely unresolved.

One of the major barriers to progress in developing such understanding has been the lack of tools for precise editing of the molecular structure of mucins. Genetic approaches that target glycosyltransferases can be highly effective in altering mucin glycosylation(10), but these approaches typically affect broad classes of glycoproteins, making any observed effects on cell behavior difficult or impossible to pinpoint to a particular mucin. To overcome the limitations of genetic approaches, libraries of bio-mimetic mucin polymers with plasma membrane anchors have been developed for glycocalyx editing(6, 11). While highly successful in unraveling some mechanistic details of mucin function, synthetic polymers are typically cleared from the cell-surface in hours to days and must be continuously replenished through media supplementation(12, 13). Thus, investigation of behaviors over longer time durations, particularly in vivo, are largely inaccessible with synthetic mucin mimetics.

Prior to the present disclosure, strategies for mucin engineering and glycocalyx editing that combines the important features of the synthetic chemical approach—defined backbone chemistry, tailored glycan structures, and precision glycan placement—with the power and long-term stability of genomic encoding had yet to be developed. Advances in custom gene synthesis support development of cDNA sequences to be constructed at unprecedented speed and low cost. However, custom gene synthesis is not readily applicable for the highly repetitive DNA sequences that are characteristic of most mucins. Repetitive gene sequences impede DNA fragment assembly in custom gene synthesis and are challenging to amplify through polymerase chain reaction (PCR) due to primer mispairing(14, 15).

As described in this Part I, a solution is to exploit codon redundancy to construct synonymous gene sequences with minimal codon repetitiveness, an approach that has been successfully applied for elastin-like proteins(16, 17).

In this Part I, we take advantage of codon redundancy to develop an efficient strategy to design, genetically encode, and fabricate cDNAs for synthesis of sequence-specific mucins in cells. The presently described combinatorial library of mucin parts enables facile construction of mucin biopolymers with tunable sizes, side-chain spacing, and glycan types for glycocalyx editing.

Part I—Results

Schematic Representation of Combinatorial Genetically Encoded Library for Sequence-Specific Mucins Part I results demonstrate a modular biology-by-parts approach for combinatorial mucin cDNA construction. Each functional motif in the mucin coding sequence was flanked by restriction sites, so that unique cDNA "bricks" for mucin leader sequences, tandem repeats, optical reporters, transmembrane domains, and cytoplasmic domains could be readily swapped to construct mucins of altered functionality (FIG. 1*a, b*). The cDNA parts catalogue included 13 unique tandem repeats for mucin biopolymers of varying size, backbone chemistry, and frequency of serine and threonine (S/T) glycosylation sites (FIG. 1*d*). The cDNAs for the mucin polymer domains were fabricated through custom gene synthesis following codon optimization (FIG. 1*c*). For optimization, codon redundancy was exploited to find synonymous gene sequences that coded the desired polypeptide with minimal codon repetition. The "codon-scrambled" cDNA sequences were synthesized through standard custom gene synthesis services offered by commercial vendors.

The tandem repeats that form the mucin polymer backbone were adapted from native mucins or newly designed (FIG. 1*d*). The repeats PDTRPAPGSTAPPAHGVTSA (SEQ ID NO:8) and KEPAPTTP (SEQ ID NO:1) have similarity to native Muc1 and Proteoglycan 4 (Lubricin), respectively. Three repeats were designed based on statistical analysis of mucin O-glycosylation sites (PPASTSAPG) (SEQ ID NO:4) or analysis of O-GalNAc transfer efficiency (DAATPAP (SEQ ID NO:2) and DAATPAPP)[20]. The base Muc1 repeat was further modified through alanine substitutions to create Muc1-like tandem repeats with altered frequencies of S/T potential glycosylation sites (Muc1_21S, D, T). Across the library, the percentage of S/T sites in the mucin backbones varied from 10% to 33% (FIG. 1*d*).

Constructing and Validating the Surface Expression of Sequence-Specific Mucins

Figure 2:
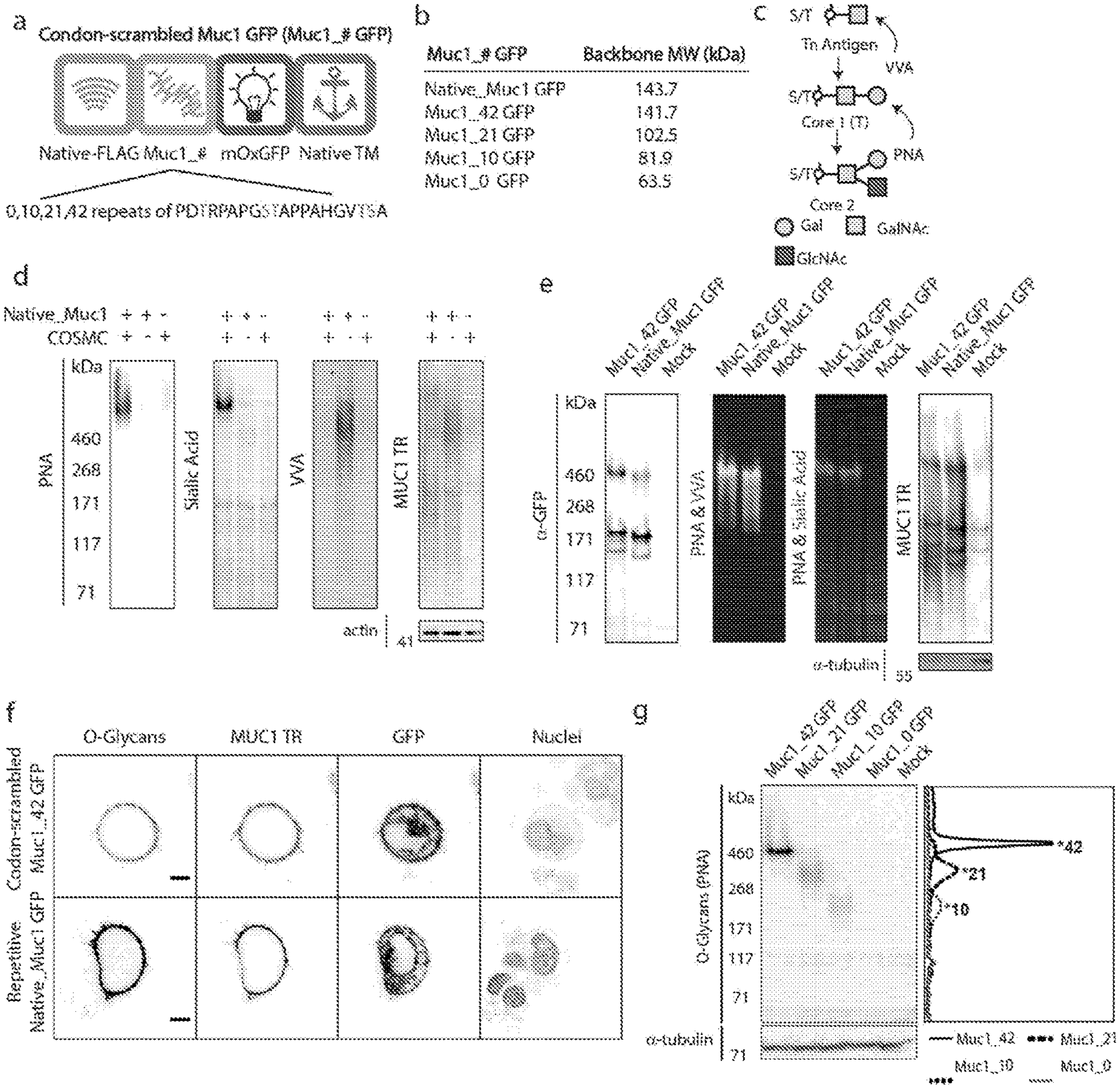
FIG. 2: Construction and Validation of Sequence-Specific Mucin Expression. (a) Components and features of codon-optimized Muc1 variants with GFP reporters. The amino acid sequence in (a) is SEQ ID NO:8. (b) Predicted Molecular Weight of the polypeptide backbone. (c) Biosynthesis of Tn antigen, Core 1, and Core 2 glycans, and specificity of relevant lectins for their detection. (d) Western Blot analysis of Native Muc1 expression and glycosylation in wild-type and Core-1 β3-T specific molecular chaperone (COSMC) knockout MCF10A cells. The MCF10A cells were stably transfected with native Muc1. The surface sialic acids were labeled with AFDye 568 through periodate labeling prior to lysate collection. The blot was stained in multiple colors with MUC1 TR (CD227 HPMV) Ab-FITC, and PNA-CF640 or biotinylated VVA (Secondary: NeutrAvidin-Dylight 650). (e) Western blot analysis of native and codon-scrambled Muc1 in extracts of transiently trnsfected HEK293T cells. (f) Immunofluorescence images of transiently transfected HEK293T cells expressing indicated constructs and probed with PNA lectin (left), anti-Muc1 antibody (center left), GFP (center right) and Hoescht nuclear stain (right) (scale bar 10 μm). (g) PNA lectin blot analysis (left) and intensity profiles (right) of mucins of varying sizes in extracts of transiently transfected HEK293T cells.

We compared the expression of codon-scrambled, synonymous mucin cDNAs to native mucin repetitive cDNAs, and evaluated the glycosylation of the protein products. We fused the cDNAs of the native and synonymous Muc1 tandem repeats with a signal/leader sequence, membrane anchor, and GFP reporter (FIG. 2*a*). Each construct was transiently expressed in HEK293 Ts. We analyzed the glycosylation patterns of the mucins through lectin blotting. Blots were probed with peanut agglutinin (PNA) to detect Core 1 glycans, *Vicia villosa* lectin (VVA) to detect the unextended Tn antigen (α-GalNAc) and Muc1 mAb (clone HMPV) to probe MUC1 tandem repeat peptide core (Muc1 TR)[21]. We also labelled Muc1 sialic acids on our blots through mild Periodate oxidation to generate aldehydes on sialic acids, followed by Aniline-catalyzed oxime Ligation (PAL) with a hydroxylamine-AF568 probe[22]. The GFP reporter were also probed via Western blot to detect expressed mucins. In order to validate the use of lectins PNA and VVA (FIG. 2*c*), we knocked out the Core 1 β3-T specific molecular chaperone (COSMC) in native Muc1 overexpressing MCF10As to inhibit elongation of the primary O-linked GalNAc[23]. We compared the glycosylation pattern of overexpressed native Muc1 (Native_Muc1) in wild-type and knockout cells. Mucin in the COSMC knockout cells had lower PNA reactivity, while VVA binding dramatically increased, presumably due to abrogation of glycan extension (FIG. 2*d*). The result confirmed that PNA can be a good indicator for extended Core 1 glycans and VVA for the unextended Tn antigen on the mucins.

Western blot analysis on native and codon-scrambled mucins confirmed that the codon-scrambled, synonymous Muc1 repeats (Muc1_42 GFP) had a molecular weight and glycosylation pattern comparable to the native repetitive Muc1 repeats (Native_Muc1 GFP) (FIG. 2*e*). Mucins ran as a nearly continuous smear in SDS-PAGE with the Muc1 TR antibody, indicating a heterogeneous mix of glycoforms (FIG. 2*e*; Muc1 TR). Predominant glycoforms with apparent molecular weights of approximately 470, 210, and 170 kDa were observed for each expression construct on the GFP blot (FIG. 2*e*; GFP). VVA staining was strong in the smeared region between the upper and lower bands, whereas PNA and sialic acid signal was strongest near the 460 kDa band at the top of the smear (FIG. 2*e*). Based on these results, we concluded that the 460 kDa band was fully glycosylated Muc1, while the smear represented a heterogenous mix of Muc1 glycoforms containing unextended O-glycan structures. The lower bands on the GFP blot were also observed on the Muc1 TR blots, but not with lectin or sialic acid probes, indicating that these bands likely represent under-glycosylated full-length Muc1. Both native and codon-scrambled Muc1 were successfully trafficked to the cell surface and incorporated into the cellular glycocalyx (FIG. 2*f*).

Figure 6:
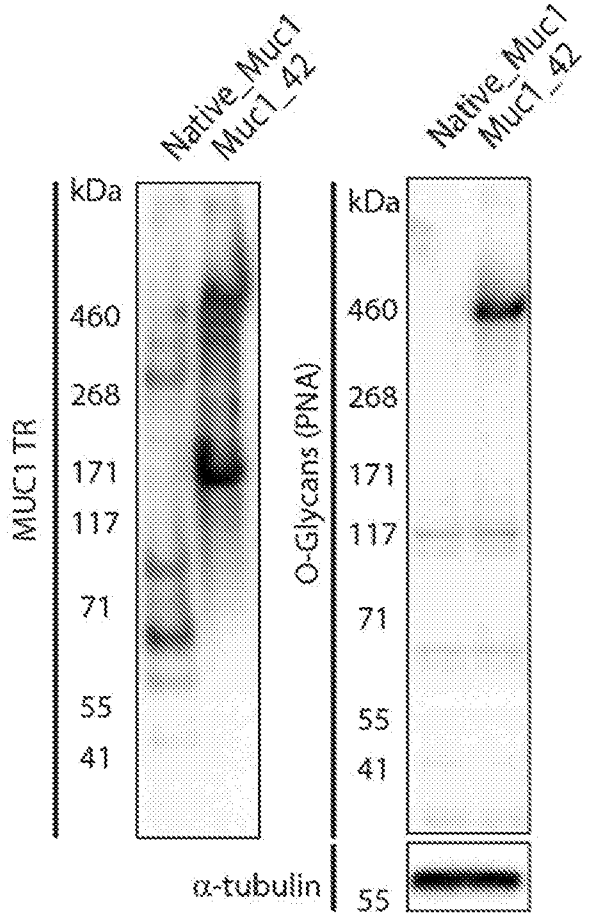
FIG. 6: Western blot analysis of MCF10A cells edited with lentivirus with native repetitive (Native_Muc1) versus codon-scrambled Muc1 cDNAs (Muc1_42).
Figure 7:
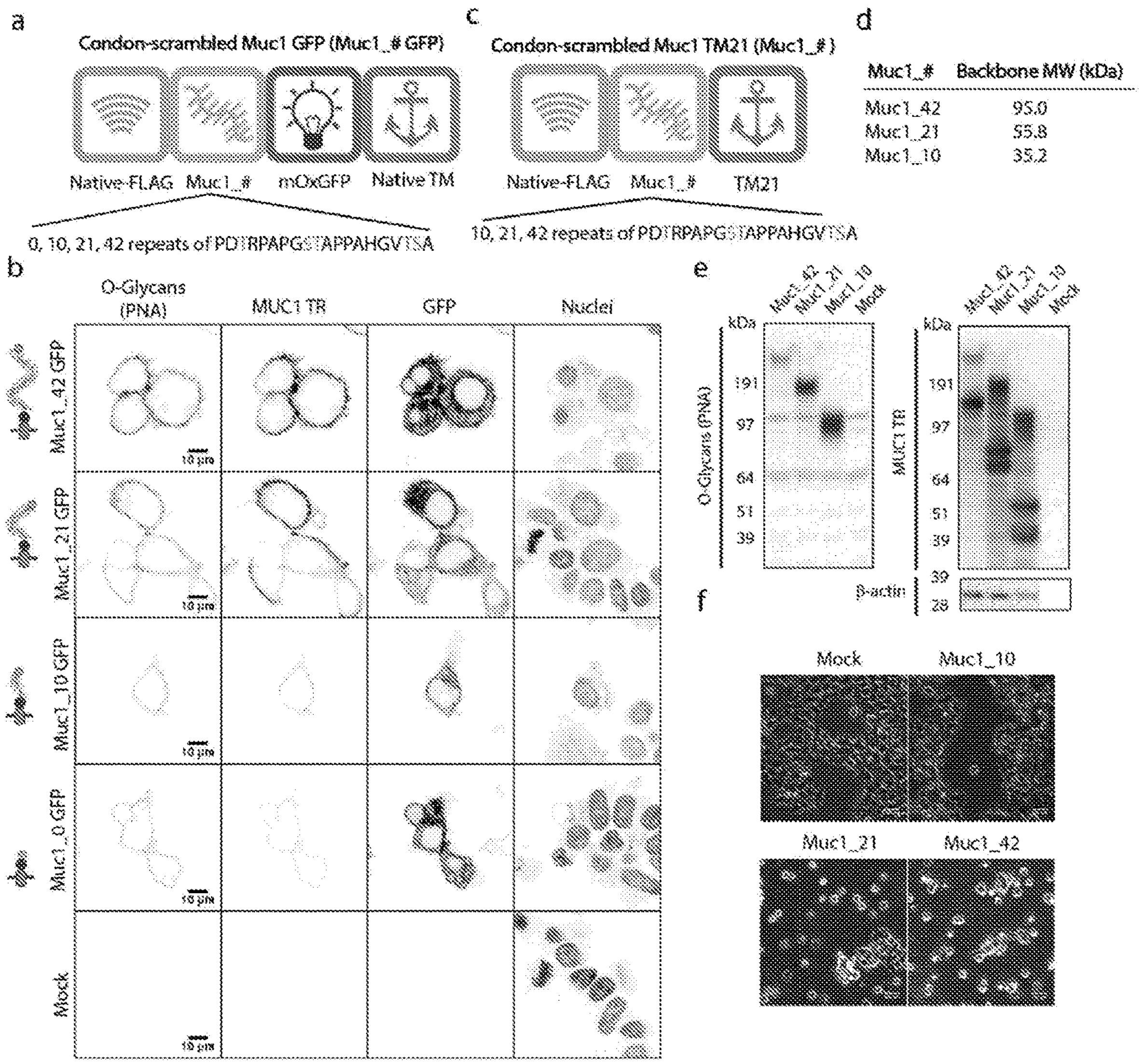
FIG. 7: Mucins with Tunable Sizes. The sequences shown in FIG. 7 are PDTRPAPGSTAPPAHGVTSA (SEQ ID NO:8). (a) Components and features of mucin constructs with GFP reporter, native Muc1 transmembrane anchor, and codon-scrambled Muc1 tandem repeats. (b) Representative immunofluorescence images of transiently transfected HEK293T cells expressing the GFP-tagged Muc1 constructs illustrated in (a) and co-stained with PNA, anti-Muc1 antibody, and Hoechst nuclear stain (scale bar 10 μm) from three independent experiments. (c) Components and features of mucin constructs with synthetic 21-amino-acid transmembrane anchor (TM21) and codon-scrambled Muc1 repeats. (d) Predicted molecular weight for mucin polypeptide backbone illustrated in (c). (e) Representative Western blot analysis (of three independent experiments) of TM21 constructs illustrated in (c) from extracts of transiently transfected HEK293T cells and probed with PNA lectin or anti-Muc1 antibody. (f) Representative phase-contrast images of HEK293 Ts expressed indicated constructs in (c) from three independent experiments (scale bar 100 μm).
Figure 8:
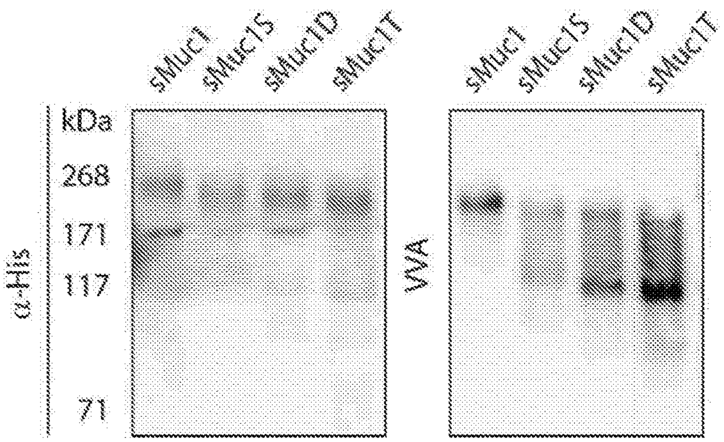
FIG. 8: Western blot Image of affinity-purified recombinant secreted mucins from FreeStyle™ 293-F cell culture media probed with anti-6×His antibody and VVA lectin

One advantage of the codon-scrambled mucin cDNAs was the potential to improve the stability of the nucleotide sequence during some DNA processing operations. Slippage during replication, transcription, reverse transcription and other nucleotide processing operations on repetitive nucleotide sequences often results in deletions or amplifications of cDNAs and mRNAs[24]. We conducted a lentiviral stability assay in which we evaluated the fidelity of cDNAs incorporated into the cellular genome following viral delivery and reverse transcription. In cells virally transduced with the native, non-optimized Muc1 cDNA, the Muc1 glycoprotein product had a significantly lower molecular weight than expected, consistent with the cDNAs being truncated. Cells transiently transfected with the native Muc1 cDNA, or those virally modified with codon-scrambled Muc1 cDNA, produced glycoproteins of the expected size (FIG. 6). While the lentiviral assay was not a direct test of genomic stability, the results indicated that non-repetitive mucin sequences are more stable throughout at least some types of nucleotide processing operations.

The tandem repeats of native mucins are often polymorphic in number in humans, resulting in a variation of mucin size amongst individuals[25] and short alleles of Muc1 have been shown to be associated with gastric cancer[26]. We designed and constructed a series of synonymous mucins with variable numbers of tandem repeats (×42, ×21, ×10, ×0; FIG. 2*a*). The polymorphic cDNAs expressed well on the cell surface and displayed the expected differences in size and extent of glycosylation. As expected based on previous reports[27], the larger mucins formed a glycocalyx that was substantial enough to dislodge epithelial cells from their substrate.

Substituting the Potential Glycosylation Sites with Alanine in the Mucin Polymer Backbone Tunes O-Glycan Maturation We next tested whether mucins with altered patterns of glycosylation, including differences in glycan extension, could be encoded by mutating away the S/T sites in the mucin backbone. Our overall strategy was to create secreted Muc1 tandem repeats in which alanine was substituted for S/T in one, two, or three of the five potential glycosylation sites in each repeat (FIG. 3*a, b*). We envisioned that the secreted mucins could then be harvested from cell culture media for subsequent glycan analysis with lectin blotting and mass spectroscopy.

cDNAs for the desired Muc1 mutants with 21 repeats each were optimized through codon scrambling and fabricated through custom gene synthesis. The single (Muc1_21S), double (Muc1_21D), and triple (Muc1_21T) glycosylation mutants had 21, 42, and 63 total S/T to alanine substitutions, respectively, and varied in potential glycosylation frequency at 20%, 15% and 10%. An IgK signal peptide and 6×-His-SUMOStar tag was fused to the 21 copies of the wild-type Muc1 repeat or the three mutant repeats (FIG. 3*a*). No transmembrane protein anchor was included, so that the IgK signal peptide would direct secretion of the recombinant mucin protein.

The secreted mucins were harvested from the media supernatant of HEK293 cells and analyzed by Western and lectin blot. The wild-type and glycosylation mutants had a considerably higher apparent molecular weight than the theoretical molecular mass of the undecorated peptide backbones (FIG. 3*b, c* and 8). The potential glycosylation site mutants migrated faster in SDS-PAGE, indicating that they had fewer glycan chains or that their glycans were shorter and, thus, less obstructive to their electrophoretic mobility (FIG. 3*c*).

We found that substituting the S/T tuned the O-glycan maturation. The secreted Muc1 glycoproteins were blotted and probed with VVA for Tn antigen, PNA for Core 1 glycans, and s-WGA for GlcNAc, a building block of Core 2, 3, 4, and 6 glycans (FIG. 3*c*). We constructed electrophoretograms by recording the fluorescence intensity of glycan probes along each lane of a single, co-stained blot (FIG. 3*d*). Core 1 (PNA) and GlcNAc-containing (s-WGA) glycans were abundant in the mucin glycoforms with the highest apparent molecular weights. The lower apparent molecular weight glycoforms contained abundant VVA-reactive glycans and minimal Core 1 and GlcNAc containing glycans. Gradual alanine substitution clearly shifted the glycoform distribution towards mucins with more unextended, VVA-reactive glycans and fewer extended Core 1 and GlcNAc containing glycans (FIG. 3*d, e*). Surprisingly, substitution of even one serine (See sMuc1S) dramatically changed the glycosylation pattern, leading to generation of more non-fully extended glycoforms (FIG. 3*c, d*).

Figure 9:
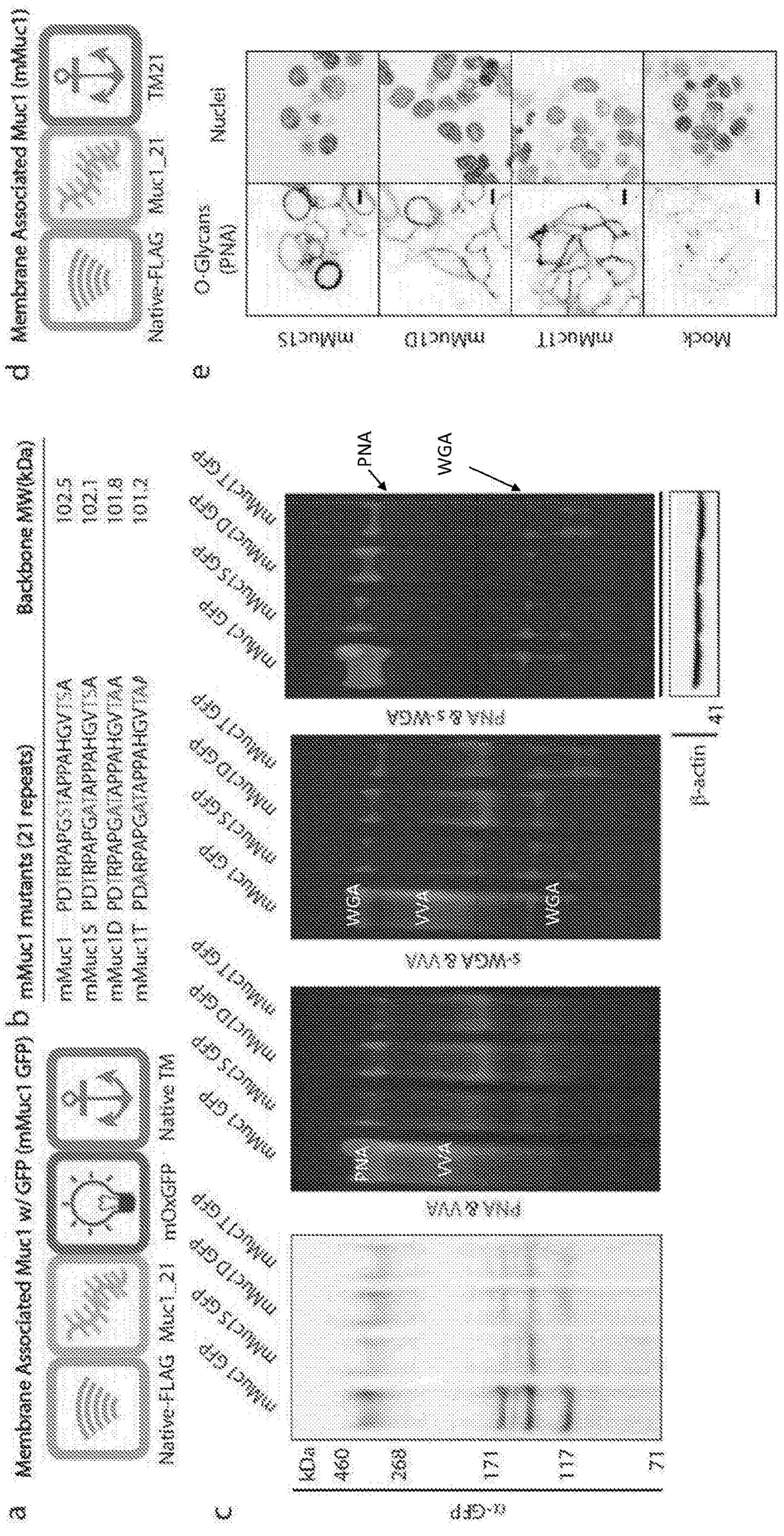
FIG. 9: Cell-Surface Mucin Mutants Derived from Muc1 Tandem Repeat Sequences. The sequences shown in FIG. 9 under mMUC1 mutants (21 repeats) from top down are PDTRPAPGSTAPPAHGVTSA (SEQ ID NO:8), PDTRPAPGATAPPAHGVTSA (SEQ ID NO:5) PDTRPAPGATAPPAHGVTAA (SEQ ID NO:6) and PDARPAPGATAPPAHGVTAA (SEQ ID NO:7). (a) Components and features of mucins constructed with 21 native or engineered Muc1 repeats, GFP reporter and native Muc1 transmembrane anchor. (b) Tandem repeats and predicted backbone molecular weight of native Muc1 (mMuc1) or engineered variants with single, double, or triple serine/threonine to alanine substitutions (mMuc1S, mMuc1D, or mMuc1T). (c) Representative Western and lectin blot analysis of indicated constructs in (a) from extracts of transiently transfected HEK293T cells and probed with anti-GFP antibody or co-stained with PNA, VVA and s-WGA lectins from three independent experiments. (d) Components and features of mucins constructed with 21 native or engineered Muc1 repeats and a synthetic 21-amino-acid transmembrane anchor (TM21). (e) Representative immunofluorescence images of transiently transfected HEK293T cells expressing the indicated constructs in (d) and co-stained with PNA lectin and Hoechst nuclear stain from three independent experiments (scale bar 10 μm)
Figure 10:
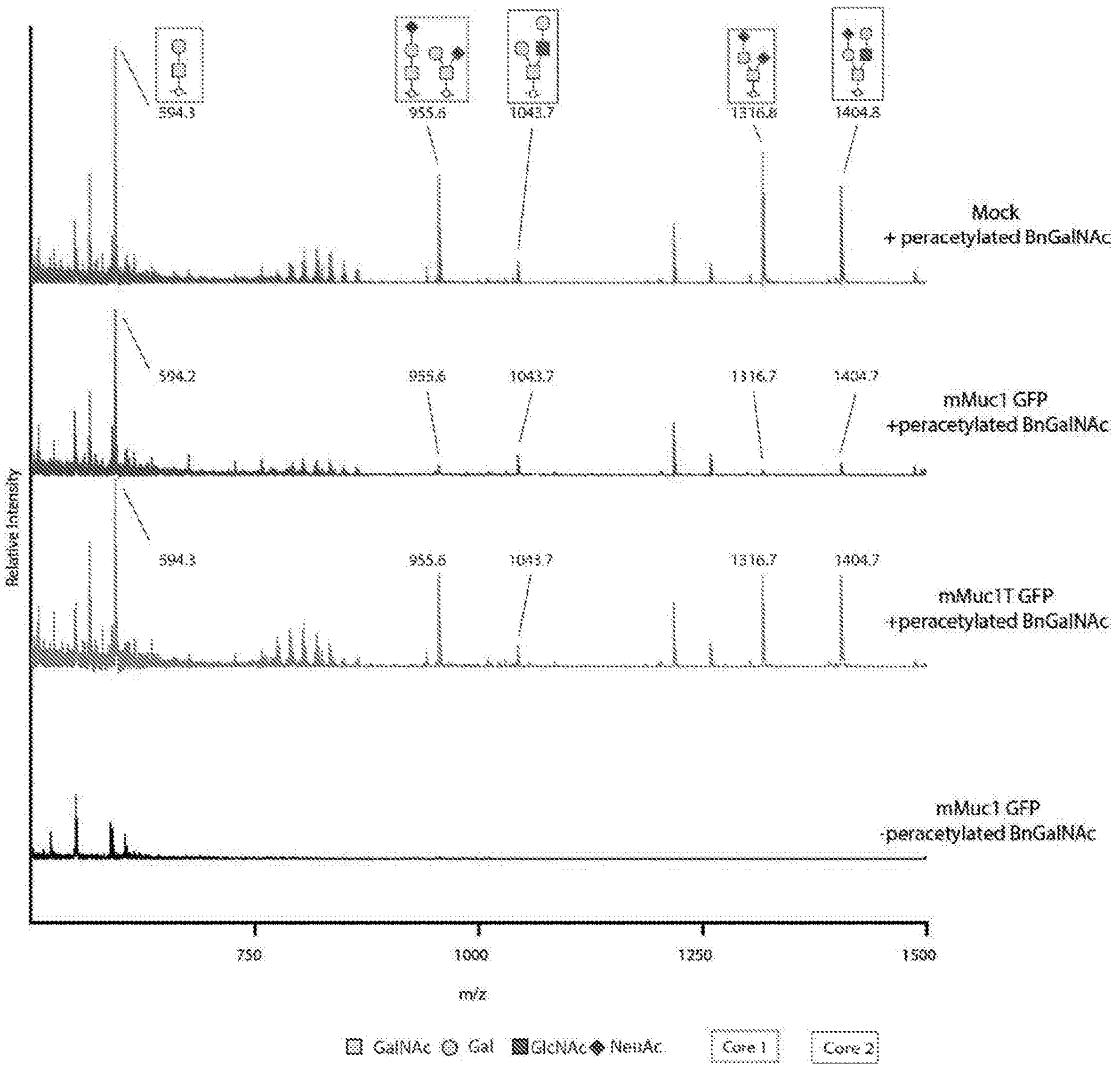
FIG. 10: MALDI-TOF_MS spectra of mucin-type O-glycans as reported by Cellular O-Glycome Reporter/Amplification (CORA). HEK293T cells were transiently transfected with the indicated synthetic mucin constructs or mock vehicle. Spectra were normalized to the matrix peak at m/z=550.
Figure 11:
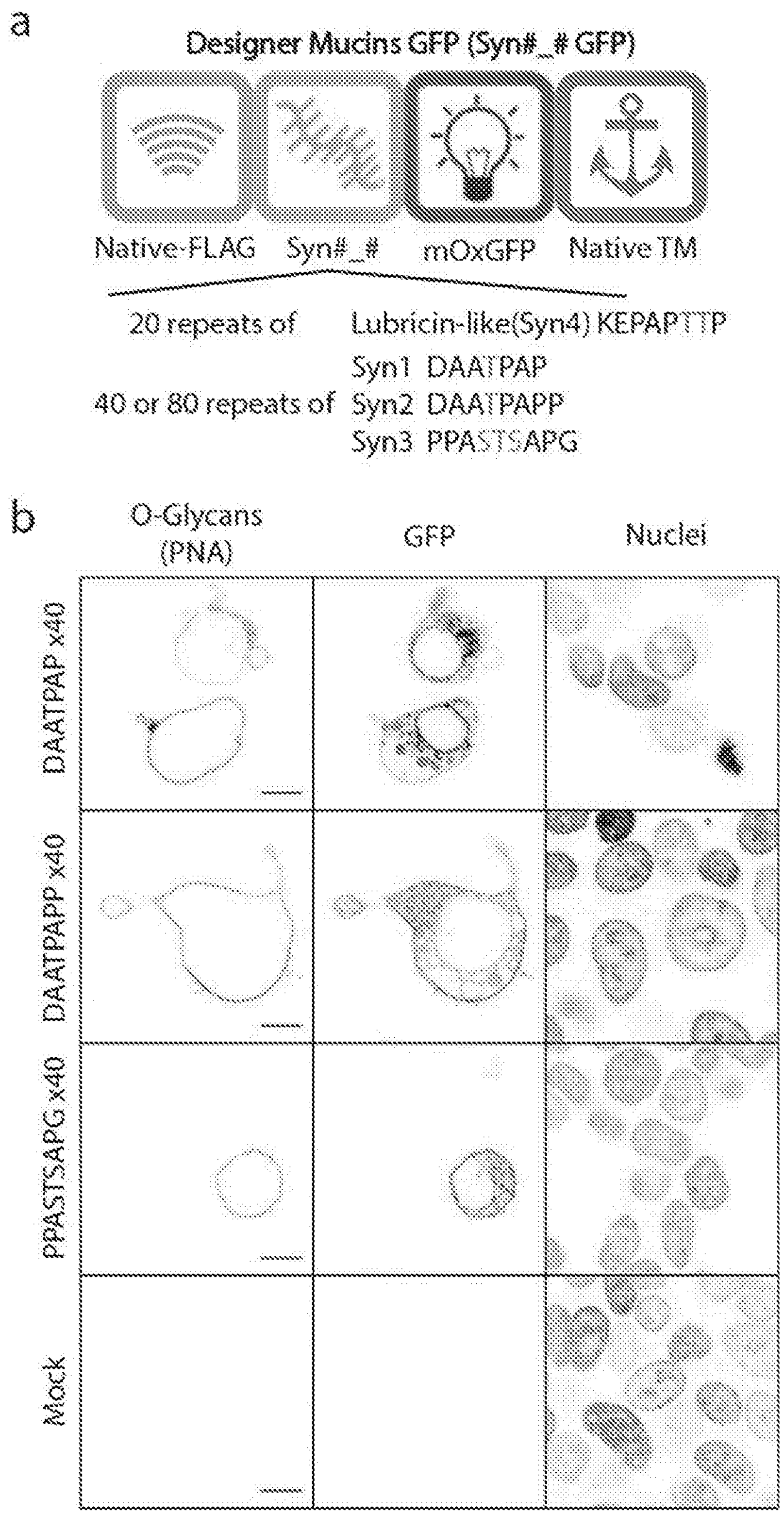
FIG. 11: Mucins Constructed with Designer Tandem Repeats. The sequences shown in FIG. 11 are DAATPAP (SEQ ID NO:2) DAATPAPP (SEQ ID NO:3) and PPASTSAPG (SEQ ID NO:4). (a) Components and features of mucin constructs with designer tandem repeats, GFP reporter and native Muc1 transmembrane anchor. (b) Representative immunofluorescence images of transiently transfected HEK293T cells expressing the indicated GFP-tagged constructs and co-stained with PNA lectin and Hoescht nuclear stain from three independent experiments (scale bar 10 μm).

To validate our lectin analysis and catalogue the specific glycan structures on the mucins, we conducted mass spectrometry to profile the O-glycans on the wild-type mucin repeats (sMuc1) and the mutant with three S/T alanine mutations per repeat (sMuc1T). We identified similar Core 1 and Core 2 glycans in both samples (FIG. 3*f*). However, the signal of extended glycans was much stronger in wild-type mucin (sMuc1) compared to the triple mutant (sMuc1T), consistent with our lectin blots. We also fused the glycosylation mutant cDNAs to a transmembrane anchor for cell-surface expression and observed a similar trend of suppression of glycan extension in the glycosylation-site mutants (FIG. 9*c*). To ensure that the overexpression of mucin constructs did not impact functionality of the glycotransferases for glycan extension, we used Cellular O-glycome Reporter/Amplification (CORA), a method which allows protein-free profiling of the overall cellular O-glycome[28]. Similar Core 1 and Core 2 glycan structures were detected in both wild-type and Muc1 overexpressing HEK293T cells, indicating that the activity of T synthase and other glycosyltransferases involved in mucin extension are not inhibited by mucin overexpression (FIG. 10). Overall, these data demonstrated that extension of glycans in both cell-surface and secreted mucins was sensitive to the alanine substitution along the polymer backbone.

Designer Mucin Domains Reveal Sequence-Specific Effects on Glycosylation

Figure 4:
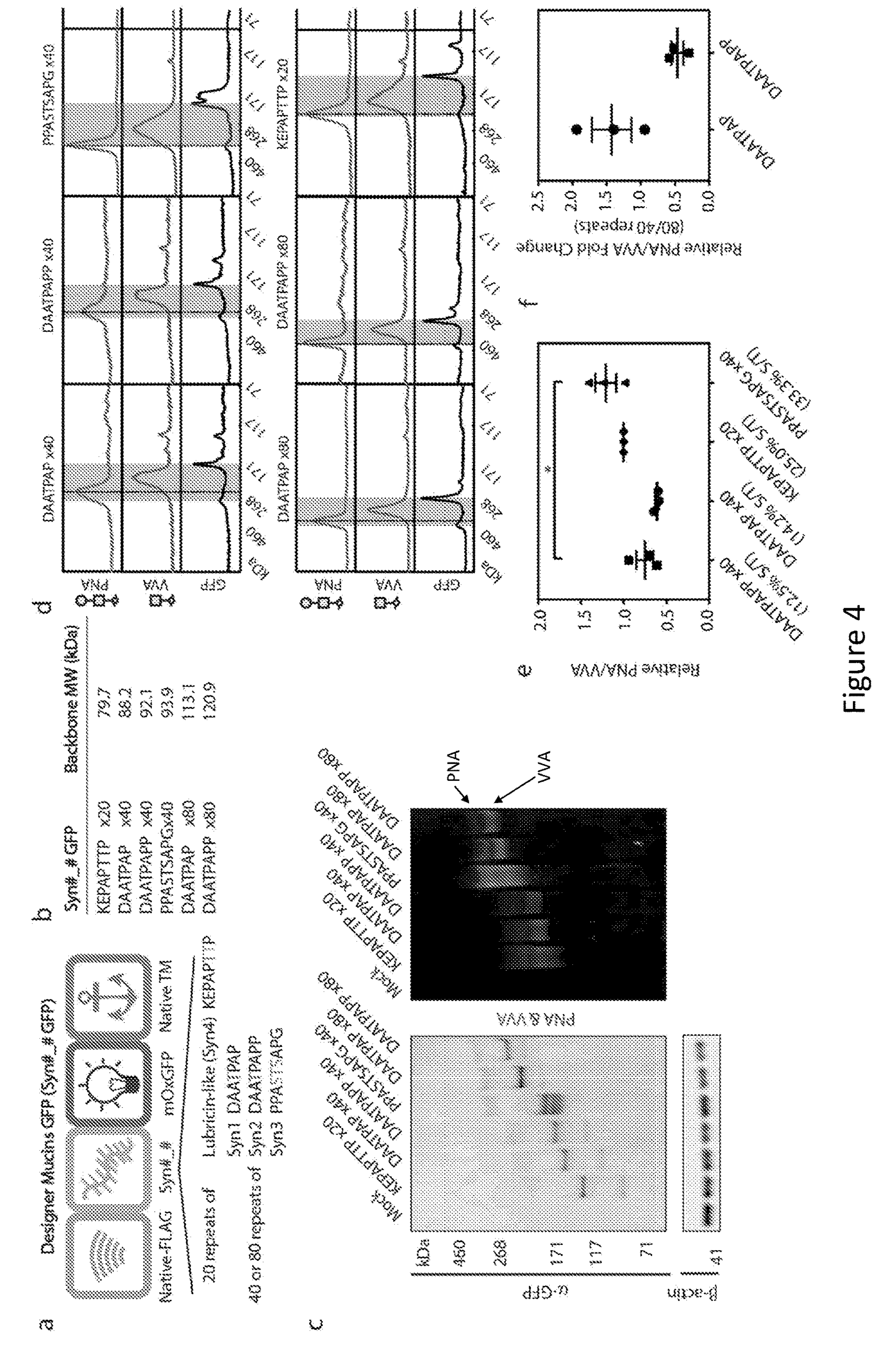
FIG. 4: Designer Mucin Domains Reveal Sequence-Specific Effects on Glycosylation. The sequences shown in FIG. 4 are KEPAPTTP (SEQ ID NO:1) DAATPAP (SEQ ID NO:2) DAATPAPP (SEQ ID NO:3) and PASTSAPG (SEQ ID NO:4). (a) Components and features of designer mucins. (b) Predicted Molecular Weight of the mucin polypeptide backbones. (c) Representative Western blot analysis (from three independent experiments) of indicated constructs in extracts of transiently transfected HEK293T cells probed with anti-GFP antibody or co-stained with PNA and VVA lectins. (d) Representative Fluorescence intensity electrophoretograms of the western blots in (c) for indicated constructs from three independent experiments. Dashed lines indicate the peak of the glycoform visible in the PNA blot. Shaded boxes indicate the regions between the bands on the anti-GFP blot with the highest and second highest apparent molecular weights. (e) Ratiometric intensity analysis of PNA to VVA staining for the indicated mucins and their corresponding frequency of serine and threonine glycosylation sites in polymer backbone. Fluorescence intensity was quantified along each lane of the dual-probed lectin blot, and the PNA:VVA ratio was normalized to that of the KEPAPTTP (SEQ ID NO:1)×20 mucin; data presented as the mean and SEM from three independent experiments. (f) The fold change in PNA:VVA ratio with doubling the indicated mucin backbone size from 40 to 80 tandem repeats; data presented as the mean and SEM from three independent experiments. *$p<0.05$

We next tested whether new types of sequence-specific mucins could be created for editing the glycocalyx. A parallel goal was to further explore the impact of specific backbone features, including glycosylation site frequency and proline number, on mucin glycosylation pattern. Cell-surface mucin cDNAs with GFP reporters were constructed for three representative designer mucin repeats: DAATPAP (SEQ ID NO:2), DAATPAPP (SEQ ID NO:3), and PPASTSAPG and KEPAPTTP (SEQ ID NO:1) which have similarity to secreted human Proteoglycan 4 (FIG. 4*a*). The three designer mucin repeats were expected to be fully glycosylated based on in vitro results[20]. The backbones varied in frequency of glycosylation sites (S/T) from 12-33%. We also created extended variants of the DAATPAP (SEQ ID NO:2) and DAATPAPP (SEQ ID NO:3) mucins through PCR-amplification of the tandem repeats and reassembly with the original cDNAs to double the number of repeats to 80. All mucins expressed well, trafficked appropriately to the cell surface, and were extensively decorated with O-glycans (FIG. 4*c* and FIG. 10*b*).

We analyzed the glycosylation patterns of the mucins through lectin blotting. Multiple bands were visible for each mucin on the anti-GFP blot, revealing a complex distribution of mucin glycoforms on and within the cell (FIG. 4*c*). The heavily glycosylated mucins, as indicated by high PNA and VVA reactivity, typically ran as a smear between the highest and second highest molecular weight bands on the anti-GFP blot (FIG. 4*c, d*). These regions were shaded in grey on the electrophoretograms to aid visualization (FIG. 4*d*). The highest molecular weight glycoforms were heavily decorated with Core 1 glycans (FIG. 4*d*; See PNA). The glycoforms enriched in unextended O-glycans were heterogenous in apparent molecular weight and ran in a smear just below the Core 1 decorated mucins (FIG. 4*d*; Compare VVA and PNA).

We then evaluated whether the frequency of O-glycosylation sites might influence the maturation and extension of O-glycans. We quantified the relative Core 1 to Tn antigen ratio among our synthetic mucins through ratiometric analysis of integrated PNA and VVA signals on our lectin blots (FIG. 4*e*). For mucins with 20 or 40 repeats, we saw a notable increase in Core 1 structures compared to Tn-antigen in mucin backbones with a higher S/T content. However, the glycoform distribution was broader for backbones with higher S/T content, as indicated by more pronounced smearing on the lectin blots and the increased width of the PNA and VVA peaks on the electrophoretograms (FIG. 4*c, d*).

We also considered whether proline content might influence the glycosylation of the mucin backbone, since proline has previously been reported to promote glycosyltransferase interactions with mucin backbones[7]. We compared glycosylation of the DAATPAP (SEQ ID NO:2) and DAATPAPP (SEQ ID NO:3) mucins, which only differed by a single proline per tandem repeat. For mucins with 40 copies of each repeat, the ratio of Core 1 glycans to unextended Tn-antigens was not significantly different between the two mucins (FIG. 4*e*). However, for mucins with 80 copies of the repeats, the relative Core 1 glycan content was significantly lower in the mucin with an extra proline per repeat (FIG. 4*f*). These results suggested that proline content may affect glycosylation in a manner that depends on the overall size of the mucin backbone.

Tuning Mucin Glycosylation Through Cytoplasmic Tail Engineering

Sialylation of O-glycans has occurs at least partially in the endosome and trans-Golgi network following endocytosis of cell-surface mucins[29]. In an attempt to exploit endocytosis and trafficking as a potential tool to alter mucin glycosylation, we created cDNA "bricks" for mucin cytoplasmic tails with different endocytosis and trafficking signals. We noted that the Muc1 cytoplasmic domain can signal for clathrin-mediated endocytosis, while the Muc1 sequence CQCRRK (SEQ ID NO:11) at the boundary of transmembrane and cytoplasmic domain signals for Muc1 recycling back to the plasma membrane[30]. We adopted a synthetic 21-amino-acid transmembrane anchor (TM21) that could anchor mucins to the plasma membrane without a cytoplasmic tail[31] or with the two different cytoplasmic tails in our library. The first cytoplasmic tail was a simple CQC motif to direct mucin recycling. The second was based on the native Muc1 cytoplasmic tail that contains the CQC motif, as well as additional motifs, YHPM and YTNP, to direct more efficient endocytosis[32].

To test their functionality, we fused the TM21 anchor with or without the cytoplasmic tails to a codon-scrambled Muc1 with 10 tandem repeats (Muc1_10) (FIG. 5*a*). All mucin cDNAs were transiently transfected into HEK293 Ts. We labelled the sialic acids on the cell surface with PAL. On lectin blots, the PAL sialic acid signal was strongest at approximately 171 kDa, overlapping with a strong PNA signal, suggesting the PNA-reactive isoforms were also sialic-acid-abundant (FIG. 5*b*). To confirm, we treated the cell lysates with sialidase prior to lectin blot analysis and analyzed the PNA-staining pattern to detect a shift in electrophoretic mobility due to removal of negatively charged sialic acids. Regardless of the cytoplasmic tail motif, the PNA reactive band in the mucins was higher and broader following sialidase treatment, indicating that the dominant PNA-reactive isoforms in all constructs were sialylated (FIG. 5*c*).

To further analyze the sialylated isoforms, we pulled down the Core-1-rich mucin glycoforms with PNA and then probed with *Maackia amurensis* lectin (MAA), which prefers to bind sialic acids in an (α-2,3) linkage[33]. Surprisingly, we did not see any MAA signal near 171 kDa, but noted ultra-high molecular weight glyoforms that were reactive to MAA (FIG. 5*d* Top). The MAA-reactive, ultra-high molecular weight glycoforms were promoted by recycling motifs. We found that the inclusion of the CQC motif led to a 2-fold increase in MAA/PNA ratio compared to the TM21 anchor only, and the longer cytoplasmic tail based on Muc1 increased the MAA/PNA ratio 3-fold (FIG. 5*d* Bottom).

Materials and Methods

Antibodies and Reagents

The following antibodies were used: anti-Human MUC1 (CD227) (clone HMPV; 555925, BD Biosciences), mouse anti-β-Actin (clone C4; 47778, Santa Cruz), chicken anti-SUMO/SUMOstar (AB7002, LifeSensors), mouse 6×His (552565, BD Biosciences), mouse anti-α-tubulin (clone B-7; 5286, Santa Cruz), mouse anti-GFP (clone 4B10; 2955, Cell Signaling Technology), m-IgGκ binding protein—horseradish peroxidase (HRP; 516102, Santa Cruz), goat anti-mouse IgG (Alexa Fluor™ 647 conjugated, A-21235; Alexa Fluor™ 488 conjugated, A-11001; Alexa Fluor™ 568 conjugated, A-11004; ThermoFisher) and goat anti-chicken IgY (Alexa Fluor 488™ conjugated; A-11039, ThermoFisher). Lectins used were: unconjugated *Arachis hypogaea* lectin/peanut agglutinin (PNA; L0881, Sigma), biotin-conjugated PNA (B-1075, Vector Laboratories), biotin-conjugated *Maackia amurensis* lectin (MAA; BA-7801, EY Lab), fluorescein-labeled succinylated Wheat Germ Agglutinin(s-WGA; FL-1021S, Vector Lab), and biotin-conjugated *Vicia villosa* lectin (VVL,VVA; B-1235, Vector Lab). Fluorescent dyes used were: Alexa Fluor™ 647 NHS Ester (A20006, Invitrogen), Alexa Fluor™ 568 NHS Ester (A20003, Invitrogen) and AFDye 568 Hydroxylamine. Biotinylated lectins were detected using ExtrAvidin-Peroxidase (E2886, Sigma) or NeutrAvidin Protein (Dylight 650 conjugated; 84607, ThermoFisher). For tetracycline-inducible systems, doxycycline was used for induction (204734, Santa Cruz). Streptavidin Sepharose® beads (3419, Cell Signaling Technology) was used for immunoprecipitation assays. Cell lysis buffer (9803) and LumiGLO® reagent and peroxide (7003) were from Cell Signaling Technology. Normal goat serum (S-1000) for sample blocking was from Vector Lab. Polyethylenimine (PEI) (25 kDa linear PEI, 23966, Polysciences) was used for FreeStyle™ 293-F cell transfection.

Gene Design and Assembly of MUC1 Tandem Repeat Domains cDNAs for cytoplasmic-tail-deleted human Muc1 (Muc1 dCT) and Muc1 tandem-repeat fusion with the synthetic membrane domain TM21 (Muc1 TM21) were generated and cloned into the tetracycline-inducible piggybac expression vector with Puromycin resistance cassette (pPB tetOn Puro) as previously described[27]. cDNA of Muc1 TM21 was also inserted into the pcDNA3.1 vector using BamHI and EcoRI restriction sites. For generation of pPB Muc1 mOxGFP dCT TetOn Puro, the cDNA for mOxGFP (Addgene #68070) was first amplified with primers: 5'-GGCAGCTCAGC-TATGGTGTCCAAGGGCGAGGAGCTGT-3' (SEQ ID NO:12) (forward) and 5'-GGCAGCTGAGCCCTTATA-CAGCTCGTCCATGCCGTGAGT-3' (reverse) (SEQ ID NO:13). The PCR product was then cloned into pJET1.2 and subcloned non-directionally into the BlpI site of pPB Muc1 dCT TetOn Puro. To fabricate the cDNAs of secreted mucins (sMuc1), synthetic oligos containing a IgK signal peptide and 6×-His-SUMOStar tag (6×His Sumostar Muc1) was created through custom gene synthesis (General Biosystems) and cloned into the tetracycline-inducible piggybac expression vector with Neomycin resistance cassette (pPB tetOn Neo). The lentiviral vector pLV puro Muc1 dCT was fabricated as previously reported[4].

cDNAs for mutant and rationally designed mucins tandem repeats were generated through custom gene synthesis following codon optimization. The least repetitive gene sequence for the desired mucin repeats was found using Codon Scrambler (chilkotilab.pratt.duke.edu/codon-scrambler)[18]. The scrambled DNA sequence was adjusted for human codon bias by swapping any codons with less than 10% frequency usage in humans for randomly selected synonymous codons with higher usage. Synthetic oligos for the desired tandem repeats were then synthesized by custom gene synthesis (General Biosystems and Genscript) and cloned in place of the Muc1 tandem repeats in either pPB Muc1 mOxGFP dCT TetOn Puro using the BamHI and Bsu36I restriction sites, pcDNA3.1 Muc1 TM21 using the BsrGI and Bsu36I restriction sites, or pPB 6×His Sumostar Muc1 using BsrGI and Bsu36I restriction sites (See Supporting Information for cDNA sequences). To generate a lentiviral vector for Muc1 dCT with 42 codon-optimized tandem repeats pLV Muc_42 dCT construct, the synthesized cDNA for the codon-optimized repeats was inserted into pLV puro Muc1 dCT using BamHI and Bsu36I restriction sites. The Muc1 construct with 0 tandem repeats was generated through deletion of the tandem repeats in pcDNA3.1 Muc1_10 TM21 through Q5 site-directed mutagenesis with 5'-TGGAGGAGCCTCAGGCATACTTTATTG-3' (forward) (SEQ ID NO:14) and 5'-CCACCGCCG ACCGA GGTGACATCCTG-3' (reverse) (SEQ ID NO:15) primers.

The cDNA with recycling motif CQCRRK (SEQ ID NO:11) pcDNA3.1 Muc1_10 TM21 CQC was generated from pcDNA3.1 Muc1_10 TM21 through Q5 site-directed mutagenesis with 5'-CCGAAAGTAGGAATTCGGGCCCG TTTAAACCCGC-3' (forward) (SEQ ID NO:16) and 5'-CGGCACTGACATCTAGAGTACCACAACAAAGC CAGGC-3' (reverse) (SEQ ID NO:17) primers. The cDNA of native CT was subcloned into the XbaI and EcoRI site of pcDNA3.1 Muc_10 TM21 CQC.

PCR and Golden Gate Assembly of Extended Synthetic Tandem Repeats

The 40 tandem repeats of DAATPAP (SEQ ID NO:2) and DAATPAPP (SEQ ID NO:3) mucin cDNAs in pcDNA3.1 were doubled in size to 80 repeats using Golden Gate Assembly. Two pairs of custom primers for tandem repeats and complete mucin vector were designed to attach BsmbI recognition sites with unique 4 bp overhangs so that the PCR products of the 40 tandem repeats and complete mucin expression vector would ligate in a Golden Gate Assembly reaction to amplify the tandem repeat number (Table S2). Golden Gate Assembly reaction was conducted as previously reported[47].

Cell Lines, Culture and Transfection

MCF10A human mammary epithelial cells and HEK293T SV40-transformed human embryonic kidney cells were obtained from ATCC. MCF10A cells were cultured in DMEM/F12 media (ThermoFisher) supplemented with 5% horse serum (ThermoFisher), 20 ng/mL EGF (Peprotech), 10 μg/ml insulin (Sigma), 500 ng/mL hydrocortisone (Sigma), and 100 ng/mL cholera toxin (Sigma). HEK293T cells were cultured in DMEM (ThermoFisher) supplemented with 10% fetal bovine serum (ThermoFisher). Cells were maintained at 37° C., 5% $CO_2$, and 90% Relative humidity (RH). FreeStyle™ 293-F cells were cultured in suspension in FreeStyle™ 293 Expression Medium (ThermoFisher). Suspension cultures were maintained in an orbital shaker at 37° C., 8% $CO_2$, and 90% RH. Lentiviral transduction was conducted as previously reported in MCF10A cells with stably integrated gene cassettes for expression of the tetracycline transactivator, rtTA-M2, and neomycin resistance gene[48]. HEK293T cells were transiently transfected with the calcium phosphate method according to standard protocols. FreeStyle™ 293-F cells were transiently transfected with PEI as previously described[49]. CRISPR/Cas9 mediated knockout of COSMC in MCF10A Muc1 dCT cells were generated as previously reported[50].

Western Blot Analysis

HEK293T cells were plated at 55,000 cells/cm$^2$ and transfected with calcium phosphate for 24-36 hrs before lysis with cell lysis buffer. MCF10A cells were plated at 20,000 cells/cm$^2$ and induced with 0.2 μg/mL doxycycline for 24 hrs before lysis with cell lysis buffer. Lysates were separated on NuPAGE 3-8% or 7% Tris-Acetate gels and transferred to PVDF membranes. Primary antibodies were diluted at 1:1000 and fluorophore-conjugated or biotinylated lectins were diluted to 2 μg/mL in 5% BSA TBST and incubated overnight at 4° C. Secondary antibodies, ExtrAvidin-HRP or Neutravidin-Dylight 650 were diluted at 1:2000 or 1 μg/mL in 5% BSA TBST and incubated for 1 hr at room temperature. Blots were either imaged on a ChemiDoc MP Imaging System (Bio-Rad) or after being developed in LumiGLO® reagent and peroxide. Integrated blot intensity was quantified with the FIJI distribution of ImageJ[51,52] The statistical significance of the differences among the data was calculated using a one-way ANOVA with repeated measures or two-tailed t-test.

Periodate Labeling of Cell Surface Sialic Acids

HEK293T cells were collected after 36 hrs of transfection. Cells were washed with cold DPBS with $Ca^{2+}$ and $Mg^{2+}$ followed by a 10-minute incubation with 1 mM sodium periodate (Sigma) in DPBS. The periodate was quenched by 1 mM glycerol in cold DPBS and washed with cold DPBS. Samples were stained with 25 μM AFDye-568-hydroxylamine (Fluoroprobes) in the presence of 10 mM aniline (Sigma) in sterile filtered DPBS+5% FBS pH 6.7 for 30 min at 4° C. in the dark with gentle agitation.

Immunoprecipitation

HEK293T cells were plated at 55,000 cells/cm$^2$ and transfected with the calcium phosphate method for 24-36 hrs before lysis with cell lysis buffer. The lysates were incubated with 125 μg/mL biotinylated lectin PNA at 4° C. with gentle rocking overnight. Streptavidin Sepharose© beads were added to the cell lysates following manufacturer's instructions and the suspension was incubated at 4° C. for 3 hrs. The beads were washed 2 times with lysis buffer and then resuspended in 4×LDS loading buffer. The resuspension was subsequently analyzed by Western blot.

Sialidase Treatment of HEK293 Ts

HEK293T cells were collected 24 hrs after transfection and incubated with *Arthrobacter ureafaciens* sialidase (Roche, 10 mU, 100 μl final volume) in sialidase buffer[53] for 30 mins at 37° C. before lysis with cell lysis buffer.

Immunofluorescence

HEK293T cells were plated at 45,000 cells/$cm^2$ and transfected with calcium phosphate for 24 hrs before being fixed with 4% paraformaldehyde. Antibodies were diluted at 1:100 in 5% normal goat serum in PBS and incubated overnight at 4° C. Lectins were diluted to 2 μg/mL in 5% normal goat serum in PBS and incubated for 2 hrs at room temperature. Samples were imaged on a Zeiss LSM inverted 880 confocal microscope using a 40× water immersion objective (NA 1.1).

Secreted Mucin Protein Expression, Purification 16.25 μg pPB 6×His Sumostar Muc1 DNAs were transfected into HEK293T cells in 10-cm culture dishes for 48 hrs. 30 μg pPB 6× His Sumostar Muc1 DNAs were transfected into 20 mL FreeStyle™ 293-F cell culture for 4 days. Culture media was collected and clarified by centrifugation at 2000 rpm for 5 min. The clarified culture media was bound to Ni-NTA agarose (Qiagen) at 4° C. overnight, washed (20 mM sodium phosphate pH 8.0, 0.5 M sodium chloride (NaCl), 20 mM imidazole), and eluted with imidazole (20 mM sodium phosphate pH 8.0, 0.5 M NaCl, 250 mM imidazole). The eluted sample was diafiltrated into PBS with Amicon Ultra-4 Centrifugal Filter (10 kDa cutoff) and then desalted by using Zeba™ Spin desalting columns (7K MWCO). The salt-free protein solution was lyophilized and stored at −80° C.

O-Glycan Profiling of Secreted Mucin Protein

All reagents were purchased from Sigma unless otherwise mentioned. Purified mucin proteins (600 ug, each) was denatured by heating at 100° C. for 5 min. The denatured proteins were subsequently treated with 19 mg sodium borohydride ($NaBH_4$) in 500 μL of 50 mM sodium hydroxide (NaOH) solution at 45° C. for 18 hrs[54]. The samples were cooled, neutralized with 10% acetic acid, passed through a Dowex H+ resin column, and lyophilized with borates removed under the stream of nitrogen. The glycans were permethylated for structural characterization by mass spectrometry using previously reported methods[55]. Briefly, the dried eluate was dissolved with dimethyl sulfoxide (DMSO) and methylated by using methyl iodide and NaOH-DMSO base (prepared by mixing DMSO and 50% w/w NaOH solution). The reaction was quenched with water and the reaction mixture was extracted with methylene chloride and dried. The permethylated glycans were dissolved in methanol and crystallized with α-dihydroxybenzoic acid (DHBA, 20 mg/mL in 50% v/v methanol:water) matrix. Analysis of glycans present in the samples was performed in the positive ion mode by MALDI-TOF/TOF-MS using an AB SCIEX TOF/TOF 5800 (Applied Biosystem MDS Analytical Technologies) mass spectrometer. Permethylated glycans from the samples were infused on an Orbitrap Fusion Tribrid mass spectrometer through an ESI probe with HCD and CID fragmentation option for further structural confirmation. The MS1 and MS2 spectra of the glycans were acquired at high resolution by a simple precursor scan and respective ions were selected manually for further MS/MS scanning. Assignment of glycan structures were done manually and by using Glycoworkbench software, based on the fragmentation patterns and common biosynthetic pathways.

Cellular O-Glycome Reporter/Amplification (CORA)

All chemicals were purchased from Millipore Sigma except where noted. Solvents were of HPLC grade or higher, and 0.1% (v/v) trifluoroacetic acid was included in all chromatography steps. Benzyl 2-acetamido-2-deoxy-α-D-galactopyranoside (BnGalNAc) was peracetylated by heating in a molar excess of 33% (v/v) acetic anhydride in anhydrous pyridine for 1 hour at 65° C. The product was dried by speedvac (Thermo Scientific SPD1010) and used without further purification. Peracetylation was confirmed by LC-MS (Agilent 1100 Series LC and G1956B MS, m/z calculated: 438.18 observed: 438.10 [M+H]+).

CORA was performed as previously reported[28]. Briefly, 500,000 HEK293T cells were plated in a 6 cm culture dish and transfected as above. Following transfection cultures were incubated in full media supplemented with 50 μM peracetylated BnGalNAc. After 48 hours the media was aspirated and loose cells and debris removed by centrifugation. The supernatant was then filtered (Millipore Amicon Ultra 4, 10 kDa MWCO) and benzyl glycans collected by gravity chromatography (Waters Sep-Pak C18 3 cc). The eluent was dried by speedvac before permethylation2. A sodium hydroxide slurry in DMSO was freshly prepared and 200 μL added to each dry sample followed by 100 μL methyl iodide (ACROS). The samples were mixed continuously for 10 mins then the reaction halted by the addition of 600 μL deionized water. Permethylated benzyl glycans were recovered by extraction with 200 μL chloroform then washed 4 times with 800 μL deionized water. The samples were further purified by C18 gravity chromatography (Waters Sep-Pak C18 1 cc) and dried by speedvac. Dried samples were dissolved in 50% methanol, and spotted 1:1 (v/v) with a matrix of 10 mg/mL 2,5-dihydrobenzoic acid in 50% acetonitrile. Benzyl glycans were analyzed using a MicroFlex MALDI-TOF-MS (Bruker) in positive ion mode. Two external standards of permethylated maltotetraose (Cayman Chemical, m/z calculated: 885.43 observed: 885.65 [M+Na}+) and maltoheptaose (Cayman Chemical, m/z calculated: 1497.73 observed: 1497.90 μM+Na}+) were included to confirm instrument performance and calibration. Benzyl glycan compositions were assigned on the basis of predicted masses of the sodium adducts of known structures ([M+Na}+}. Data was analyzed using Mnova (Mestrelab Research) and prepared for presentation with Prism8 (GraphPad).

Discussion of Part I

The O-glycosylation of mucins determines their physical and biochemical characteristics, and, thus, their biological functions. This Part I provides a genetically encoded system to edit the mucin biopolymers, and can be used as a tool for glycocalyx engineering, among other significant utilities that are discussed above. Factors that are known to influence mucin glycosylation include the cellular repertoire of glycosyltransferases and their substrates[1,34], frequency of O-glycosylation sites on the polypeptide backbone[35,36], primary peptide sequences around the O-glycosylation sites[37-39], and trafficking of the glycoprotein[32,40,41]. In this Part I we modify signals and motifs in the mucin backbone sequences and cytoplasmic tails to encode mucins with varying physical features, backbone chemistries, and glycosylation patterns.

Using codon degeneracy to design mucin cDNAs with minimal repetition, we were able to apply custom gene synthesis for construction of 13 representative unique mucin repeats, each of which could be readily combined with other functional domains for cell-surface anchorage and control of trafficking. All repeat sequences tested were successfully fabricated with no failures. The disclosure therefore includes using the described design strategy to produce other constructs as described herein. By combining these cDNAs in a modular fashion with other functional cDNA "bricks," mucins of modified structure and functionality, given the benefit of this disclosure, can readily be constructed with known molecular techniques, including Gibson Assembly, Golden Gate Assembly, and other modern DNA assembly approaches.

An observation in this Part I was that extension of O-glycans from the Tn antigen to Core ½ glycans is discouraged by alanine substitution along the polymer backbone. Given that the effect was observed in both membrane-associated and secreted mucins, altered endocytosis and trafficking likely do not account for the differences in glycan maturation. Differences in glycosylation also are not likely explained by potential effects of mucin overexpression on the functionality of T-synthase and other glycosyltransferases involved in early O-glycan extension. As shown in the Cellular O-Glycome Reporter/Amplification analysis, similar Core 1 or Core 2 glycan structures were observed for both mucin-overexpressing and wild-type HEK293 Ts (FIG. 10).

Analyses of O-glycosylation in this Part 1 were partly based on lectin blots. Controls were used to validate the main lectin-based analyses. Knock-out of COSMC to abrogate glycan extension, lead to decreased PNA binding and elevated VVA staining, suggesting the appropriateness of these lectins for detecting Core 1 O-glycans and Tn-antigen, respectively (FIG. 2*d*). O-glycomic analysis on purified mucins also validated conclusions that were based on lectin analysis regarding the types of glycan structures present on mucins (FIG. 3*f*).

We modified the mucin cytoplasmic tail for glyco-engineering. Based on a shift in electrophoretic mobility following sialidase treatment, we concluded that recycling motifs were not required for mucin sialylation. However, inclusion of recycling motifs promoted the generation of ultra-high molecular weight mucin glycoforms that react with MAA lectin. It is considered that swapping mucin cytoplasmic tails may be a viable strategy to at least partially engineer emergent glycoforms.

TABLE S1

Repetitiveness Analysis of Mucin cDNA sequences
Repetition analysis of native and codon-scrambled cDNAs were conducted with the Tandem Repeat Finder algorithm[1]. Agreement between the queried sequence and detected tandem repeats were weighed by assigning alignment scores of +2 for nucleotide sequence matches and −7 for mismatches and indels. The high alignment score indicates high-level repetitiveness of the repeats.

| Native_Muc1 | | | | | | |
|---|---|---|---|---|---|---|
| Indices | Period Size | Copy Number | Consensus Size | Percent Matches | Percent Indels | Score |
| 6-2577 | 60 | 42.9 | 60 | 99 | 0 | 4982 |

| Muc1_42 | | | | | | |
|---|---|---|---|---|---|---|
| Indices | Period Size | Copy Number | Consensus Size | Percent Matches | Percent Indels | Score |
| 146-468 | 60 | 5.4 | 60 | 75 | 3 | 220 |
| 146-468 | 120 | 2.7 | 120 | 80 | 2 | 328 |
| 149-513 | 120 | 3.0 | 120 | 79 | 5 | 294 |
| 728-897 | 60 | 2.8 | 60 | 80 | 1 | 171 |
| 746-984 | 60 | 4.0 | 60 | 75 | 4 | 169 |
| 1013-1233 | 60 | 3.7 | 60 | 77 | 0 | 208 |
| 794-1200 | 120 | 3.4 | 120 | 75 | 4 | 273 |
| 1205-1347 | 60 | 2.4 | 59 | 74 | 8 | 135 |
| 1097-1530 | 180 | 2.4 | 180 | 77 | 2 | 379 |
| 1304-1521 | 60 | 3.6 | 59 | 76 | 2 | 175 |
| 1514-1714 | 60 | 3.3 | 60 | 78 | 0 | 204 |
| 1709-1965 | 120 | 2.1 | 120 | 80 | 1 | 273 |
| 1781-2067 | 60 | 4.8 | 60 | 71 | 5 | 177 |
| 1733-2067 | 120 | 2.8 | 120 | 77 | 1 | 269 |
| 2150-2406 | 60 | 4.3 | 60 | 73 | 3 | 140 |
| 2222-2439 | 120 | 1.8 | 120 | 79 | 2 | 258 |

Table Explanation:
Indices of the repeat relative to the start of the sequence.
Period size of the repeat.
Number of copies aligned with the consensus pattern.
Size of consensus pattern (may differ slightly from the period size).
Percent of matches between adjacent copies overall.
Percent of indels between adjacent copies overall.
Alignment score.

REFERENCE (1) Benson, G. Tandem Repeats Finder: A Program to Analyze DNA Sequences. *Nucleic Acids Res* 1999, 27 (2), 573-580.

TABLE S2

| Golden Gate assembly primers. | | |
|---|---|---|
| Name | Sequence | SEQ ID NO: |
| pcDNA3.1 Syn1 FWD | AGGTAGCGTCTCGTCCCGCCTCAGGCATACTTTATTG | 18 |
| pcDNA3.1 Syn1 REV | AGGTAGCGTCTCGTCGGGAGCAGGGGTAGCG | 19 |
| Syn1 FWD | AGGTAGCGTCTCGCCGATGCAGCTACTCCAGCTCCGGACGCC | 20 |
| Syn1 REV | AGGTAGCGTCTCGGGGAGCAGGGGTAGCG | 21 |
| pcDNA3.1 Syn2 FWD | CTTCTGCGTCTCGTCCCGCCTCAGGCATACTTTATTGGCGA | 22 |
| pcDNA3.1 Syn2 REV | CTTCTGCGTCTCGTCGGGAGGAGCTGGTGTAGCCGCG | 23 |
| Syn2 FWD | CTTCTGCGTCTCCCCGATGCAGCTACCCCGGCTCCACCC | 24 |
| Syn2 REV | CTTCTGCGTCTCCGGGAGGAGCTGGTGTAGCCGCG | 25 |

TABLE S2-continued

```
Summary of cDNA "Biobricks" as described in Part I.
Leader Tag
1. Native-FLAG
Amino acid sequence:
MTPGTQSPFFLLLLLTVLTVVTGSGHASSTPGGEKETSATQRSSVPSSTEKNADYKDDDDLY
(SEQ ID NO: 26)

cDNA sequence:
GGATCCATGACACCGGGCACCCAGTCTCCTTTCTTCCTGCTGCTGCTCCTCACAGTGCTTAC
AGTTGTTACAGGTTCTGGTCATGCAAGCTCTACCCCAGGTGGAGAAAAGGAGACTTCGGCTA
CCCAGAGAAGTTCAGTGCCCAGCTCTACTGAGAAGAATGCTGATTACAAGGATGACGACGAC
CTGTACA (SEQ ID NO: 27)

2. His-SUMO
Amino acid sequence:
METDTLLLWVLLLWVPGSTGDGHHHHHHGSLQDSEVNQEAKPEVKPEVKPETHINLKVSDGS
SEIFFKIKKTTPLRRLMEAFAKRQGKEMDSLTFLYDGIEIQADQAPEDLDMEDNDITEAHRE
QIGGGSGSGHASSTPGGEKETSATQRSSVPSSTEKNADYKDDDDLY (SEQ ID NO: 28)

cDNA sequence:
GGATCCGCCACCATGGAGACAGACACACTCCTGCTATGGGTACTGCTGCTCTGGGTTCCAGG
TTCCACTGGTGACGGTCATCACCATCATCATCACGGGTCCCTGCAGGACTCAGAAGTCAATC
AAGAAGCTAAGCCAGAGGTCAAGCCAGAAGTCAAGCCTGAGACTCACATCAATTTAAAGGTG
TCCGATGGATCTTCAGAGATCTTCTTCAAGATCAAAAAGACCACTCCTTTAAGAAGGCTGAT
GGAAGCGTTCGCTAAAAGACAGGGTAAGGAAATGGACTCCTTAACGTTCTTGTACGACGGTA
TTGAAATTCAAGCTGATCAGGCCCCTGAAGATTTGGACATGGAGGATAACGATATTATTGAG
GCTCACAGAGAACAGATTGGAGGTGGCTCCGGCTCCGGTCATGCAAGCTCTACCCCAGGTGG
AGAAAAGGAGACTTCGGCTACCCAGAGAAGTTCAGTGCCCAGCTCTACTGAGAAGAATGCTG
ATTACAAGGATGACGACGACCTGTACA (SEQ ID NO: 29)
```

In the representative polymer backbone segment sequences presented immediately below, repeat sequences are proceeded by the following sequence: LYMDMVA-VSMTSSVLSSHSPGSGSSTTQGQDVTLAPATEPASGS-AATWGQDVTSV (SEQ ID NO:30) with the pertinent repeat sequence designated with the pertinent SEQ ID and the number of its repeats designated in brackets with a subscript, the subscript indicating the number of repeats. The alphnuermic names given above each sequence are names of the sequences, rather than sequences themselves.

Polymer Backbone
1. Codon-Scrambled Muc1 x42 (Muc1_42)
2. Amino acid sequence:
3. LYMDMVAVSMTSSVLSSHSPGSGSSTTQGQDVTLAPATEPASGSAATWGQD

VTSV[PDTRPAPGSTAPPAHGVTSA]$_{42}$ASG (SEQ ID NO: 30 [SEQ ID NO: 8]$_{42}$ASG cDNA sequence:

(SEQ ID NO: 50)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCGGATACGCGACCCGCCCCAGGGTCAACAGCGCCC

CCAGCCCACGGCGTTACATCTGCACCTGACACTAGACCTGCGCCAGGATC

AACAGCTCCACCGGCTCACGGGGTCACCAGTGCCCCCGACACTCGACCAG

CTCCGGGGTCTACCGCTCCCCCGGCTCATGGTGTCACTAGCGCGCCTGACA

CACGCCCGGCACCAGGGAGTACGGCCCCTCCTGCGCACGGCGTAACTTCA

GCCCCAGATACTCGACCTGCTCCGGGCTCAACAGCCCCGCCTGCACATGG

AGTTACATCAGCCCCTGATACTAGACCGGCTCCAGGTTCAACTGCTCCGCC

AGCACATGGTGTAACGTCTGCGCCCGATACTCGCCCAGCACCTGGGTCCA

CAGCTCCCCCTGCGCATGGAGTAACATCAGCACCTGATACCAGACCTGCC

CCGGGCAGCACTGCACCCCCAGCACATGGCGTAACATCAGCACCAGATAC

TCGCCCCGCTCCTGGTTCCACGGCTCCCCCCGCGCATGGCGTTACTTCAGC

TCCAGATACACGGCCGGCACCCGGCAGTACGGCTCCACCCGCACATGGAG

TAACGAGTGCTCCGGACACTCGGCCTGCTCCAGGAAGTACCGCACCTCCG

-continued

GCCCATGGCGTGACAAGTGCTCCCGACACCAGACCAGCGCCTGGTTCAAC

AGCACCGCCAGCTCATGGTGTAACCTCAGCTCCCGATACTAGACCCGCGC

CAGGTTCCACCGCTCCACCTGCACACGGGGTGACGAGCGCACCTGATACG

CGCCCGGCACCGGGAAGCACAGCGCCTCCCGCTCACGGAGTCACTAGCGC

CCCGGATACAAGACCCGCACCTGGATCTACAGCTCCTCCAGCTCACGGCG

TCACGAGTGCACCCGATACACGACCGGCCCCAGGCTCTACAGCCCCACCA

GCACATGGAGTCACGAGTGCACCTGATACTAGGCCCGCTCCGGGTTCCAC

AGCACCTCCTGCACATGGTGTTACATCCGCTCCTGATACGAGACCCGCTCC

AGGCTCTACTGCCCCACCGGCACACGGCGTGACCAGTGCTCCAGATACCC

GGCCAGCTCCTGGGAGTACTGCGCCTCCAGCTCATGGCGTCACTAGTGCA

CCTGATACAAGACCAGCCCCCGGTTCCACTGCTCCACCAGCCCATGGTGT

AACAAGTGCACCGGACACAAGGCCAGCCCCTGGTAGTACTGCTCCTCCTG

CTCACGGTGTTACTAGTGCTCCTGACACCAGACCTGCCCCTGGAAGTACTG

CACCGCCTGCTCATGGAGTCACATCAGCTCCGGATACTCGGCCGGCTCCG

GGATCAACCGCTCCTCCGGCTCATGGAGTAACCTCCGCACCGGATACTAG

GCCTGCACCGGGGAGTACAGCACCACCTGCTCATGGTGTGACTAGCGCTC

CTGACACTCGCCCCGCTCCCGGTAGCACTGCCCCCCCTGCACATGGGGTG

ACTTCAGCTCCTGATACTCGGCCTGCACCCGGAAGCACAGCCCCCCCAGC

TCATGGGGTCACAAGCGCTCCAGATACTAGGCCAGCGCCGGGAAGTACAG

CCCCTCCAGCGCACGGTGTAACTTCCGCGCCAGACACACGCCCTGCTCCC

GGATCAACGGCACCTCCAGCACACGGTGTGACGTCCGCACCCGACACAAG

ACCGGCACCTGGTTCTACTGCACCTCCCGCGCACGGAGTTACTTCAGCACC

AGATACAAGACCTGCTCCTGGCTCAACTGCCCCTCCGGCGCATGGTGTAA

CTAGTGCGCCTGATACACGCCCAGCACCGGGTAGTACGGCACCACCAGCT

CATGGAGTTACGTCAGCTCCAGATACGCGCCCTGCACCAGGCAGTACAGC

TCCGCCGGCCCACGGAGTAACTAGCGCACCAGATACCAGGCCAGCACCCG

GTAGTACCGCGCCTCCTGCCCATGGAGTAACTTCCGCCCCCGATACCCGA

CCTGCACCTGGCAGTACCGCCCCTCCCGCCCACGGGGTAACCAGTGCACC

AGACACGCGGCCCGCACCAGGATCTACTGCTCCCCCAGCGCATGGGGTAA

CTTCTGCACCAGATACGAGGCCTGCCCCAGGTAGTACAGCGCCACCTGCC

CACGGTGTCACCTCCGCTCCTGATACAAGGCCTGCGCCTGGATCAACTGC

ACCACCGGCGCACGGGGTTACAAGTGCCCCTGACACGAGACCAGCACCA

GGTTCTACGGCGCCTCCGGCACATGGAGTGACTAGTGCCCCAGACACTAG

GCCGGCTCCTGGATCAACCGCACCACCCGCTCATGGAGTGACATCAGCGC

CAGATACTAGACCAGCTCCCGGGTCAACTGCGCCGCCCGCCCATGGGGTT

ACTTCTGCTCCAGACACTCGCCCAGCCCCAGGATCAACGGCTCCTCCCGC

ACACGGAGTGACCTCTGCTCCTGATACCAGGCCAGCTCCAGGGTCTACAG

CACCCCCTGCTCATGGGGTAACATCTGCCGCCTCAGG

-continued

4. Codon-Scrambled Muc1 x21 (Muc1_21)
Amino acid sequence:
LYMDMVAVSMTSSVLSSHSPGSGSSTTQGQDVTLAPATEPASGSAATWGQD

VTSV[PDTRPAPGSTAPPAHGVTSA]$_{21}$ASG (SEQ ID NO: 30)[SEQ ID NO: 8]$_{21}$ASG cDNA sequence:
(SEQ ID NO: 51)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCAGACACTCGGCCTGCACCGGGATCAACCGCCCCA

CCGGCTCATGGTGTAACTAGTGCGCCTGATACCAGACCAGCACCAGGGAG

TACTGCACCTCCTGCTCATGGGGTTACTAGTGCCCCCGATACGCGACCTGC

TCCTGGAAGCACAGCACCGCCGGCTCACGGCGTAACGAGTGCTCCTGACA

CAAGGCCCGCTCCAGGGTCAACTGCACCACCTGCACACGGAGTGACATCA

GCGCCAGATACGAGACCTGCACCAGGAAGTACAGCGCCGCCAGCCCACG

GAGTAACTTCAGCCCCGGACACTAGGCCAGCACCTGGTTCAACGGCGCCT

CCAGCCCATGGAGTAACATCCGCTCCCGATACTCGTCCTGCTCCGGGTTCC

ACAGCTCCTCCCGCACATGGGGTGACTAGTGCTCCAGATACTCGCCCAGC

ACCCGGTAGTACCGCTCCTCCTGCACATGGCGTCACTAGTGCACCAGACA

CGCGTCCGGCTCCTGGGTCTACAGCTCCACCAGCTCACGGAGTTACCAGT

GCACCTGACACTAGACCTGCGCCCGGTTCGACGGCTCCGCCCGCCCATGG

GGTAACGTCTGCGCCGGATACACGCCCTGCACCTGGATCTACCGCACCTC

CGGCCCATGGTGTCACGAGCGCACCTGATACGAGGCCTGCTCCAGGTAGT

ACTGCTCCCCCCGCTCATGGAGTTACTAGCGCTCCTGATACTCGACCGGCA

CCTGGCAGCACTGCTCCTCCAGCACATGGTGTTACATCGGCTCCAGACAC

ACGTCCCGCGCCAGGATCGACTGCTCCACCCGCTCACGGGGTCACATCTG

CACCCGATACACGGCCAGCTCCCGGTTCCACTGCCCCGCCTGCCCATGGC

GTTACTTCGGCACCAGATACCCGACCCGCACCAGGCAGTACAGCACCTCC

AGCGCATGGTGTGACAAGCGCCCCTGATACACGACCAGCTCCAGGCTCAA

CAGCACCACCAGCACACGGTGTAACCTCAGCTCCGGATACCCGTCCAGCT

CCTGGTAGTACAGCCCCTCCTGCGCACGGAGTCACAAGTGCTCCCGACAC

AAGACCAGCCCCAGGTTCTACTGCGCCACCTGCTCACGGTGTTACCTCTGC

CCCAGATACAAGACCTGCCCCTGGCTCTACGGCACCCCCGGCACATGGAG

TCACTTCCGCACCGGATACTAGACCAGCGCCTGGGAGTACGGCCCCCCCA

GCTCATGGCGTGACTTCTGCTGCCTCAGG

5. Codon-Scrambled Muc1 x10(Muc1_10)
Amino acid sequence:
LYMDMVAVSMTSSVLSSHSPGSGSSTTQGQDVTLAPATEPASGSAATWGQD

VTSV[PDTRPAPGSTAPPAHGVTSA]$_{10}$ASG (SEQ ID NO: 30)[SEQ ID NO: 8]$_{10}$ASG cDNA sequence:
(SEQ ID NO: 52)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCAGATACAAGACCGGCCCCAGGATCTACGGCTCCT

-continued

CCGGCTCATGGAGTCACTTCTGCTCCAGACACAAGGCCCGCGCCGGGTTC

TACAGCACCGCCTGCTCATGGTGTTACTAGCGCACCCGATACGAGACCTG

CTCCGGGATCAACGGCACCTCCTGCCCACGGGGTAACATCTGCACCGGAC

ACTCGCCCTGCGCCCGGTTCAACCGCTCCACCCGCACACGGAGTGACAAG

CGCTCCTGACACTAGACCAGCACCAGGTTCTACAGCCCCACCAGCCCATG

GAGTTACCAGTGCACCAGATACTAGGCCAGCTCCAGGTAGTACTGCACCC

CCAGCTCATGGGGTTACATCAGCTCCCGACACGCGACCAGCTCCTGGAAG

CACTGCCCCTCCAGCTCACGGTGTGACCTCAGCACCTGATACACGCCCTGC

ACCTGGCTCTACTGCTCCCCCCGCTCATGGCGTAACTAGTGCCCCGGATAC

TCGACCCGCCCCTGGTTCCACAGCTCCGCCAGCACATGGTGTAACAAGTG

CTCCTGATACCCGACCAGCGCCTGGAAGTACCGCACCACCTGCACATGGA

GTAACTTCAGCCGCCTCAGG

6. Codon-Scrambled Muc1 x0 (Muc1_0)
Amino acid sequence:
(SEQ ID NO: 31)
LYMDMVAVSMTSSVLSSHSPGSGSSTTQGQDVTLAPATEPASGSAATWGQD

VTSVGGGGGASG cDNA sequence:
(SEQ ID NO: 52)
TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCGGCGGTGGTGGAGGAGCCTCAGG

7. Codon-Scrambled Muc1 Single Glycosylation Mutant x21 (Muc1_21S)
Amino acid sequence:
8. LYMDMVAVSMTSSVLSSHSPGSGSSTTQGQDVTLAPATEPASGSAATWGQD

VTSV[PDTRPAPGATAPPAHGVTSA]$_{21}$ASG (SEQ ID NO: 30)[SEQ ID NO: 5]$_{21}$ASG cDNA sequence:
TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCAGATACCAGACCTGCGCCTGGAGCCACAGCTCCT

CCTGCCCATGGCGTCACAAGTGCCCCTGACACACGCCCAGCTCCCGGGGC

TACAGCCCCACCTGCACATGGTGTTACTAGTGCACCAGACACCAGACCGG

CTCCGGGAGCCACGGCACCCCCCGCTCATGGTGTCACTTCCGCACCGGAT

ACGAGGCCAGCACCTGGGGCCACTGCGCCGCCGGCACATGGGGTGACTA

GTGCGCCAGATACTCGCCCTGCTCCAGGGGCTACTGCCCCTCCAGCTCATG

GCGTAACCTCAGCGCCTGATACCCGACCAGCGCCAGGTGCCACTGCACCG

CCAGCCCATGGGGTCACTAGTGCTCCTGACACTAGACCTGCACCTGGAGC

TACAGCACCTCCAGCGCATGGTGTGACAAGCGCCCCAGACACGAGACCAG

CCCCCGGTGCCACCGCTCCTCCCGCACATGGAGTTACTAGCGCTCCGGAC

ACAAGACCGGCACCAGGTGCGACTGCACCACCGGCTCATGGAGTAACTTC

AGCACCAGATACACGGCCTGCTCCCGGCGCTACAGCTCCACCAGCACATG

GCGTTACCTCCGCACCTGACACGAGGCCCGCTCCAGGAGCCACTGCTCCC

-continued

CCTGCACACGGTGTTACGTCAGCTCCAGATACGCGGCCAGCTCCGGGCGC

AACAGCTCCCCCGGCTCACGGTGTAACCAGTGCTCCCGACACAAGGCCTG

CACCCGGAGCAACCGCACCTCCGGCCCATGGTGTAACAAGTGCACCTGAT

ACTAGGCCCGCGCCTGGTGCTACTGCTCCACCTGCTCACGGCGTGACATC

AGCCCCTGATACGAGACCTGCCCCAGGGGCAACTGCACCTCCTGCTCATG

GGGTAACTAGTGCCCCCGATACAAGACCAGCACCGGGAGCGACCGCCCCC

CCAGCACACGGAGTAACGAGCGCACCCGATACTCGACCTGCACCAGGAG

CGACGGCTCCACCCGCTCACGGAGTCACGAGTGCTCCAGACACTCGACCT

GCTCCTGGCGCGACAGCACCACCAGCTCACGGGGTTACTAGTGCTCCTGA

TACACGACCCGCACCAGGGGCGACTGCTCCTCCAGCCCACGGAGTTACAT

CTGCCCCGGATACAAGGCCAGCACCCGGTGCAACTGCTCCGCCCGCCCAT

GGAGTCACAAGTGCTCCGGATACTAGACCAGCTCCTGGGGCTACGGCGCC

TCCTGCGCACGGAGTGACTTCTGCTGCCTCAGG

9. Codon-Scrambled Muc1 Double Glycosylation Mutant x21 (Muc1_21D)
Amino acid sequence:
LYMDMVAVSMTSSVLSSHSPGSGSSTTQGQDVTLAPATEPASGSAATWGQD

VTSV[PDTRPAPGATAPPAHGVTAA]$_{21}$ASG (SEQ ID NO: 30)[SEQ ID NO: 6]$_{21}$ASG cDNA sequence:

(SEQ ID NO: 53)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCAGACACGCGACCCGCACCAGGCGCGACTGCTCCT

CCTGCGCATGGTGTAACAGCGGCCCCTGATACGAGGCCAGCCCCTGGAGC

CACCGCACCTCCAGCACACGGAGTGACTGCAGCTCCCGATACTAGACCCG

CGCCAGGAGCAACAGCTCCTCCAGCTCATGGTGTGACGGCCGCCCCAGAT

ACCAGACCTGCCCCAGGGGCGACAGCACCCCCCGCTCACGGCGTAACTGC

AGCCCCGGATACGAGACCAGCTCCTGGGGCCACTGCACCTCCGGCTCATG

GGGTAACAGCTGCCCCCGATACCCGACCTGCACCCGGAGCTACAGCGCCG

CCTGCACACGGTGTAACCGCAGCTCCGGATACTAGACCTGCGCCTGGAGC

AACGGCGCCTCCTGCACATGGGGTTACTGCTGCGCCAGATACAAGGCCTG

CCCCTGGTGCAACAGCACCTCCTGCTCATGGCGTGACAGCTGCACCAGAC

ACAAGACCAGCGCCAGGTGCTACTGCACCACCTGCTCACGGGGTAACTGC

TGCTCCAGATACTCGCCCTGCACCGGGAGCGACGGCTCCACCAGCTCACG

GAGTAACGGCAGCACCTGACACTAGGCCGGCTCCGGGAGCTACGGCACC

GCCCGCACATGGCGTCACTGCGGCTCCTGACACACGACCAGCACCCGGTG

CCACAGCTCCGCCAGCACATGGTGTTACGGCTGCTCCCGACACGAGACCC

GCTCCTGGAGCTACTGCTCCCCCGGCTCACGGTGTTACTGCAGCGCCTGAT

ACACGCCCAGCACCGGGGGCTACAGCACCACCAGCCCATGGGGTCACAG

CAGCTCCAGACACTCGGCCAGCCCCAGGTGCAACTGCTCCACCCGCCCAT

GGTGTCACTGCTGCACCTGATACCAGGCCGGCACCAGGAGCCACGGCCCC

GCCGGCACATGGAGTGACCGCGGCACCCGATACAAGACCTGCTCCGGGCG

CTACAGCCCCCCCAGCCCACGGAGTCACCGCTGCTCCTGATACTCGACCG

-continued

GCACCTGGTGCTACAGCTCCACCGGCCCATGGCGTTACAGCAGCACCAGA

TACGAGGCCCGCTCCAGGTGCGACCGCTCCTCCCGCTCATGGAGTAACAG

CCGCTCCGGACACTAGACCGGCTCCCGGCGCAACTGCGCCCCCTGCCCAT

GGAGTTACTGCCGCACCGGATACACGCCCTGCCCCGGGAGCAACTGCCCC

TCCAGCGCACGGAGTTACAGCTGCTGCCTCAGG

10. Codon-Scrambled Muc1 Triple Glycosylation Mutant x21 (Muc1_21T)
Amino acid sequence:
11. LYMDMVAVSMTSSVLSSHSPGSGSSTTQGQDVTLAPATEPASGSAATWGQD

VTSV[PDARPAPGATAPPAHGVTAA]$_{21}$ASG (SEQ ID NO: 30[SEQ ID NO: 7]$_{21}$ASG cDNA sequence:

(SEQ ID NO: 54)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCAGATGCAAGGCCTGCCCCGGGAGCGACAGCACCA

CCAGCACATGGAGTGACGGCCGCCCCAGACGCTCGACCGGCACCAGGAG

CAACTGCTCCTCCCGCACATGGGGTCACTGCGGCCCCTGATGCGAGGCCG

GCACCTGGAGCTACTGCTCCACCGGCCCATGGTGTCACTGCAGCCCCGGA

TGCTAGACCGGCTCCGGGCGCAACTGCGCCGCCAGCCCATGGAGTTACTG

CTGCGCCAGATGCGCGGCCTGCCCCAGGTGCTACAGCCCCCCCTGCCCAT

GGCGTAACAGCTGCCCCCGATGCTCGCCCTGCACCGGGAGCAACGGCGCC

TCCAGCGCACGGAGTAACGGCAGCACCAGATGCTCGGCCAGCACCGGGG

GCTACAGCTCCACCTGCTCACGGTGTAACTGCAGCGCCTGATGCACGACC

AGCCCCTGGAGCAACAGCTCCGCCTGCACACGGAGTGACTGCTGCACCTG

ATGCTAGGCCAGCCCCAGGGGCGACTGCACCTCCAGCACACGGTGTTACA

GCTGCTCCAGACGCACGCCCAGCACCCGGTGCCACAGCTCCTCCTGCGCA

TGGTGTGACAGCTGCACCAGACGCCCGACCCGCGCCAGGAGCCACGGCTC

CACCAGCTCACGGCGTGACCGCGGCTCCTGACGCTAGGCCAGCTCCTGGA

GCCACCGCTCCTCCAGCTCATGGCGTTACAGCAGCTCCCGACGCAAGACC

CGCTCCTGGGGCCACTGCTCCCCCCGCTCACGGGGTAACAGCCGCTCCGG

ATGCAAGACCTGCCCCTGGTGCTACTGCACCACCCGCCCATGGGGTTACT

GCAGCTCCGGACGCTAGACCTGCTCCGGGAGCTACAGCGCCCCCAGCCCA

CGGAGTCACAGCAGCACCTGACGCGAGACCAGCGCCAGGTGCAACTGCC

CCTCCTGCACATGGTGTTACTGCCGCACCGGATGCCAGACCTGCACCCGG

AGCTACGGCCCCGCCGGCTCATGGGGTAACTGCTGCTCCTGATGCCCGAC

CCGCTCCAGGCGCGACCGCACCTCCTGCTCATGGAGTAACAGCGGCACCC

GATGCACGGCCGGCTCCCGGCGCTACAGCACCTCCGGCACATGGCGTCAC

CGCAGCTCCAGATGCCAGGCCCGCACCAGGTGCGACGGCACCGCCCGCTC

ATGGTGTAACCGCTGCTCCCGATGCGAGACCTGCGCCTGGTGCAACAGCA

CCCCCGGCTCACGGAGTTACGGCTGCTGCCTCAGG

-continued

12. Lubricin consensus, KEPAPTTP x20 (Syn4_20)
Amino acid sequence:
13. LYMDMVAVSMTSSVLSSHSPGSGSSTTQGQDVTLAPATEPASGSAATWGQD

VTSV[KEPAPTTP]$_{20}$ASG (SEQ ID NO: 30)[SEQ ID NO: 1]$_{20}$ASG cDNA sequence:

(SEQ ID NO: 55)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCAAGGAACCTGCACCTACAACCCCGAAGGAGCCCGCA

CCGACCACCCCAAAAGAACCTGCGCCGACAACTCCAAAGGAGCCAGCTCC

AACGACGCCAAAGGAACCAGCACCTACGACCCCCAAGGAACCCGCCCCG

ACGACTCCGAAGGAGCCTGCACCAACAACTCCTAAAGAACCAGCGCCTAC

TACGCCTAAAGAACCTGCTCCTACTACACCAAAAGAGCCAGCACCCACGA

CACCGAAAGAACCTGCCCCTACTACCCCTAAAGAACCCGCTCCTACCACA

CCAAAGGAACCGGCTCCCACTACTCCCAAAGAACCAGCCCCAACTACACC

TAAAGAACCGGCCCCCACCACTCCTAAAGAGCCGGCGCCAACTACTCCAA

AAGAACCAGCTCCTACAACTCCCAAGGAGCCGGCACCTACTACTCCGAAA

GAGCCCGCGCCCACAACACCCAAAGAGCCTGCTCCGACTACTCCTGCCTC

AGG

14. Synthetic 1, DAATPAP x40 (Syn1_40)
Amino acid sequence:
LYMDMVAVSMTSSVLSSHSPGSGSSTTQGQDVTLAPATEPASGSAATWGQD

VTSV[DAATPAP]$_{40}$ASG (SEQ ID NO: 30)[SEQ ID NO: 2]$_{40}$ASG cDNA sequence:

(SEQ ID NO: 56)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCGATGCAGCTACTCCAGCTCCGGACGCCGCAACACCC

GCTCCAGACGCCGCCACCCCAGCTCCAGATGCTGCTACACCTGCACCTGA

TGCCGCAACTCCCGCGCCGGATGCCGCGACTCCAGCACCGGACGCTGCGA

CGCCAGCCCCTGATGCTGCAACACCGGCTCCTGATGCTGCGACTCCTGCG

CCAGATGCAGCTACACCAGCCCCGGATGCTGCAACGCCTGCTCCTGACGC

AGCTACTCCGGCCCCCGACGCTGCTACCCCGGCGCCTGATGCTGCTACTCC

CGCTCCTGATGCGGCCACTCCAGCCCCAGACGCAGCAACCCCAGCCCCCG

ATGCTGCTACGCCTGCACCCGACGCGGCCACACCTGCGCCGGACGCAGCG

ACACCTGCCCCTGACGCTGCCACGCCCGCACCTGATGCAGCTACGCCAGC

TCCCGATGCGGCAACACCTGCTCCAGATGCCGCCACTCCTGCTCCGGATG

CGGCGACACCAGCGCCTGACGCCGCTACGCCGGCACCTGATGCTGCCACT

CCGGCTCCAGATGCAGCGACCCCAGCGCCAGACGCGGCAACTCCAGCGCC

CGATGCAGCTACCCCAGCACCAGATGCTGCAACCCCTGCACCGGATGCAG

CAACGCCAGCACCTGACGCGGCTACTCCTGCACCAGATGCAGCAACTCCT

GCCCCGGACGCGGCGACTCCCGCACCAGACGCTGCAACTCCGGCACCAGA

-continued

TGCGGCTACCCCCGCTCCCGACGCAGCCACTCCCGCCCCAGATGCAGCCA

CACCAGCTCCTGATGCAGCAACACCAGCACCCGATGCCGCTACCCCTGCT

CCCGCCTCAGG

15. Synthetic 1, DAATPAP x80 (Syn1_80)
Amino acid sequence:
LYMDMVAVSMTSSVLSSHSPGSGSSTTQGQDVTLAPATEPASGSAATWGQD

VTSV$[DAATPAP]_{80}$ASG (SEQ ID NO: 30)$[SEQ\ ID\ NO:\ 2]_{80}$ASG cDNA sequence:
(SEQ ID NO: 57)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCGATGCAGCTACTCCAGCTCCGGACGCCGCAACACCC

GCTCCAGACGCCGCCACCCCAGCTCCAGATGCTGCTACACCTGCACCTGA

TGCCGCAACTCCCGCGCCGGATGCCGCGACTCCAGCACCGGACGCTGCGA

CGCCAGCCCCTGATGCTGCAACACCGGCTCCTGATGCTGCGACTCCTGCG

CCAGATGCAGCTACACCAGCCCCGGATGCTGCAACGCCTGCTCCTGACGC

AGCTACTCCGGCCCCCGACGCTGCTACCCCGGCGCCTGATGCTGCTACTCC

CGCTCCTGATGCGGCCACTCCAGCCCCAGACGCAGCAACCCCAGCCCCCG

ATGCTGCTACGCCTGCACCCGACGCGGCCACACCTGCGCCGGACGCAGCG

ACACCTGCCCCTGACGCTGCCACGCCCGCACCTGATGCAGCTACGCCAGC

TCCCGATGCGGCAACACCTGCTCCAGATGCCGCCACTCCTGCTCCGGATG

CGGCGACACCAGCGCCTGACGCCGCTACGCCGGCACCTGATGCTGCCACT

CCGGCTCCAGATGCAGCGACCCCAGCGCCAGACGCGGCAACTCCAGCGCC

CGATGCAGCTACCCCAGCACCAGATGCTGCAACCCCTGCACCGGATGCAG

CAACGCCAGCACCTGACGCGGCTACTCCTGCACCAGATGCAGCAACTCCT

GCCCCGGACGCGGCGACTCCCGCACCAGACGCTGCAACTCCGGCACCAGA

TGCGGCTACCCCCGCTCCCGACGCAGCCACTCCCGCCCCAGATGCAGCCA

CACCAGCTCCTGATGCAGCAACACCAGCACCCGATGCCGCTACCCCTGCT

CCCGATGCAGCTACTCCAGCTCCGGACGCCGCAACACCCGCTCCAGACGC

CGCCACCCCAGCTCCAGATGCTGCTACACCTGCACCTGATGCCGCAACTC

CCGCGCCGGATGCCGCGACTCCAGCACCGGACGCTGCGACGCCAGCCCCT

GATGCTGCAACACCGGCTCCTGATGCTGCGACTCCTGCGCCAGATGCAGC

TACACCAGCCCCGGATGCTGCAACGCCTGCTCCTGACGCAGCTACTCCGG

CCCCCGACGCTGCTACCCCGGCGCCTGATGCTGCTACTCCCGCTCCTGATG

CGGCCACTCCAGCCCCAGACGCAGCAACCCCAGCCCCCGATGCTGCTACG

CCTGCACCCGACGCGGCCACACCTGCGCCGGACGCAGCGACACCTGCCCC

TGACGCTGCCACGCCCGCACCTGATGCAGCTACGCCAGCTCCCGATGCGG

CAACACCTGCTCCAGATGCCGCCACTCCTGCTCCGGATGCGGCGACACCA

GCGCCTGACGCCGCTACGCCGGCACCTGATGCTGCCACTCCGGCTCCAGA

TGCAGCGACCCCAGCGCCAGACGCGGCAACTCCAGCGCCCGATGCAGCTA

CCCCAGCACCAGATGCTGCAACCCCTGCACCGGATGCAGCAACGCCAGCA

CCTGACGCGGCTACTCCTGCACCAGATGCAGCAACTCCTGCCCCGGACGC

-continued

GGCGACTCCCGCACCAGACGCTGCAACTCCGGCACCAGATGCGGCTACCC

CCGCTCCCGACGCAGCCACTCCCGCCCCAGATGCAGCCACACCAGCTCCT

GATGCAGCAACACCAGCACCCGATGCCGCTACCCCTGCTCCCGCCTCAGG

16. Synthetic 2, DAATPAPP x40 (Syn2_40)
Amino acid sequence:
LYMDMVAVSMTSSVLSSHSPGSGSSTTQGQDVTLAPATEPASGSAATWGQD

VTSV[DAATPAPP]$_{40}$ASG (SEQ ID NO: 30)[SEQ ID NO: 3]$_{40}$ASG cDNA sequence:

(SEQ ID NO: 58)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCGATGCAGCTACCCCGGCTCCACCCGATGCGGCAACA

CCAGCCCCTCCCGATGCAGCAACACCTGCTCCCCCCGATGCTGCTACCCCT

GCTCCGCCTGATGCTGCAACTCCAGCTCCGCCCGATGCCGCTACACCTGCC

CCCCCTGACGCCGCCACGCCCGCTCCTCCGGATGCTGCAACCCCAGCACC

CCCAGACGCCGCTACCCCAGCTCCACCAGATGCTGCTACACCCGCACCAC

CTGATGCCGCAACACCGGCGCCTCCTGATGCTGCTACTCCAGCCCCACCTG

ATGCAGCAACTCCTGCGCCACCAGACGCTGCCACACCTGCACCACCAGAT

GCAGCCACACCAGCACCGCCAGACGCAGCAACGCCGGCTCCGCCAGATG

CAGCGACACCAGCGCCACCTGACGCAGCGACTCCAGCACCACCGGATGCG

GCTACCCCCGCTCCGCCGGACGCGGCGACTCCTGCCCCTCCTGACGCGGC

AACTCCGGCCCCTCCAGATGCGGCGACCCCAGCCCCGCCGGATGCCGCGA

CTCCGGCTCCCCCGGACGCTGCAACACCCGCTCCACCTGATGCTGCCACTC

CCGCGCCTCCAGATGCTGCAACGCCAGCTCCCCCTGATGCTGCGACGCCT

GCTCCTCCAGATGCAGCTACACCGGCTCCTCCTGATGCAGCTACGCCTGCA

CCGCCTGACGCTGCTACGCCAGCACCTCCCGACGCAGCCACTCCTGCACC

TCCTGATGCGGCCACTCCAGCGCCCCCGGATGCAGCTACTCCTGCTCCACC

GGACGCCGCAACTCCCGCCCCTCCGGACGCAGCTACTCCCGCTCCCCCAG

ATGCAGCAACCCCTGCACCCCCCGACGCGGCCACCCCTGCCCCACCAGAT

GCCGCCACTCCGGCACCACCCGACGCTGCGACTCCCGCACCTCCAGACGC

GGCTACACCAGCTCCTCCCGCCTCAGG

17. Synthetic 2, DAATPAPP x80 (Syn2_80)
Amino acid sequence:
LYMDMVAVSMTSSVLSSHSPGSGSSTTQGQDVTLAPATEPASGSAATWGQD

VTSV[DAATPAPP]$_{80}$ASG (SEQ ID NO: 30)[SEQ ID NO: 3]$_{80}$ASG cDNA sequence:

(SEQ ID NO: 59)

TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCGATGCAGCTACCCCGGCTCCACCCGATGCGGCAACA

CCAGCCCCTCCCGATGCAGCAACACCTGCTCCCCCCGATGCTGCTACCCCT

GCTCCGCCTGATGCTGCAACTCCAGCTCCGCCCGATGCCGCTACACCTGCC

-continued

CCCCCTGACGCCGCCACGCCCGCTCCTCCGGATGCTGCAACCCCAGCACC

CCCAGACGCCGCTACCCCAGCTCCACCAGATGCTGCTACACCCGCACCAC

CTGATGCCGCAACACCGGCGCCTCCTGATGCTGCTACTCCAGCCCCACCTG

ATGCAGCAACTCCTGCGCCACCAGACGCTGCCACACCTGCACCACCAGAT

GCAGCCACACCAGCACCGCCAGACGCAGCAACGCCGGCTCCGCCAGATG

CAGCGACACCAGCGCCACCTGACGCAGCGACTCCAGCACCACCGGATGCG

GCTACCCCCGCTCCGCCGGACGCGGCGACTCCTGCCCCTCCTGACGCGGC

AACTCCGGCCCCTCCAGATGCGGCGACCCCAGCCCCGCCGGATGCCGCGA

CTCCGGCTCCCCCGGACGCTGCAACACCCGCTCCACCTGATGCTGCCACTC

CCGCGCCTCCAGATGCTGCAACGCCAGCTCCCCCTGATGCTGCGACGCCT

GCTCCTCCAGATGCAGCTACACCGGCTCCTCCTGATGCAGCTACGCCTGCA

CCGCCTGACGCTGCTACGCCAGCACCTCCCGACGCAGCCACTCCTGCACC

TCCTGATGCGGCCACTCCAGCGCCCCCGGATGCAGCTACTCCTGCTCCACC

GGACGCCGCAACTCCCGCCCCTCCGGACGCAGCTACTCCCGCTCCCCCAG

ATGCAGCAACCCCTGCACCCCCCGACGCGGCCACCCCTGCCCCACCAGAT

GCCGCCACTCCGGCACCACCCGACGCTGCGACTCCCGCACCTCCAGACGC

GGCTACACCAGCTCCTCCCGATGCAGCTACCCCGGCTCCACCCGATGCGG

CAACACCAGCCCCTCCCGATGCAGCAACACCTGCTCCCCCCGATGCTGCT

ACCCCTGCTCCGCCTGATGCTGCAACTCCAGCTCCGCCCGATGCCGCTACA

CCTGCCCCCCCTGACGCCGCCACGCCCGCTCCTCCGGATGCTGCAACCCCA

GCACCCCCAGACGCCGCTACCCCAGCTCCACCAGATGCTGCTACACCCGC

ACCACCTGATGCCGCAACACCGGCGCCTCCTGATGCTGCTACTCCAGCCC

CACCTGATGCAGCAACTCCTGCGCCACCAGACGCTGCCACACCTGCACCA

CCAGATGCAGCCACACCAGCACCGCCAGACGCAGCAACGCCGGCTCCGCC

AGATGCAGCGACACCAGCGCCACCTGACGCAGCGACTCCAGCACCACCG

GATGCGGCTACCCCCGCTCCGCCGGACGCGGCGACTCCTGCCCCTCCTGA

CGCGGCAACTCCGGCCCCTCCAGATGCGGCGACCCCAGCCCCGCCGGATG

CCGCGACTCCGGCTCCCCCGGACGCTGCAACACCCGCTCCACCTGATGCT

GCCACTCCCGCGCCTCCAGATGCTGCAACGCCAGCTCCCCCTGATGCTGC

GACGCCTGCTCCTCCAGATGCAGCTACACCGGCTCCTCCTGATGCAGCTAC

GCCTGCACCGCCTGACGCTGCTACGCCAGCACCTCCCGACGCAGCCACTC

CTGCACCTCCTGATGCGGCCACTCCAGCGCCCCCGGATGCAGCTACTCCTG

CTCCACCGGACGCCGCAACTCCCGCCCCTCCGGACGCAGCTACTCCCGCT

CCCCCAGATGCAGCAACCCCTGCACCCCCCGACGCGGCCACCCCTGCCCC

ACCAGATGCCGCCACTCCGGCACCACCCGACGCTGCGACTCCCGCACCTC

CAGACGCGGCTACACCAGCTCCTCCCGCCTCAGG

-continued

18. Synthetic 3, PPASTSAPG x40 (Syn3_40)
Amino acid sequence:
LYMDMVAVSMTSSVLSSHSPGSGSSTTQGQDVTLAPATEPASGSAATWGQD

VTSV[PPASTSAPG]$_{40}$ASG (SEQ ID NO: 30)[SEQ ID NO: 4]$_{40}$ASG cDNA sequence:
(SEQ ID NO: 60)
TGTACATGGACATGGTCGCTGTGAGTATGACCAGCAGCGTACTCTCCAGC

CACAGCCCCGGTTCAGGCTCCTCCACCACTCAGGGACAGGATGTCACTCT

GGCCCCGGCCACGGAACCAGCTTCAGGTTCAGCTGCCACCTGGGGACAGG

ATGTCACCTCGGTCCCACCTGCATCTACCAGTGCCCCGGGTCCACCTGCCT

CTACTAGCGCCCCAGGACCTCCGGCAAGTACATCAGCGCCAGGACCCCCT

GCTTCCACTAGTGCACCCGGTCCCCCGGCATCTACGTCTGCCCCTGGCCCA

CCTGCTTCAACTTCAGCACCAGGACCACCCGCAAGCACATCAGCCCCAGG

CCCTCCCGCCTCTACAAGCGCTCCGGGGCCTCCGGCCTCTACCTCAGCTCC

AGGCCCACCAGCCAGCACTTCAGCCCCTGGTCCACCCGCTTCAACCTCAG

CACCCGGACCTCCTGCCTCAACTTCCGCTCCCGGTCCACCAGCTAGTACCT

CTGCTCCGGGCCCTCCGGCGAGCACGTCAGCACCGGGACCACCTGCGAGT

ACAAGTGCACCTGGCCCGCCCGCTAGCACAAGTGCCCCCGGTCCTCCAGC

ATCCACTAGTGCACCAGGGCCTCCAGCCAGCACTAGTGCGCCGGGTCCCC

CCGCGAGTACGTCAGCTCCGGGACCTCCAGCTTCTACATCTGCTCCTGGGC

CCCCTGCATCAACTAGTGCCCCTGGACCACCGGCTAGTACGTCAGCTCCTG

GTCCCCCTGCCAGTACTAGCGCTCCAGGGCCACCAGCAAGTACGAGCGCA

CCAGGCCCCCCAGCCTCTACGAGTGCACCGGGTCCTCCTGCAAGTACCTC

CGCTCCAGGTCCTCCGGCTTCAACGTCCGCACCTGGACCTCCCGCGTCCAC

ATCAGCTCCCGGCCCTCCAGCGAGTACTTCTGCTCCCGGACCACCAGCGTC

CACATCTGCGCCTGGTCCTCCCGCTAGTACCTCTGCACCTGGTCCGCCGGC

CAGTACAAGTGCTCCCGGGCCTCCCGCATCAACATCTGCACCAGGTCCAC

CGGCGTCTACTAGTGCCCCAGGTCCCCCAGCTTCAACATCAGCACCTGGG

CCGCCTGCTAGTACATCCGCTCCTGGACCCCCAGCAAGTACTTCCGCCCCT

GGGCCTCCTGCTTCTACTTCAGCTCCTGGCCCTCCTGCGTCAACTAGTGCT

CCAGGACCGCCAGCTAGTACTTCCGCGCCCGGTGCCTCAGG

Optical Reporter
1. mOxGFP
Amino acid sequence:
(SEQ ID NO: 31)
SGSASGSAMVSKGEELFTGVVPILVELDGDVNGHKFSVRGEGEGDATNGKLT

LKFISTTGKLPVPWPTLVTTLTYGVQSFSRYPDHMKRHDFFKSAMPEGYVQE

RTISFKDDGTYKTRAEVKFEGDTLVNRIELKGIDFKEDGNILGHKLEYNFNSH

NVYITADKQKNGIKANFKIRHNVEDGSVQLADHYQQNTPIGDGPVLLPDNHY

LSTQSKLSKDPNEKRDHMVLLEFVTAAGITHGMDELYKGSA cDNA sequence:
(SEQ ID NO: 61)
CCTCAGGCTCTGCATCAGGCTCAGCTATGGTGTCCAAGGGCGAGGAGCTG

TTCACCGGGGTGGTGCCCATCCTGGTCGAGCTGGACGGCGACGTAAACGG

CCACAAGTTCTCCGTGCGGGGCGAGGGCGAGGGCGATGCCACCAACGGC

AAGCTGACCCTGAAGTTCATCAGCACCACCGGCAAGCTGCCCGTGCCCTG

-continued

GCCCACCCTCGTGACCACCCTGACCTACGGCGTGCAGAGCTTCTCCCGCTA

CCCCGACCACATGAAGCGCCACGACTTCTTCAAGAGCGCCATGCCCGAAG

GCTACGTCCAGGAGCGCACCATCTCCTTCAAGGACGACGGCACCTACAAG

ACCCGCGCCGAGGTGAAGTTCGAGGGCGACACCCTGGTGAACCGCATCGA

GCTGAAGGGCATCGACTTCAAGGAGGACGGCAACATCCTGGGGCACAAG

CTGGAGTACAACTTCAACTCCCACAACGTCTATATCACCGCCGACAAGCA

GAAGAACGGCATCAAGGCCAACTTCAAGATCCGCCACAACGTGGAGGAC

GGCTCCGTGCAGCTCGCCGACCACTACCAGCAGAACACCCCCATCGGCGA

CGGCCCCGTGCTGCTGCCCGACAACCACTACCTGTCCACCCAGTCCAAGC

TGTCCAAAGACCCCAACGAGAAGCGCGATCACATGGTCCTTCTGGAATTC

GTGACCGCCGCCGGGATCACTCACGGCATGGACGAGCTGTATAAGGGCTC

AGC

Membrane Anchor
1. Native TM
Amino acid sequence:

(SEQ ID NO: 32)

SASTLVHNGTSARATTTPASKSTPFSIPSHHSDTPTTLASHSTKTDASSTHHSSV

PPLTSSNHSTSPQLSTGVSFFFLSFHISNLQFNSSLEDPSTDYYQELQRDISEMFL

QIYKQGGFLGLSNIKFRPGSVVVQLTLAFREGTINVHDVETQFNQYKTEAASR

YNLTISDVSVSDVPFPFSAQSGAGVPGWGIALLVLVCVLVALAIVYLIALAVC

QCRRK* cDNA sequence:

(SEQ ID NO: 62)

GCTCAGCTTCTACTCTGGTGCACAACGGCACCTCTGCCAGGGCTACCACA

ACCCCAGCCAGCAAGAGCACTCCATTCTCAATTCCCAGCCACCACTCTGA

TACTCCTACCACCCTTGCCAGCCATAGCACCAAGACTGATGCCAGTAGCA

CTCACCATAGCTCGGTACCTCCTCTCACCTCCTCCAATCACAGCACTTCTC

CCCAGTTGTCTACTGGGGTCTCTTTCTTTTTCCTGTCTTTTCACATTTCAAA

CCTCCAGTTTAATTCCTCTCTGGAAGATCCCAGCACCGACTACTACCAAGA

GCTGCAGAGAGACATTTCTGAAATGTTTTTGCAGATTTATAAACAAGGGG

GTTTTCTGGGCCTCTCCAATATTAAGTTCAGGCCAGGATCTGTGGTGGTAC

AATTGACTCTGGCCTTCCGAGAAGGTACCATCAATGTCCACGACGTGGAG

ACACAGTTCAATCAGTATAAAACGGAAGCAGCCTCTCGATATAACCTGAC

GATCTCAGACGTCAGCGTGAGTGATGTGCCATTTCCTTTCTCTGCCCAGTC

TGGGGCTGGGGTGCCAGGCTGGGGCATCGCGCTGCTGGTGCTGGTCTGTG

TTCTGGTTGCGCTGGCCATTGTCTATCTCATTGCCTTGGCTGTCTGTCAGTG

CCGCCGAAAGTAGGGAATTC

2. Synthetic TM TM21
Amino acid sequence:

(SEQ ID NO: 49)

ASGILYWRNPTESDSIVLAIIVPSLLLLLCLALLWYMRRRSM* cDNA sequence:

(SEQ ID NO: 63)

CCTCAGGCATACTTTATTGGCGAAACCCAACGGAAAGTGATAGCATCGTT

TTGGCAATTATCGTCCCCAGTCTGCTCCTCTTGCTCTGCCTGGCTTTGTTGT

GGTACATGCGCCGACGAAGTATGTAGGAATTC

-continued

```
Cytoplasmic Motif
1. Native CT
Amino acid sequence:
                                                           (SEQ ID NO: 33)
SRCQCRRKNYGQLDIFPARDTYHPMSEYPTYHTHGRYVPPSSTDRSPYEKVS

AGNGGSSLSYTNPAVAAASANL*

cDNA sequence:
                                                           (SEQ ID NO: 64)
TCTAGATGTCAGTGCCGCCGAAAGAACTACGGGCAGCTGGACATCTTTCC

AGCCCGGGATACCTACCATCCTATGAGCGAGTACCCCACCTACCACACCC

ATGGGCGCTATGTGCCCCCTAGCAGTACCGATCGTAGCCCCTATGAGAAG

GTTTCTGCAGGTAAtGGTGGCAGCAGCCTCTCTTACACAAACCCAGCAGTG

GCAGCCGCTTCTGCCAACTTGTAGGAATTC

2. CQC
Amino acid sequence:
                                                           (SEQ ID NO: 34)
SRCQCRRK*

cDNA sequence:
                                                           (SEQ ID NO: 65)
TCTAGATGTCAGTGCCGCCGAAAGTAGGAATTC
```

List of Constructs

Membrane Associated Mucin 1. pcDNA3.1+_Muc1_0_TM21
2. pcDNA3.1+_Muc1_10_TM21
3. pcDNA3.1+_Muc1_21_TM21
4. pcDNA3.1+_Muc1_42_TM21
5. pcDNA3.1+_Muc1_21S_TM21
6. pcDNA3.1+_Muc1_21D_TM21
7. pcDNA3.1+_Muc1_21T_TM21
8. pcDNA3.1+_Muc1_10_TM21_CT
9. pcDNA3.1+_Muc1_10_TM21_CQC
10. pcDNA3.1+_Muc1_10_dCT
11. pcDNA3.1+_Muc1_10_FL
12. pcDNA3.1+_Muc1_Syn4_20_TM21
13. pcDNA3.1+_Muc1_Syn1_40_TM21
14. pcDNA3.1+_Muc1_Syn2_40_TM21
15. pcDNA3.1+_Muc1_Syn3_40_TM21
16. pcDNA3.1+_Muc1_Syn1_80_TM21
17. pcDNA3.1+_Muc1_Syn2_80_TM21
18. pPB_Tet_Muc1_TM21_IRES2_copGFP_rtTAsM2_IRES_NeoR
19. pPB_Tet_Muc1_42_TM21_IRES2_copGFP_rtTAsM2_IRES_NeoR
20. pPB_Tet_Muc1_21_TM21_IRES2_copGFP_rtTAsM2_IRES_NeoR
21. pPB_Tet_Muc1_10_TM21_IRES2_copGFP_rtTAsM2_IRES_NeoR
22. pPB_Tet_Muc1_0_TM21_IRES2_copGFP_rtTAsM2_IRES_NeoR
23. pPB_Tet_Muc1_21D_TM21_IRES2_copGFP_rtTAsM2_IRES_NeoR
24. pPB_Tet_Muc1_21T_TM21_IRES2_copGFP_rtTAsM2_IRES_NeoR
25. pLV_puro_teton_Muc1_42_dCT
26. pLV_puro_teton_Muc1_dCT
27. pPB_Muc1_mOxGFP_dCT_BlpI
28. pPB_Muc1_42_mOxGFP_dCT_BlpI
29. pPB_Muc1_21_mOxGFP_dCT_BlpI
30. pPB_Muc1_10_mOxGFP_dCT_BlpI
31. pPB_Muc1_0_mOxGFP_dCT_BlpI
32. pPB_Muc1_21S_mOxGFP_dCT_BlpI
33. pPB_Muc1_21D_mOxGFP_dCT_BlpI
34. pPB_Muc1_21T_mOxGFP_dCT_BlpI
35. pPB_Muc1_Syn4_20_mOxGFP_dCT_BlpI
36. pPB_Muc1_Syn1_40_mOxGFP_dCT_BlpI
37. pPB_Muc1_Syn2_40_mOxGFP_dCT_BlpI
38. pPB_Muc1_Syn3_40_mOxGFP_dCT_BlpI
39. pPB_Muc1_Syn1_80_mOxGFP_dCT_BlpI
40. pPB_Muc1_Syn2_80_mOxGFP_dCT_BlpI Secreted Mucin 41. pPB_Tet_SumoStar_Muc1_42_rtTAsM2_IRES_NeoR
42. pPB_Tet_SumoStar_Muc1_21T_rtTAsM2_IRES_NeoR
43. pPB_Tet_SumoStar_Muc1_21D_rtTAsM2_IRES_NeoR
44. pPB_Tet_SumoStar_Muc1_21S_rtTAsM2_IRES_NeoR
45. pPB_Tet_SumoStar_Muc1_21_rtTAsM2_IRES_NeoR
46. pPB_Tet_SumoStar_Muc1_0_rtTAsM2_IRES_NeoR
47. pPB_Tet_SumoStar_Muc1_Syn1_40_rtTAsM2_IRES_NeoR
48. pPB_Tet_SumoStar_Muc1_Syn2_40_rtTAsM2_IRES_NeoR
49. pPB_Tet_SumoStar_Muc1_Syn3_40_rtTAsM2_IRES_NeoR
50. pPB_Tet_SumoStar_Muc1_Syn1_80_rtTAsM2_IRES_NeoR
51. pPB_Tet_SumoStar_Muc1_Syn2_80_rtTAsM2_IRES_NeoR The following sequence are representative amino acid sequences for mucin and lubricin constructs, as further described herein, and for which the entire sequences, including the N-terminal signal sequence, tandem repeat domain, fluorescent optical reporter (GFP in these sequence), the transmembrane domain to the cytoplasmic tail domain. It will be recognized that the GFP sequence may be, omitted or substituted by any other amino acid sequence, including but not limited to the sequence of other detectable proteins, or second polypeptides, as described above. The alphnuermic names given above each sequence are names of the sequences, rather than sequences themselves.

1. PDTRPAPGSTAPPAHGVTSA_42
Muc1_42_mOxGFP_dCT_BlpI (SEQ ID NO: 35)

MTPGTQSPFFLLLLLTVLTVVTGSGHASSTPGGEKETSATQRSSVPSSTEKNADYK
DDDDLYMDMVAVSMTSSVLSSHSPGSGSSTTQGQDVTLAPATEPASGSAATWG
QDVTSVPDTRPAPGSTAPPAHGVTSAPDTRPAPGSTAPPAHGVTSAPDTRPAPGS
TAPPAHGVTSAPDTRPAPGSTAPPAHGVTSAPDTRPAPGSTAPPAHGVTSAPDTR
PAPGSTAPPAHGVTSAPDTRPAPGSTAPPAHGVTSAPDTRPAPGSTAPPAHGVTS
APDTRPAPGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRPAPGST
APPAHGVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAHGVTSA
PDTRPAPGSTAPPAHGVTSAPDTRPAPGSTAPPAHGVTSAPDTRPAPGSTAPPAHG
VTSAPDTRPAPGSTAPPAHGVTSAPDTRPAPGSTAPPAHGVTSAPDTRPAPGSTAP
PAHGVTSAPDTRPAPGSTAPPAHGVTSAPDTRPAPGSTAPPAHGVTSAPDTRPAP
GSTAPPAHGVTSAPDTRPAPGSTAPPAHGVTSAPDTRPAPGSTAPPAHGVTSAPD
TRPAPGSTAPPAHGVTSAPDTRPAPGSTAPPAHGVTSAPDTRPAPGSTAPPAHGV
TSAPDTRPAPGSTAPPAHGVTSAPDTRPAPGSTAPPAHGVTSAPDTRPAPGSTAPP
AHGVTSAPDTRPAPGSTAPPAHGVTSAPDTRPAPGSTAPPAHGVTSAPDTRPAPG
STAPPAHGVTSAPDTRPAPGSTAPPAHGVTSAPDTRPAPGSTAPPAHGVTSAPDT
RPAPGSTAPPAHGVTSAASGSASGSAMVSKGEELFTGVVPILVELDGDVNGHKFS
VRGEGEGDATNGKLTLKFISTTGKLPVPWPTLVTTLTYGVQSFSRYPDHMKRHD
FFKSAMPEGYVQERTISFKDDGTYKTRAEVKFEGDTLVNRIELKGIDFKEDGNIL
GHKLEYNFNSHNVYITADKQKNGIKANFKIRHNVEDGSVQLADHYQQNTPIGDG
PVLLPDNHYLSTQSKLSKDPNEKRDHMVLLEFVTAAGITHGMDELYKGSASTLV
HNGTSARATTTPASKSTPFSIPSHHSDTPTTLASHSTKTDASSTHHSSVPPLTSSNH
STSPQLSTGVSFFFLSFHISNLQFNSSLEDPSTDYYQELQRDISEMFLQIYKQGGFL
GLSNIKFRPGSVVVQLTLAFREGTINVHDVETQFNQYKTEAASRYNLTISDVSVS
DVPFPFSAQ

2. PDTRPAPGSTAPPAHGVTSA_21
Muc1_21_mOxGFP_dCT_BlpI (SEQ ID NO: 36)

MTPGTQSPFFLLLLLTVLTVVTGSGHASSTPGGEKETSATQRSSVPSSTEKNADYK
DDDDLYMDMVAVSMTSSVLSSHSPGSGSSTTQGQDVTLAPATEPASGSAATWG
QDVTSVPDTRPAPGSTAPPAHGVTSAPDTRPAPGSTAPPAHGVTSAPDTRPAPGS
TAPPAHGVTSAPDTRPAPGSTAPPAHGVTSAPDTRPAPGSTAPPAHGVTSAPDTR
PAPGSTAPPAHGVTSAPDTRPAPGSTAPPAHGVTSAPDTRPAPGSTAPPAHGVTS
APDTRPAPGSTAPPAHGVTSAPDTRPAPGSTAPPAHGVTSAPDTRPAPGSTAPPAH
GVTSAPDTRPAPGSTAPPAHGVTSAPDTRPAPGSTAPPAHGVTSAPDTRPAPGST
APPAHGVTSAPDTRPAPGSTAPPAHGVTSAPDTRPAPGSTAPPAHGVTSAPDTRP
APGSTAPPAHGVTSAPDTRPAPGSTAPPAHGVTSAPDTRPAPGSTAPPAHGVTSA
PDTRPAPGSTAPPAHGVTSAPDTRPAPGSTAPPAHGVTSAASGSASGSAMVSKGE
ELFTGVVPILVELDGDVNGHKFSVRGEGEGDATNGKLTLKFISTTGKLPVPWPTL
VTTLTYGVQSFSRYPDHMKRHDFFKSAMPEGYVQERTISFKDDGTYKTRAEVKF

-continued

EGDTLVNRIELKGIDFKEDGNILGHKLEYNFNSHNVYITADKQKNGIKANFKIRH

NVEDGSVQLADHYQQNTPIGDGPVLLPDNHYLSTQSKLSKDPNEKRDHMVLLEF

VTAAGITHGMDELYKGSASTLVHNGTSARATTTPASKSTPFSIPSHHSDTPTTLAS

HSTKTDASSTHHSSVPPLTSSNHSTSPQLSTGVSFFFLSFHISNLQFNSSLEDPSTDY

YQELQRDISEMFLQIYKQGGFLGLSNIKFRPGSVVVQLTLAFREGTINVHDVETQF

NQYKTEAASRYNLTISDVSVSDVPFPFSAQSGAGVPGWGIALLVLVCVLVALAIV

YLIALAVCQCRRK*

3. PDTRPAPGSTAPPAHGVTSA_10
Muc1_10_TM21_CT (SEQ ID NO: 37)
MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVPDTRPAPGSTAPPAHGVTSAPDTRPAPGSTAPPAHGVTSAPDTRPAPGS

TAPPAHGVTSAPDTRPAPGSTAPPAHGVTSAPDTRPAPGSTAPPAHGVTSAPDTR

PAPGSTAPPAHGVTSAPDTRPAPGSTAPPAHGVTSAPDTRPAPGSTAPPAHGVTS

APDTRPAPGSTAPPAHGVTSAPDTRPAPGSTAPPAHGVTSAASGILYWRNPTESD

SIVLAIIVPSLLLLLCLALLWYSRCQCRRKNYGQLDIFPARDTYHPMSEYPTYHTH

GRYVPPSSTDRSPYEKVSAGNGGSSLSYTNPAVAAASANL*

4. PDTRPAPGSTAPPAHGVTSA_0
Muc1_0_mOxGFP_dCT_BlpI (SEQ ID NO: 38)
MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVGGGGGASGSASGSAMVSKGEELFTGVVPILVELDGDVNGHKFSVRGEG

EGDATNGKLTLKFISTTGKLPVPWPTLVTTLTYGVQSFSRYPDHMKRHDFFKSA

MPEGYVQERTISFKDDGTYKTRAEVKFEGDTLVNRIELKGIDFKEDGNILGHKLE

YNFNSHNVYITADKQKNGIKANFKIRHNVEDGSVQLADHYQQNTPIGDGPVLLP

DNHYLSTQSKLSKDPNEKRDHMVLLEFVTAAGITHGMDELYKGSASTLVHNGTS

ARATTTPASKSTPFSIPSHHSDTPTTLASHSTKTDASSTHHSSVPPLTSSNHSTSPQL

STGVSFFFLSFHISNLQFNSSLEDPSTDYYQELQRDISEMFLQIYKQGGFLGLSNIK

FRPGSVVVQLTLAFREGTINVHDVETQFNQYKTEAASRYNLTISDVSVSDVPFPFS

AQSGAGVPGWGIALLVLVCVLVALAIVYLIALAVCQCRRK**

5. PDTRPAPGATAPPAHGVTSA_21
Muc1_21S_mOxGFP_dCTBlpI (SEQ ID NO: 39)
MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVPDTRPAPGATAPPAHGVTSAPDTRPAPGATAPPAHGVTSAPDTRPAPGA

TAPPAHGVTSAPDTRPAPGATAPPAHGVTSAPDTRPAPGATAPPAHGVTSAPDTR

PAPGATAPPAHGVTSAPDTRPAPGATAPPAHGVTSAPDTRPAPGATAPPAHGVTS

APDTRPAPGATAPPAHGVTSAPDTRPAPGATAPPAHGVTSAPDTRPAPGATAPPA

HGVTSAPDTRPAPGATAPPAHGVTSAPDTRPAPGATAPPAHGVTSAPDTRPAPGA

TAPPAHGVTSAPDTRPAPGATAPPAHGVTSAPDTRPAPGATAPPAHGVTSAPDTR

PAPGATAPPAHGVTSAPDTRPAPGATAPPAHGVTSAPDTRPAPGATAPPAHGVTS

APDTRPAPGATAPPAHGVTSAPDTRPAPGATAPPAHGVTSAASGSASGSAMVSK

-continued

GEELFTGVVPILVELDGDVNGHKFSVRGEGEGDATNGKLTLKFISTTGKLPVPWP

TLVTTLTYGVQSFSRYPDHMKRHDFFKSAMPEGYVQERTISFKDDGTYKTRAEV

KFEGDTLVNRIELKGIDFKEDGNILGHKLEYNFNSHNVYITADKQKNGIKANFKIR

HNVEDGSVQLADHYQQNTPIGDGPVLLPDNHYLSTQSKLSKDPNEKRDHMVLLE

FVTAAGITHGMDELYKGSASTLVHNGTSARATTTPASKSTPFSIPSHHSDTPTTLA

SHSTKTDASSTHEISSVPPLTSSNHSTSPQLSTGVSFFFLSFHISNLQFNSSLEDPSTD

YYQELQRDISEMFLQIYKQGGFLGLSNIKFRPGSVVVQLTLAFREGTINVHDVET

QFNQYKTEAASRYNLTISDVSVSDVPFPFSAQSGAGVPGWGIALLVLVCVLVALA

IVYLIALAVCQCRRK*

6. PDTRPAPGATAPPAHGVTAA_21
Muc1_21D_mOxGFP_dCT_BlpI (SEQ ID NO: 40)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVPDTRPAPGATAPPAHGVTAAPDTRPAPGATAPPAHGVTAAPDTRPAPG

ATAPPAHGVTAAPDTRPAPGATAPPAHGVTAAPDTRPAPGATAPPAHGVTAAPD

TRPAPGATAPPAHGVTAAPDTRPAPGATAPPAHGVTAAPDTRPAPGATAPPAHG

VTAAPDTRPAPGATAPPAHGVTAAPDTRPAPGATAPPAHGVTAAPDTRPAPGAT

APPAHGVTAAPDTRPAPGATAPPAHGVTAAPDTRPAPGATAPPAHGVTAAPDTR

PAPGATAPPAHGVTAAPDTRPAPGATAPPAHGVTAAPDTRPAPGATAPPAHGVT

AAPDTRPAPGATAPPAHGVTAAPDTRPAPGATAPPAHGVTAAPDTRPAPGATAP

PAHGVTAAPDTRPAPGATAPPAHGVTAAPDTRPAPGATAPPAHGVTAAASGSAS

GSAMVSKGEELFTGVVPILVELDGDVNGHKFSVRGEGEGDATNGKLTLKFISTTG

KLPVPWPTLVTTLTYGVQSFSRYPDHMKRHDFFKSAMPEGYVQERTISFKDDGT

YKTRAEVKFEGDTLVNRIELKGIDFKEDGNILGHKLEYNFNSHNVYITADKQKNG

IKANFKIRHNVEDGSVQLADHYQQNTPIGDGPVLLPDNHYLSTQSKLSKDPNEKR

DHMVLLEFVTAAGITHGMDELYKGSASTLVHNGTSARATTTPASKSTPFSIPSHE

SDTPTTLASHSTKTDASSTHEISSVPPLTSSNHSTSPQLSTGVSFFFLSFHISNLQFNS

SLEDPSTDYYQELQRDISEMFLQIYKQGGFLGLSNIKFRPGSVVVQLTLAFREGTI

NVHDVETQFNQYKTEAASRYNLTISDVSVSDVPFPFSAQSGAGVPGWGIALLVL

VCVLVALAIVYLIALAVCQCRRK*

7. PDARPAPGATAPPAHGVTAA_21
Muc1_21T_mOxGFP_dCT_BlpI (SEQ ID NO: 41)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVPDARPAPGATAPPAHGVTAAPDARPAPGATAPPAHGVTAAPDARPAPG

ATAPPAHGVTAAPDARPAPGATAPPAHGVTAAPDARPAPGATAPPAHGVTAAPD

ARPAPGATAPPAHGVTAAPDARPAPGATAPPAHGVTAAPDARPAPGATAPPAHG

VTAAPDARPAPGATAPPAHGVTAAPDARPAPGATAPPAHGVTAAPDARPAPGAT

APPAHGVTAAPDARPAPGATAPPAHGVTAAPDARPAPGATAPPAHGVTAAPDA

RPAPGATAPPAHGVTAAPDARPAPGATAPPAHGVTAAPDARPAPGATAPPAHGV

TAAPDARPAPGATAPPAHGVTAAPDARPAPGATAPPAHGVTAAPDARPAPGATA

-continued

PPAHGVTAAPDARPAP GATAPPAHGVTAAPDARPAPGATAPPAHGVTAAASGSA

SGSAMVSKGEELFTGVVPILVELDGDVNGHKFSVRGEGEGDATNGKLTLKFISTT

GKLPVPWPTLVTTLTYGVQSFSRYPDHMKRHDFFKSAMPEGYVQERTISFKDDG

TYKTRAEVKFEGDTLVNRIELKGIDFKEDGNILGHKLEYNFNSHNVYITADKQKN

GIKANFKIRHNVEDGSVQLADHYQQNTPIGDGPVLLPDNHYLSTQSKLSKDPNEK

RDHMVLLEFVTAAGITHGMDELYKGSASTLVHNGTSARATTTPASKSTPFSIPSH

HSDTPTTLASHSTKTDASSTHEISSVPPLTSSNHSTSPQLSTGVSFFFLSFHISNLQFN

SSLEDPSTDYYQELQRDISEMFLQIYKQGGFLGLSNIKFRPGSVVVQLTLAFREGTI

NVHDVETQFNQYKTEAASRYNLTISDVSVSDVPFPFSAQSGAGVPGWGIALLVL

VCVLVALAIVYLIALAVCQCRRK*

8. KEPAPTTP_20 (Syn4_20)
Muc1_Syn4_20_mOxGFP_dCT_BlpI
(SEQ ID NO: 42)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVKEPAPTTPKEPAPTTPKEPAPTTPKEPAPTTPKEPAPTTPKEPAPTTPKEP

APTTPKEPAPTTPKEPAPTTPKEPAPTTPKEPAPTTPKEPAPTTPKEPAPTTPKEPAP

TTPKEPAPTTPKEPAPTTPKEPAPTTPKEPAPTTPKEPAPTTPKEPAPTTPASGSASG

SAMVSKGEELFTGVVPILVELDGDVNGHKFSVRGEGEGDATNGKLTLKFISTTGK

LPVPWPTLVTTLTYGVQSFSRYPDHMKRHDFFKSAMPEGYVQERTISFKDDGTY

KTRAEVKFEGDTLVNRIELKGIDFKEDGNILGHKLEYNFNSHNVYITADKQKNGI

KANFKIRHNVEDGSVQLADHYQQNTPIGDGPVLLPDNHYLSTQSKLSKDPNEKR

DHMVLLEFVTAAGITHGMDELYKGSASTLVHNGTSARATTTPASKSTPFSIPSHE

SDTPTTLASHSTKTDASSTHEISSVPPLTSSNHSTSPQLSTGVSFFFLSFHISNLQFNS

SLEDPSTDYYQELQRDISEMFLQIYKQGGFLGLSNIKFRPGSVVVQLTLAFREGTI

NVHDVETQFNQYKTEAASRYNLTISDVSVSDVPFPFSAQSGAGVPGWGIALLVL

VCVLVALAIVYLIALAVCQCRRK*

9. DAATPAP_40 (Syn1_40)
Muc1_Syn1_40_mOxGFP_dCT_BlpI
(SEQ ID NO: 43)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVDAATPAPDAATPAPDAATPAPDAATPAPDAATPAPDAATPAPDAATPA

PDAATPAPDAATPAPDAATPAPDAATPAPDAATPAPDAATPAPDAATPAPDAAT

PAPDAATPAPDAATPAPDAATPAPDAATPAPDAATPAPDAATPAPDAATPAPDA

ATPAPDAATPAPDAATPAPDAATPAPDAATPAPDAATPAPDAATPAPDAATPAP

DAATPAPDAATPAPDAATPAPDAATPAPDAATPAPDAATPAPDAATPAPDAATP

APDAATPAPDAATPAPASGSASGSAMVSKGEELFTGVVPILVELDGDVNGHKFS

VRGEGEGDATNGKLTLKFISTTGKLPVPWPTLVTTLTYGVQSFSRYPDHMKRHD

FFKSAMPEGYVQERTISFKDDGTYKTRAEVKFEGDTLVNRIELKGIDFKEDGNIL

GHKLEYNFNSHNVYITADKQKNGIKANFKIRHNVEDGSVQLADHYQQNTPIGDG

PVLLPDNHYLSTQSKLSKDPNEKRDHMVLLEFVTAAGITHGMDELYKGSASTLV

HNGTSARATTTPASKSTPFSIPSHHSDTPTTLASHSTKTDASSTHEISSVPPLTSSNH

STSPQLSTGVSFFFLSFHISNLQFNSSLEDPSTDYYQELQRDISEMFLQIYKQGGFL

-continued

GLSNIKFRPGSVVVQLTLAFREGTINVHDVETQFNQYKTEAASRYNLTISDVSVS

DVPFPFSAQSGAGVPGWGIALLVLVCVLVALAIVYLIALAVCQCRRK*

10. DAATPAP_80 (Syn1_80)
Muc1_Syn1_80_mOxGFP_dCT_BlpI (SEQ ID NO: 44)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVDAATPAPDAATPAPDAATPAPDAATPAPDAATPAPDAATPAPDAATPA

PDAATPAPDAATPAPDAATPAPDAATPAPDAATPAPDAATPAPDAATPAPDAAT

PAPDAATPAPDAATPAPDAATPAPDAATPAPDAATPAPDAATPAPDAATPAPDA

ATPAPDAATPAPDAATPAPDAATPAPDAATPAPDAATPAPDAATPAPDAATPAP

DAATPAPDAATPAPDAATPAPDAATPAPDAATPAPDAATPAPDAATPAPDAATP

APDAATPAPDAATPAPDAATPAPDAATPAPDAATPAPDAATPAPDAATPAPDAA

TPAPDAATPAPDAATPAPDAATPAPDAATPAPDAATPAPDAATPAPDAATPAPD

AATPAPDAATPAPDAATPAPDAATPAPDAATPAPDAATPAPDAATPAPDAATPA

PDAATPAPDAATPAPDAATPAPDAATPAPDAATPAPDAATPAPDAATPAPDAAT

PAPDAATPAPDAATPAPDAATPAPDAATPAPDAATPAPDAATPAPDAATPAPDA

ATPAPDAATPAPDAATPAPDAATPAPASGSASGSAMVSKGEELFTGVVPILVELD

GDVNGHKFSVRGEGEGDATNGKLTLKFISTTGKLPVPWPTLVTTLTYGVQSFSR

YPDHMKRHDFFKSAMPEGYVQERTISFKDDGTYKTRAEVKFEGDTLVNRIELKG

IDFKEDGNILGHKLEYNFNSHNVYITADKQKNGIKANFKIRHNVEDGSVQLADH

YQQNTPIGDGPVLLPDNHYLSTQSKLSKDPNEKRDHMVLLEFVTAAGITHGMDE

LYKGSASTLVHNGTSARATTTPASKSTPFSIPSHHSDTPTTLASHSTKTDASSTHHS

SVPPLTSSNHSTSPQLSTGVSFFFLSFHISNLQFNSSLEDPSTDYYQELQRDISEMFL

QIYKQGGFLGLSNIKFRPGSVVVQLTLAFREGTINVHDVETQFNQYKTEAASRYN

LTISDVSVSDVPFPFSAQSGAGVPGWGIALLVLVCVLVALAIVYLIALAVCQCRRK*

11. DAATPAPP_40 (Syn2_40)
Muc1_Syn1_40_mOxGFP_dCT_BlpI (SEQ ID NO: 45)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVDAATPAPPDAATPAPPDAATPAPPDAATPAPPDAATPAPPDAATPAPPD

AATPAPPDAATPAPPDAATPAPPDAATPAPPDAATPAPPDAATPAPPDAATPAPP

DAATPAPPDAATPAPPDAATPAPPDAATPAPPDAATPAPPDAATPAPPDAATPAP

PDAATPAPPDAATPAPPDAATPAPPDAATPAPPDAATPAPPDAATPAPPDAATPA

PPDAATPAPPDAATPAPPDAATPAPPDAATPAPPDAATPAPPDAATPAPPDAATP

APPDAATPAPPDAATPAPPDAATPAPPDAATPAPPDAATPAPPDAATPAPPASGS

ASGSAMVSKGEELFTGVVPILVELDGDVNGHKFSVRGEGEGDATNGKLTLKFIST

TGKLPVPWPTLVTTLTYGVQSFSRYPDHMKRHDFFKSAMPEGYVQERTISFKDD

GTYKTRAEVKFEGDTLVNRIELKGIDFKEDGNILGHKLEYNFNSHNVYITADKQK

NGIKANFKIRHNVEDGSVQLADHYQQNTPIGDGPVLLPDNHYLSTQSKLSKDPNE

KRDHMVLLEFVTAAGITHGMDELYKGSASTLVHNGTSARATTTPASKSTPFSIPS

HHSDTPTTLASHSTKTDASSTHHSSVPPLTSSNHSTSPQLSTGVSFFFLSFHISNLQF

-continued

NSSLEDPSTDYYQELQRDISEMFLQIYKQGGFLGLSNIKFRPGSVVVQLTLAFREG

TINVHDVETQFNQYKTEAASRYNLTISDVSVSDVPFPFSAQSGAGVPGWGIALLV

LVCVLVALAIVYLIALAVCQCRRK*

12. DAATPAPP_80 (Syn2_80)
Muc1_Syn1_40_mOxGFP_dCT_BlpI (SEQ ID NO: 46)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVDAATPAPPDAATPAPPDAATPAPPDAATPAPPDAATPAPPDAATPAPPD

AATPAPPDAATPAPPDAATPAPPDAATPAPPDAATPAPPDAATPAPPDAATPAPP

DAATPAPPDAATPAPPDAATPAPPDAATPAPPDAATPAPPDAATPAPPDAATPAP

PDAATPAPPDAATPAPPDAATPAPPDAATPAPPDAATPAPPDAATPAPPDAATPA

PPDAATPAPPDAATPAPPDAATPAPPDAATPAPPDAATPAPPDAATPAPPDAATP

APPDAATPAPPDAATPAPPDAATPAPPDAATPAPPDAATPAPPDAATPAPPDAAT

PAPPDAATPAPPDAATPAPPDAATPAPPDAATPAPPDAATPAPPDAATPAPPDAA

TPAPPDAATPAPPDAATPAPPDAATPAPPDAATPAPPDAATPAPPDAATPAPPDA

ATPAPPDAATPAPPDAATPAPPDAATPAPPDAATPAPPDAATPAPPDAATPAPPD

AATPAPPDAATPAPPDAATPAPPDAATPAPPDAATPAPPDAATPAPPDAATPAPP

DAATPAPPDAATPAPPDAATPAPPDAATPAPPDAATPAPPDAATPAPPDAATPAP

PDAATPAPPDAATPAPPDAATPAPPDAATPAPPDAATPAPPASGSASGSAMVSKG

EELFTGVVPILVELDGDVNGHKFSVRGEGEGDATNGKLTLKFISTTGKLPVPWPT

LVTTLTYGVQSFSRYPDHMKRHDFFKSAMPEGYVQERTISFKDDGTYKTRAEVK

FEGDTLVNRIELKGIDFKEDGNILGHKLEYNFNSHNVYITADKQKNGIKANFKIRH

NVEDGSVQLADHYQQNTPIGDGPVLLPDNHYLSTQSKLSKDPNEKRDHMVLLEF

VTAAGITHGMDELYKGSASTLVHNGTSARATTTPASKSTPFSIPSHHSDTPTTLAS

HSTKTDASSTHHSSVPPLTSSNHSTSPQLSTGVSFFFLSFHISNLQFNSSLEDPSTDY

YQELQRDISEMFLQIYKQGGFLGLSNIKFRPGSVVVQLTLAFREGTINVHDVETQF

NQYKTEAASRYNLTISDVSVSDVPFPFSAQSGAGVPGWGIALLVLVCVLVALAIV

YLIALAVCQCRRK*

13. PPASTSAPG_40 (Syn3_40)
Muc1_Syn1_40_mOxGFP_dCT_BlpI (SEQ ID NO: 47)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVPPASTSAPGPPASTSAPGPPASTSAPGPPASTSAPGPPASTSAPGPPASTS

APGPPASTSAPGPPASTSAPGPPASTSAPGPPASTSAPGPPASTSAPGPPASTSAPGP

PASTSAPGPPASTSAPGPPASTSAPGPPASTSAPGPPASTSAPGPPASTSAPGPPAST

SAPGPPASTSAPGPPASTSAPGPPASTSAPGPPASTSAPGPPASTSAPGPPASTSAPG

PPASTSAPGPPASTSAPGPPASTSAPGPPASTSAPGPPASTSAPGPPASTSAPGPPAS

TSAPGPPASTSAPGPPASTSAPGPPASTSAPGPPASTSAPGPPASTSAPGPPASTSAP

GPPASTSAPGPPASTSAPGASGSASGSAMVSKGEELFTGVVPILVELDGDVNGHK

FSVRGEGEGDATNGKLTLKFISTTGKLPVPWPTLVTTLTYGVQSFSRYPDHMKRH

DFFKSAMPEGYVQERTISFKDDGTYKTRAEVKFEGDTLVNRIELKGIDFKEDGNI

LGHKLEYNFNSHNVYITADKQKNGIKANFKIRHNVEDGSVQLADHYQQNTPIGD

-continued

GPVLLPDNHYLSTQSKLSKDPNEKRDHMVLLEFVTAAGITHGMDELYKGSASTL

VHNGTSARATTTPASKSTPFSIPSHHSDTPTTLASHSTKTDASSTHHSSVPPLTSSN

HSTSPQLSTGVSFFFLSFHISNLQFNSSLEDPSTDYYQELQRDISEMFLQIYKQGGF

LGLSNIKFRPGSVVVQLTLAFREGTINVHDVETQFNQYKTEAASRYNLTISDVSVS

DVPFPFSAQSGAGVPGWGIALLVLVCVLVALAIVYLIALAVCQCRRK*

14. PPASTSAPG_80 (Syn3_80)
Muc1_Syn1_40_mOxGFP_dCT_BlpI (SEQ ID NO: 48)

MTPGTQSPFFLLLLLTVLTVVTGSGHASSTPGGEKETSATQRSSVPSSTEKNADYK

DDDDLYMDMVAVSMTSSVLSSHSPGSGSSTTQGQDVTLAPATEPASGSAATWG

QDVTSVPPASTSAPGPPASTSAPGPPASTSAPGPPASTSAPGPPASTSAPGPPASTS

APGPPASTSAPGPPASTSAPGPPASTSAPGPPASTSAPGPPASTSAPGPPASTSAPGP

PASTSAPGPPASTSAPGPPASTSAPGPPASTSAPGPPASTSAPGPPASTSAPGPPAST

SAPGPPASTSAPGPPASTSAPGPPASTSAPGPPASTSAPGPPASTSAPGPPASTSAPG

PPASTSAPGPPASTSAPGPPASTSAPGPPASTSAPGPPASTSAPGPPASTSAPGPPAS

TSAPGPPASTSAPGPPASTSAPGPPASTSAPGPPASTSAPGPPASTSAPGPPASTSAP

GPPASTSAPGPPASTSAPGPPASTSAPGPPASTSAPGPPASTSAPGPPASTSAPGPPA

STSAPGPPASTSAPGPPASTSAPGPPASTSAPGPPASTSAPGPPASTSAPGPPASTSA

PGPPASTSAPGPPASTSAPGPPASTSAPGPPASTSAPGPPASTSAPGPPASTSAPGPP

ASTSAPGPPASTSAPGPPASTSAPGPPASTSAPGPPASTSAPGPPASTSAPGPPASTS

APGPPASTSAPGPPASTSAPGPPASTSAPGPPASTSAPGPPASTSAPGPPASTSAPGP

PASTSAPGPPASTSAPGPPASTSAPGPPASTSAPGPPASTSAPGPPASTSAPGPPAST

SAPGPPASTSAPGPPASTSAPGPPASTSAPGASGSASGSAMVSKGEELFTGVVPILV

ELDGDVNGHKFSVRGEGEGDATNGKLTLKFISTTGKLPVPWPTLVTTLTYGVQS

FSRYPDHMKRHDFFKSAMPEGYVQERTISFKDDGTYKTRAEVKFEGDTLVNRIE

LKGIDFKEDGNILGHKLEYNFNSHNVYITADKQKNGIKANFKIRHNVEDGSVQLA

DHYQQNTPIGDGPVLLPDNHYLSTQSKLSKDPNEKRDHMVLLEFVTAAGITHGM

DELYKGSASTLVHNGTSARATTTPASKSTPFSIPSHHSDTPTTLASHSTKTDASST

HEISSVPPLTSSNHSTSPQLSTGVSFFFLSFHISNLQFNSSLEDPSTDYYQELQRDISE

MFLQIYKQGGFLGLSNIKFRPGSVVVQLTLAFREGTINVHDVETQFNQYKTEAAS

RYNLTISDVSVSDVPFPFSAQSGAGVPGWGIALLVLVCVLVALAIVYLIALAVCQ

CRRK

List of Constructs Used in Part I
Membrane Associated Mucin 52. pcDNA3.1+_Muc1_0_TM21
53. pcDNA3.1+_Muc1_10_TM21
54. pcDNA3.1+_Muc1_21_TM21
55. pcDNA3.1+_Muc1_42_TM21
56. pcDNA3.1+_Muc1_21S_TM21
57. pcDNA3.1+_Muc1_21D_TM21
58. pcDNA3.1+_Muc1_21T_TM21
59. pcDNA3.1+_Muc1_10_TM21_CT
60. pcDNA3.1+_Muc1_10_TM21_CQC
61. pcDNA3.1+_Muc1_10_dCT
62. pcDNA3.1+_Muc1_10_FL
63. pcDNA3.1+_Muc1_Syn4_20_TM21
64. pcDNA3.1+_Muc1_Syn1_40_TM21
65. pcDNA3.1+_Muc1_Syn2_40_TM21
66. pcDNA3.1+_Muc1_Syn3_40_TM21
67. pcDNA3.1+_Muc1_Syn1_80_TM21
68. pcDNA3.1+_Muc1_Syn2_80_TM21
69. pcDNA3.1+_Muc1_Syn3_80_TM21
70. pPB_Tet_Muc1_TM21_IRES2_copGFP_rtTAsM2_IRES_NeoR
71. pPB_Tet_Muc1_42_TM21_IRES2_copGFP_rtTAsM2_IRES_NeoR
72. pPB_Tet_Muc1_21_TM21_IRES2_copGFP_rtTAsM2_IRES_NeoR
73. pPB_Tet_Muc1_10_TM21_IRES2_copGFP_rtTAsM2_IRES_NeoR
74. pPB_Tet_Muc1_0_TM21_IRES2_copGFP_rtTAsM2_IRES_NeoR 75. pPB_Tet_Muc1_21D_TM21_IRES2_copGFP_rtTAsM2_IRES_NeoR
76. pPB_Tet_Muc1_21T_TM21_IRES2_copGFP_rtTAsM2_IRES_NeoR
77. pLV_puro_teton_Muc1_42_dCT
78. pLV_puro_teton_Muc1_dCT
79. pPB_Muc1_mOxGFP_dCT_BlpI
80. pPB_Muc1_42_mOxGFP_dCT_BlpI
81. pPB_Muc1_21_mOxGFP_dCT_BlpI
82. pPB_Muc1_10_mOxGFP_dCT_BlpI
83. pPB_Muc1_0_mOxGFP_dCT_BlpI
84. pPB_Muc1_21S_mOxGFP_dCT_BlpI
85. pPB_Muc1_21D_mOxGFP_dCT_BlpI
86. pPB_Muc1_21T_mOxGFP_dCT_BlpI
87. pPB_Muc1_Syn4_20_mOxGFP_dCT_BlpI
88. pPB_Muc1_Syn1_40_mOxGFP_dCT_BlpI
89. pPB_Muc1_Syn2_40_mOxGFP_dCT_BlpI
90. pPB_Muc1_Syn3_40_mOxGFP_dCT_BlpI
91. pPB_Muc1_Syn1_80_mOxGFP_dCT_BlpI
92. pPB_Muc1_Syn2_80_mOxGFP_dCT_BlpI Secreted Mucin 93. pPB_Tet_SumoStar_Muc1_42_rtTAsM2_IRES_NeoR
94. pPB_Tet_SumoStar_Muc1_21T_rtTAsM2_IRES_NeoR
95. pPB_Tet_SumoStar_Muc1_21D_rtTAsM2_IRES_NeoR
96. pPB_Tet_SumoStar_Muc1_21S_rtTAsM2_IRES_NeoR
97. pPB_Tet_SumoStar_Muc1_21_rtTAsM2_IRES_NeoR
98. pPB_Tet_SumoStar_Muc1_0_rtTAsM2_IRES_NeoR
99. pPB_Tet_SumoStar_Muc1_Syn1_40_rtTAsM2_IRES_NeoR
100. pPB_Tet_SumoStar_Muc1_Syn2_40_rtTAsM2_IRES_NeoR
101. pPB_Tet_SumoStar_Muc1_Syn3_40_rtTAsM2_IRES_NeoR
102. pPB_Tet_SumoStar_Muc1_Syn1_80_rtTAsM2_IRES_NeoR
103. pPB_Tet_SumoStar_Muc1_Syn2_80_rtTAsM2_IRES_NeoR References cited in Part I—references listed in any part of this disclosure is not an indication that any of the references are material to patentability.

REFERENCES (1) Brockhausen, I.; Schachter, H.; Stanley, P. O-GalNAc Glycans. In *Essentials of Glycobiology*; Varki, A., Cummings, R. D., Esko, J. D., Freeze, H. H., Stanley, P., Bertozzi, C. R., Hart, G. W., Etzler, M. E., Eds.; Cold Spring Harbor Laboratory Press: Cold Spring Harbor (NY), 2009.

(2) Lichtenberger, L. M. The Hydrophobic Barrier Properties of Gastrointestinal Mucus. *Annu. Rev. Physiol.* 1995, 57 (1), 565-583. //doi.org/10.1 146/annurev.ph.57.030195.003025.

(3) Hudak, J. E.; Canham, S. M.; Bertozzi, C. R. Glycocalyx Engineering Reveals a Siglec-Based Mechanism for NK Cell Immunoevasion. *Nature Chemical Biology* 2014, 10 (1), 69-75. //doi.org/10.1038/nchembio.1388.

(4) Paszek, M. J.; DuFort, C. C.; Rossier, O.; Bainer, R.; Mouw, J. K.; Godula, K.; Hudak, J. E.; Lakins, J. N.; Wijekoon, A. C.; Cassereau, L.; et al. The Cancer Glycocalyx Mechanically Primes Integrin-Mediated Growth and Survival. *Nature* 2014, 511 (7509), 319-325. //doi.org/10.1038/nature13535.

(5) Polefka, T. G.; Garrick, R. A.; Redwood, W. R.; Swislocki, N. I.; Chinard, F. P. Solute-Excluded Volumes near the Novikoff Cell Surface. *American Journal of Physiology-Cell Physiology* 1984, 247 (5), C350-C356. //doi.org/10.1152/ajpcell.1984.247.5.C350.

(6) Kramer, J. R.; Onoa, B.; Bustamante, C.; Bertozzi, C. R. Chemically Tunable Mucin Chimeras Assembled on Living Cells. *PNAS* 2015, 112 (41), 12574-12579. //doi.org/10.1073/pnas.1516127112.

(7) Coltart, D. M.; Royyuru, A. K.; Williams, L. J.; Glunz, P. W.; Sames, D.; Kuduk, S. D.; Schwarz, J. B.; Chen, X.-T.; Danishefsky, S. J.; Live, D. H. Principles of Mucin Architecture: Structural Studies on Synthetic Glycopeptides Bearing Clustered Mono-, Di-, Tri-, and Hexasaccharide Glycodomains. *J. Am. Chem. Soc.* 2002, 124 (33), 9833-9844. //doi.org/10.1021/ja020208f.

(8) Dennis, J. W.; Granovsky, M.; Warren, C. E. Protein Glycosylation in Development and Disease. *BioEssays* 1999, 21 (5), 412-421. //doi.org/10.1002/(SICI)1521-1878(199905)21:5<412::AID-BIES8>3.0.CO; 2-5.

(9) Reis, C. A.; Osorio, H.; Silva, L.; Gomes, C.; David, L. Alterations in Glycosylation as Biomarkers for Cancer Detection. *Journal of Clinical Pathology* 2010, 63 (4), 322-329. //doi.org/10.1136/jcp.2009.071035.

(10) Steentoft, C.; Vakhrushev, S. Y.; Vester-Christensen, M. B.; Schjoldager, K. T.-B. G.; Kong, Y.; Bennett, E. P.; Mandel, U.; Wandall, H.; Levery, S. B.; Clausen, H. Mining the O-Glycoproteome Using Zinc-Finger Nuclease-Glycoengineered SimpleCell Lines. *Nature Methods* 2011, 8 (11), 977-982. //doi.org/10.1038/nmeth.1731.

(11) Julien, S.; Adriaenssens, E.; Ottenberg, K.; Furlan, A.; Courtand, G.; Vercoutter-Edouart, A.-S.; Hanisch, F.-G.; Delannoy, P.; Le Bourhis, X. ST6GalNAc I Expression in MDA-MB-231 Breast Cancer Cells Greatly Modifies Their O-Glycosylation Pattern and Enhances Their Tumourigenicity. *Glycobiology* 2006, 16 (1), 54-64. //doi.org/10.1093/glycob/cwj033.

(12) Pérez-Garay, M.; Arteta, B.; Pagès, L.; Llorens, R. de; Bolòs, C. de; Vidal-Vanaclocha, F.; Peracaula, R. A2,3-Sialyltransferase ST3Gal III Modulates Pancreatic Cancer Cell Motility and Adhesion In Vitro and Enhances Its Metastatic Potential In Vivo. *PLOS ONE* 2010, 5 (9), e12524. //doi.org/10.1371/journal.pone.0012524.

(13) Parthasarathy, R.; Rabuka, D.; Bertozzi, C. R.; Groves, J. T. Molecular Orientation of Membrane-Anchored Mucin Glycoprotein Mimics. *J. Phys. Chem. B* 2007, 111 (42), 12133-12135. //doi.org/10.1021/jp072136q.

(14) Rabuka, D.; Forstner, M. B.; Groves, J. T.; Bertozzi, C. R. Noncovalent Cell Surface Engineering: Incorporation of Bioactive Synthetic Glycopolymers into Cellular Membranes. *J. Am. Chem. Soc.* 2008, 130 (18), 5947-5953. //doi.org/10.1021/ja710644g.

(15) Woods, E. C.; Yee, N. A.; Shen, J.; Bertozzi, C. R. Glycocalyx Engineering with a Recycling Glycopolymer That Increases Cell Survival In Vivo. *Angewandte Chemie International Edition* 2015, 54 (52), 15782-15788. //doi.org/10.1002/anie.201508783.

(16) Brakenhoff, R. H.; Schoenmakers, J. G.; Lubsen, N. H. Chimeric CDNA Clones: A Novel PCR Artifact. *Nucleic Acids Res* 1991, 19 (8), 1949.

(17) Meyerhans, A.; Vartanian, J.-P.; Wain-Hobson, S. DNA Recombination during PCR. *Nucleic Acids Res* 1990, 18 (7), 1687-1691. //doi.org/10.1093/nar/18.7.1687.

(18) Tang, N. C.; Chilkoti, A. Combinatorial Codon Scrambling Enables Scalable Gene Synthesis and Amplification of Repetitive Proteins. *Nat Mater* 2016, 15 (4), 419-424. //doi.org/10.1038/nmat4521.

(19) Ferrari, F. A.; Cappello, J. Biosynthesis of Protein Polymers. In *Protein-Based Materials*; Bioengineering of Materials; Birkhäuser Boston, 1997; pp 37-60. //doi.org/10.1007/978-1-4612-4094-5_2.

(20) Yoshida, A.; Suzuki, M.; Ikenaga, H.; Takeuchi, M. Discovery of the Shortest Sequence Motif for High Level Mucin-Type O-Glycosylation. *J. Biol. Chem.* 1997, 272 (27), 16884-16888. //doi.org/10.1074/jbc.272.27.16884.

(21) Pei-Xiang, X.; Prenzoska, J.; Mckenzie, I. F. C. Epitope Mapping of Anti-Breast and Anti-Ovarian Mucin Monoclonal Antibodies. *Molecular Immunology* 1992, 29 (5), 641-650. //doi.org/10.1016/0161-5890(92)90201-8.

(22) Zeng, Y.; Ramya, T. N. C.; Dirksen, A.; Dawson, P. E.; Paulson, J. C. High-Efficiency Labeling of Sialylated Glycoproteins on Living Cells. *Nature Methods* 2009, 6 (3), 207-209. //doi.org/10.1038/nmeth.1305.

(23) Wang, Y.; Ju, T.; Ding, X.; Xia, B.; Wang, W.; Xia, L.; He, M.; Cummings, R. D. Cosmc Is an Essential Chaperone for Correct Protein O-Glycosylation. *Proc. Natl. Acad. Sci. U.S.A.* 2010, 107 (20), 9228-9233. //doi.org/10.1073/pnas.0914004107.

(24) Bzymek, M.; Lovett, S. T. Instability of Repetitive DNA Sequences: The Role of Replication in Multiple Mechanisms. *PNAS* 2001, 98 (15), 8319-8325. //doi.org/10.1073/pnas.111008398.

(25) Swallow, D. M.; Gendler, S.; Griffiths, B.; Corney, G.; Taylor-Papadimitriou, J.; Bramwell, M. E. The Human Tumour-Associated Epithelial Mucins Are Coded by an Expressed Hypervariable Gene Locus PUM. *Nature* 1987, 328 (6125), 82-84. //doi.org/10.1038/328082a0.

(26) Carvalho, F.; Seruca, R.; David, L.; Amorim, A.; Seixas, M.; Bennett, E.; Clausen, H.; Sobrinho-Simoes, M. MUC1 Gene Polymorphism and Gastric Cancer—an Epidemiological Study. *Glycoconj J* 1997, 14 (1), 107-111. //doi.org/10.1023/A:1018573201347.

(27) Shurer, C. R.; Colville, M. J.; Gupta, V. K.; Head, S. E.; Kai, F.; Lakins, J. N.; Paszek, M. J. Genetically Encoded Toolbox for Glycocalyx Engineering: Tunable Control of Cell Adhesion, Survival, and Cancer Cell Behaviors. *ACS Biomater. Sci. Eng.* 2017. //doi.org/10.1021/acsbiomaterials.7b00037.

(28) Cellular O-Glycome Reporter/Amplification to explore O-glycans of living cells Nature Methods //www.nature-.com/articles/nmeth.3675 (accessed Jun. 1, 2019).

(29) Litvinov, S. V.; Hilkens, J. The Epithelial Sialomucin, Episialin, Is Sialylated during Recycling. *J. Biol. Chem.* 1993, 268 (28), 21364-21371.

(30) Kinlough, C. L.; McMahan, R. J.; Poland, P. A.; Bruns, J. B.; Harkleroad, K. L.; Stremple, R. J.; Kashlan, O. B.; Weixel, K. M.; Weisz, O. A.; Hughey, R. P. Recycling of MUC1 Is Dependent on Its Palmitoylation. *J. Biol. Chem.* 2006, 281 (17), 12112-12122. //doi.org/10.1074/jbc.M512996200.

(31) Mercanti, V.; Marchetti, A.; Lelong, E.; Perez, F.; Orci, L.; Cosson, P. Transmembrane Domains Control Exclusion of Membrane Proteins from Clathrin-Coated Pits. *J Cell Sci* 2010, 123 (19), 3329-3335. //doi.org/10.1242/jcs.073031.

(32) Kinlough, C. L.; Poland, P. A.; Bruns, J. B.; Harkleroad, K. L.; Hughey, R. P. MUC1 Membrane Trafficking Is Modulated by Multiple Interactions. *J. Biol. Chem.* 2004, 279 (51), 53071-53077. //doi.org/10.1074/jbc.M409360200.

(33) Geisler, C.; Jarvis, D. L. Letter to the Glyco-Forum: Effective Glycoanalysis with *Maackia amurensis* Lectins Requires a Clear Understanding of Their Binding Specificities. *Glycobiology* 2011, 21 (8), 988-993. //doi.org/10.1093/glycob/cwr080.

(34) Brockhausen, I.; Yang, J.-M.; Burchell, J.; Whitehouse, C.; Taylor-Papadimitriou, J. Mechanisms Underlying Aberrant Glycosylation of MUC1 Mucin in Breast Cancer Cells. *European Journal of Biochemistry* 1995, 233 (2), 607-617. //doi.org/10.1111/j.1432-1033.1995.607_2.x.

(35) Gerken, T. A.; Gilmore, M.; Zhang, J. Determination of the Site-Specific Oligosaccharide Distribution of the O-Glycans Attached to the Porcine Submaxillary Mucin Tandem Repeat FURTHER EVIDENCE FOR THE MODULATION OF O-GLYCAN SIDE CHAIN STRUCTURES BY PEPTIDE SEQUENCE. *J. Biol. Chem.* 2002, 277 (10), 7736-7751. //doi.org/10.1074/jbc.M111690200.

(36) Gerken, T. A. Kinetic Modeling Confirms the Biosynthesis of Mucin Core 1 ((3-Gal(1-3) α-GalNAc-O-Ser/Thr) 0-Glycan Structures Are Modulated by Neighboring Glycosylation Effects. *Biochemistry* 2004, 43 (14), 4137-4142. //doi.org/10.1021/bi036306a.

(37) Clausen, H.; Bennett, E. P. A Family of UDP-GalNAc: Polypeptide N-Acetylgalactosaminyl-Transferases Control the Initiation of Mucin-Type O-Linked Glycosylation. *Glycobiology* 1996, 6 (6), 635-646. //doi.org/10.1093/glycob/6.6.635.

(38) Granovsky, M.; Bielfeldt, T.; Peters, S.; Paulsen, H.; Meldal, M.; Brockhausen, J.; Brockhausen, I. UDPgalactose:Glycoprotein-N-Acetyl-d-Galactosamine 3-β-d-Galactosyltransferase Activity Synthesizing O-Glycan Core 1 Is Controlled by the Amino Acid Sequence and Glycosylation of Glycopeptide Substrates. *European Journal of Biochemistry* 1994, 221 (3), 1039-1046. H//doi.org/10.1111/j.1432-1033.1994.tb18822.x.

(39) Brockhausen, I.; Dowler, T.; Paulsen, H. Site Directed Processing: Role of Amino Acid Sequences and Glycosylation of Acceptor Glycopeptides in the Assembly of Extended Mucin Type O-Glycan Core 2. *Biochimica et Biophysica Acta* (BBA)—*General Subjects* 2009, 1790 (10), 1244-1257. //doi.org/10.1016/j.bbagen.2009.05.020.

(40) Huang, K. M.; Snider, M. D. Glycoprotein Recycling to the Galactosyltransferase Compartment of the Golgi Complex. *J. Biol. Chem.* 1993, 268 (13), 9302-9310.

(41) Engelmann, K.; Kinlough, C. L.; Müller, S.; Razawi, H.; Baldus, S. E.; Hughey, R. P.; Hanisch, F.-G. Transmembrane and Secreted MUC1 Probes Show Trafficking-Dependent Changes in O-Glycan Core Profiles. *Glycobiology* 2005, 15 (11), 1111-1124. //doi.org/10.1093/glycob/cwiO99.

(42) Elhammer, A. P.; Poorman, R. A.; Brown, E.; Maggiora, L. L.; Hoogerheide, J. G.; Kźdy, F. J. The Specificity of UDP-GalNAc:Polypeptide N-Acetylgalactosaminyltransferase as Inferred from a Database of in Vivo Substrates and from the in Vitro Glycosylation of Proteins and Peptides. *J. Biol. Chem.* 1993, 268 (14), 10029-10038.

(43) Hema Thanka Christlet, T.; Veluraja, K. Database Analysis of O-Glycosylation Sites in Proteins. *Biophysical Journal* 2001, 80 (2), 952-960. //doi.org/10.1016/S0006-3495(01)76074-2.

(44) Gerken, T. A.; Owens, C. L.; Pasumarthy, M. Site-Specific Core 1 O-Glycosylation Pattern of the Porcine Submaxillary Gland Mucin Tandem Repeat EVIDENCE FOR THE MODULATION OF GLYCAN LENGTH BY PEPTIDE SEQUENCE. *J. Biol. Chem.* 1998, 273 (41), 26580-26588. //doi.org/10.1074/jbc.273.41.26580.
(45) Sihlbom, C.; van Dijk Härd, I.; Lidell, M. E.; Noll, T.; Hansson, G. C.; Bäckström, M. Localization of O-Glycans in MUC1 Glycoproteins Using Electron-Capture Dissociation Fragmentation Mass Spectrometry. *Glycobiology* 2009, 19 (4), 375-381. //doi.org/10.1093/glycob/cwn144.
(46) Nicholls, J. M.; Bourne, A. J.; Chen, H.; Guan, Y.; Peiris, J. M. Sialic Acid Receptor Detection in the Human Respiratory Tract: Evidence for Widespread Distribution of Potential Binding Sites for Human and Avian Influenza Viruses. *Respir Res* 2007, 8 (1), 73. //doi.org/10.1186/1465-9921-8-73.
(47) Lee, M. E.; DeLoache, W. C.; Cervantes, B.; Dueber, J. E. A Highly Characterized Yeast Toolkit for Modular, Multipart Assembly. *ACS Synth. Biol.* 2015, 4 (9), 975-986. //doi.org/10.1021/sb500366v.
(48) Paszek, M. J.; DuFort, C. C.; Rubashkin, M. G.; Davidson, M. W.; Thorn, K. S.; Liphardt, J. T.; Weaver, V. M. Scanning Angle Interference Microscopy Reveals Cell Dynamics at the Nanoscale. *Nat Meth* 2012, 9 (8), 825-827. //doi.org/10.1038/nmeth.2077.
(49) Subedi, G. P.; Johnson, R. W.; Moniz, H. A.; Moremen, K. W.; Barb, A. High Yield Expression of Recombinant Human Proteins with the Transient Transfection of HEK293 Cells in Suspension. *J Vis Exp* 2015, No. 106. //doi.org/10.3791/53568.
(50) Shurer, C. R.; Kuo, J. C.-H.; Roberts, L. M.; Gandhi, J. G.; Colville, M. J.; Enoki, T. A.; Pan, H.; Su, J.; Noble, J. M.; Hollander, M. J.; et al. Physical Principles of Membrane Shape Regulation by the Glycocalyx. *Cell* 2019, 177 (7), 1757-1770.e21. //doi.org/10.1016/j.cell.2019.04.017.
(51) Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; et al. Fiji: An Open-Source Platform for Biological-Image Analysis. *Nature Methods* 2012, 9 (7), 676-682. //doi.org/10.1038/nmeth.2019.
(52) Schneider, C. A.; Rasband, W. S.; Eliceiri, K. W. NIH Image to ImageJ: 25 years of image analysis //www.nature.com/articles/nmeth.2089 (accessed Oct. 31, 2018). //doi.org/10.1038/nmeth.2089.
(53) Reichner, J. S.; Whiteheart, S. W.; Hart, G. W. Intracellular Trafficking of Cell Surface Sialoglycoconjugates. *J. Biol. Chem.* 1988, 263 (31), 16316-16326.
(54) Fukuda, M. Beta-Elimination for Release of O-GalNAc-Linked Oligosaccharides from Glycoproteins and Glycopeptides. *Curr Protoc Mol Biol* 2001, Chapter 17, Unit17.15B. //doi.org/10.1002/0471142727.mb1715bs31.
(55) Shajahan, A.; Heiss, C.; Ishihara, M.; Azadi, P. Glycomic and Glycoproteomic Analysis of Glycoproteins-a Tutorial. *Anal Bioanal Chem* 2017, 409 (19), 4483-4505. //doi.org/10.1007/s00216-017-0406-7.

Part II

This Part II of the disclosure illustrates mucin-coating technologies for protection and reduced aggregation of cellular production systems.

In connection with this Part II, optimization of host-cell production systems with improved yield and production reliability is desired in order to meet the increasing demand for biologics with complex post-translational modifications. Prior to the present disclosure, aggregation of suspension-adapted mammalian cells remained a significant problem that can limit the cellular density and per volume yield of bio-reactors. This Part II provides a genetically encoded technology that directs the synthesis of anti-adhesive and protective coatings on the cellular surface. We genetically encode new cell-surface coatings through the fusion of engineered mucin domains to synthetic transmembrane anchors. Combined with appropriate expression systems, the mucin coating technology directs the assembly of thick, highly hydrated barriers to strongly mitigate cell aggregation and protect cells in suspension against fluid shear stresses. The coating technology is demonstrated on suspension adapted human 293-F cells, which resist clumping even in media formulations that otherwise would induce extreme cell aggregation and show improved performance over commercially available anti-clumping agent. The stable biopolymer coatings do not show deleterious effects on cell proliferation rate, efficiency of transient transfection with cDNAs, or recombinant protein expression. Overall, the mucin coating technology and engineered cell lines described herein exhibit the ability to improve the single-cell growth and viability of suspended cells in bioreactors.

This Part II, as well as other parts of this disclosure, pertain to biopolymers referred to in the art as mucins, which are utilized to reduce adhesion and fouling at biological interfaces. Mucins are characterized by amino acid sequences rich in serine and threonine residues, which are post-translationally modified with O-linked pendant glycan structures (Thornton, Rousseau, & McGuckin, 2008). The bottlebrush molecular structure of mucins confers an anti-adhesive characteristic that is used by biological systems for diverse purposes, including antifouling coatings, lubrication, and modulation of cellular interactions (Jay & Waller, 2014; Kuo, Gandhi, Zia, & Paszek, 2018; Paszek et al., 2014). Of the mucin family members, Mucin-1 (Muc1) is recognized as an anti-adhesive protein that can interfere with integrin- and cadherin-mediated cell interactions (Klinken, Dekker, Buller, & Einerhand, 1995; Wesseling, Valk, & Hilkens, 1996; Wesseling, van der Valk, Vos, Sonnenberg, & Hilkens, 1995). The anti-adhesive properties of Muc1 are conferred by its large ectodomain, which is heavily 0-glycosylated during trafficking to the cell surface. Neutral and anionic sugar residues of the glycans can coordinate with water to form a highly hydrated barrier on the cell surface (Gendler & Spicer, 1995).

In this Part II, novel mucin cDNAs and mucins encoded by them are described and used to create a genetically-encoded technology for reduction of aggregation of human-cell host production systems. In particular, the presently described mucin technology is improved, tested, and refined for use, for example, as an anti-adhesive coating on host-cell production systems. As a non-limiting demonstration, we develop new 293-F cell lines with stable anti-adhesive coatings and evaluate their performance in regards to proliferation rate, cell aggregation, resistance to shear stress, and efficiency of transfection with plasmid DNA.

Materials and Methods

Antibodies and Reagents

The following antibodies were used: Human CD227 (555925, BD Biosciences) (Muc1), β-Actin (sc-4778, Santa Cruz), Goat anti-Mouse IgG-HRP (sc-2005, Santa Cruz). Lectins used were: Biotinylated Peanut Agglutinin (PNA; B-1075, Vector Laboratories), CF568 PNA (29061, Biotium), CF640R PNA (29063, Biotium), CF633 Wheat Germ Agglutinin (WGA; 29024, Biotium). Biotinylated lectins were detected using ExtrAvidin-Peroxidase (E2886, Sigma). To induce transactivator cell lines, doxycycline was used (sc-204734, Santa Cruz). For gentamycin selection, G418 was used (10131035, Thermo Fisher).

Constructs

A tetracycline-inducible, transposon based Piggybac expression vector with an integrated, co-expressed reverse tetracycline transactivator gene (pPB tet rtTA NeoR) was used for stable line generation. The pPB tet rtTA NeoR plasmid was modified by the insertion of the internal ribosome entry site (IRES) of the encephalomyocarditis virus followed by the fluorescent protein copGFP into the NotI and XbaI sites (pPB tet IRES GFP rtTA NeoR). Synthetic cDNAs containing either 21 or 42 tandem repeats (TR) of the amino acid sequence PDTRPAPGSTAPPAHGVTSA (SEQ ID NO:8) were codon optimized with codon scrambler (Tang & Chilkoti, 2016), generated through custom gene synthesis (General Biosystems), and cloned in place of the native tandem repeats in pcDNA3.1 Muc1 TM21—previously described in (Paszek et al., 2014; Shurer et al., 2017)—using the BamHI and Bsu36I restriction sites. The Muc1 gene containing the engineered 21 or 42 tandem repeats was then cloned into the pPB tet IRES GFP rtTA NeoR plasmid using the BamHI and EcoRI sites to generate Muc1 42TR TM21 pPB tet IRES GFP rtTA NeoR and Muc1 21TR TM21 pPB tet IRES GFP rtTA NeoR plasmids used to make the Mucin-270 and Mucin-135 biopolymer cell lines, respectively. To produce the Mucin-0 cell line, the native Muc1 tandem repeats were deleted from the pcDNA3.1 Muc1 TM21 through Q5 site directed mutagenesis with 5'-TGGAGGAGCCTCAGGCATACTTTATTG-3' ((SEQ ID NO:14) forward) and 5'-CCACCGCCGACCGAGGTGACATCCTG-3' ((SEQ ID NO:15) reverse) primers. The Muc1 gene with 0TR was then cut from the pcDNA3.1 Muc1 0TR TM21 and cloned into the pPB tet IRES GFP rtTA NeoR plasmid via the BamHI and EcoRI sites. The plasmid pLV puro mRuby2 was used for transient transfection experiments with cytoplasmic red fluorescent protein (RFP). For secreted RFP experiments, SS-mScarlet-I pPB tet TRES GFP rtTA NeoR plasmid was used. To construct this plasmid, the backbone was linearized using BamHI-HF and EcoRI-HF. A dsDNA oligo encoding the Muc1 signal sequence (MTPGTQSPFFLLLLLTVLTVVTGS (SEQ ID NO:26)) fused by a linker (four Glycines followed by a Serine) to mScarlet-I was ordered from Integrated DNA Technologies. This fragment was inserted into the linearized backbone via NEB HiFi Assembly.

Cell Lines and Culture

FreeStyle 293-F Cells were obtained from Thermo Fisher Scientific. Cells were cultured and maintained according to the manufacturer's guidelines in an Eppendorf New Brunswick s4li incubator in Erlenmeyer flasks. Cells were maintained between $0.5\times10^6$ and $3\times10^6$ cells/mL at 120 rpm, 37° C., and 8% $CO_2$ in FreeStyle 293 Expression Medium (Thermo). Transfections were performed using polyethyleneimine (PEI) as previously reported (Durocher et al., 2002). Genetically-encoded stable cell lines were created by co-transfection of the pPB tet IRES GFP rtTA NeoR plasmids described above with a hyperactive transposase plasmid (Shurer et al., 2017) and subsequently selected with 750 g/mL of gentamycin for two weeks. Cell proliferation was quantified by cell counting on a hemocytometer with trypan blue exclusion.

Confocal Microscopy

Samples were collected, pelleted at 200 rcf for 5 min, and fixed in 4% paraformaldehyde for 10 minutes at room temperature. Samples were washed three times with PBS. Cells were labeled with 1:1000 CF568 PNA for O-glycans and 1:1000 CF633 WGA for the cell membrane in PBS for 30 minutes at room temperature. Samples were washed three times with PBS and imaged on a Zeiss LSM800 with a 63× water immersion objective.

Flow Cytometry Analysis

All samples were measured using live cells, unless otherwise indicated. Cells were harvested from suspension culture, pelleted at 200 rcf for 5 min, and resuspended in 0.5% BSA PBS. Samples were filtered through a 0.22 μm filter cap and analyzed on a BD FACS Aria Fusion. For the doxycycline time-course, cells were induced with 1 μg/mL of doxycycline. Cellular samples from the cultures were taken at the indicated time points, pelleted at 200 rcf for 5 min, and fixed with 4% paraformaldehyde for 10 min at room temperature. Samples were rinsed three times with PBS and stored at 4° C. until flow cytometry analysis. Analysis of all flow cytometry data was performed using FlowJo software.

Immuno- and Lectin Blot Analysis

Cells are inoculated at $0.5\times10^6$ cells/mL and grown overnight, 16-18 hr. Biopolymer expression was then induced with 1 μg/mL doxycycline, and cells were grown with doxycycline for an additional 48 hr. After 48 hr, a sample was taken for each cell line, pelleted at 200 rcf for 5 min before the supernatant was separated, and the cell pellet was lysed by resuspending in RIPA lysis buffer (Abcam), vortexing the sample for 30 seconds, and heating to 98° C. for 10 min. Lysates were frozen on liquid nitrogen and stored at −80° C. Lysates were separated on Nupage 3-8% Tris-Acetate gels (Invitrogen) and transferred to PVDF membranes. Membranes were blocked with 3% BSA TBST for 2 hr. Primary antibodies were diluted 1:1000 and lectins were diluted to 1 μg/mL in 3% BSA TBST and incubated on membranes overnight at 4° C. Secondary antibodies or ExtrAvidin were diluted 1:2000 in 3% BSA TBST and incubated for 2 hr at room temperature. Blots were developed in Clarity ECL (BioRad) substrate and imaged on a ChemiDoc (BioRad) documentation system.

PCR Amplification of Mucin-270 Transgene in the Transfected 293F Cells

To test for amplification or deletion of stably integrated Mucin-270 cDNAs in 293F genomes, PCR amplification was performed with Q5 Hot start high-fidelity DNA polymerase (New England Biolabs Inc., Ipswich, MA) using extracted genomic DNA as the template. Genomic DNA was extracted with GeneJET genomic DNA purification kit (Thermo Scientific., Waltham, MA). A total of 60 ng of genomic DNA was used for PCR amplification. Primers: Mucin-270 FWD 5'-ATGACACCGGGCACCCAGTC-3' (SEQ NO:85) and Mucin-270 REV 5'-CTACATACTTCGTCGGCGCATGTAC-3' (SEQ NO:86). Size of amplicon is 2994 bp.

Cell Clumping Analysis

Cells were inoculated at $0.75\times10^6$ cells/mL and induced with 1 μg/mL doxycycline after overnight growth (16-18 hr). Cells were then grown to a high cell density for an additional 48 or 72 hr in the presence of 1μ/mL doxycycline. Cell density was quantified by collecting sample of the culture, mixing thoroughly to dissociate large clumps, and counting viable cells with a hemocytometer and trypan blue exclusion. For imaging, samples were drawn with wide-bore pipette tips to reduce dissociation of large clumps and diluted in PBS to approximately $6.75\times10^4$ cells/cm$^2$ for imaging in 2D. Phase contrast images were acquired on an Olympus IX81 microscope with a 10× objective. Fiji was used for image processing (Schindelin et al., 2012). Two independent samples were collected and prepared as technical replicates for imaging with three regions of interest imaged per technical replicate. Three biological replicates were performed. Automated image analysis was performed using custom analysis software adapted from a previous publication (Shurer et al., 2017). Briefly, the analysis software located the center of each circular object. The coordinates of each cell's center were then used to calculate the Ripley's K function in MATLAB. The percent of single cells was calculated by counting the total number of cells which do not have any neighboring cells within 19 μm and dividing by the total number of cells in the image. Similarly, the percent of cells in various cluster sizes was calculated by binning the cells into clusters based on the number of neighboring cells within 19 μm.

To evaluate resistance to calcium induced cell aggregation, cultures were inoculated at $0.5\times10^6$ cells/mL and induced with 1 μg/mL doxycycline after overnight growth (16-18 hr). After 48 hr, cells were resuspended at $4\times10^6$ cells/mL. The culture media was then supplemented with 2 mM $CaCl_2$), 1:300 anti-clumping agent (Thermo Fisher, 0010057AE), or both. Still images and videos of the cell suspension were acquired after 24 hr of treatment by transferring the culture to a glass test tube. The concentration of cells in suspension was determined by collecting duplicate samples from each culture after allowing the largest aggregates to settle out of suspension for 20 seconds. Cell concentration was measured using a hemocytometer and Trypan blue.

Shear Stress Experiments

Cells were inoculated at $0.5\times10^6$ cells/mL, grown overnight (16-18 hr), and induced with 1 μg/mL doxycycline for 48 hr. Using a 5 mL syringe with a 16-gauge needle connected to 6.5 in of 1.02 mm silicon tubing, cell suspensions were sheared by flowing through a 500 m constriction (Teflon tubing) at a constant force generated by a 1 kg mass applied to a syringe with gravity. Samples were passed through the constriction five times. Cells were then stained with 1 μg/mL CF640R PNA for 15 min at 4° C. Cells were washed with 0.5% BSA PBS three times and then stained with Ethidium homodimer-1 (dead cell stain, Thermo Fisher, L3224). Three biological replicates were performed, with two technical replicates for each biological replicate. Percent dead cells was determined by measuring the fraction of cells that had taken up the dead cell stain on a BD FACS Aria Fusion. A control sample without shear was used to subtract background cell death for each cell line. For Mucin-135 and Mucin-270 cell lines, only PNA positive cells were considered for analysis. Data analysis was performed using FlowJo software.

Transfection Experiments

Cells were inoculated at $0.5\times10^6$ cells/mL, grown overnight (16-18 hr), and induced with 1 μg/mL doxycycline for 48 hr. Cells were then diluted to $2\times10^6$ cells/mL in fresh medium containing 1 μg/mL doxycycline and transfected with 1 μg DNA per $10^6$ cells. The next day (16-18 hr post-transfection), cells were diluted 1:1 with fresh medium containing 1 g/mL doxycycline. To measure transfection efficiency, cells were transfected with the pLV puro mRuby2 plasmid and transfection efficiency was calculated by flow cytometry as the fraction of cells expressing RFP 72 hr post transfection. For production and secretion of recombinant RFP, cells were transfected with SS-mScarlet-I pPB tet IRES GFP rtTA NeoR. After 24 hr, secreted RFP fluorescence in the media supernatant was quantified using a Tecan M1000 Pro plate reader.

Statistical Analysis

Statistical significance was determined by ordinary one-way ANOVA or Student's t test (two-tailed) as appropriate using Prism (GraphPad). All graphs were generated in Prism (Graphpad) except for boxplot which were generated in R.

Results

Genetically-Encoded Biopolymers Expressed on the Surface of 293-F Cell Lines

This Part II demonstrates creation of cDNAs that encode Muc1-like biopolymers with transmembrane domains for anchorage to the cell surface. The biopolymer domains consisted of an unstructured protein backbone with 0-42 perfect repeats of PDTRPAPGSTAPPAHGVTSA (SEQ ID NO:8), which is recognized by the O-glycosylation machinery of the endoplasmic reticulum and Golgi apparatus and heavily glycosylated while trafficked to the cell surface. Each biopolymer was targeted to the extracellular space by the native Muc1 signal sequence. The biopolymers were anchored to the cell membrane with a 21-amino acid transmembrane domain (Mercanti et al., 2010; C. R. Shurer et al., 2017). By replacing the native autocatalytic domain of Muc1 (Levitin et al., 2005) with the engineered 21-amino acid transmembrane domain, we mitigated the risk of ectodomain shedding from the cell surface. The described engineered constructs also lacked a cytoplasmic tail to avoid inadvertent transduction of biochemical or physical stimuli by the mucins.

The genetic modification of the 293-F cell line was performed non-virally with an "all-in-one plasmid" that contained all necessary elements for selection and tetracycline-inducible expression (FIG. 12A). The vector included a tetracycline-responsive promoter for expression of the biopolymer coating and an additional cassette for constitutive expression of the reverse tetracycline transactivator (rtTA-M2) and neomycin-resistance gene (Gossen, Bender, Muller, al, & Freundlieb, 1995). A bicistronic green fluorescent protein (GFP) reporter was also included for visual confirmation of transcription of the mucin cDNA. The cDNA for the biopolymers was stably incorporated into the genome at random locations by transposon mediated integration (X. Li et al., 2013; Wilson, Coates, & George, 2007; Woodard & Wilson, 2015). This approach avoided the use of any viral technology, which poses a serious safety concern in bio-manufacturing (Dumont et al., 2016). We predicted that the modified cells would be coated with a dense, inducible layer of mucin biopolymers on their surface (FIG. 12B).

We tested three different representative biopolymers size for their effects on 293-F cell aggregation. Mucin-like genes with 0, 21, and 42 tandem repeats were constructed. The contour lengths of the polymers with 21 and 42 repeats were predicted to be 135 nm and 270 nm, respectively. We therefore designated the biopolymers Mucin-0, Mucin-135, and Mucin-270 based on the relative length of the biopolymer (FIG. 12C). Because it lacks the large, glycosylated biopolymer domain, the Mucin-0 construct served as a control for any effects related to expression of the transmembrane anchor of the biopolymer.

We confirmed the expression and localization of the biopolymers to the cell surface. Fluorescent microscopy showed expression of the cDNA, reported by the bicistronic GFP signal, and the presence of O-glycans on the membrane of cells expressing the Mucin-135 and Mucin-270 semi-synthetic genes (FIG. 13A). We observed a large distribution of biopolymer expression levels, which without intended to be constrained by any particular theory is attributed to the randomized transposition of the cDNAs into the genome (FIG. 2B). Despite the broad distribution, a large portion of the cell populations had stably integrated the cDNA, as shown by the GFP reporter (FIG. 13A-C). The expression and size of the biopolymers was further validated by Western blot (FIG. 13D). Both the Mucin-135 and Mucin-270 could be probed with antibodies against the native Muc1 tandem repeats (FIG. 13D, left). Wild-type (w.t.) cells had no detectable level of endogenous Muc1 expression and no significant O-linked mucin-like glycosylation (FIG. 13D). The Mucin-135 and Mucin-270 were heavily glycosylated when expressed. This is shown by the protein bands which are detected above the protein sequence molecular weight when probing with anti-Muc1 antibodies (FIG. 13D, left; predicted molecular weights 81 kDa and 120 kDa for Mucin-135 and Mucin-270, respectively). O-glycosylation is further demonstrated by the detection of the biopolymer with PNA which binds specifically to O-linked glycans such as those found on Muc1 (FIG. 13D, right).

No significant difference in cell proliferation rate was observed for any of our biopolymer-coated cell lines (FIG. 13E). We concluded that the additional protein load of our biopolymers did not adversely affect the rapid growth rate of parental 293-F cells. For a stable cell line, we used the well characterized reverse-tetracycline inducible promoter (Gossen et al., 1995) which initiates gene transcription upon addition of doxycycline and halts transcription on withdrawal of doxycycline. This cell line responded as predicted to induction by doxycycline, demonstrating temporal control over expression of the mucin coating (FIG. 13F).

Highly repetitive cDNAs, such as mucins, are reported to have higher frequencies of amplification and deletion in the cellular genome (Gemayel, Vinces, Legendre, & Verstrepen, 2010; Oren et al., 2016). The cDNAs for our Mucin-135 and Mucin-270 constructs were codon optimized to minimize their repetitiveness. We found that the optimized cDNAs were stable when integrated in the host cell genome. Notably, no noticeable amplification or deletion of stably integrated Mucin-270, the largest and most repetitive of our biopolymer cDNAs, was observed after 2 months of cell culture (FIG. 13G).

Biopolymer Coatings Reduced Cell Aggregation

After establishing stable populations, we analyzed whether the biopolymer coatings could reduce cell aggregation in suspension cell cultures. Phase contrast images of the cell lines qualitatively showed more cell aggregates in the w.t. and Mucin-0 cell lines than in the Mucin-135 and Mucin-270 lines (FIG. 14A). Quantification of the fraction of single cells in the sample showed an increase in the percent of single cells for the Mucin-135 and Mucin-270 coatings compared to the w.t. cells, while the Mucin-0 line showed no difference compared to w.t. cells (FIG. 12B, FIG. 19A). Correspondingly, w.t. and Mucin-0 coated cell lines were much more likely to form clusters of two or more cells than Mucin-135 or Mucin-270 cell lines (FIG. 14C, FIG. 19B).

Inspection of phase contrast images of our 293-F lines engineered with Mucin-135 or Mucin-270 revealed that the majority of cells were singlets or doublets with few detectable higher order aggregates (FIG. 14B). Because of the absence of higher order aggregates, we reasoned that the doublets in the Mucin-135 and Mucin-270 samples may be actively dividing cells or cells that have yet to full disassociate following cytokinesis. The appearance of doublets can also result from single cells randomly settling out of suspension too near each other to resolve in the 2D plane of the image formed on our microscope. To approximate the frequency of single cells which could randomly settle out of suspension in such a way, we created a simulated dataset of randomly placed centroids and conducted our clustering analysis. On average, the simulated centroids would be counted as singlets 66% of the time. By comparison, 57% of the Mucin-270 cells were singlets (FIG. 14B).

To quantify the extent of cell clustering, we analyzed the spatial distribution of cells in the image using the Ripley's K function, a spatial distribution statistic that counts the frequency at which neighboring particles are found within a given distance of any given particle. Using this statistical tool, we observed that the Mucin-135 and Mucin-270 biopolymers show decreased clustering compared to the w.t. and Mucin-0 cell lines (FIG. 14D, FIG. 19C).

Mucin-270 Coatings Outperformed Commercially Available Anti-Clumping Agent

We found that the Mucin-270 biopolymer coating could reduce cell aggregation even in extreme pro-clumping conditions. Suspension adapted cell lines have previously been shown to significantly aggregate under specific media conditions, such as high calcium concentrations that are known to promote engagement of cadherins (Dee et al., 1997; Han et al., 2006b; Kim, Tai, Mok, Mosser, & Schuman, 2011; Meissner et al., 2001; Peshwa et al., 1993; Sjaastad & Nelson, 1997; Tolbert et al., 1980; Yamamoto et al., 2000; Zanghi et al., 2000). When cultured in high calcium conditions (2 mM $CaCl_2$)), the Mucin-270 biopolymer coated cells showed qualitatively less aggregation than w.t. cells (FIG. 15A). Notably, cultures with Mucin-270 biopolymer coatings retained their turbidity in the pro-clumping conditions, whereas unmodified cells assembled into large clusters easily visible to the naked eye (FIG. 15A). Mucin-270-coated cells show a slight decrease in concentration of cells in suspension upon calcium treatment while w.t. cells have essentially no cells remaining in suspension (FIG. 15B).

Further, the Mucin-270 coating outperforms a commercially available anti-clumping agent in highly aggregating conditions. Under high calcium conditions, anti-clumping agent had no discernable efficacy in mitigating cell clumping (FIG. 15A). Addition of commercial anti-clumping agent to Mucin-270 coated cells did not further enhance their resistance to clumping in our assays (FIG. 15B). Together, these results demonstrated the ability of the presently provided genetically-encoded biopolymer coatings to reduce cell aggregation in suspension.

Biopolymer Coatings Provided Resistance to Shear Stress

The sensitivity of suspension-adapted mammalian cells to shear stresses imposes a limit on the rate of mixing and mass transfer in typical bioreactors (Hu, Berdugo, & Chalmers, 2011). Large volume bioreactors operated at high-cell densities require increased mixing to overcome mass transfer limitations (Hu et al., 2011). Thus, cellular sensitivity to shear places another limit on bioreactor productivity. Because protection of ductal epithelial cells to shear stress is a physiological function of mucins, we considered whether, as an added benefit, our biopolymer coatings protect cells from shear stresses. To test this, suspended cells were sheared by passage through a narrow constriction and then analyzed for viability after reintroduction into culture (FIG. 16A). A 1 kg mass was applied to a vertically-oriented syringe to generate a constant and controlled pressure that drove the flow of suspended cells through a 7.6 cm length of 500 μm diameter Teflon tubing. Cell death was analyzed by flow cytometry using a live/dead cell stain. We found that the Mucin-135 and Mucin-270 biopolymer-coated cell lines had significantly greater viability after shearing compared to both w.t. and Mucin-0 cell lines (FIG. 16B), suggesting that the mucin coatings could allow for higher mixing rates in the bioreactor.

Biopolymer Coated Cell Lines can be Transiently Transfected and Produced Comparable Levels of Recombinant Protein The use of transient transfection of cells for recombinant protein production has recently become of interest to avoid the long development times associated with selection and isolation of stable cell lines for production of new pharmaceuticals (Derouazi et al., 2004; Durocher et al., 2002; Swiech et al., 2011). Given the potential barrier effect of a mucopolysaccharide coating on the cell surface, we tested whether expression of the presently provided biopolymers would affect transfection efficiency of the cell lines. To test, we transiently transfected cell lines with a plasmid for expression of cytoplasmic red-fluorescent protein. We observed no statistically significant difference in the transfection efficiency of the Mucin-0, Mucin-135, or Mucin-270 cell lines compared to the w.t. cells (FIG. 17A). Single-cell analysis revealed similar distributions of recombinant protein production across the engineered and parental cell populations (FIG. 17B). Further, there is no significant difference in the RFP signal of transfected cells, indicating comparable expression of transiently transfected proteins in the different cell lines (FIG. 17C). We also tested the performance of the engineered cells for production of secreted recombinant proteins. As non-limiting example, we fused a signal peptide to the fluorescent protein, mScarlet-I, and measured production of the secreted protein in medium supernatant from transiently transfected cultures. Mucin-270 coated cells produced the same quantities of secreted recombinant protein as w.t. cells (FIG. 18). Thus, the described biopolymer coatings did not adversely affect transfection efficiency and high protein production rate of the 293-F cell system.

Discussion of Part II

This Part II demonstrates, among other features, that established cell lines can be genetically modified to express engineered mucin biopolymers for anti-adhesion. Expression of these biopolymers does not negatively impact the desirable characteristics of 293-F cells, including their fast proliferation rates (FIG. 12E) and high transfection efficiencies (FIG. 15A, B). Moreover, the expression of the biopolymers significantly reduces undesirable cell clumping (FIG. 14, FIG. 15, FIG. 19) and enhances resistance of the cells to shear forces (FIG. 6). Mucin-135 coating and thicker Mucin-270 coatings performed similarly in head-to-head tests and are expected to be equally well-suited for the applications described herein.

The described biopolymer coatings provide a significant reduction of cell aggregation in serum-free media formulations that are typically used for production in bioreactor formulations. Notably, the coatings could reduce aggregation further even in media formulations that were designed to minimize cell clumping (eg. Invitrogen Freestyle 293-F media). The disclosure includes biopolymer expression on cell aggregation in media formulations that have historically been avoided due to issues of cell aggregation. For example, highly efficient transient transfections have long been performed with DNA-calcium phosphate precipitates (Jordan & Wurm, 2004). However, at the high calcium concentrations required, 293-F cells are known to form large cell aggregates (Meissner et al., 2001; Peshwa et al., 1993). Based on results of this Part II results (FIG. 15), use of the Mucin-135 or Mucin-270 coatings significantly reduce cell aggregation in such conditions for improved protein production from transiently transfected cultures.

The disclosure includes further improvements of the described mucin coating can be achieved through additional optimization of the engineered mucins and their regulated expression. Notably, excessive over-production of highly glycosylated mucin-like proteins could possibly compete with recombinant glycoproteins for the cellular glycosylation machinery and the nucleotide sugar building blocks of glycans. Shedding of the engineered mucins from the cell surface is mitigated by the described selection of a membrane anchor, which lacks a proteolytic cleavage site.

The mucin approached described herein can be employed as a solution for suspension-adapted suspension systems that tend to aggregate in the bio-reactor. But it will be recognized that the ability of these compositions to protect cells and strongly resist clumping could also benefit current bio-manufacturing platforms, like CHO cells, which can still aggregate under non-ideal reactor conditions or in non-optimal media formulations. As bio-manufacturing looks beyond CHO systems for next-generation production platforms that mitigate the risk of non-human glyco-conjugates and other antigenic epitopes, adaptation to growth in suspension remains a significant and time-consuming challenge for human, primate, and many other mammalian cell lines (Amaral et al., 2016; Rodrigues et al., 2013). By promoting cell viability and minimizing aggregation, the presently provided compositions can be expected to help overcome some of the significant barriers to suspension adaptation.

Taken together, this Part II presents a mucin coating technology for improved single-cell growth of cells in suspension. The system was largely successful in mitigating cell aggregation.

REFERENCES

Amaral, R. L. F. do, Bomfim, A. de S., Abreu-Neto, M. S. de, Picanço-Castro, V., Russo, E. M. de S., Covas, D. T., & Swiech, K. (2016). Approaches for recombinant human factor IX production in serum-free suspension cultures. *Biotechnology Letters,* 38(3), 385-394. //doi.org/10.1007/s10529-015-1991-1

Carter, P. J. (2011). Introduction to current and future protein therapeutics: A protein engineering perspective. *Experimental Cell Research,* 317(9), 1261-1269. //doi.org/10.1016/j.yexcr.2011.02.013

Casademunt, E., Martinelle, K., Jernberg, M., Winge, S., Tiemeyer, M., Biesert, L., . . . Schroder, C. (2012). The first recombinant human coagulation factor VIII of human origin: human cell line and manufacturing characteristics. *European Journal of Haematology,* 89(2), 165-176. //doi.org/10.1111/j.1600-0609.2012.01804.x Dee, K. U., Shuler, M. L., & Wood, H. A. (1997). Inducing single-cell suspension of BTI-TN5B1-4 insect cells: I. The use of sulfated polyanions to prevent cell aggregation and enhance recombinant protein production. *Biotechnology and Bioengineering,* 54(3), 191-205. //doi.org/10.1002/(SICI)1097-0290(19970505)54:3<191::AID-BIT1>3.0.CO; 2-A Derouazi, M., Girard, P., Van Tilborgh, F., Iglesias, K., Muller, N., Bertschinger, M., & Wurm, F. M. (2004). Serum-free large-scale transient transfection of CHO cells. *Biotechnology and Bioengineering,* 87(4), 537-545. //doi.org/10.1002/bit.20161

Dumont, J., Euwart, D., Mei, B., Estes, S., & Kshirsagar, R. (2016). Human cell lines for biopharmaceutical manufacturing: history, status, and future perspectives. *Critical Reviews in Biotechnology,* 36(6), 1110-1122. //doi.org/10.3109/07388551.2015.1084266

Durocher, Y., Perret, S., & Kamen, A. (2002). High-level and high-throughput recombinant protein production by transient transfection of suspension-growing human 293-EBNA1 cells. *Nucleic Acids Research,* 30(2), e9.
Gemayel, R., Vinces, M. D., Legendre, M., & Verstrepen, K. J. (2010). Variable tandem repeats accelerate evolution of coding and regulatory sequences. *Annual Review of Genetics,* 44, 445-477. //doi.org/10.1146/annurev-genet-072610-155046
Gendler, S. J., & Spicer, A. P. (1995). Epithelial Mucin Genes. *Annual Review of Physiology,* 57(1), 607-634. //doi.org/10.1146/annurev.ph.57.030195.003135
Ghaderi, D., Zhang, M., Hurtado-Ziola, N., & Varki, A. (2012). Production platforms for biotherapeutic glycoproteins. Occurrence, impact, and challenges of non-human sialylation. *Biotechnology & Genetic Engineering Reviews,* 28, 147-175.
Gossen, M., Bender, G., Muller, G., al, et, & Freundlieb, S. (1995). Transcriptional activation by tetracyclines in mammalian cells. *Science,* 268(5218), 1766.
Han, Y., Liu, X.-M., Liu, H., Li, S.-C., Wu, B.-C., Ye, L.-L., . . . Chen, Z.-L. (2006a). Cultivation of Recombinant Chinese hamster ovary cells grown as suspended aggregates in stirred vessels. *Journal of Bioscience and Bioengineering,* 102(5), 430-435. //doi.org/10.1263/jbb.102.430
Han, Y., Liu, X.-M., Liu, H., Li, S.-C., Wu, B.-C., Ye, L.-L., . . . Chen, Z.-L. (2006b). *Journal of Bioscience and Bioengineering,* 102(5), 430-435. //doi.org/10.1263/jbb.102.430
Hu, W., Berdugo, C., & Chalmers, J. J. (2011). The potential of hydrodynamic damage to animal cells of industrial relevance: current understanding. *Cytotechnology,* 63(5), 445-460. //doi.org/10.1007/s10616-011-9368-3
Jay, G. D., & Waller, K. A. (2014). The biology of Lubricin: Near frictionless joint motion. *Matrix Biology,* 39, 17-24. //doi.org/10.1016/j.matbio.2014.08.008
Jordan, M., & Wurm, F. (2004). Transfection of adherent and suspended cells by calcium phosphate. *Methods,* 33(2), 136-143. //doi.org/10.1016/j.ymeth.2003.11.011
Kim, S. A., Tai, C.-Y., Mok, L.-P., Mosser, E. A., & Schuman, E. M. (2011). Calcium-dependent dynamics of cadherin interactions at cell-cell junctions. *Proceedings of the National Academy of Sciences,* 108(24), 9857-9862. //doi.org/10.1073/pnas.1019003108
Klinken, B. J. V., Dekker, J., Buller, H. A., & Einerhand, A. W. (1995). Mucin gene structure and expression: protection vs. adhesion. *American Journal of Physiology—Gastrointestinal and Liver Physiology,* 269(5), G613-G627.
Kuo, J. C.-H., Gandhi, J. G., Zia, R. N., & Paszek, M. J. (2018). Physical biology of the cancer cell glycocalyx. *Nature Physics,* 14(7), 658-669. //doi.org/10.1038/s41567-018-0186-9
Leader, B., Baca, Q. J., & Golan, D. E. (2008). Protein therapeutics: a summary and pharmacological classification. *Nature Reviews Drug Discovery,* 7(1), 21-39. //doi.org/10.1038/nrd2399
Levitin, F., Stem, O., Weiss, M., Gil-Henn, C., Ziv, R., Prokocimer, Z., . . . Wreschner, D. H. (2005). The MUC1 SEA module is a self-cleaving domain. *The Journal of Biological Chemistry,* 280(39), 33374-33386. //doi.org/10.1074/jbc.M506047200
Li, L., Qin, J., Feng, Q., Tang, H., Liu, R., Xu, L., & Chen, Z. (2011). Heparin Promotes Suspension Adaptation Process of CHO-TS28 Cells by Eliminating Cell Aggregation. *Molecular Biotechnology,* 47(1), 9-17. //doi.org/10.1007/si2033-010-9306-1
Li, X., Burnight, E. R., Cooney, A. L., Malani, N., Brady, T., Sander, J. D., . . . Craig, N. L. (2013). piggyBac transposase tools for genome engineering. *Proceedings of the National Academy of Sciences,* 110(25), E2279-E2287. //doi.org/10.1073/pnas.1305987110
Liu, M., & Goudar, C. T. (2013). Gene expression profiling for mechanistic understanding of cellular aggregation in mammalian cell perfusion cultures. *Biotechnology and Bioengineering,* 110(2), 483-490. //doi.org/10.1002/bit.24730
Meissner, P., Pick, H., Kulangara, A., Chatellard, P., Friedrich, K., & Wurm, F. M. (2001). Transient gene expression: recombinant protein production with suspension-adapted HEK293-EBNA cells. *Biotechnology and Bioengineering,* 75(2), 197-203.
Mercanti, V., Marchetti, A., Lelong, E., Perez, F., Orci, L., & Cosson, P. (2010). Transmembrane domains control exclusion of membrane proteins from clathrin-coated pits. *J Cell Sci,* 123(19), 3329-3335. //doi.org/10.1242/jcs.073031
Oren, M., Barela Hudgell, M. A., D'Allura, B., Agronin, J., Gross, A., Podini, D., & Smith, L. C. (2016). Short tandem repeats, segmental duplications, gene deletion, and genomic instability in a rapidly diversified immune gene family. *BMC Genomics,* 17. //doi.org/10.1186/s12864-016-3241-x
Park, J. H., Lim, M. S., Woo, J. R., Kim, J. W., & Lee, G. M. (2016). The molecular weight and concentration of dextran sulfate affect cell growth and antibody production in CHO cell cultures. *Biotechnology Progress,* 32(5), 1113-1122. //doi.org/10.1002/btpr.2287
Paszek, M. J., DuFort, C. C., Rossier, O., Bainer, R., Mouw, J. K., Godula, K., . . . Weaver, V. M. (2014). The cancer glycocalyx mechanically primes integrin-mediated growth and survival. *Nature,* 511(7509), 319-325. //doi.org/10.1038/nature13535
Peshwa, M. V., Kyung, Y.-S., McClure, D. B., & Hu, W.-S. (1993). Cultivation of mammalian cells as aggregates in bioreactors: Effect of calcium concentration of spatial distribution of viability. *Biotechnology and Bioengineering,* 41(2), 179-187. //doi.org/10.1002/bit.260410203
Rodrigues, M. E., Costa, A. R., Henriques, M., Cunnah, P., Melton, D. W., Azeredo, J., & Oliveira, R. (2013). Advances and Drawbacks of the Adaptation to Serum-Free Culture of CHO-K1 Cells for Monoclonal Antibody Production. *Applied Biochemistry and Biotechnology,* 169 (4), 1279-1291. //doi.org/10.1007/s12010-012-0068-z
Sandberg, H., Kannicht, C., Stenlund, P., Dadaian, M., Oswaldsson, U., Cordula, C., & Walter, O. (2012). Functional characteristics of the novel, human-derived recombinant FVIII protein product, human-cl rhFVIII. *Thrombosis Research,* 130(5), 808-817. //doi.org/10.1016/j.thromres.2012.08.311
Schindelin, J., Arganda-Carreras, I., Frise, E., Kaynig, V., Longair, M., Pietzsch, T., . . . Cardona, A. (2012). Fiji: an open-source platform for biological-image analysis. *Nature Methods,* 9(7), 676-682. //doi.org/10.1038/nmeth.2019
Shukla, A. A., & Thömmes, J. (2010). Recent advances in large-scale production of monoclonal antibodies and related proteins. *Trends in Biotechnology,* 28(5), 253-261. //doi.org/10.1016/j.tibtech.2010.02.001
Shurer, C. R., Colville, M. J., Gupta, V. K., Head, S. E., Kai, F., Lakins, J. N., & Paszek, M. J. (2017). Genetically Encoded Toolbox for Glycocalyx Engineering: Tunable Control of Cell Adhesion, Survival, and Cancer Cell Behaviors. *ACS Biomaterials Science & Engineering*. //doi.org/10.1021/acsbiomaterials.7b00037

Sjaastad, M. D., & Nelson, W. J. (1997). Integrin-mediated calcium signaling and regulation of cell adhesion by intracellular calcium. *BioEssays: News and Reviews in Molecular, Cellular and Developmental Biology,* 19(1), 47-55. //doi.org/10.1002/bies.950190109

Swiech, K., Kamen, A., Ansorge, S., Durocher, Y., Picanço-Castro, V., Russo-Carbolante, E. M., . . . Covas, D. T. (2011). Transient transfection of serum-free suspension HEK 293 cell culture for efficient production of human rFVIII. *BMC Biotechnology,* 11, 114. //doi.org/10. 1186/1472-6750-11-114

Tang, N. C., & Chilkoti, A. (2016). Combinatorial codon scrambling enables scalable gene synthesis and amplification of repetitive proteins. *Nature Materials,* 15(4), 419-424. //doi.org/10.1038/nmat4521

Thornton, D. J., Rousseau, K., & McGuckin, M. A. (2008). Structure and Function of the Polymeric Mucins in Airways Mucus. *Annual Review of Physiology,* 70(1), 459-486. //doi.org/10.1146/annurev-.physiol.70.113006.100702

Tolbert, W. R., Hitt, M. M., & Feder, J. (1980). Cell aggregate suspension culture for large-scale production of biomolecules. *In Vitro,* 16(6), 486-490. //doi.org/10.1007/BF02626461

Tsao, Y. S., Condon, R., Schaefer, E., Lio, P., & Liu, Z. (2001). Development and improvement of a serum-free suspension process for the production of recombinant adenoviral vectors using HEK293 cells. *Cytotechnology,* 37(3), 189-198. //doi.org/10.1023/A:1020555310558

Vink, T., Oudshoorn-Dickmann, M., Roza, M., Reitsma, J.-J., & de Jong, R. N. (2014). A simple, robust and highly efficient transient expression system for producing antibodies. *Methods,* 65(1), 5-10. //doi.org/10.1016/j.ymeth.2013.07.018

Wesseling, J., Valk, S. W. van der, & Hilkens, J. (1996). A mechanism for inhibition of E-cadherin-mediated cell-cell adhesion by the membrane-associated mucin episialin/MUC1. *Molecular Biology of the Cell,* 7(4), 565-577. //doi.org/10.1091/mbc.7.4.565

Wesseling, J., van der Valk, S. W., Vos, H. L., Sonnenberg, A., & Hilkens, J. (1995). Episialin (MUC1) overexpression inhibits integrin-mediated cell adhesion to extracellular matrix components. *The Journal of Cell Biology,* 129(1), 255-265.

Wilson, M. H., Coates, C. J., & George, A. L. (2007). PiggyBac transposon-mediated gene transfer in human cells. *Molecular Therapy: The Journal of the American Society of Gene Therapy,* 15(1), 139-145. //doi.org/10.1038/sj.mt.6300028

Woodard, L. E., & Wilson, M. H. (2015). piggyBac-ing models and new therapeutic strategies. *Trends in Biotechnology,* 33(9), 525-533. //doi.org/10.1016/j.tibtech.2015.06.009

Wurm, F., & Bernard, A. (1999). Large-scale transient expression in mammalian cells for recombinant protein production. *Current Opinion in Biotechnology,* 10(2), 156-159. //doi.org/10.1016/S0958-1669(99)80027-5

Wurm, F. M. (2004). Production of recombinant protein therapeutics in cultivated mammalian cells. *Nature Biotechnology,* 22(11), 1393-1398. //doi.org/10.1038/nbt1026

Yamamoto, S., Matsuda, H., Takahashi, T., Xing, X.-H., Tanji, Y., & Unno, H. (2000). Aggregate formation of rCHO cells and its maintenance in repeated batch culture in the absence of cell adhesion materials. *Journal of Bioscience and Bioengineering,* 89(6), 534-538. //doi.org/10.1016/S1389-1723(00)80052-3

Zanghi, J. A., Renner, W. A., Bailey, J. E., & Fussenegger, M. (2000). The Growth Factor Inhibitor Suramin Reduces Apoptosis and Cell Aggregation in Protein-Free CHO Cell Batch Cultures. *Biotechnology Progress,* 16(3), 319-325. //doi.org/10.1021/bp0000353

Zhu, J. (2012). Mammalian cell protein expression for biopharmaceutical production. *Biotechnology Advances,* 30(5), 1158-1170. //doi.org/10.1016/j.biotechadv.2011.08.022

Part III

This Part III provides representative and non-limiting approaches to stable recombinant production of codon-scrambled lubricin and mucin in human cells. In connection with this, it is known that widespread therapeutic and commercial interest in recombinant mucin technology has emerged due to the unique ability of mucin glycoproteins to hydrate, protect, and lubricate biological surfaces. However, prior to the present disclosure, recombinant production of the large, highly repetitive domains that are characteristic of mucins remained a challenge in bio-manufacturing likely due, at least in part, to the inherent instability of DNA repeats in the cellular genome. To overcome this challenge, this Part III demonstrates exploitation of codon redundancy to encode desired mucin polypeptides with minimal nucleotide repetition. The codon-scrambling strategy was applied to generate synonymous genes, or "synDNAs," for two representative mucins of commercial interest: lubricin and Muc1. Stable, long-term recombinant production in suspension-adapted human 293-F cells was demonstrated for the synonymous lubricin cDNA, which is referred to herein from time to time as "SynLubricin." Under optimal conditions, a 293-F sub-population produced recombinant SynLubricin at more than 200 mg/L of media and was stable throughout two months of continuous culture. Functionality tests confirmed that the recombinant lubricin could effectively inhibit cell adhesion and lubricate cartilage explants. Together, this Part III provides, among other aspects, a viable workflow for cDNA design and stable mucin production in mammalian host production systems.

Part III Introduction

As will be recognized from the foregoing description, mucins are membrane-bound or secreted glycoproteins containing a variable number of tandem repeats that are defined by their densely clustered sites for O-glycosylation (Hang & Bertozzi, 2005). This extensive glycosylation gives rise to a bottlebrush molecular structure that confers mucins with remarkable physical properties (Kuo, Gandhi, Zia, & Paszek, 2018). Mucins at biological interfaces can coordinate with water molecules to form hydrated layers that protect delicate cellular or tissue structures, deter biofouling, and resist pathological cellular deposition (Hattrup & Gendler, 2008). For instance, transmembrane mucins such as Muc1 and Muc16 are densely grafted on the ocular surface, where they maintain hydration, resist abrasion, and provide a selective barrier to macromolecules (Gipson, Spurr-Michaud, Tisdale, & Menon, 2014; Mauris & Argueso, 2012) Similarly, the secreted mucin-like glycoprotein called proteoglycan 4 (PRG4), or lubricin, can bind to cells and tissue interfaces, including the articular cartilage and ocular surfaces, enabling low friction lubrication and protection from pathological cellular deposition and biofouling (Rhee et al., 2005; Schmidt, Sullivan, Knop, & et al., 2013).

Alterations in mucin expression and glycosylation are observed in various pathological conditions, ranging from cancer and inflammatory bowel disease to ocular disease (Dhanisha, Guruvayoorappan, Drishya, & Abeesh, 2018). Patients with genetic mutations that preclude functional lubricin synthesis demonstrate symptoms of Camptodactyly-Arthropathy-Coxa Vara-Pericarditis (CACP) syndrome, including early-onset polyarthropathy as a result of pannus formation and impaired joint lubrication (Bahabri et al., 1998; Marcelino et al., 1999). Decreased synovial fluid lubricin concentrations have also been observed in patients with anterior cruciate ligament injury, osteoarthritis, and rheumatoid arthritis (Elsaid et al., 2008; Kosinska et al., 2015). As such, there has been significant interest in the development of recombinant lubricin and other mucins as injectable therapeutics for osteoarthritis and rheumatic diseases (Le Graverand-Gastineau, 2010) and as topical treatments for chronic dry eye and other conditions that require application of exogenous lubricants (Schmidt et al., 2013).

Despite this commercial interest, recombinant production has proven challenging for Muc1, lubricin, and other mucins that contain a high number of tandem repeats. Although highly productive clones of Chinese Hamster Ovary (CHO) cells have been isolated for a truncated Muc1 with approximately ⅓ of its native tandem repeats, similar attempts to isolate clones for full-length recombinant Muc1 have failed (Backstrom et al., 2003). Likewise, stable clones for recombinant lubricin with the complete 76-78 native tandem repeats produced the glycoprotein at low levels (Jones et al., 2007), but a modified recombinant lubricin protein construct (LUB:1), which contained only ⅓ of the tandem repeats, was more amenable to large scale production (Flannery et al., 2009). More recently, the production of full-length recombinant human lubricin expressed in suspension-adapted CHO cells has been reported and has demonstrated potential as an ocular lubricant for treating dry eye disease or hydrating contact lenses (Samsom et al., 2014). The precise details of how recombinant production was achieved for the full-length lubricin remain proprietary, and at the time of filing of this application or patent, it is believed no published strategy for large-scale lubricin production is available.

The exact biology that underlies the difficulty of producing mucins at high levels remains unclear. However, long, repetitive DNA sequences, such as those common in the cDNAs of mucin tandem repeats, are relatively unstable in the cellular genome (Pearson, Edamura, & Cleary, 2005). The fidelity of nearly all DNA processing steps can be compromised by slippage and other errors linked to repetitive sequences (López Castel, Cleary, & Pearson, 2010). Consequently, repeats can mutate by addition or loss of their unit nucleotide sequence up to 100,000 times more frequently than point mutations in non-repetitive regions (Oren et al., 2016). The variation in tandem repeat numbers for Muc1 and other mucins in humans and mammals provides an evolutionary argument that these genomic cDNAs are mutational hotspots (Gemayel, Vinces, Legendre, & Verstrepen, 2010). Recombination and truncation of exogenous Muc1 cDNAs in bacteria have also been reported, suggesting a high level of instability for these repetitive sequences in host microbial cells, as well (Backstrom et al., 2003).

Now that advances in custom gene synthesis (CGS) enable fast and cost-effective synthesis of long cDNAs (Kosuri & Church, 2014), a new approach to providing improved genomic stability of mucins is provided herein, and in certain embodiments exploits codon redundancy to identify and use synonymous gene sequences that are less repetitive but encode the same desired polypeptide. Such codon optimization algorithms have been developed and successfully applied for elastin-like proteins and some other repetitive protein domains (Tang & Chilkoti, 2016). However, it is believed that, prior to the present disclosure, optimized synthetic cDNAs had not been designed, synthesized and tested for bio-manufacturing of large mucins of commercial interest.

Also, prior to the present disclosure, most biologics, including mucins, have been produced in CHO cells due to their fast growth, adaptability to suspension culture, and capacity for glycosylation and other important post-translational modifications. However, CHO cells can generate glycan epitopes that are now suspected to elicit adverse immunological responses in humans (Butler & Spearman, 2014). Namely, the α1,3-galactosyltransferases of CHO and other non-primate cells produce glycans with Galα1,3-Gal residues that can be immunogenic to humans, apes, and other old-world monkeys that have lost α1,3-galactosyltransferase activity (Bosques et al., 2010; Brooks, 2004). CHO cells also can generate Neu5Gc, a terminal sialic acid that is common in most mammalian cells but has been lost in humans and primates (Ghaderi, Zhang, Hurtado-Ziola, & Varki, 2012). These glycans are of particular concern for recombinant mucins, which can consist of 75% or more carbohydrate by mass and are often highly sialylated (Estrella, Whitelock, Packer, & Karlsson, 2010). Recombinant production of the glycoproteins in human cells would avoid the risk of Galα1,3-Gal and Neu5Gc residues; but, it is beleieved that prior to the present disclosure, no successful attempts at large-scale mucin production in a human cell host production system has been reported.

Thus, the present disclosure demonstrates, in addition to other aspects, that cDNA optimization through codon scrambling is an effective strategy to achieve stable recombinant production of mucins and mucin-like glycoproteins, and that this strategy is viable in suspension-adapted human 293-F cells. Notably, the United States Food and Drug Administration (FDA) has recently approved several biologics produced in 293-F cells, establishing the cell platform as a viable alternative to CHO and other non-human systems for manufacturing specialized therapeutics (Dumont, Euwart, Mei, Estes, & Kshirsagar, 2016). In this disclosure, the codon-scrambling approach is demonstrated for Muc1 and lubricin, and the production strategy is further developed to achieve stable production of a functional, full-length recombinant lubricin. It will be recognized by those skilled in the art, when given the benefit of the present disclosure, the presently described approaches can be used for stable and robust expression of other mucins and mucin-like proteins.

Part II Results

Design and Synthesis of cDNA for Synonymous Lubricin

As an approach for recombinant mucin production, we applied a codon-scrambling and optimization strategy to design synthetic mucin cDNAs within minimal codon repetition (FIG. 20A). A global codon optimization algorithm was applied to find the least repetitive gene sequence that encoded the desired mucin tandem repeats (Tang & Chilkoti, 2016). To tailor the sequences for production in a human host system, such as 293-F, a subsequent optimization was conducted to replace any codons with less than 10% usage frequency in humans (FIG. 20A). We envisioned that the optimized mucin cDNAs could be synthesized through rapid and low-cost services for CGS (Kosuri & Church, 2014; Tang & Chilkoti, 2016). We first tested the strategy for human lubricin, which has approximately 59 tandem repeats with a consensus sequence of KXPXPTTX (SEQ ID NO:87), with KEPAPTTP (SEQ ID NO:1) being the most frequent repeat. For our synthetic lubricin, we optimized the codons for 59 perfect repeats of the KEPAPTTP (SEQ ID NO:1) consensus sequence (FIG. 20B). The protein sequence for the perfect repeats had approximately 88% similarity to the native human PRG4 repeats (FIG. 20C). The synthetic tandem repeats were flanked by additional sequences encoding the native N- and C-termini of human PRG4. These sequences included the native somatomedin and hemopexin domains of lubricin. We also included an IgK leader sequence, 6× histidine tag, and N-terminal SumoStar tag to aid in protein secretion and purification (FIG. 20B). We named the new semi-synthetic gene encoded by the codon-optimized cDNA "synonymous lubricin" or "SynLubricin."

The nucleotides encoding SynLubricin were significantly less repetitive than native PRG4. We analyzed the nucleotide sequences with an alignment algorithm that detects tandem repeats and scores their degree of repetitiveness based on how frequently they repeat and how closely the identified consensus matches the nucleotides of the queried sequence (Benson, 1999). The detected repeats were aligned with the queried sequence through a Smith-Waterman style local alignment, and the overall repetitiveness was scored by assigning +2 for each nucleotide match and −7 for each mismatch or indel (Benson, 1999). Thus, a higher score was indicative of more nucleotide repetition. The tandem repeats of SynLubricin had a modest score of 168, whereas the native PRG4 repeats had a much higher repetition score of 1001. The present disclosure encompasses such sequences, wherein the overall repetitiveness score of a polynucleotide is compared to a suitable control.

We also aligned the amino acids of the SynLubricin tandem repeats to the 59 tandem repeats of human PRG4 isoform A (FIG. 20D). We noted that the perfect repeats of SynLubricin and the native repeats of human PRG4-A have similar compositions of alanine, glutamic acid, lysine, and threonine, while proline content is slightly higher in the SynLubricin repeats (37% vs 30.5%; Part III Supplemental Table 1). The native repeats contain small amounts of asparagine (0.2%), aspartic acid (0.4%), glycine (0.8%), isoleucine (0.2%), leucine (1.4%) and serine (2.6%), which are not contained in SynLubricin (Part III Supplemental Table 1). Thus, in addition to a distinct coding sequence, the amino acid sequence of SynLubricin is distinct from that of human PRG4.

The low-repetition of nucleotides in the SynLubricin gene enabled synthesis of the desired cDNA using available techniques. We also had a cDNA for the native human lubricin/PRG4 sequence through a commercial vendor. However, our attempts to subsequently clone the native PRG4 cDNA sequence into a mammalian expression vector and recombinantly express the product in mammalian cells failed. Consequently, we discontinued further efforts at recombinant production of lubricin with the full-length, native cDNA.

Efforts to produce SynLubricin in transiently transfected mammalian cells were successful. The SynLubricin cDNA was fused to a bicistronic copGFP reporter and transiently transfected into adherent human embryonic kidney 293-T cells. The protein product of the SynLubricin gene was highly glycosylated, as desired, and exhibited the anti-adhesive properties that we predicted. Transfected cells maintained large gaps between cells in the monolayer, particularly at locations where visible copGFP fluorescence reported high expression levels of the bicistronic mRNA (FIG. 26A). We noted that these observations were consistent with the known anti-adhesive functionality of native lubricin (Rhee et al., 2005). In contrast, mock transfected cells grew to a highly confluent monolayer in culture (FIG. 26A). A western blot of the media supernatant from the SynLubricin-transfected cultures revealed a high molecular weight protein of approximately 460 kDa, which was similar in size to the native lubricin that we detected in equine synovial fluid (FIG. 26B). The expected molecular weight of the peptide backbone of SynLubricin was 145 kDa, indicating that SynLubricin was extensively glycosylated.

We next developed strategies for stable production of the synthetic mucins in 293-F suspension cultures. In one embodiment, we created a non-viral transposon vector for "all-in-one" inducible expression of mucins. The vector contained a tetracycline-responsive promoter for inducible expression of the desired gene and a bicistronic copGFP reporter. The vector also contained a second cassette under control of an EF1alpha promoter for expression of the rtTA-M2 tetracycline transactivator and a bicistronic neomycin resistance gene for selection (FIG. 20E). To test the performance of the expression system, we cloned mCherry2 into the vector and transfected 293-F cells with cationic polyethylenimine (PEI) condensates following standard protocols (Boussif et al., 1995; de los Milagros Bassani Molinas, Beer, Hesse, Wirth, & Wagner, 2014; Sonawane, Szoka Jr., & Verkman, 2003). Stable cell populations were isolated after two weeks of selection, and mCherry2 production was validated by flow cytometry. Based on the flow cytometric analysis, we found that stable cells produced high levels of mCherry2, and that the fluorescence readout of the copGFP reporter was generally a good indicator of recombinant protein production (FIG. 27).

Design and Synthesis of cDNA for Synonymous Muc1

We tested whether the described strategy for mucin-type cDNAs was generalizable and could be applied to other mucins. We chose the mucin Muc1, which is important in the hydration and protection of the cornea and other epithelial surfaces (Mantelli & Argüeso, 2008). We noted that the native tandem repeats of Muc1 are polymorphic, with 42 perfect repeats being most frequent in humans (Nath & Mukherjee, 2014). We applied the codon optimization strategy to design a cDNA for 42-perfect Muc1 repeats, PDTRPAPGSTAPPAHGVTSA (SEQ ID NO:8). The optimized sequence was fused to the codons for the native N-terminus of human Muc1. We also added the IgK leader sequence, 6× histidine tag, and SumoStar tag, similarly to SynLubricin (FIG. 28A). We calculated a very high repetition score of 4997 for the nucleotide coding sequence of the native human Muc1 tandem repeats. The repetition score was reduced to 220 in our synthetic cDNA, which we referred to as SynMuc1 (FIG. 28B).

The optimized coding sequence for SynMuc1 was synthesized through standard CGS services, whereas efforts to synthesize the extremely repetitious sequence of the native Muc1 cDNA were not able to be carried out by commercial vendors. The custom synthesized SynMuc1 cDNA was transfected into 293-F cells. The recombinant protein was purified from the media supernatant via immobilized metal affinity chromatography (IMAC) and detected by Western blot with an antibody against the native human tandem repeats (FIG. 28C). The recombinant mucin was extensively O-glycosylated, as indicated by the strong signal when probed with peanut agglutinin (PNA), a lectin that is specific for a core-1, mucin-type disaccharide (FIG. 28D).

During purification, we noticed that a significant percentage of the mucin failed to bind to the IMAC resin and was detected in the flow through (FIG. 28C, D). Western blotting confirmed the presence of the 6×-histidine SumoStar purification tag on the recombinant protein in the flow through and eluted fractions, suggesting that the N-terminus and purification tag were present but inaccessible to the immobilized IMAC cations as would be the case, for example, if the tag was buried in the random coil of the mucin biopolymer (FIG. 28E). Since an objective was to demonstrate the production of the recombinant SynMuc1 and not optimize its purification, alternative chromatography approaches were not explored.

Stable Host Production of Recombinant SynLubricin

Using a transposon system, we tested its application for SynLubricin production (FIG. 21A). Unexpectedly, we found that after selection with G418, comparatively few cells exhibited high copGFP reporter levels following doxycycline induction (FIG. 21). To overcome the issue, we applied a two-round sorting strategy using the copGFP reporter to isolate a sub-population of cells that expressed SynLubricin at high levels. Stable cells were expanded and sorted for the top 5% copGFP expressers, which were then expanded and sorted a second time for the top 10% expressers. We found that the sorting strategy improved SynLubricin production 15-fold and did not impact the molecular weight of the glycosylated protein product (FIG. 21B, C). The sorted cell populations displayed noticeably higher levels of the copGFP reporter after induction with doxycycline, indicating successful isolation of a polyclonal population with higher gene expression levels.

To confirm the cDNA stability of the integrated SynLubricin gene in our stable 293-F cells, genomic DNA was extracted from modified 293-F cells after two months of continuous culture. The SynLubricin cDNA was then amplified by polymerase chain reaction (PCR) using primers that were specific to SynLubricin (FIG. 22). The amplified gene was approximately 4 kb in length, as expected for full-length lubricin, and indistinguishable in size from similarly amplified genes obtained using the original SynLubricin plasmid as the template or DNA extracted from transiently transfected cells (FIG. 22). Even after culture for 2 months, the polyclonal cell population exhibited no indications of SynLubricin gene application or deletion, indicating a high level of genomic stability (FIG. 22).

Optimization of SynLubricin Production

We analyzed whether SynLubricin productivity could be improved through addition of the histone deacetylase inhibitor, valproic acid (VPA), which has previously been shown to drastically increase production of some recombinant proteins in 293-F cells (Backliwal et al., 2008). Our sorted cell population was induced with doxycycline in the presence or absence of 3.5 mM VPA, and media supernatants were sampled each subsequent day from batch cultures. The molecular weights of the protein products were similar, suggesting that VPA did not appreciably affect the total extent of glycosylation of the protein product (FIG. 23A). Interestingly, the recombinant protein levels peaked at approximately 2-3 days post-induction in cultures without VPA and declined rapidly thereafter (FIG. 23B). In VPA treated cultures, SynLubricin levels in the media did not decline as significantly over time. We ruled out protein degradation as a likely explanation for the decline of recombinant protein in cultures without VPA, since we saw no prominent degradation products for lubricin on Western blots (FIG. 23A). We instead considered the possibility that the 293-F culture might consume the recombinant protein in conditions of reduced nutrient availability. Consistent with this possibility, we observed that the decline in recombinant protein levels coincided with the depletion of glucose in the cultures without VPA (FIG. 23C). Metabolic activity largely ceased in VPA treated cultures after 3 days, as indicated by a sharp decline in glucose consumption (FIG. 23C). Thus, VPA may prevent the loss of recombinant protein in batch cultures through slowing 293-F cellular metabolism.

We next scaled up production to 1-liter bioreactors operated in batch mode and conducted two independent production runs with VPA added. Each production run yielded plentiful recombinant protein that was comparable in molecular weight to both recombinant protein isolated from transiently transfected cultures and native lubricin detected in equine synovial fluid (FIG. 23D). An ELISA using purified bovine lubricin as a standard reported approximately 200 mg/L of SynLubricin in the batch runs with our stable 293-F lines. Less than 50% of the stable cell population showed strong expression of the copGFP reporter in the batch bioreactors, suggesting that increases in productivity could likely be achieved with clonal expansion of the production cell line (FIG. 21D). It is possible that ELISA-based quantification with bovine standard may over- or under-estimate SynLubricin levels.

We tested whether stable protein production could be achieved with periodic media changes to avoid nutrient depletion. Conditioned media was harvested from doxycycline-induced cultures that were maintained for 10 consecutive days in the absence of VPA. Media in the batch cultures was exchanged every 48 hrs to replenish nutrients and remove metabolic waste products. Viable cell concentration was also reduced to $1\times10^6$ cells/mL every 48 hrs. SynLubricin production levels were stable over the 10 days of culture, and the SynLubricin molecular weight was constant, indicating that glycosylation was also stable (FIG. 23E). While there appears to potentially be a slight decrease in SynLubricin production with time, there is no significant difference in protein yield (FIG. 23F).

SynLubricin is a Functional Biolubricant

Recombinant SynLubricin was effectively purified with anion-exchange chromatography following our previously reported strategy for isolation of native lubricin from equine synovial fluid, with slight modification from using DEAE-Sepharose® to using Q Sepharose® (Reesink et al., 2016). We also attempted IMAC to purify the native lubricin, but the recombinant SynLubricin had poor affinity to IMAC resins (FIG. 29). As for SynMuc1, we reasoned that the N-terminal histidine-tag could be buried in the large, random coil of the SynLubricin tandem repeats and abandoned the IMAC approach. In contrast, SynLubricin bound to the anion-exchange resin strongly and eluted continuously over high salt concentrations ranging from approximately 350 mM to 1.5 M (FIG. 24A, B). The continuous elution of SynLubricin was likely explained by a varying frequency of anionic sialic acids in the O-glycans of the recombinant SynLubricin (Estrella et al., 2010). We found that a stringent wash step of approximately 500 mM NaCl could remove most protein contaminants detectable by silver stain, although some SynLubricin was inevitably lost to this high-salt wash (FIG. 24C, D).

To ensure functionality of our recombinant SynLubricin, we tested its ability to lubricate cartilage and reduce friction. Recombinant SynLubricin was purified via anion exchange chromatography using the stringent 500 mM NaCl wash step to eliminate most protein contaminants (FIG. 24D). Following purification, SynLubricin was dialyzed in saline and diluted to physiological concentrations. Lubrication was tested on bovine articular cartilage explants where the native lubricin boundary layer had been extracted using a custom linear reciprocating tribometer (Jones et al., 2007). Compared to a saline control, we found that SynLubricin-containing solutions, as well as control synovial fluid, significantly reduced the boundary friction of cartilage explants (FIG. 25; p<0.001 and 0.0001, respectively).

We also tested a small quantity of a second SynLubricin sample that was purified without the stringent wash of the anion exchange column with 500 mM NaCl. Notably, cartilage friction coefficients were markedly lower for this SynLubricin preparation than any of the measured friction coefficients for the more stringently washed SynLubricin preparations (FIG. 25). Low sample volume for the unwashed SynLubricin preparation hindered obtaining enough independent measurements for meaningful statistical comparisons (FIG. 25). However, further optimization of purification conditions using techniques that will be apparent to those skilled in the art, given the benefit of this disclosure, are expected to produce recombinant lubricin fractions with improved performance in bio lubrication. For instance, less negatively charged lubricin fractions that elute at lower salt concentrations (350-500 mM NaCl) are important for cartilage biolubriction either by acting independently or in synergy with more negatively charged lubricin fractions. Alternatively, contaminants that are eliminated with the 500 mM NaCl wash might act synergistically with lubricin in cartilage lubrication.

This Part III example provides an approach to larger-scale, mucin bio-manufacturing. Success in the design and synthesis of new semi-synthetic genes for both Muc1 and lubricin, combined with our success in isolating highly stable, lubricin-expressing cell populations, indicates that this approach may be broadly applicable for recombinant mucins with long, repetitive domains. The successful demonstration of recombinant production in a human cell system that avoids the risk of immunogenic Galα1,3-Gal and Neu5Gc epitopes. We find that the recombinant product of our SynLubricin gene is functional in its ability to resist cellular adhesion (FIG. 26A) and lubricate biological surfaces, such as cartilage (FIG. 25). Thus, SynLubricin can be expected to be suitable for diverse applications ranging from injectables for osteoarthritis to topical treatments for chronic dry eye. Moreover, given the speed and low cost of CGS, the approach described herein can be expected to be applied to rapidly prototype designer mucins with new or modified functional domains.

Materials and Methods

Antibodies and Reagents

The following antibodies were used: mouse anti-human CD227 (555925, BD Biosciences) (Muc1), mouse anti-human lubricin (MABT401, EMD Millipore), goat anti-mouse IgG-HRP (sc-2005, Santa Cruz), mouse anti-SUMO (4G11E9, GenScript). Lectins used were biotinylated Peanut Agglutinin (PNA; B-1075, Vector Laboratories). Biotinylated lectins were detected using ExtrAvidin-Peroxidase (E2886, Sigma). To induce transactivator cell lines, doxycycline was used (sc-204734, Santa Cruz). For neomycin selection, G418 was used (10131035, Thermo Fisher). Valproic acid (VPA) was used as a histone deacetylase inhibitor (Sigma P4543-100G).

Constructs

A tetracycline-inducible, transposon based Piggybac expression vector with an integrated, co-expressed reverse tetracycline transactivator gene (pPB tet rtTA NeoR) was used for stable line generation. The pPB tet rtTA NeoR plasmid was modified by the insertion of the internal ribosome entry site (IRES) of the encephalomyocarditis virus followed by the fluorescent protein copGFP into the NotI and XbaI sites of the plasmid (pPB tet IRES copGFP rtTA NeoR). Synthetic cDNA for a lubricin analog with 78 perfect repeats of KEPAPTTP (SEQ ID NO:1), native N- and C-terminal domains, and an N-terminal SumoStar tag (lifesensors) were generated through custom gene synthesis (General Biosystems) and cloned into the multiple cloning site of pPB tet IRES copGFP rtTA NeoR using BamHI and EcoRI restriction sites. Similarly, cDNA for a soluble, codon-scrambled Muc1 having 42 perfect repeats of PDTRPAPGSTAPPAHGVTSA (SEQ ID NO:8) and a native human Muc1 N-terminus with SumoStar tag was generated by custom gene synthesis in the pcDNA3 plasmid. For construction of an mCherry2 IRES2 copGFP expression plasmid, an mCherry2 cDNA was isolated by EcoRI and NotI digestion of pmCherry2 N1 and cloned into the EcoRI and NotI digested pPB tet IRES copGFP rtTA NeoR vector to create pPB tet mCherry2 IRES copGFP rtTA NeoR.

Cell Lines and Culture

FreeStyle 293-F (293-F) cells were obtained from Thermo Fisher Scientific. Cells were cultured and maintained according to the manufacturer's guidelines in 100-ml Wheaton Celstir glass spinner flasks. Cells were maintained between $0.5\times10^6$ and $3\times10^6$ cells/mL at 120 rpm, 37° C., and 8% $CO_2$ in FreeStyle 293 Expression Medium (Thermo). 293-F transfections were performed using polyethyleneimine (PEI) as previously reported (Durocher, Perret, & Kamen, 2002). Stable cell lines were created by co-transfection of the pPB tet IRES copGFP rtTA NeoR plasmids described above with a hyperactive transposase plasmid (Shurer et al., 2018) and subsequently selected with 750 μg/mL of G418 for two weeks. Human embryonic kidney cells transformed with the SV40 large T antigen (293-T; ATCC) were maintained in high-glucose DMEM supplemented with 10% fetal bovine serum and penicillin/streptomycin. 293-T cells were transfected through a standard calcium phosphate transfection protocol. Cell proliferation was quantified by cell counting on a hemocytometer with trypan blue exclusion.

Cell Sorting and SynLubricin Production

293-F cells with stable incorporation of PRG4 IRES copGFP were expanded and induced at $1\times10^6$ cells/mL with 1 μg/mL doxycycline for 24 hours. The top 5% of copGFP-expressing cells were collected through Fluorescence Activated Cell Sorting (FACS) on a FACSAria Fusion (BD Biosciences). Cells were subsequently expanded in the absence of doxycycline to $1\times10^6$ cells/mL. Cells were induced with 1 μg/mL doxycycline for 24 hours and sorted a second time, collecting the top 10% of copGFP-expressing cells. For PRG4 production, cells were transferred to a 1 L ProCulture glass spinner flask (Corning) and induced at $2\times10^6$ cells/mL with 1 μg/mL doxycycline and 3.5 mM VPA. Smaller scale production of lubricin was also conducted in 100-ml Wheaton Celstir glass spinner flasks for measurement of lubricin production rates and glucose consumption rates in the presence or absence of VPA. Glucose levels were recorded with a GlucCell glucose monitoring system (CESCO BioProducts).

Immuno- and Lectin Blot Analysis

Protein in culture supernatants or purified samples were separated on NuPAGE 3-8% Tris-Acetate gels (Invitrogen) and transferred to PVDF membranes. Membranes were blocked with 3% BSA TBST for 2 hours. Primary antibodies were diluted 1:1000 and lectins were diluted to 1 μg/mL in 3% BSA TBST and incubated on membranes overnight at 4° C. Secondary antibodies or ExtrAvidin were diluted 1:2000 in 3% BSA TBST and incubated for 2 hours at room temperature. Blots were developed in Clarity ECL (BioRad)

substrate and imaged on a ChemiDoc (BioRad) documentation system. Fiji was used for image processing (Schindelin et al., 2012).

Enzyme-linked immunosorbent Assay (ELISA)

A custom sandwich ELISA was used to assess the concentration of SynLubricin, similarly to previous descriptions. A 96-well plate (Costar) was incubated overnight at 4° C. with 10 μg/mL peanut agglutinin (Sigma) in 50 mM sodium bicarbonate buffer, pH 9.5. Plates were blocked with 3% BSA PBS for 1 hour at room temperature. Serial dilutions of FPLC-purified bovine synovial fluid lubricin were used as standards. Samples were loaded at 1:200 dilution in DPBS for 1 hour at room temperature, followed by three washes in PBS+0.1% Tween20. The primary antibody used (Millipore MABT401) binds to the native PRG4 tandem repeats of human and bovine lubricin, which have approximately 90% sequence similarity to the repeats of SynLubricin. Primary antibody and secondary antibody (Millipore AP126P) were diluted 1:5000 and 1:2000, respectively, and each incubated for 1 hour at room temperature, with three washes with PBS-T in between antibody incubations and following the secondary antibody incubation. The ELISA was developed at room temperature with 1-Step Ultra TMB (ThermoFisher) for 9-12 minutes or until a royal blue color appeared, at which point the reaction was stopped with 2N $H_2SO_4$. Absorbance was measured at 450 nm with 540 nm background subtraction on a Tecan Spark® 3M microplate reader, and concentrations were calculated using Magellan software with a four parameter Marquardt fit.

Purification of Recombinant SynMuc1

293-F cells were transiently transfected using the PEI protocol previously described. After 24 hours, the media supernatant was collected. The media supernatant was diluted 1:4 in 20 mM sodium phosphate, 0.5 M NaCl, pH 7.4 and incubated with 100 μL Ni Sepharose excel resin (17371201, GE) overnight at 4° C. Sample flow through was collected using a gravity column (29922, Thermo). The resin was washed with 5 mL 20 mM sodium phosphate, 0.5 M NaCl, 5 mM imidazole, pH 7.4. SynMuc1 was eluted with 5 mL of 20 mM sodium phosphate, 0.5 M NaCl, 500 mM imidazole, pH 7.4. SynMuc1 was desalted into PBS using a Zeba Spin Desalting Column (87766, Thermo).

Purification of Recombinant SynLubricin

SynLubricin was purified from PRG4 IRES copGFP positive 293-F cell culture supernatant by fast protein liquid chromatography (FPLC) with Q Sepharose® resin (GE). The supernatant was diluted 1:10 with 50 mM Tri-HCl buffer, pH 7.5, and loaded onto the column. The column was washed with 50 mM Tris-HCl, 525 mM NaCl, pH7.5. Purified SynLubricin was collected by eluting with 50 mM Tris-HCl, 1M NaCl, pH 7.5. The purified SynLubricin was dialyzed into PBS using a Tube-O-Dialyzer (G-Biosciences) overnight at 4° C. The final purified product was obtained by concentrating with a SpeedVac on the low setting.

Tribology

The performance of SynLubricin as a boundary lubricant was assessed using a custom linear reciprocating tribometer as previously described (Gleghorn & Bonassar, 2008). Briefly, cylindrical cartilage explants (6 mm diameter×2 mm thickness) were harvested from the femoral condyles of neonatal bovine stifles. Endogenous cartilage-bound lubricin was extracted using a 30 min incubation in 1.5M NaCl, followed by a 1-hour equilibration step in PBS. Explants were incubated in either PBS, SynLubricin, or bovine synovial fluid for 15-20 min prior to loading onto a tribometer in a 1 mL bath of the respective fluid. Explants were compressed to approximately 30% strain against a glass counter-face and permitted to depressurize over the course of one hour. After reaching an equilibrium normal load, the counter-face was linearly reciprocated at a speed of 0.3 mm/s for three cycles. Simultaneously, a biaxial load recorded the normal and shear loads. For both the forward and reverse directions and at each speed, the friction coefficient was calculated as the mean shear force while sliding divided by the equilibrium normal load.

Statistical Analysis

Statistical significance was determined by one-way ANOVA or Student's t test (two-tailed) as appropriate using Prism (GraphPad). For the lubrication data, a one-way ANOVA with Tukey's post-hoc tests were performed to compare mean friction coefficients across all lubricants. All graphs were generated in Prism (GraphPad, La Jolla, CA).

PART III SUPPLEMENTAL TABLE 1

Amino acid compositions in the tandem repeats of human PRG4 isoform A and SynLubricin.

| Human PRG4A Repeats Amino acid composition | | | Synimbricin Repeats Amino acid composition | | |
|---|---|---|---|---|---|
| Ala (A) | 58 | 11.4% | Ala (A) | 59 | 12.5% |
| Arg (R) | 0 | 0.0% | Arg (R) | 0 | 0.0% |
| Asn (N) | 1 | 0.2% | Asn (N) | 0 | 0.0% |
| Asp (D) | 2 | 0.4% | Asp (D) | 0 | 0.0% |
| Cys (C) | 0 | 0.0% | Cys (C) | 0 | 0.0% |
| Gln (Q) | 0 | 0.0% | Gln (Q) | 0 | 0.0% |
| Glu (E) | 48 | 9.4% | Glu (E) | 59 | 12.5% |
| Gly (G) | 4 | 0.8% | Gly (G) | 0 | 0.0% |
| His (H) | 0 | 0.0% | His (H) | 0 | 0.0% |
| Ile (I) | 1 | 0.2% | Ile (I) | 0 | 0.0% |
| Leu (L) | 7 | 1.4% | Leu (L) | 0 | 0.0% |
| Lys (K) | 69 | 13.6% | Lys (K) | 59 | 12.5% |
| Met (M) | 0 | 0.0% | Met (M) | 0 | 0.0% |
| Phe (F) | 0 | 0.0% | Phe (F) | 0 | 0.0% |
| Pro (P) | 155 | 30.5% | Pro (P) | 177 | 37.5% |
| Ser (S) | 13 | 2.6% | Ser (S) | 0 | 0.0% |
| Thr (T) | 150 | 29.5% | Thr (T) | 118 | 25.0% |
| Trp (W) | 0 | 0.0% | Trp (W) | 0 | 0.0% |
| Tyr (Y) | 0 | 0.0% | Tyr (Y) | 0 | 0.0% |
| Val (V) | 0 | 0.0% | Vol (V) | 0 | 0.0% |

REFERENCES

Backliwal, G., Hildinger, M., Kuettel, I., Delegrange, F., Hacker, D. L., & Wurm, F. M. (2008). Valproic acid: a viable alternative to sodium butyrate for enhancing protein expression in mammalian cell cultures. *Biotechnol Bioeng,* 101(1), 182-189. //doi.org/10.1002/bit.21882

Backstrom, M., Link, T., Olson, F. J., Karlsson, H., Graham, R., Picco, G., . . . Hansson, G. C. (2003). Recombinant MUC1 mucin with a breast cancer-like O-glycosylation produced in large amounts in Chinese-hamster ovary cells. *Biochem J,* 376(Pt 3), 677-686. //doi.org/10.1042/bj20031130

Bahabri, S. A., Suwairi, W. M., Laxer, R. M., Polinkovsky, A., Dalaan, A. A., & Warman, M. L. (1998). The camptodactyly-arthropathy-coxa vara-pericarditis syndrome: Clinical features and genetic mapping to human chromosome 1. *Arthritis & Rheumatism,* 41(4), 730-735. //doi.org/10.1002/1529-0131(199804)41:4<730::AID-ART22>3.0.CO; 2-Y Benson, G. (1999). Tandem repeats finder: a program to analyze DNA sequences. *Nucleic Acids Research,* 27(2), 573-580. //doi.org/10.1093/nar/27.2.573

Bosques, C. J., Collins, B. E., Meador, J. W., Sarvaiya, H., Murphy, J. L., DelloRusso, G., . . . Venkataraman, G. (2010). Chinese hamster ovary cells can produce galactose-α-1,3-galactose antigens on proteins. *Nature Biotechnology,* 28(11), 1153-1156. //doi.org/10.1038/nbt1110-1153
Boussif, O., Lezoualc'h, F., Zanta, M. A., Mergny, M. D., Scherman, D., Demeneix, B., & Behr, J. P. (1995). A versatile vector for gene and oligonucleotide transfer into cells in culture and in vivo: polyethylenimine. *Proc Natl Acad Sci USA,* 92(16), 7297-7301. //doi.org/10.1073/pnas.92.16.7297
Brooks, S. A. (2004). Appropriate glycosylation of recombinant proteins for human use. *Molecular Biotechnology,* 28(3), 241-255. //doi.org/10.1385/MB:28:3:241
Butler, M., & Spearman, M. (2014). The choice of mammalian cell host and possibilities for glycosylation engineering. *Current Opinion in Biotechnology,* 30, 107-112. //doi.org/10.1016/j.copbio.2014.06.010
de los Milagros Bassani Molinas, M., Beer, C., Hesse, F., Wirth, M., & Wagner, R. (2014). Optimizing the transient transfection process of HEK-293 suspension cells for protein production by nucleotide ratio monitoring. *Cytotechnology,* 66(3), 493-514. //doi.org/10.1007/s10616-013-9601-3
Dhanisha, S. S., Guruvayoorappan, C., Drishya, S., & Abeesh, P. (2018). Mucins: Structural diversity, biosynthesis, its role in pathogenesis and as possible therapeutic targets. *Critical Reviews in Oncology/Hematology,* 122, 98-122. //doi.org/10.1016/j.critrevonc.2017.12.006
Dumont, J., Euwart, D., Mei, B., Estes, S., & Kshirsagar, R. (2016). Human cell lines for biopharmaceutical manufacturing: history, status, and future perspectives. *Crit Rev Biotechnol,* 36(6), 1110-1122. //doi.org/10.3109/07388551.2015.1084266
Durocher, Y., Perret, S., & Kamen, A. (2002). High-level and high-throughput recombinant protein production by transient transfection of suspension-growing human 293-EBNA1 cells. *Nucleic Acids Res,* 30(2), E9.
Elsaid, K. A., Fleming, B. C., Oksendahl, H. L., Machan, J. T., Fadale, P. D., Hulstyn, M. J., . . . Jay, G. D. (2008). Decreased lubricin concentrations and markers of joint inflammation in the synovial fluid of patients with anterior cruciate ligament injury. *Arthritis & Rheumatism,* 58(6), 1707-1715. //doi.org/10.1002/art.23495
Estrella, R. P., Whitelock, J. M., Packer, N. H., & Karlsson, N. G. (2010). The glycosylation of human synovial lubricin: implications for its role in inflammation. *Biochemical Journal,* 429(2), 359-367. //doi.org/10.1042/bj20100360
Flannery, C. R., Zollner, R., Corcoran, C., Jones, A. R., Root, A., Rivera-Bermudez, M. A., . . . Glasson, S. S. (2009). Prevention of cartilage degeneration in a rat model of osteoarthritis by intraarticular treatment with recombinant lubricin. *Arthritis Rheum,* 60(3), 840-847. //doi.org/10.1002/art.24304
Gemayel, R., Vinces, M. D., Legendre, M., & Verstrepen, K. J. (2010). Variable Tandem Repeats Accelerate Evolution of Coding and Regulatory Sequences. *Annual Review of Genetics,* 44(1), 445-477. //doi.org/10.1146/annurev-genet-072610-155046
Ghaderi, D., Zhang, M., Hurtado-Ziola, N., & Varki, A. (2012). Production platforms for biotherapeutic glycoproteins. Occurrence, impact, and challenges of non-human sialylation. *Biotechnol Genet Eng Rev,* 28, 147-175. //doi.org/10.5661/bger-28-147
Gipson, I. K., Spurr-Michaud, S., Tisdale, A., & Menon, B. B. (2014). Comparison of the Transmembrane Mucins MUC1 and MUC16 in Epithelial Barrier Function. *PLOS ONE,* 9(6), e100393. //doi.org/10.1371/journal-.pone.0100393
Gleghorn, J. P., & Bonassar, L. J. (2008). Lubrication mode analysis of articular cartilage using Stribeck surfaces. *J Biomech,* 41(9), 1910-1918. //doi.org/10.1016/j.jbiomech.2008.03.043
Hang, H. C., & Bertozzi, C. R. (2005). The chemistry and biology of mucin-type O-linked glycosylation. *Bioorganic & Medicinal Chemistry,* 13(17), 5021-5034. //doi.org/10.1016/j.bmc.2005.04.085
Hattrup, C. L., & Gendler, S. J. (2008). Structure and Function of the Cell Surface (Tethered) Mucins. *Annual Review of Physiology,* 70(1), 431-457. //doi.org/10.1146/annurev.physiol.70.113006.100659
Jones, A. R. C., Gleghorn, J. P., Hughes, C. E., Fitz, L. J., Zollner, R., Wainwright, S. D., . . . Flannery, C. R. (2007). Binding and localization of recombinant lubricin to articular cartilage surfaces. *Journal of Orthopaedic Research,* 25(3), 283-292. //doi.org/doi:10.1002/jor.20325
Kosinska, M. K., Ludwig, T. E., Liebisch, G., Zhang, R., Siebert, H.-C., Wilhelm, J., . . . Steinmeyer, J. (2015). Articular Joint Lubricants during Osteoarthritis and Rheumatoid Arthritis Display Altered Levels and Molecular Species. *PLOS ONE,* 10(5), e0125192. //doi.org/10.1371/journal.pone.0125192
Kosuri, S., & Church, G. M. (2014). Large-scale de novo DNA synthesis: technologies and applications. *Nature Methods,* 11, 499. //doi.org/10.1038/nmeth.2918
Kuo, J. C.-H., Gandhi, J. G., Zia, R. N., & Paszek, M. J. (2018). Physical biology of the cancer cell glycocalyx. *Nature Physics,* 14(7), 658-669. //doi.org/10.1038/s41567-018-0186-9
Le Graverand-Gastineau, M. P. (2010). Disease modifying osteoarthritis drugs: facing development challenges and choosing molecular targets. *Curr Drug Targets,* 11(5), 528-535. //doi.org/10.2174/138945010791011893
López Castel, A., Cleary, J. D., & Pearson, C. E. (2010). Repeat instability as the basis for human diseases and as a potential target for therapy. *Nature Reviews Molecular Cell Biology,* 11, 165. //doi.org/10.1038/nrm2854
Mantelli, F., & Argueso, P. (2008). Functions of ocular surface mucins in health and disease. *Current Opinion in Allergy and Clinical Immunology,* 8(5), 477-483. //doi.org/10.1097/ACI.0b013e32830e6b04
Marcelino, J., Carpten, J. D., Suwairi, W. M., Gutierrez, O. M., Schwartz, S., Robbins, C., . . . Warman, M. L. (1999). CACP, encoding a secreted proteoglycan, is mutated in camptodactyly-arthropathy-coxa vara-pericarditis syndrome. *Nature Genetics,* 23, 319. //doi.org/10.1038/15496
Mauris, J., & Argüeso, P. (2012). Mucins and Galectin-3 in Ocular Surface Health and Disease. In *Galectins and Disease Implications for Targeted Therapeutics* (Vol. 1115, pp. 409-414). American Chemical Society. //doi.org/10.1021/bk-2012-1115.ch025
Nath, S., & Mukherjee, P. (2014). Muc1: a multifaceted oncoprotein with a key role in cancer progression. *Trends in Molecular Medicine,* 20(6), 332-342. //doi.org/10.1016/j.molmed.2014.02.007
Oren, M., Barela Hudgell, M. A., D'Allura, B., Agronin, J., Gross, A., Podini, D., & Smith, L. C. (2016). Short tandem repeats, segmental duplications, gene deletion, and genomic instability in a rapidly diversified immune gene family. *BMC Genomics,* 17, 900. //doi.org/10. 1186/s12864-016-3241-x
Pearson, C. E., Edamura, K. N., & Cleary, J. D. (2005). Repeat instability: mechanisms of dynamic mutations. *Nature Reviews Genetics,* 6, 729. //doi.org/10.1038/nrg1689

Reesink, H. L., Bonnevie, E. D., Liu, S., Shurer, C. R., Hollander, M. J., Bonassar, L. J., & Nixon, A. J. (2016). Galectin-3 Binds to Lubricin and Reinforces the Lubricating Boundary Layer of Articular Cartilage. *Scientific Reports,* 6, 25463. //doi.org/10.1038/srep25463

Rhee, D. K., Marcelino, J., Baker, M., Gong, Y., Smits, P., Lefebvre, V., . . . Carpten, J. D. (2005). The secreted glycoprotein lubricin protects cartilage surfaces and inhibits synovial cell overgrowth. *J Clin Invest,* 115(3), 622-631. //doi.org/10.1172/jci22263

Samsom, M. L., Morrison, S., Masala, N., Sullivan, B. D., Sullivan, D. A., Sheardown, H., & Schmidt, T. A. (2014). Characterization of full-length recombinant human Proteoglycan 4 as an ocular surface boundary lubricant. *Experimental Eye Research,* 127, 14-19. //doi.org/10.1016/j.exer.2014.06.015

Schindelin, J., Arganda-Carreras, I., Frise, E., Kaynig, V., Longair, M., Pietzsch, T., . . . Cardona, A. (2012). Fiji: An open-source platform for biological-image analysis. *Nature Methods.* //doi.org/10.1038/nmeth.2019

Schmidt, T. A., Sullivan, D. A., Knop, E., & et al. (2013). Transcription, translation, and function of lubricin, a boundary lubricant, at the ocular surface. *JAMA Ophthalmology,* 131(6), 766-776. //doi.org/10.1001/jamaophthalmol.2013.2385

Shurer, C. R., Colville, M. J., Gupta, V. K., Head, S. E., Kai, F., Lakins, J. N., & Paszek, M. J. (2018). Genetically Encoded Toolbox for Glycocalyx Engineering: Tunable Control of Cell Adhesion, Survival, and Cancer Cell Behaviors. *ACS Biomaterials Science & Engineering,* 4(2), 388-399. //doi.org/10.1021/acsbiomaterials.7b00037

Sonawane, N. D., Szoka Jr., F. C., & Verkman, A. S. (2003). Chloride accumulation and swelling in endosomes enhances DNA transfer by polyamine-DNA polyplexes. *J Biol Chem,* 278(45), 44826-44831. //doi.org/10.1074/jbc.M308643200

Tang, N. C., & Chilkoti, A. (2016). Combinatorial codon scrambling enables scalable gene synthesis and amplification of repetitive proteins. *Nature Materials,* 15(4), 419-424. //doi.org/10.1038/nmat4521

Part IV

This Part IV provides, among other aspects, a description of the physical principles of membrane shape regulation by the glycocalyx.

In connection with this Part IV, it is known that cells bend their plasma membranes into highly curved forms to interact with the local environment, but how shape generation is regulated is not fully resolved. This Part IV describes a broad synergy between shape-generating processes in the cell interior and the external organization and composition of the cell-surface glycocalyx. Mucin biopolymers and long-chain polysaccharides within the glycocalyx can generate entropic forces that favor or disfavor the projection of spherical and finger-like extensions from the cell surface. A polymer brush model of the glycocalyx successfully predicts the effects of polymer size and cell-surface density on membrane morphologies. Specific glycocalyx compositions can also induce plasma membrane instabilities to generate more exotic undulating and pearled membrane structures and drive secretion of extracellular vesicles. Together, results presented in this Part IV suggest a fundamental role for the glycocalyx in regulating curved membrane features that serve in diverse modes of communication between cells and with the extracellular matrix.

Introduction to Part IV

Tubular and spherical extensions of the plasma membrane play vital roles in human development and everyday cellular functions. While curved membrane protrusions have long been recognized to increase cell-surface area for secretion, absorption, and receptor-mediated communication, modern research has provided compelling examples of much more diverse and sophisticated functionalities (Marshall, 2012). For instance, T-cells of the adaptive immune system generate a high density of tubular microvilli to engage antigen presenting cells, and such structures may be similarly important for the recognition of tumor cells by engineered immune cell therapies (D'Aloia et al., 2018; Jung et al., 2016). Membrane projections also enable cell-to-cell communication over long ranges and at precise three-dimensional locations in tissues. During development, long and thin membrane projections called cytonemes pinpoint delivery of morphogens from 'sender' cells to specific 'receiver' cells up to 40-microns away (Bischoff et al., 2013; Kornberg and Roy, 2014). Stem cells, immune cells, and many other cell types are also known to bend their plasma membranes into spherical microvesicles that are directly shed and can deliver macromolecular cargoes over long distances (Tricarico et al., 2017). Moreover, curved membrane features are ubiquitous in physical cell behaviors, including migration and mechanotransduction. For example, spherical membrane expansions called blebs are generated by primordial germ cells, tumor cells, and other cell types for protrusion and frictional coupling with the tissue matrix during migration (Paluch and Raz, 2013).

Deregulation of membrane-shape generating processes can contribute directly to disease progression. As a notable example, aggressive tumor cells frequently extend numerous microvilli for adhesion and rolling in the vasculature (Kramer and Nicolson, 1979; Liu et al., 2018). Aggressive tumor cells can also project blebs for amoeboid migration (Bergert et al., 2015; Friedl and Wolf, 2010). Microvesicles often bud from the plasma membrane of tumor cells at abnormally high rates (Antonyak et al., 2011; Becker et al., 2016). Cargoes carried by these particles are now recognized to have diverse modulatory roles, including reprogramming of other cell types in the stroma and the preparation of distant metastatic niches for colonization (Becker et al., 2016).

Forces originating from cytoskeletal dynamics are posited to generate membrane curvature for the diverse spherical and tubular structures on the cell surface. Polymerizing cytoskeletal filaments are envisioned to push out at discrete points along the plasma membrane for extension of microvilli, cilia, filapodia and other finger-like projections (Footer et al., 2007; Gupton and Gertler, 2007; Peskin et al., 1993). Contraction of the cytoskeleton generates the hydrostatic pressure for spherical expansion of the membrane during bleb formation (Charras et al., 2005). The physical dynamics that bend sub-regions of the plasma membrane into microvesicles remain poorly understood; however, reports have implicated the actin cytoskeleton in their biogenesis (Tricarico et al., 2017).

While the cell-surface glycocalyx is not featured in canonical models of membrane shape regulation, correlations abound between glycocalyx composition and cell-surface morphology in both normal and disease states. In normal cell physiology, polypeptide and sugar co-polymers called mucins are frequently anchored at high densities on the surfaces of epithelial microvilli (Hattrup and Gendler, 2008; Kesavan et al., 2009; Kesimer et al., 2013), cilia (Button et al., 2012), and filapodia (Bennett et al., 2001); while hyaluronan polymers densely coat the microvilli of oocytes and mesothelium (Evanko et al., 2007; Makabe Sayoko et al., 2006); and long chains of sialic acid and hyaluronan decorate the highly curved surfaces of neuronal axons (Fowke et al., 2017; van den Pol and Kim, 1993; Zhang et al., 1992). T-cells and dendritic cells express cell-surface mucins upon activation or maturation, which coincides often with the dramatic changes in membrane tubularization and microvilli generation (Agrawal et al., 1998; Cloosen et al., 2004; Jung et al., 2016; Pilon et al., 2009). Aggressive tumor cells frequently produce an abundance of mucins and hyaluronan on their cell surface (Kufe, 2009; Turley et al., 2016), and the expression of these polymers has been anecdotally linked to their unique membrane features, such as extensive microvilli (Polefka et al., 1984). Mucins and hyaluronan polymers are also densely arrayed on the surfaces of enterocytes, reactive astrocytes, dendritic cells, and tumor cells that are known to secrete high levels of microvesicles (Cloosen et al., 2004, 2004; Gangoda et al.; McConnell et al., 2009; Paszek et al., 2014; Pelaseyed et al.; Tricarico et al., 2017). While the ubiquity of these correlations suggests a possible causal relationship between glycocalyx polymer composition and plasma membrane morphologies, a specific mechanism of action has not been delineated. The present disclosure contributes to an understanding of this mechanism of action.

Mucins and long-chain polysaccharides are anchored to the membrane in such a way that long polymer chains or loops are expected to extend from the cell surface (Hattrup and Gendler, 2008; Lee et al., 1993). The ensemble resembles a well-studied structure in polymer physics called a brush, where polymers are grafted on one end to a surface (Chen et al., 2017). Polymer brush theory has long recognized that steric interactions in a densely crowded brush restrict the number of molecular configurations each polymer can explore, thereby increasing the free energy of the system through reduced entropy (de Gennes, 1980). Similar to the thermodynamic basis of gas pressure, the entropic penalty associated with molecular crowding can theoretically generate sufficient pressure to deform a flexible surface, like a membrane (Hiergeist and Lipowsky, 1996; Lipowsky, 1995).

Results

Glycocalyx Polymers and Membrane Morphology:

In this Part IV, we analyzed whether glycocalyx polymers may generate an entropic bending force to favor the formation of specific membrane forms. As a corollary to this, we tested whether emergent membrane structures could be tuned through rational manipulation of the glycocalyx.

To test this, we constructed a genetically encoded library of native, semi-synthetic, and rationally designed mucin polymers of varying size, backbone sequence, and membrane anchorage (FIG. 30A and FIG. 36A). Each construct encoded a mucin polymer domain comprised of an unstructured polypeptide backbone with a high density of serine and threonine sites for O-glycosylation. When expressed in cells, the mucin domains were post-translationally modified with O-linked sugar side chains to form a bottlebrush molecular structure that defines mucins (FIG. 35A, B).

Polymer domains in the library included the 42 native tandem repeats (TR) of Mucin-1 (Muc1-42TR), the serine and threonine-rich polymer domain of Podocalyxin (Podxl; S/T-Rich), and a new synthetic mucin that we rationally designed and constructed through the tandem fusion of 80 perfect repeats based on a consensus of mucin O-glycosylation sequence, PPASTSAPGA (Rational) (FIG. 30A and FIG. 35A). Each polymer domain was fused to the native Muc1 transmembrane anchor with the cytoplasmic tail deleted (ΔCT), or a 21-amino acid synthetic transmembrane anchor (TM21), or a native mucin anchor with a membrane proximal green fluorescent protein for imaging (GFP-ΔCT) (FIG. 30A and FIG. 35A).

When expressed and assembled at high levels on the epithelial cell surface, each mucin polymer in our library triggered a dramatic tubularization of the plasma membrane, as observed by scanning electron microscopy (SEM) (FIG. 30B, C and FIG. 35B). Without intending to be bound by any particular theory, we concluded that this tubularization was likely a general consequence of polymer anchorage to the plasma membrane and did not require a specific biopolymer sequence or transmembrane anchor. Notably, the Muc1-42TR ΔCT was identical to native Mucin-1 except for the cytoplasmic tail, indicating that native glycocalyx constituents can influence plasma membrane morphology in addition to our rationally designed polymers. Mucin expression did not have a significant effect on endocytosis, arguing against lipid recycling and the regulation of membrane tension as a primary mechanism for the morphological changes (FIG. 35C, D).

The tubularization phenomenon was relatively insensitive to the length of the mucin polymer domain, provided that the polymers were expressed on the cell surface at moderate to high densities. cDNAs for 0, 10, or 42 Muc1 repeats were fused with a GFP-tagged transmembrane anchor to encode cell-surface mucins with expected contour lengths of 0, 65, and 270 nm, respectively (FIG. 30D and FIG. 35E). Cell lines expressing the constructs were sorted into populations with similar mucin surface densities using a nanobody that probed cell-surface GFP (FIG. 30D). The flexible polymer domain was required for efficient membrane tubularization, and the 10- and 42-TR mucins induced comparable levels of membrane tubularization despite their size difference (FIG. 30E and FIG. 35F). We compared cells of similar spread area to rule out the possibility that changes in membrane surface tension and other effects associated with cell spreading could explain the morphological differences (FIG. 30E).

Similar to mucins, we found that a glycocalyx rich in large, linear polysaccharides could also trigger dramatic changes in plasma membrane morphology. Notably, hyaluronic acid synthase 3 (HAS3) expression increased the density of high molecular weight hyaluronic acid (HA) polymers on the cell surface and led to the protrusion of many finger-like membrane extensions (FIG. 36A-D), consistent with prior observations by others (Koistinen et al., 2015). Together, these results suggested that diverse glycocalyx polymer types and sizes might influence cell morphological states.

We next tested whether glycocalyx biopolymers could induce spontaneous curvature in model membranes independent of intracellular machinery. When anchored to the surface of giant unilamellar vesicles (GUVs), we found that the S/T-rich polymer domain of Podxl triggered spontaneous generation of spherical and tubular membrane structures (FIG. 30F and FIG. 37A, B). Tubules were also observed at very high densities of a folded protein, human serum albumin (HSA), consistent with previous findings that the extensive crowding of folded or intrinsically disordered proteins could induce spontaneous membrane curvatures in GUVs (Stachowiak et al., 2010) (FIG. 30F and FIG. 37B, C). However, the surface density required to induce spontaneous tubularization was significantly lower for Podxl mucin compared to HSA (FIG. 30F and FIG. 37B).

Specialized Cells In Vivo:

Motivated by these observations in vitro, we considered whether glycocalyx polymers might play a role in shaping the morphology of specialized cell types in vivo. We elected to evaluate synoviocytes, since these secretory cells are known to produce large quantities of HA for joint lubrication and, thus, are expected to display a high density of HA polymers on their surface. We isolated synovial tissues from equine carpus (FIG. 31A) and found that primary synoviocytes expressing HAS3 were highly tubulated, but treatment with hyaluronidase (HyA) to degrade HA resulted in the rapid destabilization and disappearance of membrane tubules (FIG. 31B, C). We also evaluated synoviocyte morphology in tissues that were freshly extracted and briefly cultured ex vivo (<1 h). The synoviocytes in native synovial tissue displayed an HA-rich head that appeared highly tubulated and protruded from the tissue matrix (FIG. 31D, E). Brief treatment of the tissue with HyA ex vivo resulted in a dramatic retraction of synoviocyte tubules, suggesting a role for the glycocalyx in the maintenance of membrane projections in vivo (FIG. 31E).

Polymer Brush Framework:

We considered whether the observed membrane shapes and their frequencies could be rationalized through the framework of polymer brush theory. We noted that two limiting regimes are classically described in polymer physics for end-grafted polymers: the "mushroom" regime, where polymers at low grafting densities have limited interactions with each other, and the "brush" regime, where crowded polymers can interact sterically and electrostatically with each other to exert larger pressures on the anchoring surface (Milner, 1991) (FIG. 32A). For mucins, we expected the transition from the mushroom to brush regime to occur at a surface density where the average distance between the polymers was approximately two times their radius of gyration in solution (FIG. 32A).

To measure the radius of gyration and flexibility of individual mucins, we produced recombinant Muc1-42TR with a terminal purification tag in place of its transmembrane anchor (FIG. 38A-C). Size-exclusion chromatography coupled to multi-angle light scattering (SEC-MALS) reported 32 nm±0.4% for the mucin radius of gyration in physiological buffer. Based on the estimated Muc1-42TR contour length of approximately 270 nm, and again without intending to be bound by any particular theory, we concluded that the mucin had a persistence length of approximately 7.5 nm and adopted the extended random coil configuration expected for a semi-flexible polymer in solution.

We next tested whether polymer brush theory could capture the physical behavior of mucin ensembles on the cell surface. We tested whether mucins stretch and extend in a predictable manner as they become progressively more crowded, a characteristic physical behavior originally described by Alexander and de Gennes in their seminal theories on polymer brushes (Alexander, 1977; Milner, 1991). We chose to evaluate mucin extension on actin-containing tubules that resembled microvilli, since the curvature of these structures was highly uniform and essentially independent of the mucin surface density (FIG. 38D). As such, we were able to approximate the tubule surface as a rigid cylinder of fixed radius for direct comparison to classical theory. A cDNA for Muc1-42TR with complimentary epitope tags flanking the mucin polymer domain was constructed. Following cellular expression, the encoded tags were labeled with fluorophore-conjugated probes and resolved on microvilli cross-sections using a super-resolution optical technique called expansion microscopy (ExM) (FIG. 32B and FIG. 38E). We found that the mucin extension had an exponential dependence, or 'scaled,' with fluorescence intensity, and hence surface density, with an exponent of 0.48±0.10 (FIG. 32B). This value compared well to the theoretically derived power law exponent of between 0.33 and 0.5 for polyelectrolytes grafted on a rigid cylindrical surface at physiological salt concentrations (Zhulina and Borisov, 1996).

We created a polymer brush model to describe the physical behavior of a mucin-rich glycocalyx assembled on the plasma membrane. The entropic pressure contributed by the mucin brush generated a spontaneous membrane curvature that strongly scaled with polymer density and weakly with polymer chain length (Hiergeist and Lipowsky, 1996) (FIG. 32C and FIG. 39). The weak dependence on polymer length was consistent with findings that mucins with 10 and 42 repeats had comparable effects on cell-surface morphology despite their 4-fold difference in size (FIG. 30E and FIG. 35F). For these two mucins, our brush model predicted only a ~20% difference in induction of spontaneous membrane curvature (FIG. 39).

Preferred Membrane Shapes:

We tested whether the polymer model could explain the frequency of finger-like and spherical protrusions from the cell surface. We reasoned that protrusion of a specific membrane feature would be disfavored when high intracellular forces were required to extend or maintain the protrusion and favored when these force requirements were minimal. Minimizing the standard Helfrich free energy function for membranes with induced spontaneous curvature, we calculated the equilibrium cytosolic pressure required to maintain a spherical membrane bleb and the point force required to maintain a membrane tubule (FIG. 33D). For experimental comparison, we evaluated the types, sizes, and frequencies of plasma membrane features as a function of mucin cell-surface density. Cells expressing Muc1-42TR GFP were labeled with an anti-GFP nanobody and sorted into populations of varying mucin surface levels (FIG. 33A). The average mucin surface density in each population was estimated by SDS-PAGE through interpolation using a nanobody standard curve (FIG. 40). Molecular surface densities in the sorted populations ranged from 180 to ~50,000 mucins per $\mu m^2$. For reference, we expected the mushroom to brush transition to occur around 250 mucins per $\mu m^2$ based on the measured radius of gyration of recombinant Muc1-42TR in solution.

Initially, we evaluated membrane blebs. Using physical parameters measured for Muc1-42TR, we predicted that the pressure required for maintaining a bleb with a typical radius of 250 nm would be minimal at moderate mucin densities near the mushroom-brush transition (FIG. 32D). A surprising model prediction was that the required maintenance pressure would rise sharply at higher mucin densities, quickly reaching pressures that exceed the known limits of the cell's contractile machinery (Charras et al., 2008). Thus, theory suggested that blebbing would be suppressed by a highly dense glycocalyx (FIG. 32D). Our experimental observations showed good qualitative agreement with these predictions. Cells with a mucin density near the estimated mushroom-brush transition displayed a significant number of large, bleb-like forms with an average radius of 260±100 nm (FIG. 33B-D; 180 mucins per $\mu m^2$). Upon crossover into the brush regime, the bleb frequency plummeted precipitously, consistent with the model's prediction of a quadratic rise in the necessary bleb maintenance pressure (FIG. 33B, D).

The glycocalyx polymer model predicted a much different dependence of tubule projection on mucin density. The predicted point force required for maintaining an extended tubule decreased progressively with high mucin densities and exhibited no sharp transitions (FIG. 32D). Accordingly, the frequency of cell-surface tubules observed in our sorted cell populations increased steadily with mucin density throughout the mushroom and brush regimes until the cell was fully saturated with tubes at very high mucin densities (FIG. 33B-E). Notably, theory predicted that at these high densities, the required force for tubule extension is comparable to the polymerization force of a single cytoskeletal filament, ~1 pN (Footer et al., 2007). Based on the experimentally measured mucin densities, we estimated the theoretical point force, f, required to maintain tubules. Remarkably, the experimentally observed tube frequency had a nearly perfect inverse correlation with the theoretical point force (FIG. 33F). The Pearson's correlation coefficient describing the relationship between tube density and 1/f was 0.97.

The polymer model also predicted that the spontaneous curvatures generated by high mucin surface densities exceeded the curvature of finger-like projections that we observed on the cell surface. We noted that the tubular membrane projections on our cells typically contained a filamentous actin (F-actin) core and did not contain microtubules (FIG. 34A, B, FIG. 41A-D). Disruption of F-actin assembly with the drug Latrunculin A (LatA) led to a reduction in tubule diameter by approximately 30 nm (FIG. 34C, D and FIG. 41E, F), indicating that the mucin-induced spontaneous curvature exceeded the curvature of the stable, actin-filled projections. It should be noted that our measurement of LatA-treated cells likely excluded very thin and delicate membrane tubules that were difficult to preserve throughout the SEM sample preparation. Nevertheless, these results clearly indicated that spontaneous curvatures generated by the glycocalyx can meet or exceed the curvature requirements for thin, finger-like projections, such as microtubules, cilia, filapodia, axons, and cytonemes, which have characteristic diameters of approximately 100-200 nm.

Membrane Instabilities and Extracellular Vesicle Generation:

We next considered whether other functional membrane shapes could be generated through actions of the glycocalyx. We noted that a progressive increase in spontaneous curvature has been known to trigger membrane instabilities and morphological changes in membrane vesicles (Campelo and Hernández-Machado, 2007; Tsafrir et al., 2001). Therefore, we reasoned that membrane instabilities could arise if the F-actin cores that physiologically resist the spontaneous curvatures of mucins were disrupted. Indeed, our model suggested that ~400 mucins per $\mu m^2$ or more would be sufficient to drive membrane instabilities in tubules. Accordingly, we observed that LatA treatment triggered formation of pearled and undulating structures that are characteristic of membrane instabilities (FIG. 34D).

Deuling, Helfrich, and others theoretically considered instabilities in membrane tubules with volume to area ratio, λ, and found that for certain spontaneous curvatures, $c_0$, the membrane bending energy vanished through the adoption of one of three "Delaunay" shapes: a cylinder for $c_0=\frac{1}{2}\lambda$ (Shape 1), a smoothly varying set of unduloids for $\frac{1}{2}\lambda<c_0<\frac{2}{3}\lambda$ (Shape 2), and a set of equal-sized "pearls" for $c_0=\frac{2}{3}\lambda$ (Shape 3) (Campelo and Hernández-Machado, 2007; Tsafrir et al., 2001). For spontaneous curvatures that exceeded $\frac{2}{3}\lambda$, the lowest energy shapes that satisfied the constraints of volume and surface area were found to include a set of small pearls of the preferred curvature with one or more big pearls necessary to hold excess volume (Shape 4) and a set of pearls with a gradient in size (Shape 5) (Campelo and Hernández-Machado, 2007; Tsafrir et al., 2001). We evaluated whether the minimal energy surfaces, Shapes 1-5, would be formed on cells expressing moderate to high levels of mucin without exogenous treatments, and found commonplace examples of each expected shape (FIG. 34E). The observation of these shapes provided a compelling argument that membrane instabilities can be driven by specific compositions of the glycocalyx.

Remarkably, we discovered that membrane pearling was an intermediate step towards the secretion of extracellular vesicles directly from the plasma membrane (FIG. 34F). Compared to controls, the conditioned media from Muc1-42TR-expressing cells contained massive concentrations of particles ranging in size from approximately 100-nm to 400-nm (FIG. 5G), which is characteristic of microvesicles (Pol et al., 2016). Particle generation was further enhanced by LatA treatment to disrupt the supporting F-actin cores of surface projections and locally destabilize the plasma membrane (FIG. 34H). Cryo-transmission electron microscopy (cryo-TEM) confirmed that the secreted particles were indeed membrane vesicles and grafted with a distinct glycocalyx ultrastructure on their surfaces (FIG. 34I). These observations are consistent with previous reports of vesicle generation from microvilli in enterocytes and other mucin expressing cells (McConnell et al., 2009). However, and without intending to be bound by any particular theofy, our results now suggest a possible three-step mechanism for microvesicle generation: (1) cytoskeletal filaments help extend and stabilize long and thin protrusions from the plasma membrane in a glycocalyx-dependent manner; (2) following disassembly of the cytoskeletal core, spontaneous curvature imposed by the glycocalyx induces membrane instabilities of the tubules; and (3) membrane pearls pinch off to release vesicles (FIG. 5E, F).

Discussion

The description presented in this Part IV implicates an entropic mechanism through which the glycocalyx can strongly influence the favorability of diverse plasma membrane shapes and protrusions. The morphological changes regulated by the glycocalyx could, in principle, have broad consequences on membrane processes, ranging from absorption and secretion to cellular communication, signaling, and motility (Lange, 2011; Paluch and Raz, 2013; Sauvanet et al., 2015; Schmick and Bastiaens, 2014). Given that glycosylation changes dramatically and in tandem with cell fate transitions (Buck et al., 1971; Freeze, 2013; Satomaa et al., 2009), and that the pool of monomers for construction of glycocalyx polymers is tightly coupled to specific metabolic programs (Dennis et al., 2009; Koistinen et al., 2015; Ying et al., 2012), this Part IV raises the intriguing possibility that the glycocalyx may serve as a conduit linking physical morphology to specific cell states.

Contemporary frameworks for understanding membrane shape regulation largely lack a physical description of the glycocalyx. However, long-chain biopolymers in the glycocalyx are almost universally found anchored to the surfaces of curved membrane features and cell-surface organelles (Bennett et al., 2001; Button et al., 2012; Evanko et al., 2007; Fowke et al., 2017; Hattrup and Gendler, 2008; Kesavan et al., 2009; Kesimer et al., 2013; Makabe Sayoko et al., 2006; van den Pol and Kim, 1993; Zhang et al., 1992). The results in this Part IV suggests that the principles and theories of polymer physics can be adopted to understand, at least to a first approximation, the physical regulation of membrane shape generation by the glycocalyx. A model of end-anchored polymer mushrooms and polymer brushes is a simple physical representation of the glycocalyx. The actual glycocalyx architecture can include additional hierarchies of crosslinking, entanglement, and molecular inhomogeneity (Tammi et al., 2002). However, the nearly perfect inverse relationships between the force requirements for membrane extension, as estimated using a relatively simple model of the glycocalyx, and the experimentally observed frequencies of these extensions argue that at least some of the physical behaviors of the glycocalyx can be captured using polymer network models. Indeed, we found that glycocalyx polymer extension correlates with cell surface density according to the classic scaling laws developed by de Gennes and others for polymer brushes (Gennes, 1979; Zhulina and Borisov, 1996).

How the glycocalyx and intracellular shape-generating processes coordinate in space and time to control membrane protrusions is not fully resolved. In particular, the Rho family of GTPases are master regulators of cytoskeletal dynamics and cell-surface morphology (Hall, 1998). The description in this Part IV suggests that by modulating the barrier to membrane bending, the glycocalyx primes the membrane for expansion into specific types of spherical or tubular forms that are subject to regulation by Rho GTPases. This integrated view suggests that perturbation of normal cell-surface morphology could be achieved through deregulation of intracellular shape generating processes, glycocalyx polymer assembly, or both. For instance, deregulation of Rho GTPase signaling, cytoskeletal dynamics, and glycocalyx assembly are all common hallmarks of cancer cells (Paszek et al., 2014; Pinho and Reis, 2015; Porter et al., 2016; Yamaguchi and Condeelis, 2007) and may each contribute to the unique cell-surface dynamics that contribute to the lethality of metastatic cancer cells.

Bending of surfaces by anchored polymers is a general physical phenomenon. As such, membrane shape regulation by the glycocalyx could be a universal feature relevant in all cell types. Future efforts may unravel physical function of the glycocalyx in the biogenesis of specific membrane organelles and signaling structures, including cilia, axons, cytonemes, and microvilli. Nevertheless, the description in this Part IV supports a more holistic model of membrane shape regulation that includes consideration of forces on both the intracellular and extracellular faces of the plasma membrane.

Methods

Antibodies and reagents. The following antibodies were used: FITC-Human CD227 (Muc1) (559774, BD Biosciences), Human CD227 (555925, BD Biosciences) (Muc1), Alexa Flour 488 Human Podocalyxin (222328, R&D Systems), Actin (sc1615, Santa Cruz), GFP (4B10, 2955S, Cell Signaling), 6×His (9000012, BD Biosciences), Goat anti-Mouse IgG-HRP (sc-2005, Santa Cruz), Mouse anti-Goat IgG-HRP (sc-2354, Santa Cruz). Lectins used were: Biotinylated Peanut Agglutinin (PNA; B-1075, Vector Laboratories), CF568 PNA (29061, Biotium), CF640R PNA (29063, Biotium), CF633 Wheat Germ Agglutinin (WGA; 29024, Biotium). Biotinylated lectins were detected using ExtrAvidin-Peroxidase (E2886, Sigma). Hyaluronic acid (HA) was probed in blots with fluorescently labeled or biotinylated bovine nasal hyaluronic acid binding protein (HABP; Millipore). Biotin-HABP was detected with horseradish peroxidase conjugated streptavidin (HRP-streptavidin; R&D Systems). For HA ELISAs, the DuoSet Hyaluronan kit was from R&D Systems. Actin depolymerization was induced through treatment with Latrunculin A (LatA; 76343-93-6; *Cayman Chemicals*).

For formation of giant unilamellar vesicles (GUVs), 1,2-dioleoyl-sn-glycero-3-phosphocholine (DOPC) and 1,2-dioleoyl-sn-glycero-3-((N-(5-amino-1-carboxypentyl)iminodiacetic acid)succinyl), with nickel salt (DOGS-NTA-Ni) were purchased from Avanti Polar Lipids; 2-(4,4-difluoro-5,7-dimethyl-4-bora-3a,4a-diaza-s-indacene-3-pentanoyl)-1-hexadecanoyl-sn-glycero-2-phosphocholine (Bodipy-PC) was purchased from Invitrogen; His-tagged recombinant human Podocalyxin (Ser23-Arg427; accession number AAB61574.1) was from R&D Systems; and His-tagged human serum albumin (accession number NP_000468) was from ACROBiosystems.

GFP binding protein (nanobody) came from Chromotek. NHS-esters of Alexa Fluor 488, Alexa Fluor 568, and Alexa Fluor 647 were from Invitrogen. Electron microscopy-grade 16% paraformaldehyde, 10% glutaraldehyde, and 2% $OsO_4$ for scanning electron microscopy (SEM) were obtained from Electron Microscopy Sciences.

Cloning and constructs. cDNAs for cytoplasmic-tail-deleted human Muc1 with 42 tandem repeats (Muc1-42TR ΔCT), Muc1-42TR polymer domain fusion with the TM21 synthetic membrane domain (Muc1-42TR TM21), cytoplasmic-tail-deleted human Podocalyxin (S/T-Rich ΔCT) were generated and cloned into the tetracycline-inducible PiggyBac expression vector (pPB TetOn Puro) or mammalian expression vector pcDNA3.1 as previously described (Paszek et al., 2014; Shurer et al.). To make lentiviral vector pLV Hygro TetOn HAS3, the cDNA for human HAS3 (accession NP_005320) was obtained from R&D Systems and amplified via PCR with the forward primer, 5'-GGCACCTCGAGGATGCCGGTGCAGCTGACGACA-3' (SEQ ID NO:88), and reverse primer, 5'-GGCAGAATTCTTACACCTCAGCAAAAGCCAAGCT-3' (SEQ ID NO:89). The PCR product was cloned into pJET1.2 (ThermoFisher) according to manufacturer's protocol, and subcloned into the AbsI and EcoRI sites of pLV Hygro TetOn (Paszek et al., 2012). For generation of pPB Muc1 GFP ΔCT TetOn Puro with varying number of tandem repeats, the cDNA for mOxGFP (Addgene #68070; heretofore mOxGFP is referred to as GFP) was amplified with primers: 5'-GGCAGCTCAGCTATGGTGTCCAAGGGCGAGGAGCTGT-3' ((SEQ ID NO:90) forward) and 5'-GGCAGCTGAGCCCTTATACAGCTCGTCCATGCCGTGAGT-3' ((SEQ ID NO:91) reverse). The PCR product was cloned into pJET1.2 and subcloned non-directionally into the BlpI site of pPB Muc1-42TR ΔCT TetOn Puro. For constructs with 10 and 42 native tandem repeats (PDTRPAPGSTAPPAHGVTSA ((SEQ ID NO:8)), synthetic cDNAs for the desired repeat units were generated through custom gene synthesis (General Biosystems) and cloned in place of the tandem repeats in pPB Muc1 GFP ΔCT TetOn Puro using the BamHI and Bsu36I restriction sites. Muc1 tandem repeats were deleted through Q5 site directed mutagenesis with 5'-TGGAGGAGCCTCAGGCATACTTTATTG-3' (SEQ ID NO:92) forward) and 5'-CCACCGCCGACCGAGGTGACATCCTG-3' ((SEQ ID NO:93) reverse) primers to generate pPB Muc1 0TR GFP ΔCT TetOn Puro. To add a SumoStar tag to the Muc1-42TR GFP ΔCT N-terminus, a cDNA encoding the IgG kappa leader sequence, SumoStar tag, and Muc1 N-terminus was generated through custom gene synthesis (General Biosystems) and inserted in place of the Muc1 N-terminus in pPB Muc1 GFP TetOn Puro using the BamHI and BsrGI restriction sites. For recombinant production of the mucin polymer domain, 42 tandem repeats from Muc1 were fused to an N-terminal S6 tag (GDSLSWLLRLLN) and C-terminal 10×-histidine purification tag to make Muc1-42TR 10× His.

To insert the S6 tag, Q5 site directed mutagenesis was performed using 5'-GTTGCGACTGCTTAACGGACA-GATCTCGATGGTGAGC-3' (SEQ ID NO:94) forward) AND 5'-AGCCAGCTCAGGGAATCCCCAGCATTCT-TCTCAGTAGAG-3' ((SEQ ID NO:95) reverse) on a pcDNA3.1 plasmid containing the Muc1 N-terminus from pPB Muc1-42TR ΔCT TetOn Puro between BamHI and BglII sites. The S6 tag was subsequently cut at these sites and replaced in the Muc1-42TR ΔCT N-terminus in pPB Muc1-42TR ΔCT TetOn Puro. The 10×-histidine tag was added by annealing the oligos, 5'-TCAGGCCACCACCAC-CATCACCATCATCACCACCATTAGGG-3' (SEQ ID NO:96) and 3'-CC- GGTGGTGGTGGTAGTG-GTAGTAGTGGTGGTAATCCCTTAA-5' (SEQ ID NO:97), and inserting in place of the Muc1-42TR ΔCT C-terminus in pPB Muc1-42TR ΔCT TetOn Puro using the Bsu36I and EcoRI restriction sites.

Cell lines and culture. MCF10A and HEK293T cells were obtained from ATCC. MCF10A cells were cultured in DMEM/F12 media supplemented with 5% horse serum, 20 ng/mL EGF, 10 μg/ml insulin, 500 ng/mL hydrocortisone, 100 ng/mL cholera toxin and penicillin/streptomycin. HEK293T cells were cultured in DMEM high glucose supplemented with 10% fetal bovine serum and penicillin/streptomycin. Equine synoviocytes were cultured in low glucose (1.0 g/L) DMEM media supplemented with 40 mM HEPES, 4 mM L-Glutamine, 110 mg/L sodium pyruvate, 10% fetal bovine serum and penicillin/streptomycin. Subculture of the synoviocytes was performed every 3-4 days. All adherent cells were maintained at 37° C., 5% $CO_2$, and 90% RH. Suspension-adapted 293F cells obtained from Thermo Fisher (R79007) and were maintained in Freestyle 293F Expression Medium (Thermo Fisher, 12338018) in spinner flasks at 37° C., 8% $CO_2$, 120 RPM, and 80% RH according to manufacturer's protocol. Stable MCF10A, primary equine synoviocyte, and 293F cells expressing the rtTA-M2 tetracycline transactivator were prepared by lentiviral transduction using the pLV rtTA-NeoR plasmid as previously described (Paszek et al., 2012). For preparation of mucin expressing cell lines, plasmids with ITR-flanked expression cassettes (i.e. PiggyBac vectors) were co-transfected with the PiggyBac hyperactive transposase using Nucleofection Kit V (Lonza) or FreeStyle Max Reagent (Thermo Fisher) according to manufacturer's protocols and selected with 1 μg/ml puromycin or 200 μg/mL hygromycin.

Equine synovial tissue resection and primary synoviocyte isolation. Primary equine synoviocytes were obtained from the shoulder, stifle, carpal, tarsal and fetlock joints of a yearling horse (*Equus caballus*). To isolate the fibroblast-like type B synovial cells (synoviocytes), synovial membrane tissues were digested with 0.15% collagenase (Worthington Biochemical, Lakewood, NJ) supplemented with 0.015% DNase I (Roche, Indianapolis, IN) for 3 h at 37° C. in Ham's F12 media, followed by filtration and centrifugation at 250×g for 10 minutes as previously described (Saxer et al., 2001).

Freshly resected synovial tissues were either incubated for 30 min in Ham's F12 media with or without 1 U/mL Hyaluronidase (Sigma) and fixed or immediately fixed for 24 h with 4% paraformaldehyde and 1% glutaraldehyde in PBS. Tissues were then either processed for SEM or reduced with 0.1 mg/mL $NaBH_4$ for 20 min on ice and further processed for confocal imaging.

Scanning electron microscopy (SEM) and analysis. All samples were fixed for 24 h with 4% paraformaldehyde and 1% glutaraldehyde in PBS, post-fixed for 45 min with 1% osmium tetraoxide in $dH_2O$, washed and subsequently dehydrated stepwise in ethanol of 25%, 50%, 70%, 95%, 100%, 100% before drying in a critical point dryer (CPD 030, Bal-Tec). Samples were coated with gold-palladium in a Desk V sputter system (Denton Vacuum) and imaged on a field emission scanning electron microscope (Mira3 FE-SEM, Tescan or FE-SEM LEO 1550, Carl Zeiss Inc.). For actin depolymerization studies, cells were treated for 60 min with 10 μM LatA before fixation, where indicated.

Cellular tube density, diameter, and length were analyzed in ImageJ Fiji (Schindelin et al., 2012). For quantification of tube density per area, a ~2 μm×2 μm region of interest was drawn and the encompassed tubes counted manually. Tube diameter was measured by drawing a strain line through the tube cross section at its mid-point. Tube length was measured for tubes extending approximately parallel to the image plane, as identified by visual inspection, using the ImageJ line segment tool.

Confocal microscopy for cells and tissues. Cells were plated at 5,000 cells/cm$^2$ and subsequently induced with 0.2 μg/mL of doxycycline for 24 h before being fixed with 4% paraformaldehyde. Antibodies were diluted 1:200 in 5% normal goat serum PBS and incubated overnight at 4° C. Lectins were diluted to 1 μg/mL in 5% normal goat serum PBS and incubated for 2 h at room temperature. For hyaluronic acid staining of cells and tissues, HABP was diluted to 0.125 μg/ml in 0.5% normal goat serum in PBS and incubated on samples for 24 h. Cell samples were imaged on a Zeiss LSM inverted 880 confocal microscope using a 40× water immersion objective (NA 1.1). In addition to HABP, $NaBH_4$-treated tissues were stained with 1 μg/mL Hoechst for 10 min and imaged on a Zeiss 880 upright confocal microscope with a 40× water dipping lens. Unstained tissue collagen was visualized with second harmonic generation using non-descan detectors.

Immuno- and lectin blot analysis. Cells were plated at 20,000 cells/cm$^2$ and induced with 0.2 μg/mL doxycycline for 24 h before lysis with Tris-Triton lysis buffer (Abcam). Lysates were separated on Nupage 4-12% Bis-Tris or 3-8% Tris-Acetate gels (Thermo Fisher) and transferred to PVDF membranes. Primary antibodies were diluted 1:1000 and lectins were diluted to 1 μg/mL in 3% BSA TBST and incubated 4 h at room temperature or overnight at 4° C. Secondary antibodies or ExtrAvidin were diluted 1:2000 in 3% BSA TBST and incubated for 2 h at room temperature. Blots were developed in Clarity ECL (BioRad) substrate, imaged on a ChemiDoc (BioRad) documentation system, and quantified in ImageJ Fiji (Schindelin et al., 2012).

Flow cytometry. Cells were plated at 20,000 cells/cm$^2$ and grown for 24 h. Cells were then induced with 0.2 μg/mL doxycycline for 24 h. Adherent cells were non-enzymatically detached by incubating with 1 mM EGTA in PBS at 37° C. for 20 min and added to the population of floating cells, if present. Antibodies were diluted 1:200 and lectins were diluted to 1 μg/mL in 0.5% BSA PBS and incubated with cells at 4° C. for 30 min. The BD Accuri C6 flow cytometer was used for analysis.

Analysis of HA synthesis and molecular size. Control and lentiviral transduced MCF10A and primary equine synoviocytes were plated and induced with 0.2 μg/mL doxycycline for 24 h. Total levels of HA secreted into the cell culture media were measured via the DuoSet Hyaluronan ELISA kit following manufacturer's protocol. Briefly, a 96-well microplate was coated with recombinant human Aggrecan. HA in cell culture media was captured by the coated Aggrecan and detected with Biotin-HABP/HRP-Streptavidin. HA concentration was measured using *S. pyogenes* HA standard (R&D Systems). HA molecular mass was assayed by electrophoresis and blot analysis essentially as described (Yuan et al., 2013), using agarose instead of polyacrylamide for gel electrophoresis. Briefly, cell culture media containing HA was loaded in a 0.6% agarose gel in TBE buffer. Following electrophoresis, samples were transferred to HyBond N+ membrane (GE Healthcare). HA was probed with biotin-HABP (0.125 μg/ml in 0.1% BSA-PBS, 1 h) and subsequently detected with HRP-Streptavidin (0.025 μg/ml in 0.1% BSA-PBS, 1 h). Blots were developed in ECL substrate (Amresco), imaged on a ChemiDoc (BioRad) documentation system, and quantified in ImageJ Fiji (Schindelin et al., 2012).

Analysis of mucin radius of gyration. The Muc1 polymer domain with 42 tandem repeats (S6 Muc1-42TR 10×His) was produced recombinantly in suspension adapted Freestyle 293F cells. Stable 293F cell lines were prepared with the pPB Muc1-42TR 10×His Puro TetOn Puro vector as described above. Production of Muc1 biopolymer was induced with 1 μg/mL doxycycline in 30 mL of suspension culture in Freestyle 293F media. Induced media was collected after 24 h and purified on HisPur Ni-NTA resin (Thermo Fisher) according to standard protocols. Briefly, 1 mL bed volume of Ni-NTA resin was rinsed with equilibration buffer (20 mM sodium phosphate, 0.5 M NaCl, pH=7.4). Equilibrated resin was incubated overnight at 4° C. with 10 μmL harvested 293F media diluted in 30 mL of equilibration buffer. Beads were washed in equilibration buffer with 5 mM imidazole and eluted in equilibration buffer with 500 mM imidazole. Eluted protein was dialyzed against PBS and analyzed by SDS-PAGE. Gels were stained with Sypro Ruby (Thermo Fisher) according to manufacturer's instructions to confirm protein size and purity. Gels were blotted and probed with Muc1 and His antibodies to confirm mucin identity and PNA lectin to confirm mucin O-glycosylation. Purified recombinant Muc1 was dialyzed against PBS to remove imidazole.

The radius of gyration of the recombinant Muc1 polymer domain was measured with size-exclusion chromatography-coupled to multiangle light scattering (SEC-MALS). Purified protein (40 μL of Muc1 with a concentration of 5 μg/L) was subjected to SEC using a Superdex 200 Increase 10/300 column (GE Healthcare) equilibrated in MALS buffer (20 mM sodium phosphate, 0.5 M NaCl, pH 7.4). The SEC was coupled to a static 18-angle light scattering detector (DAWN HELEOS-II) and a refractive index detector (Optilab T-rEX, Wyatt Technology). Data were collected every second at a flow rate of 0.7 mL/min. Data analysis was carried out using ASTRA VI, yielding the molar mass, mass distribution (polydispersity), and radius of gyration of the sample (32.0 nm±0.4%). For normalization of the light scattering detectors and data quality control, monomeric BSA (Sigma) was used.

Variation of mucin lengths and cell-surface densities. Mucin lengths: MCF10As expressing Muc1 mOxGFP with 0, 10, or 42 tandem repeats were sorted for similar levels of GFP on a BD FACs Aria II. Stable populations were created from these sorted lines. Cells were plated onto 8 mm coverslips at 10,000 cells/$cm^2$ for 16-18 h, then induced with 0.2 g/mL of doxycycline for 24 h and fixed for SEM analysis.

Mucin cell surface density: A nanobody with an approximate size of 2 nm (15 kDa) and picomolar affinity for GFP was obtained from ChromoTech and labeled with NHS-Alexa Fluor 647 according to manufacturer's protocol. MCF10A cells expressing Muc1 mOxGFP with 42 tandem repeats were labeled in 5 μg/ml 647-nanobody for 20 min on ice to label only cell surface mucins. Cells were sorted onto poly-l-lysine treated 8 mm coverslips at 5,000 to 10,000 cells/$cm^2$ for SEM, allowed to adhere for 4 h at 37° C., and fixed for SEM imaging. Alternatively, cells were sorted into 1.7 mL Eppendorf tubes, resuspended in 100 μL 0.5% BSA PBS, and lysed with 100 μL 2×RIPA lysis buffer for estimation of mucin surface densities via SDS-PAGE. Lysed samples were run simultaneously with Alexa Fluor 647-nanobody standards of known molecular concentration. Nanobody fluorescence in lysed samples and standards were imaged on a Typhoon 9400 imaging system (GE Healthcare). Total fluorescence in each sample or standard was quantified in ImageJ Fiji (Schindelin et al., 2012). A standard curve was constructed by relating fluorescence from nanobody standards to their known concentration. The number of labeled mucins in each lysate were estimated based on the standard curve. The mucin surface density was estimated by dividing the total number of mucins by the known number of cells in each sample and their average surface area of 5,000 $\mu m^2$ based on an average radius of 20 μm and spherically shaped wild-type cells in suspension. A standard curve was constructed based on the number of mucins per area and the known mean fluorescence signal from the FACS collected population. This standard curve was then applied to calculate the number of mucins per area of populations collected subsequently.

Giant unilamellar vesicles. Preparation. Giant Unilamellar Vesicles (GUVs) were prepared by electroformation as described previously (Angelova and Dimitrov, 1986). Briefly, lipids and dye dissolved in chloroform were spread on glass slides coated with ITO (Indium-Tin-Oxide). The slides were placed under vacuum for 2 h to remove all traces of organic solvents. The lipid films were hydrated and swelled in 120 mM sucrose at 55° C. GUVs were electroformed by the application of an oscillating potential of 1.4 V (peak-to-peak) and 12 Hz for 3 h (Busch et al., 2015). GUVs compositions were prepared with DOPC and increasing molar fractions of DOGS-Ni-NTA lipid (5, 10, 15, and 20 mol %). Bodipy-PC was used to label the lipids at a dye/lipid ratio of 1/2500. Recombinant His-tagged Podocalyxin and human serum albumin (HSA) were conjugated with NHS-Alexa Fluor 568, and the degree of labelling quantified according to the manufacturer's protocol. GUVs were diluted in 20 mM HEPES, 50 mM NaCl, pH=7.4 (120 mOsm) and then mixed with labeled Podocalyxin (~2 μM) or HSA (0.125 or 0.375 μM) for at least 20 minutes before imaging (GUVs/proteins=1/1 by volume).

Imaging and analysis. GUVs were imaged on a Nikon C2plus confocal microscope using a 60× water immersion objective (NA 1.2). Lipids and (Bodipy-PC) and protein (Alexa Fluor 568) were imaged through excitation at wavelength λ=488 and 561 nm, respectively. Dye fluorescent intensity was measured by taking 5 different line scans across the GUV in ImageJ Fiji (Schindelin et al., 2012). The intensity profile of each line was analyzed using Mathematica 10.3, where the integral of the intensity peak was calculated and averaged for 5 different lines per GUV.

Expansion microscopy. Expansion microscopy (ExM) was performed as described previously (Tillberg et al., 2016) and involved steps of anchoring fluorescent dyes and proteins, gelation, digestion and expansion to achieve dye retention and separation. Briefly, fixed and stained cells were anchored with 0.1 mg/ml Acryloyl-X, SE (6-((acryloyl) amino)hexanoic acid, succinimidyl ester (ThermoFisher) in PBS for 16 h at RT, washed twice and further incubated 1 h at 37° C. in a monomer solution (1×PBS, 2 M NaCl, 8.625% (w/w) sodium acrylate, 2.5% (w/w) acrylamide, 0.15% (w/w) N,N'-methylenebisacrylamide) mixed with ammonium persulfate 0.2% (w/w) initiator and tetramethylethylenediamine 0.2% (w/w) accelerator for gelation. For digestion, gelled samples were gently transferred into 6 well glass bottom plates (Cellvis) and treated with Proteinase K (New England Biolabs) at 8 units/mL in digestion buffer (50 mM Tris (pH 8), 1 mM EDTA, 0.5% Triton X-100, 1 M NaCl) for 16 h at room temperature. For expansion, digested gels were washed in large excess volume of $ddH_2O$ for 1 h. This was repeated 4-6 times until the expansion plateaued. Samples were imaged on a Zeiss LSM inverted 880 confocal microscope using a 40× water immersion objective (NA 1.1) in Airyscan mode to optimize resolution.

Isolation of extracellular vesicles. Cell were plated at 10,000 cells/$cm^2$ in appropriate dishes. Following induction with 1 μg/ml doxycycline for 18 h, cells were rinsed with PBS twice then serum-starved for an additional 6 h with 1 μg/mL doxycycline treatment. Conditioned media from serum-starved cells was clarified by pelleting cellular debris through two consecutive centrifugations at 600×g for 5 min.

Nanoparticle tracking analysis. Extracellular vesicles in the clarified media were analyzed using a Malvern NS300 NanoSight. Imaging was performed for 60 s with five captures per sample. Particle analysis was performed using Malvern Nanoparticle Tracking Analysis software.

Plunge-freezing vitrification. From clarified media, 3-5 μl of sample was pipetted onto holey carbon-coated 200 mesh copper grids (Quantifoil Micro Tools, Jena, Germany) with hole sizes of ~2 μm. The grids were blotted from the reverse side and immediately plunged into a liquid ethane/propane mixture cooled to liquid nitrogen temperature using a custom-built vitrification device (MPI, Martinsried, Germany). The plunge-frozen grids were stored in sealed cryo-boxes in liquid nitrogen until used.

Cryogenic transmission electron microscopy. Cryogenic transmission electron microscopy (cryo-TEM) was performed on a Titan Themis (Thermo Fisher Scientific, Waltham, MA) operated at 300 kV in energy-filtered mode, equipped with a field-emission gun, and 3838×3710 pixel Gatan K2 Summit direct detector camera (Gatan, Pleasanton, CA) operating in Counted, dose-fractionated modes. Images were collected at a defoci of between −1 μm and −3 μm. Images were binned by 2, resulting in pixel sizes of 0.72-1.1 nm.

Statistics. Statistics were calculated in Graphpad Prism. One-way ANOVA and post-hoc two-tailed student's t-test were used where appropriate as indicated by figure legends. For boxplots—center lines show the medians; box limits indicate the 25th and 75th percentiles as determined by R software; whiskers extend 1.5 times the interquartile range from the 25th and 75th percentiles, and notches, where shown, indicate the 95% confidence interval.

REFERENCES

Agrawal, B., Krantz, M. J., Parker, J., and Longenecker, B. M. (1998). Expression of MUC1 Mucin on Activated Human T Cells: Implications for a Role of MUC1 in Normal Immune Regulation. Cancer Res. 58, 4079-4081.

Alexander, S. (1977). Adsorption of chain molecules with a polar head a scaling description. J. Phys. 38, 983-987.

Angelova, M. I., and Dimitrov, D. S. (1986). Liposome electroformation. Faraday Discuss. Chem. Soc. 81, 303-311.

Antonyak, M. A., Li, B., Boroughs, L. K., Johnson, J. L., Druso, J. E., Bryant, K. L., Holowka, D. A., and Cerione, R. A. (2011). Cancer cell-derived microvesicles induce transformation by transferring tissue transglutaminase and fibronectin to recipient cells. Proc. Natl. Acad. Sci. 108, 4852-4857.

Becker, A., Thakur, B. K., Weiss, J. M., Kim, H. S., Peinado, H., and Lyden, D. (2016). Extracellular Vesicles in Cancer: Cell-to-Cell Mediators of Metastasis. Cancer Cell 30, 836-848.

Bennett, R., Jarvela, T., Engelhardt, P., Kostamovaara, L., Sparks, P., Carpén, O., Turunen, O., and Vaheri, A. (2001). Mucin MUC1 is seen in cell surface protrusions together with ezrin in immunoelectron tomography and is concentrated at tips of filopodial protrusions in MCF-7 breast carcinoma cells. J. Histochem. Cytochem. Off. J. Histochem. Soc. 49, 67-77.

Bergert, M., Erzberger, A., Desai, R. A., Aspalter, I. M., Oates, A. C., Charras, G., Salbreux, G., and Paluch, E. K. (2015). Force transmission during adhesion-independent migration. Nat. Cell Biol. 17, 524-529.

Bischoff, M., Gradilla, A.-C., Seijo, I., Andrés, G., Rodríguez-Navas, C., González-Méndez, L., and Guerrero, I. (2013). Cytonemes are required for the establishment of a normal Hedgehog morphogen gradient in *Drosophila* epithelia. Nat. Cell Biol. 15, 1269-1281.

Buck, C. A., Glick, M. C., and Warren, L. (1971). Glycopeptides from the surface of control and virus-transformed cells. Science 172, 169-171.

Busch, D. J., Houser, J. R., Hayden, C. C., Sherman, M. B., Lafer, E. M., and Stachowiak, J. C. (2015). Intrinsically disordered proteins drive membrane curvature. Nat. Commun. 6, 7875.

Button, B., Cai, L.-H., Ehre, C., Kesimer, M., Hill, D. B., Sheehan, J. K., Boucher, R. C., and Rubinstein, M. (2012). A periciliary brush promotes the lung health by separating the mucus layer from airway epithelia. Science 337, 937-941.

Campelo, F., and Hernández-Machado, A. (2007). Model for Curvature-Driven Pearling Instability in Membranes. Phys. Rev. Lett. 99, 088101.

Charras, G. T., Yarrow, J. C., Horton, M. A., Mahadevan, L., and Mitchison, T. J. (2005). Non-equilibration of hydrostatic pressure in blebbing cells. Nature 435, 365-369.

Charras, G. T., Coughlin, M., Mitchison, T. J., and Mahadevan, L. (2008). Life and Times of a Cellular Bleb. Biophys. J. 94, 1836-1853.

Chen, W.-L., Cordero, R., Tran, H., and Ober, C. K. (2017). 50th Anniversary Perspective: Polymer Brushes: Novel Surfaces for Future Materials. Macromolecules 50, 4089-4113.

Cloosen, S., Thio, M., Vanclee, A., Leeuwen, V., M, E. B., Senden-Gijsbers, B. L. M. G., Oving, E. B. H., Germeraad, W. T. V., and Bos, G. M. J. (2004). Mucin-1 is expressed on dendritic cells, both in vitro and in vivo. Int. Immunol. 16, 1561-1571.

D'Aloia, M. M., Zizzari, I. G., Sacchetti, B., Pierelli, L., and Alimandi, M. (2018). CAR-T cells: the long and winding road to solid tumors. Cell Death Dis. 9, 282.

Dennis, J. W., Nabi, I. R., and Demetriou, M. (2009). Metabolism, Cell Surface Organization, and Disease. Cell 139, 1229-1241.

Evanko, S. P., Tammi, M. I., Tammi, R. H., and Wight, T. N. (2007). Hyaluronan-Dependent Pericellular Matrix. Adv. Drug Deliv. Rev. 59, 1351-1365.

Footer, M. J., Kerssemakers, J. W. J., Theriot, J. A., and Dogterom, M. (2007). Direct measurement of force generation by actin filament polymerization using an optical trap. Proc. Natl. Acad. Sci. 104, 2181-2186.

Fowke, T. M., Karunasinghe, R. N., Bai, J.-Z., Jordan, S., Gunn, A. J., and Dean, J. M. (2017). Hyaluronan synthesis by developing cortical neurons in vitro. Sci. Rep. 7, 44135.

Freeze, H. H. (2013). Understanding Human Glycosylation Disorders: Biochemistry Leads the Charge. J. Biol. Chem. 288, 6936-6945.

Friedl, P., and Wolf, K. (2010). Plasticity of cell migration: a multiscale tuning model. J. Cell Biol. 188, 11-19.

Gangoda, L., Boukouris, S., Liem, M., Kalra, H., and Mathivanan, S. Extracellular vesicles including exosomes are mediators of signal transduction: Are they protective or pathogenic? PROTEOMICS 15, 260-271.

Gennes, P.-G. (1979). Scaling Concepts in Polymer Physics (Ithaca, NY: Cornell University Press).

de Gennes, P. (1980). Conformations of polymers attached to an interace. Macromolecules 1069-1075.

Gupton, S. L., and Gertler, F. B. (2007). Filopodia: the fingers that do the walking. Sci. STKE Signal Transduct. Knowl. Environ. 2007, re5.

Hall, A. (1998). Rho GTPases and the actin cytoskeleton. Science 279, 509-514.

Hattrup, C. L., and Gendler, S. J. (2008). Structure and Function of the Cell Surface (Tethered) Mucins. Annu. Rev. Physiol. 70, 431-457.

Hiergeist, C., and Lipowsky, R. (1996). Elastic Properties of Polymer-Decorated Membranes. J. Phys. II 6, 1465-1481.

Jung, Y., Riven, I., Feigelson, S. W., Kartvelishvily, E., Tohya, K., Miyasaka, M., Alon, R., and Haran, G. (2016). Three-dimensional localization of T-cell receptors in relation to microvilli using a combination of superresolution microscopies. Proc. Natl. Acad. Sci. 113, E5916-E5924.

Kesavan, G., Sand, F. W., Greiner, T. U., Johansson, J. K., Kobberup, S., Wu, X., Brakebusch, C., and Semb, H. (2009). Cdc42-mediated tubulogenesis controls cell specification. Cell 139, 791-801.

Kesimer, M., Ehre, C., Burns, K. A., Davis, C. W., Sheehan, J. K., and Pickles, R. J. (2013). Molecular organization of the mucins and glycocalyx underlying mucus transport over mucosal surfaces of the airways. Mucosal Immunol. 6, 379-392.

Koistinen, V., Kärnä, R., Koistinen, A., Arjonen, A., Tammi, M., and Rilla, K. (2015). Cell protrusions induced by hyaluronan synthase 3 (HAS3) resemble mesothelial microvilli and share cytoskeletal features of filopodia. Exp. Cell Res. 337, 179-191.

Kornberg, T. B., and Roy, S. (2014). Cytonemes as specialized signaling filopodia. Development 141, 729-736.

Kramer, R. H., and Nicolson, G. L. (1979). Interactions of tumor cells with vascular endothelial cell monolayers: a model for metastatic invasion. Proc. Natl. Acad. Sci. U.S.A. 76, 5704-5708.

Kufe, D. W. (2009). Mucins in cancer: function, prognosis and therapy. Nat. Rev. Cancer 9, nrc2761.

Lange, K. (2011). Fundamental role of microvilli in the main functions of differentiated cells: Outline of an universal regulating and signaling system at the cell periphery. J. Cell. Physiol. 226, 896-927.

Lee, G. M., Johnstone, B., Jacobson, K., and Caterson, B. (1993). The dynamic structure of the pericellular matrix on living cells. J. Cell Biol. 123, 1899-1907.

Lipowsky, R. (1995). Bending of Membranes by Anchored Polymers. EPL Europhys. Lett. 30, 197.

Liu, T.-L., Upadhyayula, S., Milkie, D. E., Singh, V., Wang, K., Swinburne, I. A., Mosaliganti, K. R., Collins, Z. M., Hiscock, T. W., Shea, J., et al. (2018). Observing the cell in its native state: Imaging subcellular dynamics in multicellular organisms. Science 360, eaaq1392.

Makabe Sayoko, Naguro Tomonori, and Stallone Tiziana (2006). Oocyte-follicle cell interactions during ovarian follicle development, as seen by high resolution scanning and transmission electron microscopy in humans. Microsc. Res. Tech. 69, 436-449.

Marshall, W. F. (2012). Organelle Size Control Systems: From Cell Geometry to Organelle-Directed Medicine. BioEssays News Rev. Mol. Cell. Dev. Biol. 34, 721-724.

McConnell, R. E., Higginbotham, J. N., Shifrin, D. A., Tabb, D. L., Coffey, R. J., and Tyska, M. J. (2009). The enterocyte microvillus is a vesicle-generating organelle. J. Cell Biol. 185, 1285-1298.

Milner, S. T. (1991). Polymer brushes. Science 251, 905-914.

Paluch, E. K., and Raz, E. (2013). The role and regulation of blebs in cell migration. Curr. Opin. Cell Biol. 25, 582-590.

Paszek, M. J., DuFort, C. C., Rubashkin, M. G., Davidson, M. W., Thorn, K. S., Liphardt, J. T., and Weaver, V. M. (2012). Scanning angle interference microscopy reveals cell dynamics at the nanoscale. Nat. Methods 9, 825-827.

Paszek, M. J., DuFort, C. C., Rossier, O., Bainer, R., Mouw, J. K., Godula, K., Hudak, J. E., Lakins, J. N., Wijekoon, A. C., Cassereau, L., et al. (2014). The cancer glycocalyx mechanically primes integrin-mediated growth and survival. Nature 511, 319-325.

Pelaseyed, T., Bergström, J. H., Gustafsson, J. K., Ermund, A., Birchenough, G. M. H., Schutte, A., Post, S. van der, Svensson, F., Rodríguez-Piñeiro, A. M., Nyström, E. E. L., et al. The mucus and mucins of the goblet cells and enterocytes provide the first defense line of the gastrointestinal tract and interact with the immune system. Immunol. Rev. 260, 8-20.

Peskin, C. S., Odell, G. M., and Oster, G. F. (1993). Cellular motions and thermal fluctuations: the Brownian ratchet. Biophys. J. 65, 316-324.

Pilon, C., Levast, B., Meurens, F., Le Vern, Y., Kerboeuf, D., Salmon, H., Velge-Roussel, F., Lebranchu, Y., and Baron, C. (2009). CD40 engagement strongly induces CD25 expression on porcine dendritic cells and polarizes the T cell immune response toward Thl. Mol. Immunol. 46, 437-447.

Pinho, S. S., and Reis, C. A. (2015). Glycosylation in cancer: mechanisms and clinical implications. Nat. Rev. Cancer 15, 540-555.

Pol, E. van der, Böing, AN, Gool, E. L., and Nieuwland, R. (2016). Recent developments in the nomenclature, presence, isolation, detection and clinical impact of extracellular vesicles. J. Thromb. Haemost. 14, 48-56.

van den Pol, A. N., and Kim, W. T. (1993). NILE/L1 and NCAM-polysialic acid expression on growing axons of isolated neurons. J. Comp. Neurol. 332, 237-257.

Polefka, T. G., Garrick, R. A., Redwood, W. R., Swislocki, N. I., and Chinard, F. P. (1984). Solute-excluded volumes near the Novikoff cell surface. Am. J. Physiol.-Cell Physiol. 247, C350-C356.

Porter, A. P., Papaioannou, A., and Malliri, A. (2016). Deregulation of Rho GTPases in cancer. Small GTPases 7, 123-138.

Satomaa, T., Heiskanen, A., Mikkola, M., Olsson, C., Blomqvist, M., Tiittanen, M., Jaatinen, T., Aitio, O., Olonen, A., Helin, J., et al. (2009). The N-glycome of human embryonic stem cells. BMC Cell Biol. 10, 42.

Sauvanet, C., Wayt, J., Pelaseyed, T., and Bretscher, A. (2015). Structure, Regulation, and Functional Diversity of Microvilli on the Apical Domain of Epithelial Cells. Annu. Rev. Cell Dev. Biol. 31, 593-621.

Saxer, R. A., Bent, S. J., Brower-Toland, B. D., Mi, Z., Robbins, P. D., Evans, C. H., and Nixon, A. J. (2001). Gene mediated insulin-like growth factor-I delivery to the synovium. J. Orthop. Res. Off. Publ. Orthop. Res. Soc. 19, 759-767.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat. Methods 9, 676-682.

Schmick, M., and Bastiaens, P. I. H. (2014). The Interdependence of Membrane Shape and Cellular Signal Processing. Cell 156, 1132-1138.

Shurer, C., Colville, M., Gupta, V., Head, S., Kai, F., Lakins, J., and Paszek, M. A Genetically Encoded Toolbox for Glycocalyx Engineering: Tunable Control of Cell Adhesion, Survival, and Cancer Cell Behaviors. ACS Biomater. Sci. Eng.

Stachowiak, J. C., Hayden, C. C., and Sasaki, D. Y. (2010). Steric confinement of proteins on lipid membranes can drive curvature and tubulation. Proc. Natl. Acad. Sci. 107, 7781-7786.

Tammi, M. I., Day, A. J., and Turley, E. A. (2002). Hyaluronan and Homeostasis: A Balancing Act. J. Biol. Chem. 277, 4581-4584.

Tillberg, P. W., Chen, F., Piatkevich, K. D., Zhao, Y., Yu, C.-C. (Jay), English, B. P., Gao, L., Martorell, A., Suk, H.-J., Yoshida, F., et al. (2016). Protein-retention expansion microscopy of cells and tissues labeled using standard fluorescent proteins and antibodies. Nat. Biotechnol. 34, 987-992.

Tricarico, C., Clancy, J., and D'Souza-Schorey, C. (2017). Biology and biogenesis of shed microvesicles. Small GTPases 8, 220-232.

Tsafrir, I., Sagi, D., Arzi, T., Guedeau-Boudeville, M.-A., Frette, V., Kandel, D., and Stavans, J. (2001). Pearling Instabilities of Membrane Tubes with Anchored Polymers. Phys. Rev. Lett. 86, 1138-1141.

Turley, E. A., Wood, D. K., and McCarthy, J. B. (2016). Carcinoma Cell Hyaluronan as a "Portable" Cancerized Prometastatic Microenvironment. Cancer Res. 76, 2507-2512.

Yamaguchi, H., and Condeelis, J. (2007). Regulation of the actin cytoskeleton in cancer cell migration and invasion. Biochim. Biophys. Acta BBA—Mol. Cell Res. 1773, 642-652.

Ying, H., Kimmelman, A. C., Lyssiotis, C. A., Hua, S., Chu, G. C., Fletcher-Sananikone, E., Locasale, J. W., Son, J., Zhang, H., Coloff, J. L., et al. (2012). Oncogenic Kras Maintains Pancreatic Tumors through Regulation of Anabolic Glucose Metabolism. Cell 149, 656-670.

Yuan, H., Tank, M., Alsofyani, A., Shah, N., Talati, N., LoBello, J. C., Kim, J. R., Oonuki, Y., de la Motte, C. A., and Cowman, M. K. (2013). Molecular mass dependence of hyaluronan detection by sandwich ELISA-like assay and membrane blotting using biotinylated hyaluronan binding protein. Glycobiology 23, 1270-1280.

Zhang, H., Miller, R. H., and Rutishauser, U. (1992). Polysialic acid is required for optimal growth of axons on a neuronal substrate. J. Neurosci. Off. J. Soc. Neurosci. 12, 3107-3114.

Zhulina, E. B., and Borisov, O. V. (1996). Polyelectrolytes Grafted to Curved Surfaces. Macromolecules 29, 2618-2626.

Theoretical Considerations

Glycocalyx Polymer Brush Model

Without intending to be constrained by any particular theory, the disclosure provides a model to explain how biopolymers in the glycocalyx can generate entropic driving forces for membrane curvature. The model considers long chain polymers anchored on one end to the plasma membrane. Common examples of long-chain polymers in the glycocalyx include mucins and hyaluronic acid (HA), which we model specifically here. The modeling framework could be similarly applied to other types of glycocalyx polymers, including polysialic acid and other glycosaminoglycans. Hyaluronic acid is a semi-flexible linear polysaccharide comprised of repeating units of glucuronic acid and N-acetylglucosamine. Mucins have a more complex bottlebrush structure comprised of a central polypeptide backbone and densely clustered glycan side chains along the backbone. Although their structure is complex, bottlebrush polymers can be modelled as effective linear polymers with a monomer size on the order of the side chains (Paturej et al., 2016). Therefore, we consider all glycocalyx polymers in our model to be linear or effectively linear.

Biopolymers in the glycocalyx are anchored to the cell surface in several ways, including through transmembrane anchors, covalent conjugation to integral membrane proteins, and non-covalently to specific transmembrane receptors. Cell surface mucins are anchored directly near their carboxy terminus by a single transmembrane domain. Hyaluronic acid is anchored to the cell surface through specific transmembrane receptors on the cell surface. While it is possible for hyaluronic acid to be anchored at multiple points along the polymer backbone, for simplicity, we consider all glycocalyx polymers to have a single membrane anchor at one end.

The cell surface is also decorated with many types of integral and peripheral membrane proteins. These molecules could also contribute to an entropic pressure on the cell membrane, similar to a 2D gas pressure. To isolate the effects of glycocalyx polymers on the membrane, we did not include possible contributions from other cell surface proteins, as well as intracellular forces. However, the model could be extended to include these additional contributions to the system energy.

Biopolymers have excluded volumes accounting for steric interactions between monomers on the same polymer as well as between monomers on adjacent molecules (de Gennes, 1980). Large negative charges on acidic sugars, such as glucuronic acid and sialic acid, give rise to intramolecular and intermolecular electrostatic interactions (Israels et al., 1994). Finally, the polymers and the brush have entropic contributions due to the elastic energy, which captures the stretch of the molecules (de Gennes, 1980). Embedded in a deformable lipid membrane, the energy of this polymer glycocalyx and that of the membrane can minimize to yield the equilibrium configuration (Lipowsky, 1995; Stachowiak et al., 2012). Hence, in the present model below, we performed an energy minimization of the glycocalyx and the underlying membrane to describe the surface curvature.

Depending on surface density, polymers tethered to a surface exhibit two particular regimes of physical behavior—mushroom and brush. The Flory radius measures the approximate size of an entire polymer, and is given by $$R_F \approx l_a N_a^{\nu} = l^{\nu} l_a^{1-\nu},$$

where $N_a$ is the number of monomers in the polymer, $l_a$ is the size of each monomer or effective monomer, l is the fully extended length of the polymer chain, and v is called the Flory exponent. v≅0.6 for hydrophilic biopolymers in good solvents like water. At low densities, such that intermolecular spacing is larger than the polymer Flory radius, i.e. $C_G<1/(R_F)^2$, where $C_G$ is biopolymer concentration, biopolymers take up preferable conformations independent of neighbor interactions. In this regime, the flexible molecules can coil up to exhibit mushroom-like structures. On the other hand, at high surface concentrations, when the intermolecular spacing is smaller than the Flory radius, intermolecular interactions can dominate and stretch the biopolymers out into a brush-like structure. The polymer layer extension or thickness, the stored energy, and the generated membrane curvatures exhibit different scaling laws in these regimes, as described below.

In the mushroom regime, the attachment of a biopolymer to a flat, impenetrable surface reduces the number of accessible molecular conformations, cutting down the polymer shapes that penetrate the surface. Curving the impenetrable grafting surface can marginally increase the permissible configurations, and increase the entropy of the polymer. Thus, flexible biopolymers tethered to a deformable membrane can generate curvatures, as described by Lipowsky (Lipowsky, 1995). However, the additional entropy due to membrane curvature is small and consequently, curvatures generated by polymer mushrooms are also small, relative to deformations elicited by intermolecular interactions in polymer brushes. In this mushroom regime, the free energy due to the entropic contribution of each mushroom polymer tethered to a curved membrane is:

$$F_{mushroom} = -TS_{mushroom} \sim -k_B T\frac{2\pi R_{mushroom}}{R}. \quad (1)$$

where the reference configuration is the polymer tethered to a flat surface, $S_{mushroom}$ is the corresponding entropic contribution, $R_{mushroom}$ is the Flory radius of the mushroom-shaped biopolymer, and R is the radius of curvature of the underlying membrane. In the mushroom regime, we consider the formation of spherical membrane structures. The bending energy of the curved membrane is:

$$F_{membrane} = \frac{\kappa}{2C_G R^2}, \quad (2)$$

where κ is the bending stiffness of the membrane bilayer, $C_G$ is the surface density of the biopolymers, and $1/C_G$ is the area available for each polymer. Minimizing the total energy, $F_{total}=F_{mushroom}+F_{membrane}$ with respect to the radius of curvature, R, as $\partial F_{total}/\partial R=0$, we obtain the following scaling law for R:

$$R \sim \frac{\kappa}{k_B T}\frac{1}{2\pi C_G l_a N_a^v}, \quad (3)$$

where $l_a$ is the size of monomeric segments and $N_a$ is the number of such monomers in a polymer molecule.

At high surface densities, such that neighboring polymer molecules interact with each other, grafted polymers exhibit a brush-like structure (de Gennes, 1980). In this regime, we consider the formation of tubular structures from the membrane and predict the tubule curvatures generated by intermolecular crowding effects on the cell surface. An energy minimization approach elucidates the equilibrium curvature and brush extension as follows. For a tubule with radius R, the energy of the glycocalyx per length of the tubule contains elastic, excluded volume, and electrostatic components (Borisov and Zhulina, 2002; Bracha et al., 2013; Zhulina et al., 2006):

$$F_{brush} = F_{elastic} + F_{excluded\ volume} + F_{electrostatic}, \quad (4)$$

$$F_{brush} = k_B T\int_R^{R+H}\left[\frac{3}{2l_a^2 c_p s} + \left(w + \frac{\alpha_b^2}{2\Phi_{ion}}\right)c_p^2 s\right]dr, \quad (5)$$

where R is the radius of the tubule, H is the thickness of the glycocalyx brush, $l_a$ is the size of monomeric segments that form the biopolymers, $c_p$ is the monomer concentration, and s is the area per polymer. At the tubule surface, the area per polymer, s(r=R) is related to the biopolymer surface density, $C_G$, as $s(r=R)=1/C_G$. w is the excluded volume of monomer segments, $\alpha_b$ is the degree of ionization of a monomer, $\Phi_{ion}$ is the ion concentration in bulk solution, and r is a radial coordinate.

Zhulina et al. (Zhulina et al., 2006) provide expressions for $c_p$. Given the monomer length and diameter are similar (Paturej et al., 2016), we consider the monomeric segments to be cylinders with an aspect ratio close to 1. The energy per length of the underlying membrane bent into the tubular structure is (Helfrich, 2014):

$$F_{membrane} = \frac{\pi\kappa}{R}, \quad (6)$$

where κ is the membrane bending modulus. Thus, the total energy per tubule length is:

$$F_{total} = F_{brush} + F_{membrane} = k_B T\int_R^{R+H}\left[\frac{3}{2l_a^2 c_p s} + \left(w + \frac{\alpha_b^2}{2\Phi_{ion}}\right)c_p^2 s\right]dr + \frac{\pi\kappa}{R}. \quad (7)$$

Minimizing the total energy with respect to the tubule radius ($dF_{total}/dR=0$) reveals the dependence of the spontaneous curvature on the properties of the glycocalyx and the cell membrane, including the surface density of biopolymers.

We consider the implications of this theory for native Muc1, as an example mucin. We course-grain the bottlebrush biopolymer into $N_a$ effective monomers of size $l_{a,eff}$ (Paturej et al., 2016). In this work, we measure the radius of gyration, $R_G$, of Muc1 to be 32 nm. We estimate the overall stretched length, l, to be 270 nm based on electron micrographs of Muc1 purified from human HEp-2 epithelial cells (Bramwell et al., 1986). The radius of gyration is related to the Flory radius by $$R_G \approx \frac{1}{\sqrt{6}} R_F = \frac{1}{\sqrt{6}} l^\nu l_{a,eff}^{1-\nu}.$$

Using estimates of $R_G$=32 nm, l= 270 nm, and v=0.6, we estimate the mucin to be described by $N_a$=18 effective monomeric segments each having a size of $l_{a,eff}$=15 nm. We note that this effective monomer size is in good agreement with expectations based on estimates of the mucin side chain size to be 5-10 nm (Kesimer et al., 2013; McMaster et al., 1999). We assume that sialic acids on mucins contribute to a charge density of approximately 5 $e^-$ per 20 amino acid tandem repeat. Our assumption is based on most mucin O-glycosylation sites being occupied with sialylated glycans (Backström et al., 2003; Müller et al., 1999).

The scaling law for the mucin mushroom regime predicts small spontaneous curvatures for low biopolymer densities (FIG. 32C). The predicted spontaneous curvatures are comparable to the curvatures of the bleb-like protrusions observed in cells expressing low surface densities of mucins, as shown in FIG. 33B, 180 mucins/$m^2$. For higher densities, where the biopolymers form a brush, the corresponding model above predicts the generation of curvatures similar or greater to those observed in the tubules on the cells of FIG. 33B, 52000 mucins/$\mu m^2$. The curvature of such tubules is predicted to increase exponentially with biopolymer density. Notably, the continuous transition between mushroom and brush regimes predicted about a biopolymer density of 250 #/$\mu m^2$ accompanies a change in cell surface morphology from bleb-like to tubulated (FIG. 33B, D, E).

Similarly, HA molecules closely resemble linear polymer chains. For instance, a 1 MDa HA molecule has a length of 2.5 μm when stretched out, and can be modeled as a chain of 250 monomeric units approximately 10 nm long (Cleland Robert L., 2004; Hayashi et al., 1995). Polymer theory predicts such a polymer to have a large Flory radius of about 1 μm, which is more than an order of magnitude larger than that of Muc1. Thus, HA is expected to have a much larger effective volume and physical presence on the cell surface than Muc1. The consequently stronger intramolecular and intermolecular interactions in HA should render it significantly more effective at bending the membrane than Muc1. Furthermore, considerably lower surface density of HA is expected to generate the same membrane curvature as a surface densely crowded with Muc1.

We also conducted numerical calculations for the specific example of HA. Adopting the approach of Bracha et al. on DNA, also a linear polyelectrolyte, we coarse grain hyaluronic acid into $N_a$ cylindrical segments of length $l_a$ and diameter d to allow application of polymer brush theory scaling laws (Bracha et al., 2013). The Kuhn length, $l_a$, of the biopolymers is twice the persistence length and the length scale at which the molecule is straight. Hyaluronic acid is semi-rigid owing to the local stiffness that arises from intrinsically large size of the sugar ring monomers and the hindered rotations about the glycosidic linkages (Day and Sheehan, 2001). Measurements of the persistence length range from 5 to 9 nm. The diameter of the hyaluronic acid chain is about 0.6 nm (Cowman et al., 2005). In this work, we measure the molecular weight of hyaluronic acid produced by the hyaluronic acid synthase 3 (HAS3) to be approximately 3 MDa. This large size corresponds to a fully stretch length of approximately 10 μm, assuming a disaccharide size of 1 nm.

Force Requirements for Cell Surface Blebs and Tubes

To predict the relative frequencies of blebs and tubes on the cell surface, we perform energetic calculations for the cell membrane. The crowding pressure of the glycopolymers effectively increases the natural curvature of the cell membrane. Hence, we lump together the crowding effects of the glycocalyx into a spontaneous membrane curvature, $c_0$.

Intracellular forces pushing the cell membrane out, e.g. actin polymerization, can generate cylindrical tubes (Weichsel and Geissler, 2016). Here we consider a tube of length L and radius $R_{tube}$ generated due to a force f. On the other hand, a hydrostatic pressure difference p between inside and outside the cell can form spherical blebs of radius $R_{bleb}$ (Charras and Paluch, 2008). The energy of the membrane in these configurations includes the bending energy, surface tension, and contributions from the pressure p or the force f (Derényi et al., 2002; Helfrich, 2014; Seifert et al., 1991):

$$F = \int_A \frac{\kappa}{2}(c_1 + c_2 - c_0)^2 dA + \sigma A - pV - fL, \tag{8}$$

where κ is the bending stiffness of the membrane, $c_1$ and $c_2$ are the principal curvatures, $c_0$ is the spontaneous curvature of the membrane—generated due to the crowding pressure of the biopolymers, A is the area of the membrane, and σ is the surface tension of the membrane. For tubes, p=0, f≠0, and L is the length of the tube, whereas for blebs, f=0, p≠0, and V is the bleb volume.

A cylindrical tube of radius $R_{tube}$ has $c_1$=0 and $c_2$=1/$R_{tube}$, which simplify the energy:

$$F_{tube} = \left[\frac{\kappa}{2}\left(\frac{1}{R_{tube}} - c_0\right)^2 + \sigma\right] 2\pi R_{tube} L - fL. \tag{9}$$

The case of a spherical bleb with a very thin neck provides an upper limit on the energy of a bleb. For a bleb with radius $R_{bleb}$, $c_1$=$c_2$=1/$R_{bleb}$, and $$F_{bleb} = \left[\frac{\kappa}{2}\left(\frac{2}{R_{bleb}} - c_0\right)^2 + \sigma\right] 4\pi R_{bleb}^2 - \frac{4\pi R_{bleb}^3}{3} p. \tag{10}$$

At equilibrium, these energies are minimized with respect to the radii of the blebs and tubes (Derényi et al., 2002). The tube energy is also minimized with respect to the tube length L at steady state (Derényi et al., 2002). That is, $$\frac{\partial F_{tube}}{\partial R_{tube}} = 0, \frac{\partial F_{tube}}{\partial L} = 0, \tag{11}$$

and $$\frac{\partial F_{bleb}}{\partial R_{bleb}} = 0 \tag{12}$$

at equilibrium. The equilibrium equations (Eq. 11) for the tube imply:

$$R_{tube} = \frac{1}{\sqrt{c_0^2 + 2\sigma/\kappa}}, \tag{13}$$

-continued and $$f = 2\pi\kappa\left(\sqrt{c_0^2 + 2\sigma/\kappa} - c_0\right). \quad (14)$$

These equilibrium calculations predict the tube radius is completely governed by the mechanical properties of the lipid bilayer and the spontaneous curvature. These calculations do not account for the structural support of actin filaments widening the tubes.

Bleb energy minimization (Eq. 12) yields the pressure requirement for a bleb of a given size:

$$p = \frac{2\sigma}{R_{bleb}} - \frac{c_0\kappa}{R_{bleb}}\left(\frac{2}{R_{bleb}} - c_0\right). \quad (15)$$

Eq.13-15 relate the force or pressure required to maintain a tube or bleb with the spontaneous curvature generated by the biopolymers. FIG. 32C details the dependence of the spontaneous curvature on biopolymer concentration. We thus graph the force and pressure requirements against the biopolymer concentration (FIG. 32D). Comparisons with typically observed forces from actin polymerization and hydrostatic pressures explain the relative densities of tubes and blebs as a function of biopolymer density.

REFERENCES

Backström, M., Link, T., Olson, F. J., Karlsson, H., Graham, R., Picco, G., Burchell, J., Taylor-Papadimitriou, J., Noll, T., and Hansson, G. C. (2003). Recombinant MUC1 mucin with a breast cancer-like O-glycosylation produced in large amounts in Chinese-hamster ovary cells. Biochem. J. 376, 677-686.

Borisov, O. V., and Zhulina, E. B. (2002). Effect of Salt on Self-Assembly in Charged Block Copolymer Micelles. Macromolecules 35, 4472-4480.

Bracha, D., Karzbrun, E., Shemer, G., Pincus, P. A., and Bar-Ziv, R. H. (2013). Entropy-driven collective interactions in DNA brushes on a biochip. Proc. Natl. Acad. Sci. 110, 4534-4538.

Bramwell, M. E., Wiseman, G., and Shotton, D. M. (1986). Electron-microscopic studies of the CA antigen, epitectin. J. Cell Sci. 86, 249-261.

Charras, G., and Paluch, E. (2008). Blebs lead the way: how to migrate without lamellipodia. Nat. Rev. Mol. Cell Biol. 9, 730-736.

Cleland Robert L. (2004). Viscometry and sedimentation equilibrium of partially hydrolyzed hyaluronate: Comparison with theoretical models of wormlike chains. Biopolymers 23, 647-666.

Cowman, M. K., Spagnoli, C., Kudasheva, D., Li, M., Dyal, A., Kanai, S., and Balazs, E. A. (2005). Extended, relaxed, and condensed conformations of hyaluronan observed by atomic force microscopy. Biophys. J. 88, 590-602.

Day, A. J., and Sheehan, J. K. (2001). Hyaluronan: polysaccharide chaos to protein organisation. Curr. Opin. Struct. Biol. 11, 617-622.

Derényi, I., Jülicher, F., and Prost, J. (2002). Formation and interaction of membrane tubes. Phys. Rev. Lett. 88, 238101.

de Gennes, P. (1980). Conformations of polymers attached to an interace. Macromolecules 1069-1075.

Hayashi, K., Tsutsumi, K., Nakajima, F., Norisuye, T., and Teramoto, A. (1995). Chain-stiffness and excluded-volume effects in solutions of sodium hyaluronate at high ionic strength. Macromolecules 28, 3824-3830.

Helfrich, W. (2014). Elastic Properties of Lipid Bilayers: Theory and Possible Experiments. Z. Für Naturforschung C 28, 693-703.

Israels, R., Leermakers, F. A. M., Fleer, G. J., and Zhulina, E. B. (1994). Charged Polymeric Brushes: Structure and Scaling Relations. Macromolecules 27, 3249-3261.

Kesimer, M., Ehre, C., Burns, K. A., Davis, C. W., Sheehan, J. K., and Pickles, R. J. (2013). Molecular organization of the mucins and glycocalyx underlying mucus transport over mucosal surfaces of the airways. Mucosal Immunol. 6, 379-392.

Lipowsky, R. (1995). Bending of Membranes by Anchored Polymers. EPL Europhys. Lett. 30, 197.

McMaster, T. J., Berry, M., Corfield, A. P., and Miles, M. J. (1999). Atomic force microscopy of the submolecular architecture of hydrated ocular mucins. Biophys. J. 77, 533-541.

Müller, S., Alving, K., Peter-Katalinic, J., Zachara, N., Gooley, A. A., and Hanisch, F. G. (1999). High density O-glycosylation on tandem repeat peptide from secretory MUC1 of T47D breast cancer cells. J. Biol. Chem. 274, 18165-18172.

Paturej, J., Sheiko, S. S., Panyukov, S., and Rubinstein, M. (2016). Molecular structure of bottlebrush polymers in melts. Sci. Adv. 2, e1601478.

Seifert, U., Berndl, K., and Lipowsky, R. (1991). Shape transformations of vesicles: Phase diagram for spontaneous-curvature and bilayer-coupling models. Phys. Rev. A 44, 1182-1202.

Stachowiak, J. C., Schmid, E. M., Ryan, C. J., Ann, H. S., Sasaki, D. Y., Sherman, M. B., Geissler, P. L., Fletcher, D. A., and Hayden, C. C. (2012). Membrane bending by protein-protein crowding. Nat. Cell Biol. 14, 944-949.

Weichsel, J., and Geissler, P. L. (2016). The More the Tubular: Dynamic Bundling of Actin Filaments for Membrane Tube Formation. PLOS Comput. Biol. 12, e1004982.

Zhulina, E. B., Birshtein, T. M., and Borisov, O. V. (2006). Curved polymer and polyelectrolyte brushes beyond the Daoud-Cotton model. Eur. Phys. J. E 20, 243-256.

What is claimed is:

1. Modified mammalian cells present in a suspension cell culture, said culture being present in a suspended cell bioreactor, the modified mammalian cells comprising polypeptides expressed from recombinant polynucleotides introduced into the cells, wherein the polypeptides comprise a transmembrane anchor and a segment external to the cells, the segment external to the cells comprising a repeated amino acid sequence consisting of the sequence PDTRPAPGSTAPPAHGVTSA (SEQ ID NO: 8), said sequence being repeated only 21 or 42 times, and wherein the cells in the suspension cell culture exhibit less aggregation relative to a control value obtained from a suspended cell culture comprising mammalian cells that do not express the polypeptide comprising the repeated amino acid sequence.

2. The modified mammalian cells of claim 1, wherein the cells are human cells.

3. The modified mammalian cells of claim 2, wherein the cells are human embryonic kidney cells.

4. The modified mammalian cells of claim 3, wherein the modified mammalian cells further comprise an introduced polynucleotide encoding a distinct polypeptide that is different from the polypeptides comprising the repeated amino acid sequence, and wherein the modified mammalian cells are capable of producing the distinct polypeptide.

5. The modified mammalian cells of claim 3, wherein the transmembrane anchor comprises a cytoplasmic recycling motif.

6. The modified mammalian cells of claim 1, wherein the recombinant polynucleotides encoding the segment external to the cells that comprises the repeated amino acid sequence consisting of PDTRPAPGSTAPPAHGVTSA (SEQ ID NO:8) repeated only 21 times comprise a sequence consisting of SEQ ID NO:51.

7. The modified mammalian cells of claim 1, wherein the recombinant polynucleotides encoding the segment external to the cells that comprises the repeated amino acid sequence consisting of PDTRPAPGSTAPPAHGVTSA (SEQ ID NO:8) repeated only 42 times comprise a sequence consisting of SEQ ID NO:50.

8. A cell suspension bioreactor comprising a suspension cell culture comprising modified mammalian cells according to claim 3.

9. An isolated polynucleotide encoding the polypeptides comprising a transmembrane anchor and a repeated amino acid sequence according to claim 1.

10. The isolated polynucleotide of claim 9, wherein the isolated polynucleotide is present in an expression vector.

11. A method of making cells that express the polypeptides according to claim 1, comprising introducing an isolated polynucleotide encoding the polypeptides into the cells such that the polypeptide is expressed.

12. A method for producing a desired polypeptide, the method comprising expressing the desired polypeptide in the modified mammalian cells according to claim 1, such that the desired polypeptide is produced, wherein the desired polypeptide is distinct from the polypeptides comprising the repeated amino acid sequence.

13. The method of claim 12, further comprising separating the desired polypeptide from the suspension cell culture.

14. The method of claim 13, wherein the modified mammalian cells are adapted to growth in a suspension culture.

* * * * *

SEQUENCE LISTING

<160> NUMBER OF SEQ ID NOS: 99

<210> SEQ ID NO 1
<211> LENGTH: 8
<212> TYPE: PRT
<213> ORGANISM: artificial sequence
<220> FEATURE:
<223> OTHER INFORMATION: modified lubricin repeat -continued

<400> SEQUENCE: 1

Lys Glu Pro Ala Pro Thr Thr Pro
1 5

<210> SEQ ID NO 2
<211> LENGTH: 7
<212> TYPE: PRT
<213> ORGANISM: artificial sequence
<220> FEATURE:
<223> OTHER INFORMATION: modified mucin repeat

<400> SEQUENCE: 2

Asp Ala Ala Thr Pro Ala Pro
1 5

<210> SEQ ID NO 3
<211> LENGTH: 8
<212> TYPE: PRT
<213> ORGANISM: artificial sequence
<220> FEATURE:
<223> OTHER INFORMATION: modified mucin repeat

<400> SEQUENCE: 3

Asp Ala Ala Thr Pro Ala Pro Pro
1 5

<210> SEQ ID NO 4
<211> LENGTH: 9
<212> TYPE: PRT
<213> ORGANISM: artificial sequence
<220> FEATURE:
<223> OTHER INFORMATION: modified mucin repeat

<400> SEQUENCE: 4

Pro Pro Ala Ser Thr Ser Ala Pro Gly
1 5

<210> SEQ ID NO 5
<211> LENGTH: 20
<212> TYPE: PRT
<213> ORGANISM: artificial sequence
<220> FEATURE:
<223> OTHER INFORMATION: modified mucin repeat

<400> SEQUENCE: 5

Pro Asp Thr Arg Pro Ala Pro Gly Ala Thr Ala Pro Pro Ala His Gly
1 5 10 15

Val Thr Ser Ala
20

<210> SEQ ID NO 6
<211> LENGTH: 20
<212> TYPE: PRT
<213> ORGANISM: artificial sequence
<220> FEATURE:
<223> OTHER INFORMATION: modified mucin repeat

<400> SEQUENCE: 6

Pro Asp Thr Arg Pro Ala Pro Gly Ala Thr Ala Pro Pro Ala His Gly
1 5 10 15

Val Thr Ala Ala
20

<210> SEQ ID NO 7

```
<211> LENGTH: 20
<212> TYPE: PRT
<213> ORGANISM: artificial sequence
<220> FEATURE:
<223> OTHER INFORMATION: Modified mucin repeat

<400> SEQUENCE: 7

Pro Asp Ala Arg Pro Ala Pro Gly Ala Thr Ala Pro Pro Ala His Gly
1               5                   10                  15

Val Thr Ala Ala
            20


<210> SEQ ID NO 8
<211> LENGTH: 20
<212> TYPE: PRT
<213> ORGANISM: artificial sequence
<220> FEATURE:
<223> OTHER INFORMATION: Unmodified mucin repeat

<400> SEQUENCE: 8

Pro Asp Thr Arg Pro Ala Pro Gly Ser Thr Ala Pro Pro Ala His Gly
1               5                   10                  15

Val Thr Ser Ala
            20


<210> SEQ ID NO 9
<211> LENGTH: 7
<212> TYPE: PRT
<213> ORGANISM: artificial sequence
<220> FEATURE:
<223> OTHER INFORMATION: Modified mucin repeat

<400> SEQUENCE: 9

Lys Glu Pro Ala Pro Thr Pro
1               5


<210> SEQ ID NO 10
<211> LENGTH: 9
<212> TYPE: PRT
<213> ORGANISM: artificial sequence
<220> FEATURE:
<223> OTHER INFORMATION: Modified mucin repeat

<400> SEQUENCE: 10

Lys Glu Pro Ala Pro Thr Thr Thr Pro
1               5


<210> SEQ ID NO 11
<211> LENGTH: 6
<212> TYPE: PRT
<213> ORGANISM: Homo sapiens

<400> SEQUENCE: 11

Cys Gln Cys Arg Arg Lys
1               5


<210> SEQ ID NO 12
<211> LENGTH: 37
<212> TYPE: DNA
<213> ORGANISM: artificial sequence
<220> FEATURE:
<223> OTHER INFORMATION: Primer

<400> SEQUENCE: 12

ggcagctcag ctatggtgtc caagggcgag gagctgt                              37
```

-continued

<210> SEQ ID NO 13
<211> LENGTH: 39
<212> TYPE: DNA
<213> ORGANISM: artificial sequence
<220> FEATURE:
<223> OTHER INFORMATION: Primer

<400> SEQUENCE: 13
ggcagctgag cccttataca gctcgtccat gccgtgagt 39

<210> SEQ ID NO 14
<211> LENGTH: 27
<212> TYPE: DNA
<213> ORGANISM: artificial sequence
<220> FEATURE:
<223> OTHER INFORMATION: Primer

<400> SEQUENCE: 14
tggaggagcc tcaggcatac tttattg 27

<210> SEQ ID NO 15
<211> LENGTH: 26
<212> TYPE: DNA
<213> ORGANISM: artificial sequence
<220> FEATURE:
<223> OTHER INFORMATION: Primer

<400> SEQUENCE: 15
ccaccgccga ccgaggtgac atcctg 26

<210> SEQ ID NO 16
<211> LENGTH: 34
<212> TYPE: DNA
<213> ORGANISM: artificial sequence
<220> FEATURE:
<223> OTHER INFORMATION: Primer

<400> SEQUENCE: 16
ccgaaagtag gaattcgggc ccgtttaaac ccgc 34

<210> SEQ ID NO 17
<211> LENGTH: 37
<212> TYPE: DNA
<213> ORGANISM: artificial sequence
<220> FEATURE:
<223> OTHER INFORMATION: Primer

<400> SEQUENCE: 17
cggcactgac atctagagta ccacaacaaa gccaggc 37

<210> SEQ ID NO 18
<211> LENGTH: 37
<212> TYPE: DNA
<213> ORGANISM: artificial sequence
<220> FEATURE:
<223> OTHER INFORMATION: Primer

<400> SEQUENCE: 18
aggtagcgtc tcgtcccgcc tcaggcatac tttattg 37

<210> SEQ ID NO 19
<211> LENGTH: 31
<212> TYPE: DNA
<213> ORGANISM: artificial sequence
<220> FEATURE:
<223> OTHER INFORMATION: Primer

<400> SEQUENCE: 19
aggtagcgtc tcgtcgggag caggggtagc g 31

<210> SEQ ID NO 20
<211> LENGTH: 42
<212> TYPE: DNA
<213> ORGANISM: artificial sequence
<220> FEATURE:
<223> OTHER INFORMATION: Primer

<400> SEQUENCE: 20
ggtagcgtct cgccgatgca gctactccag ctccggacag cc 42

<210> SEQ ID NO 21
<211> LENGTH: 29
<212> TYPE: DNA
<213> ORGANISM: artificial sequence
<220> FEATURE:
<223> OTHER INFORMATION: Primer

<400> SEQUENCE: 21
aggtagcgtc tcggggagca ggggtagcg 29

<210> SEQ ID NO 22
<211> LENGTH: 41
<212> TYPE: DNA
<213> ORGANISM: artificial sequence
<220> FEATURE:
<223> OTHER INFORMATION: Primer

<400> SEQUENCE: 22
cttctgcgtc tcgtcccgcc tcaggcatac tttattggcg a 41

<210> SEQ ID NO 23
<211> LENGTH: 37
<212> TYPE: DNA
<213> ORGANISM: artificial sequence
<220> FEATURE:
<223> OTHER INFORMATION: Primer

<400> SEQUENCE: 23
cttctgcgtc tcgtcgggag gagctggtgt agccgcg 37

<210> SEQ ID NO 24
<211> LENGTH: 39
<212> TYPE: DNA
<213> ORGANISM: artificial sequence
<220> FEATURE:
<223> OTHER INFORMATION: Primer

<400> SEQUENCE: 24
cttctgcgtc tccccgatgc agctaccccg gctccaccc 39

<210> SEQ ID NO 25
<211> LENGTH: 35
<212> TYPE: DNA
<213> ORGANISM: artificial sequence
<220> FEATURE:
<223> OTHER INFORMATION: Primer

<400> SEQUENCE: 25
cttctgcgtc tccgggagga gctggtgtag ccgcg 35

<210> SEQ ID NO 26

<211> LENGTH: 62
<212> TYPE: PRT
<213> ORGANISM: artificial sequence
<220> FEATURE:
<223> OTHER INFORMATION: Flag Tag

<400> SEQUENCE: 26

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr
    50                  55                  60
```

<210> SEQ ID NO 27
<211> LENGTH: 193
<212> TYPE: DNA
<213> ORGANISM: artificial sequence
<220> FEATURE:
<223> OTHER INFORMATION: Flag tag cDNA

<400> SEQUENCE: 27

```
ggatccatga caccgggcac ccagtctcct ttcttcctgc tgctgctcct cacagtgctt     60

acagttgtta caggttctgg tcatgcaagc tctaccccag gtggagaaaa ggagacttcg    120

gctacccaga gaagttcagt gcccagctct actgagaaga atgctgatta caaggatgac    180

gacgacctgt aca                                                       193
```

<210> SEQ ID NO 28
<211> LENGTH: 170
<212> TYPE: PRT
<213> ORGANISM: artificial sequence
<220> FEATURE:
<223> OTHER INFORMATION: His-SUMO protein

<400> SEQUENCE: 28

```
Met Glu Thr Asp Thr Leu Leu Leu Trp Val Leu Leu Leu Trp Val Pro
1               5                   10                  15

Gly Ser Thr Gly Asp Gly His His His His His His Gly Ser Leu Gln
            20                  25                  30

Asp Ser Glu Val Asn Gln Glu Ala Lys Pro Glu Val Lys Pro Glu Val
        35                  40                  45

Lys Pro Glu Thr His Ile Asn Leu Lys Val Ser Asp Gly Ser Ser Glu
    50                  55                  60

Ile Phe Phe Lys Ile Lys Lys Thr Thr Pro Leu Arg Arg Leu Met Glu
65                  70                  75                  80

Ala Phe Ala Lys Arg Gln Gly Lys Glu Met Asp Ser Leu Thr Phe Leu
                85                  90                  95

Tyr Asp Gly Ile Glu Ile Gln Ala Asp Gln Ala Pro Glu Asp Leu Asp
            100                 105                 110

Met Glu Asp Asn Asp Ile Ile Glu Ala His Arg Glu Gln Ile Gly Gly
        115                 120                 125

Gly Ser Gly Ser Gly His Ala Ser Ser Thr Pro Gly Gly Glu Lys Glu
    130                 135                 140

Thr Ser Ala Thr Gln Arg Ser Ser Val Pro Ser Ser Thr Glu Lys Asn
145                 150                 155                 160

Ala Asp Tyr Lys Asp Asp Asp Asp Leu Tyr
```

```
                165                 170


<210> SEQ ID NO 29
<211> LENGTH: 522
<212> TYPE: DNA
<213> ORGANISM: artificial sequence
<220> FEATURE:
<223> OTHER INFORMATION: His-SUMO cDNA

<400> SEQUENCE: 29

gatccgccac catggagaca gacacactcc tgctatgggt actgctgctc tgggttccag      60

gttccactgg tgacggtcat caccatcatc atcacgggtc cctgcaggac tcagaagtca     120

atcaagaagc taagccagag gtcaagccag aagtcaagcc tgagactcac atcaatttaa     180

aggtgtccga tggatcttca gagatcttct tcaagatcaa aaagaccact cctttaagaa     240

ggctgatgga agcgttcgct aaaagacagg gtaaggaaat ggactcctta acgttcttgt     300

acgacggtat tgaaattcaa gctgatcagg cccctgaaga tttggacatg gaggataacg     360

atattattga ggctcacaga gaacagattg gaggtggctc cggctccggt catgcaagct     420

ctaccccagg tggagaaaag gagacttcgg ctacccagag aagttcagtg cccagctcta     480

ctgagaagaa tgctgattac aaggatgacg acgacctgta ca                        522


<210> SEQ ID NO 30
<211> LENGTH: 55
<212> TYPE: PRT
<213> ORGANISM: artificial sequence
<220> FEATURE:
<223> OTHER INFORMATION: Synthetic polymer backbone

<400> SEQUENCE: 30

Leu Tyr Met Asp Met Val Ala Val Ser Met Thr Ser Ser Val Leu Ser
1               5                   10                  15

Ser His Ser Pro Gly Ser Gly Ser Ser Thr Thr Gln Gly Gln Asp Val
            20                  25                  30

Thr Leu Ala Pro Ala Thr Glu Pro Ala Ser Gly Ser Ala Ala Thr Trp
        35                  40                  45

Gly Gln Asp Val Thr Ser Val
    50                  55


<210> SEQ ID NO 31
<211> LENGTH: 63
<212> TYPE: PRT
<213> ORGANISM: artificial sequence
<220> FEATURE:
<223> OTHER INFORMATION: Synthetic mucin

<400> SEQUENCE: 31

Leu Tyr Met Asp Met Val Ala Val Ser Met Thr Ser Ser Val Leu Ser
1               5                   10                  15

Ser His Ser Pro Gly Ser Gly Ser Ser Thr Thr Gln Gly Gln Asp Val
            20                  25                  30

Thr Leu Ala Pro Ala Thr Glu Pro Ala Ser Gly Ser Ala Ala Thr Trp
        35                  40                  45

Gly Gln Asp Val Thr Ser Val Gly Gly Gly Gly Gly Ala Ser Gly
    50                  55                  60


<210> SEQ ID NO 32
<211> LENGTH: 250
<212> TYPE: PRT
<213> ORGANISM: artificial sequence
```

<220> FEATURE:
<223> OTHER INFORMATION: Recombinant green fluorescent protein

<400> SEQUENCE: 32

Ser Gly Ser Ala Ser Gly Ser Ala Met Val Ser Lys Gly Glu Glu Leu
1 5 10 15

Phe Thr Gly Val Val Pro Ile Leu Val Glu Leu Asp Gly Asp Val Asn
20 25 30

Gly His Lys Phe Ser Val Arg Gly Glu Gly Glu Gly Asp Ala Thr Asn
35 40 45

Gly Lys Leu Thr Leu Lys Phe Ile Ser Thr Thr Gly Lys Leu Pro Val
50 55 60

Pro Trp Pro Thr Leu Val Thr Thr Leu Thr Tyr Gly Val Gln Ser Phe
65 70 75 80

Ser Arg Tyr Pro Asp His Met Lys Arg His Asp Phe Phe Lys Ser Ala
85 90 95

Met Pro Glu Gly Tyr Val Gln Glu Arg Thr Ile Ser Phe Lys Asp Asp
100 105 110

Gly Thr Tyr Lys Thr Arg Ala Glu Val Lys Phe Glu Gly Asp Thr Leu
115 120 125

Val Asn Arg Ile Glu Leu Lys Gly Ile Asp Phe Lys Glu Asp Gly Asn
130 135 140

Ile Leu Gly His Lys Leu Glu Tyr Asn Phe Asn Ser His Asn Val Tyr
145 150 155 160

Ile Thr Ala Asp Lys Gln Lys Asn Gly Ile Lys Ala Asn Phe Lys Ile
165 170 175

Arg His Asn Val Glu Asp Gly Ser Val Gln Leu Ala Asp His Tyr Gln
180 185 190

Gln Asn Thr Pro Ile Gly Asp Gly Pro Val Leu Leu Pro Asp Asn His
195 200 205

Tyr Leu Ser Thr Gln Ser Lys Leu Ser Lys Asp Pro Asn Glu Lys Arg
210 215 220

Asp His Met Val Leu Leu Glu Phe Val Thr Ala Ala Gly Ile Thr His
225 230 235 240

Gly Met Asp Glu Leu Tyr Lys Gly Ser Ala
245 250

<210> SEQ ID NO 33
<211> LENGTH: 222
<212> TYPE: PRT
<213> ORGANISM: artificial sequence
<220> FEATURE:
<223> OTHER INFORMATION: Recombinant transmembrane domain

<400> SEQUENCE: 33

Ser Ala Ser Thr Leu Val His Asn Gly Thr Ser Ala Arg Ala Thr Thr
1 5 10 15

Thr Pro Ala Ser Lys Ser Thr Pro Phe Ser Ile Pro Ser His His Ser
20 25 30

Asp Thr Pro Thr Thr Leu Ala Ser His Ser Thr Lys Thr Asp Ala Ser
35 40 45

Ser Thr His His Ser Ser Val Pro Pro Leu Thr Ser Ser Asn His Ser
50 55 60

Thr Ser Pro Gln Leu Ser Thr Gly Val Ser Phe Phe Phe Leu Ser Phe
65 70 75 80

His Ile Ser Asn Leu Gln Phe Asn Ser Ser Leu Glu Asp Pro Ser Thr

```
                85                  90                  95

Asp Tyr Tyr Gln Glu Leu Gln Arg Asp Ile Ser Glu Met Phe Leu Gln
            100                 105                 110

Ile Tyr Lys Gln Gly Gly Phe Leu Gly Leu Ser Asn Ile Lys Phe Arg
        115                 120                 125

Pro Gly Ser Val Val Val Gln Leu Thr Leu Ala Phe Arg Glu Gly Thr
    130                 135                 140

Ile Asn Val His Asp Val Glu Thr Gln Phe Asn Gln Tyr Lys Thr Glu
145                 150                 155                 160

Ala Ala Ser Arg Tyr Asn Leu Thr Ile Ser Asp Val Ser Val Ser Asp
                165                 170                 175

Val Pro Phe Pro Phe Ser Ala Gln Ser Gly Ala Gly Val Pro Gly Trp
            180                 185                 190

Gly Ile Ala Leu Leu Val Leu Val Cys Val Leu Val Ala Leu Ala Ile
        195                 200                 205

Val Tyr Leu Ile Ala Leu Ala Val Cys Gln Cys Arg Arg Lys
    210                 215                 220


<210> SEQ ID NO 34
<211> LENGTH: 74
<212> TYPE: PRT
<213> ORGANISM: artificial sequence
<220> FEATURE:
<223> OTHER INFORMATION: Recombinant cytoplasmic domain

<400> SEQUENCE: 34

Ser Arg Cys Gln Cys Arg Arg Lys Asn Tyr Gly Gln Leu Asp Ile Phe
1               5                   10                  15

Pro Ala Arg Asp Thr Tyr His Pro Met Ser Glu Tyr Pro Thr Tyr His
            20                  25                  30

Thr His Gly Arg Tyr Val Pro Pro Ser Ser Thr Asp Arg Ser Pro Tyr
        35                  40                  45

Glu Lys Val Ser Ala Gly Asn Gly Gly Ser Ser Leu Ser Tyr Thr Asn
    50                  55                  60

Pro Ala Val Ala Ala Ala Ser Ala Asn Leu
65                  70


<210> SEQ ID NO 35
<211> LENGTH: 8
<212> TYPE: PRT
<213> ORGANISM: artificial sequence
<220> FEATURE:
<223> OTHER INFORMATION: Recombinant cytoplasmic domain

<400> SEQUENCE: 35

Ser Arg Cys Gln Cys Arg Arg Lys
1               5


<210> SEQ ID NO 36
<211> LENGTH: 1426
<212> TYPE: PRT
<213> ORGANISM: artificial sequence
<220> FEATURE:
<223> OTHER INFORMATION: Recombinant mucin

<400> SEQUENCE: 36

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30
```

```
Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Pro Asp Thr Arg Pro Ala Pro Gly Ser Thr Ala Pro Pro
        115                 120                 125

Ala His Gly Val Thr Ser Ala Pro Asp Thr Arg Pro Ala Pro Gly Ser
    130                 135                 140

Thr Ala Pro Pro Ala His Gly Val Thr Ser Ala Pro Asp Thr Arg Pro
145                 150                 155                 160

Ala Pro Gly Ser Thr Ala Pro Pro Ala His Gly Val Thr Ser Ala Pro
                165                 170                 175

Asp Thr Arg Pro Ala Pro Gly Ser Thr Ala Pro Pro Ala His Gly Val
            180                 185                 190

Thr Ser Ala Pro Asp Thr Arg Pro Ala Pro Gly Ser Thr Ala Pro Pro
        195                 200                 205

Ala His Gly Val Thr Ser Ala Pro Asp Thr Arg Pro Ala Pro Gly Ser
    210                 215                 220

Thr Ala Pro Pro Ala His Gly Val Thr Ser Ala Pro Asp Thr Arg Pro
225                 230                 235                 240

Ala Pro Gly Ser Thr Ala Pro Pro Ala His Gly Val Thr Ser Ala Pro
                245                 250                 255

Asp Thr Arg Pro Ala Pro Gly Ser Thr Ala Pro Pro Ala His Gly Val
            260                 265                 270

Thr Ser Ala Pro Asp Thr Arg Pro Ala Pro Gly Ser Thr Ala Pro Pro
        275                 280                 285

Ala His Gly Val Thr Ser Ala Pro Asp Thr Arg Pro Ala Pro Gly Ser
    290                 295                 300

Thr Ala Pro Pro Ala His Gly Val Thr Ser Ala Pro Asp Thr Arg Pro
305                 310                 315                 320

Ala Pro Gly Ser Thr Ala Pro Pro Ala His Gly Val Thr Ser Ala Pro
                325                 330                 335

Asp Thr Arg Pro Ala Pro Gly Ser Thr Ala Pro Pro Ala His Gly Val
            340                 345                 350

Thr Ser Ala Pro Asp Thr Arg Pro Ala Pro Gly Ser Thr Ala Pro Pro
        355                 360                 365

Ala His Gly Val Thr Ser Ala Pro Asp Thr Arg Pro Ala Pro Gly Ser
    370                 375                 380

Thr Ala Pro Pro Ala His Gly Val Thr Ser Ala Pro Asp Thr Arg Pro
385                 390                 395                 400

Ala Pro Gly Ser Thr Ala Pro Pro Ala His Gly Val Thr Ser Ala Pro
                405                 410                 415

Asp Thr Arg Pro Ala Pro Gly Ser Thr Ala Pro Pro Ala His Gly Val
            420                 425                 430

Thr Ser Ala Pro Asp Thr Arg Pro Ala Pro Gly Ser Thr Ala Pro Pro
        435                 440                 445
```

-continued

```
Ala His Gly Val Thr Ser Ala Pro Asp Thr Arg Pro Ala Pro Gly Ser
    450                 455                 460

Thr Ala Pro Pro Ala His Gly Val Thr Ser Ala Pro Asp Thr Arg Pro
465                 470                 475                 480

Ala Pro Gly Ser Thr Ala Pro Pro Ala His Gly Val Thr Ser Ala Pro
                485                 490                 495

Asp Thr Arg Pro Ala Pro Gly Ser Thr Ala Pro Pro Ala His Gly Val
            500                 505                 510

Thr Ser Ala Pro Asp Thr Arg Pro Ala Pro Gly Ser Thr Ala Pro Pro
        515                 520                 525

Ala His Gly Val Thr Ser Ala Pro Asp Thr Arg Pro Ala Pro Gly Ser
    530                 535                 540

Thr Ala Pro Pro Ala His Gly Val Thr Ser Ala Pro Asp Thr Arg Pro
545                 550                 555                 560

Ala Pro Gly Ser Thr Ala Pro Pro Ala His Gly Val Thr Ser Ala Pro
                565                 570                 575

Asp Thr Arg Pro Ala Pro Gly Ser Thr Ala Pro Pro Ala His Gly Val
            580                 585                 590

Thr Ser Ala Pro Asp Thr Arg Pro Ala Pro Gly Ser Thr Ala Pro Pro
        595                 600                 605

Ala His Gly Val Thr Ser Ala Pro Asp Thr Arg Pro Ala Pro Gly Ser
    610                 615                 620

Thr Ala Pro Pro Ala His Gly Val Thr Ser Ala Pro Asp Thr Arg Pro
625                 630                 635                 640

Ala Pro Gly Ser Thr Ala Pro Pro Ala His Gly Val Thr Ser Ala Pro
                645                 650                 655

Asp Thr Arg Pro Ala Pro Gly Ser Thr Ala Pro Pro Ala His Gly Val
            660                 665                 670

Thr Ser Ala Pro Asp Thr Arg Pro Ala Pro Gly Ser Thr Ala Pro Pro
        675                 680                 685

Ala His Gly Val Thr Ser Ala Pro Asp Thr Arg Pro Ala Pro Gly Ser
    690                 695                 700

Thr Ala Pro Pro Ala His Gly Val Thr Ser Ala Pro Asp Thr Arg Pro
705                 710                 715                 720

Ala Pro Gly Ser Thr Ala Pro Pro Ala His Gly Val Thr Ser Ala Pro
                725                 730                 735

Asp Thr Arg Pro Ala Pro Gly Ser Thr Ala Pro Pro Ala His Gly Val
            740                 745                 750

Thr Ser Ala Pro Asp Thr Arg Pro Ala Pro Gly Ser Thr Ala Pro Pro
        755                 760                 765

Ala His Gly Val Thr Ser Ala Pro Asp Thr Arg Pro Ala Pro Gly Ser
    770                 775                 780

Thr Ala Pro Pro Ala His Gly Val Thr Ser Ala Pro Asp Thr Arg Pro
785                 790                 795                 800

Ala Pro Gly Ser Thr Ala Pro Pro Ala His Gly Val Thr Ser Ala Pro
                805                 810                 815

Asp Thr Arg Pro Ala Pro Gly Ser Thr Ala Pro Pro Ala His Gly Val
            820                 825                 830

Thr Ser Ala Pro Asp Thr Arg Pro Ala Pro Gly Ser Thr Ala Pro Pro
        835                 840                 845

Ala His Gly Val Thr Ser Ala Pro Asp Thr Arg Pro Ala Pro Gly Ser
    850                 855                 860

Thr Ala Pro Pro Ala His Gly Val Thr Ser Ala Pro Asp Thr Arg Pro
```

-continued

```
865                 870                 875                 880

Ala Pro Gly Ser Thr Ala Pro Pro Ala His Gly Val Thr Ser Ala Pro
                885                 890                 895

Asp Thr Arg Pro Ala Pro Gly Ser Thr Ala Pro Pro Ala His Gly Val
            900                 905                 910

Thr Ser Ala Pro Asp Thr Arg Pro Ala Pro Gly Ser Thr Ala Pro Pro
        915                 920                 925

Ala His Gly Val Thr Ser Ala Pro Asp Thr Arg Pro Ala Pro Gly Ser
    930                 935                 940

Thr Ala Pro Pro Ala His Gly Val Thr Ser Ala Ala Ser Gly Ser Ala
945                 950                 955                 960

Ser Gly Ser Ala Met Val Ser Lys Gly Glu Glu Leu Phe Thr Gly Val
                965                 970                 975

Val Pro Ile Leu Val Glu Leu Asp Gly Asp Val Asn Gly His Lys Phe
            980                 985                 990

Ser Val Arg Gly Glu Gly Glu Gly  Asp Ala Thr Asn Gly  Lys Leu Thr
        995                 1000                1005

Leu Lys  Phe Ile Ser Thr Thr  Gly Lys Leu Pro Val  Pro Trp Pro
    1010                 1015                 1020

Thr Leu  Val Thr Thr Leu Thr  Tyr Gly Val Gln Ser  Phe Ser Arg
    1025                 1030                 1035

Tyr Pro  Asp His Met Lys Arg  His Asp Phe Phe Lys  Ser Ala Met
    1040                 1045                 1050

Pro Glu  Gly Tyr Val Gln Glu  Arg Thr Ile Ser Phe  Lys Asp Asp
    1055                 1060                 1065

Gly Thr  Tyr Lys Thr Arg Ala  Glu Val Lys Phe Glu  Gly Asp Thr
    1070                 1075                 1080

Leu Val  Asn Arg Ile Glu Leu  Lys Gly Ile Asp Phe  Lys Glu Asp
    1085                 1090                 1095

Gly Asn  Ile Leu Gly His Lys  Leu Glu Tyr Asn Phe  Asn Ser His
    1100                 1105                 1110

Asn Val  Tyr Ile Thr Ala Asp  Lys Gln Lys Asn Gly  Ile Lys Ala
    1115                 1120                 1125

Asn Phe  Lys Ile Arg His Asn  Val Glu Asp Gly Ser  Val Gln Leu
    1130                 1135                 1140

Ala Asp  His Tyr Gln Gln Asn  Thr Pro Ile Gly Asp  Gly Pro Val
    1145                 1150                 1155

Leu Leu  Pro Asp Asn His Tyr  Leu Ser Thr Gln Ser  Lys Leu Ser
    1160                 1165                 1170

Lys Asp  Pro Asn Glu Lys Arg  Asp His Met Val Leu  Leu Glu Phe
    1175                 1180                 1185

Val Thr  Ala Ala Gly Ile Thr  His Gly Met Asp Glu  Leu Tyr Lys
    1190                 1195                 1200

Gly Ser  Ala Ser Thr Leu Val  His Asn Gly Thr Ser  Ala Arg Ala
    1205                 1210                 1215

Thr Thr  Thr Pro Ala Ser Lys  Ser Thr Pro Phe Ser  Ile Pro Ser
    1220                 1225                 1230

His His  Ser Asp Thr Pro Thr  Thr Leu Ala Ser His  Ser Thr Lys
    1235                 1240                 1245

Thr Asp  Ala Ser Ser Thr His  His Ser Ser Val Pro  Pro Leu Thr
    1250                 1255                 1260

Ser Ser  Asn His Ser Thr Ser  Pro Gln Leu Ser Thr  Gly Val Ser
    1265                 1270                 1275
```

```
Phe Phe Phe Leu Ser Phe His Ile Ser Asn Leu Gln Phe Asn Ser
    1280                1285                1290

Ser Leu Glu Asp Pro Ser Thr Asp Tyr Tyr Gln Glu Leu Gln Arg
    1295                1300                1305

Asp Ile Ser Glu Met Phe Leu Gln Ile Tyr Lys Gln Gly Gly Phe
    1310                1315                1320

Leu Gly Leu Ser Asn Ile Lys Phe Arg Pro Gly Ser Val Val Val
    1325                1330                1335

Gln Leu Thr Leu Ala Phe Arg Glu Gly Thr Ile Asn Val His Asp
    1340                1345                1350

Val Glu Thr Gln Phe Asn Gln Tyr Lys Thr Glu Ala Ala Ser Arg
    1355                1360                1365

Tyr Asn Leu Thr Ile Ser Asp Val Ser Val Ser Asp Val Pro Phe
    1370                1375                1380

Pro Phe Ser Ala Gln Ser Gly Ala Gly Val Pro Gly Trp Gly Ile
    1385                1390                1395

Ala Leu Leu Val Leu Val Cys Val Leu Val Ala Leu Ala Ile Val
    1400                1405                1410

Tyr Leu Ile Ala Leu Ala Val Cys Gln Cys Arg Arg Lys
    1415                1420                1425
```

<210> SEQ ID NO 37
<211> LENGTH: 1005
<212> TYPE: PRT
<213> ORGANISM: artificial sequence
<220> FEATURE:
<223> OTHER INFORMATION: Recombinant mucin

<400> SEQUENCE: 37

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Pro Asp Thr Arg Pro Ala Pro Gly Ser Thr Ala Pro Pro
        115                 120                 125

Ala His Gly Val Thr Ser Ala Pro Asp Thr Arg Pro Ala Pro Gly Ser
    130                 135                 140

Thr Ala Pro Pro Ala His Gly Val Thr Ser Ala Pro Asp Thr Arg Pro
145                 150                 155                 160

Ala Pro Gly Ser Thr Ala Pro Pro Ala His Gly Val Thr Ser Ala Pro
                165                 170                 175

Asp Thr Arg Pro Ala Pro Gly Ser Thr Ala Pro Pro Ala His Gly Val
            180                 185                 190

Thr Ser Ala Pro Asp Thr Arg Pro Ala Pro Gly Ser Thr Ala Pro Pro
        195                 200                 205
```

```
Ala His Gly Val Thr Ser Ala Pro Asp Thr Arg Pro Ala Pro Gly Ser
    210                 215                 220

Thr Ala Pro Pro Ala His Gly Val Thr Ser Ala Pro Asp Thr Arg Pro
225                 230                 235                 240

Ala Pro Gly Ser Thr Ala Pro Pro Ala His Gly Val Thr Ser Ala Pro
                245                 250                 255

Asp Thr Arg Pro Ala Pro Gly Ser Thr Ala Pro Pro Ala His Gly Val
            260                 265                 270

Thr Ser Ala Pro Asp Thr Arg Pro Ala Pro Gly Ser Thr Ala Pro Pro
        275                 280                 285

Ala His Gly Val Thr Ser Ala Pro Asp Thr Arg Pro Ala Pro Gly Ser
    290                 295                 300

Thr Ala Pro Pro Ala His Gly Val Thr Ser Ala Pro Asp Thr Arg Pro
305                 310                 315                 320

Ala Pro Gly Ser Thr Ala Pro Pro Ala His Gly Val Thr Ser Ala Pro
                325                 330                 335

Asp Thr Arg Pro Ala Pro Gly Ser Thr Ala Pro Pro Ala His Gly Val
            340                 345                 350

Thr Ser Ala Pro Asp Thr Arg Pro Ala Pro Gly Ser Thr Ala Pro Pro
        355                 360                 365

Ala His Gly Val Thr Ser Ala Pro Asp Thr Arg Pro Ala Pro Gly Ser
    370                 375                 380

Thr Ala Pro Pro Ala His Gly Val Thr Ser Ala Pro Asp Thr Arg Pro
385                 390                 395                 400

Ala Pro Gly Ser Thr Ala Pro Pro Ala His Gly Val Thr Ser Ala Pro
                405                 410                 415

Asp Thr Arg Pro Ala Pro Gly Ser Thr Ala Pro Pro Ala His Gly Val
            420                 425                 430

Thr Ser Ala Pro Asp Thr Arg Pro Ala Pro Gly Ser Thr Ala Pro Pro
        435                 440                 445

Ala His Gly Val Thr Ser Ala Pro Asp Thr Arg Pro Ala Pro Gly Ser
    450                 455                 460

Thr Ala Pro Pro Ala His Gly Val Thr Ser Ala Pro Asp Thr Arg Pro
465                 470                 475                 480

Ala Pro Gly Ser Thr Ala Pro Pro Ala His Gly Val Thr Ser Ala Pro
                485                 490                 495

Asp Thr Arg Pro Ala Pro Gly Ser Thr Ala Pro Pro Ala His Gly Val
            500                 505                 510

Thr Ser Ala Pro Asp Thr Arg Pro Ala Pro Gly Ser Thr Ala Pro Pro
        515                 520                 525

Ala His Gly Val Thr Ser Ala Ala Ser Gly Ser Ala Ser Gly Ser Ala
    530                 535                 540

Met Val Ser Lys Gly Glu Glu Leu Phe Thr Gly Val Val Pro Ile Leu
545                 550                 555                 560

Val Glu Leu Asp Gly Asp Val Asn Gly His Lys Phe Ser Val Arg Gly
                565                 570                 575

Glu Gly Glu Gly Asp Ala Thr Asn Gly Lys Leu Thr Leu Lys Phe Ile
            580                 585                 590

Ser Thr Thr Gly Lys Leu Pro Val Pro Trp Pro Thr Leu Val Thr Thr
        595                 600                 605

Leu Thr Tyr Gly Val Gln Ser Phe Ser Arg Tyr Pro Asp His Met Lys
    610                 615                 620
```

-continued

```
Arg His Asp Phe Phe Lys Ser Ala Met Pro Glu Gly Tyr Val Gln Glu
625                 630                 635                 640

Arg Thr Ile Ser Phe Lys Asp Asp Gly Thr Tyr Lys Thr Arg Ala Glu
                645                 650                 655

Val Lys Phe Glu Gly Asp Thr Leu Val Asn Arg Ile Glu Leu Lys Gly
            660                 665                 670

Ile Asp Phe Lys Glu Asp Gly Asn Ile Leu Gly His Lys Leu Glu Tyr
        675                 680                 685

Asn Phe Asn Ser His Asn Val Tyr Ile Thr Ala Asp Lys Gln Lys Asn
    690                 695                 700

Gly Ile Lys Ala Asn Phe Lys Ile Arg His Asn Val Glu Asp Gly Ser
705                 710                 715                 720

Val Gln Leu Ala Asp His Tyr Gln Gln Asn Thr Pro Ile Gly Asp Gly
                725                 730                 735

Pro Val Leu Leu Pro Asp Asn His Tyr Leu Ser Thr Gln Ser Lys Leu
            740                 745                 750

Ser Lys Asp Pro Asn Glu Lys Arg Asp His Met Val Leu Leu Glu Phe
        755                 760                 765

Val Thr Ala Ala Gly Ile Thr His Gly Met Asp Glu Leu Tyr Lys Gly
    770                 775                 780

Ser Ala Ser Thr Leu Val His Asn Gly Thr Ser Ala Arg Ala Thr Thr
785                 790                 795                 800

Thr Pro Ala Ser Lys Ser Thr Pro Phe Ser Ile Pro Ser His His Ser
                805                 810                 815

Asp Thr Pro Thr Thr Leu Ala Ser His Ser Thr Lys Thr Asp Ala Ser
            820                 825                 830

Ser Thr His His Ser Ser Val Pro Pro Leu Thr Ser Ser Asn His Ser
        835                 840                 845

Thr Ser Pro Gln Leu Ser Thr Gly Val Ser Phe Phe Phe Leu Ser Phe
    850                 855                 860

His Ile Ser Asn Leu Gln Phe Asn Ser Ser Leu Glu Asp Pro Ser Thr
865                 870                 875                 880

Asp Tyr Tyr Gln Glu Leu Gln Arg Asp Ile Ser Glu Met Phe Leu Gln
                885                 890                 895

Ile Tyr Lys Gln Gly Gly Phe Leu Gly Leu Ser Asn Ile Lys Phe Arg
            900                 905                 910

Pro Gly Ser Val Val Val Gln Leu Thr Leu Ala Phe Arg Glu Gly Thr
        915                 920                 925

Ile Asn Val His Asp Val Glu Thr Gln Phe Asn Gln Tyr Lys Thr Glu
    930                 935                 940

Ala Ala Ser Arg Tyr Asn Leu Thr Ile Ser Asp Val Ser Val Ser Asp
945                 950                 955                 960

Val Pro Phe Pro Phe Ser Ala Gln Ser Gly Ala Gly Val Pro Gly Trp
                965                 970                 975

Gly Ile Ala Leu Leu Val Leu Val Cys Val Leu Val Ala Leu Ala Ile
            980                 985                 990

Val Tyr Leu Ile Ala Leu Ala Val  Cys Gln Cys Arg Arg
        995                 1000                1005


<210> SEQ ID NO 38
<211> LENGTH: 591
<212> TYPE: PRT
<213> ORGANISM: artificial sequence
<220> FEATURE:
<223> OTHER INFORMATION: Recombinant mucin
```

<400> SEQUENCE: 38

```
Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Gly Gly Gly Gly Gly Ala Ser Gly Ser Ala Ser Gly Ser
        115                 120                 125

Ala Met Val Ser Lys Gly Glu Glu Leu Phe Thr Gly Val Val Pro Ile
    130                 135                 140

Leu Val Glu Leu Asp Gly Asp Val Asn Gly His Lys Phe Ser Val Arg
145                 150                 155                 160

Gly Glu Gly Glu Gly Asp Ala Thr Asn Gly Lys Leu Thr Leu Lys Phe
                165                 170                 175

Ile Ser Thr Thr Gly Lys Leu Pro Val Pro Trp Pro Thr Leu Val Thr
            180                 185                 190

Thr Leu Thr Tyr Gly Val Gln Ser Phe Ser Arg Tyr Pro Asp His Met
        195                 200                 205

Lys Arg His Asp Phe Phe Lys Ser Ala Met Pro Glu Gly Tyr Val Gln
    210                 215                 220

Glu Arg Thr Ile Ser Phe Lys Asp Asp Gly Thr Tyr Lys Thr Arg Ala
225                 230                 235                 240

Glu Val Lys Phe Glu Gly Asp Thr Leu Val Asn Arg Ile Glu Leu Lys
                245                 250                 255

Gly Ile Asp Phe Lys Glu Asp Gly Asn Ile Leu Gly His Lys Leu Glu
            260                 265                 270

Tyr Asn Phe Asn Ser His Asn Val Tyr Ile Thr Ala Asp Lys Gln Lys
        275                 280                 285

Asn Gly Ile Lys Ala Asn Phe Lys Ile Arg His Asn Val Glu Asp Gly
    290                 295                 300

Ser Val Gln Leu Ala Asp His Tyr Gln Gln Asn Thr Pro Ile Gly Asp
305                 310                 315                 320

Gly Pro Val Leu Leu Pro Asp Asn His Tyr Leu Ser Thr Gln Ser Lys
                325                 330                 335

Leu Ser Lys Asp Pro Asn Glu Lys Arg Asp His Met Val Leu Leu Glu
            340                 345                 350

Phe Val Thr Ala Ala Gly Ile Thr His Gly Met Asp Glu Leu Tyr Lys
        355                 360                 365

Gly Ser Ala Ser Thr Leu Val His Asn Gly Thr Ser Ala Arg Ala Thr
    370                 375                 380

Thr Thr Pro Ala Ser Lys Ser Thr Pro Phe Ser Ile Pro Ser His His
385                 390                 395                 400

Ser Asp Thr Pro Thr Thr Leu Ala Ser His Ser Thr Lys Thr Asp Ala
```

405 410 415

Ser Ser Thr His His Ser Ser Val Pro Pro Leu Thr Ser Ser Asn His
420 425 430

Ser Thr Ser Pro Gln Leu Ser Thr Gly Val Ser Phe Phe Phe Leu Ser
435 440 445

Phe His Ile Ser Asn Leu Gln Phe Asn Ser Ser Leu Glu Asp Pro Ser
450 455 460

Thr Asp Tyr Tyr Gln Glu Leu Gln Arg Asp Ile Ser Glu Met Phe Leu
465 470 475 480

Gln Ile Tyr Lys Gln Gly Gly Phe Leu Gly Leu Ser Asn Ile Lys Phe
485 490 495

Arg Pro Gly Ser Val Val Val Gln Leu Thr Leu Ala Phe Arg Glu Gly
500 505 510

Thr Ile Asn Val His Asp Val Glu Thr Gln Phe Asn Gln Tyr Lys Thr
515 520 525

Glu Ala Ala Ser Arg Tyr Asn Leu Thr Ile Ser Asp Val Ser Val Ser
530 535 540

Asp Val Pro Phe Pro Phe Ser Ala Gln Ser Gly Ala Gly Val Pro Gly
545 550 555 560

Trp Gly Ile Ala Leu Leu Val Leu Val Cys Val Leu Val Ala Leu Ala
565 570 575

Ile Val Tyr Leu Ile Ala Leu Ala Val Cys Gln Cys Arg Arg Lys
580 585 590

<210> SEQ ID NO 39
<211> LENGTH: 1005
<212> TYPE: PRT
<213> ORGANISM: artificial sequence
<220> FEATURE:
<223> OTHER INFORMATION: Recombinant mucin

<400> SEQUENCE: 39

Met Thr Pro Gly Thr Gln Ser Pro Phe Phe Leu Leu Leu Leu Leu Thr
1 5 10 15

Val Leu Thr Val Val Thr Gly Ser Gly His Ala Ser Ser Thr Pro Gly
20 25 30

Gly Glu Lys Glu Thr Ser Ala Thr Gln Arg Ser Ser Val Pro Ser Ser
35 40 45

Thr Glu Lys Asn Ala Asp Tyr Lys Asp Asp Asp Asp Leu Tyr Met Asp
50 55 60

Met Val Ala Val Ser Met Thr Ser Ser Val Leu Ser Ser His Ser Pro
65 70 75 80

Gly Ser Gly Ser Ser Thr Thr Gln Gly Gln Asp Val Thr Leu Ala Pro
85 90 95

Ala Thr Glu Pro Ala Ser Gly Ser Ala Ala Thr Trp Gly Gln Asp Val
100 105 110

Thr Ser Val Pro Asp Thr Arg Pro Ala Pro Gly Ala Thr Ala Pro Pro
115 120 125

Ala His Gly Val Thr Ser Ala Pro Asp Thr Arg Pro Ala Pro Gly Ala
130 135 140

Thr Ala Pro Pro Ala His Gly Val Thr Ser Ala Pro Asp Thr Arg Pro
145 150 155 160

Ala Pro Gly Ala Thr Ala Pro Pro Ala His Gly Val Thr Ser Ala Pro
165 170 175

Asp Thr Arg Pro Ala Pro Gly Ala Thr Ala Pro Pro Ala His Gly Val

-continued

```
            180                 185                 190

Thr Ser Ala Pro Asp Thr Arg Pro Ala Pro Gly Ala Thr Ala Pro Pro
        195                 200                 205

Ala His Gly Val Thr Ser Ala Pro Asp Thr Arg Pro Ala Pro Gly Ala
    210                 215                 220

Thr Ala Pro Pro Ala His Gly Val Thr Ser Ala Pro Asp Thr Arg Pro
225                 230                 235                 240

Ala Pro Gly Ala Thr Ala Pro Pro Ala His Gly Val Thr Ser Ala Pro
                245                 250                 255

Asp Thr Arg Pro Ala Pro Gly Ala Thr Ala Pro Pro Ala His Gly Val
            260                 265                 270

Thr Ser Ala Pro Asp Thr Arg Pro Ala Pro Gly Ala Thr Ala Pro Pro
        275                 280                 285

Ala His Gly Val Thr Ser Ala Pro Asp Thr Arg Pro Ala Pro Gly Ala
    290                 295                 300

Thr Ala Pro Pro Ala His Gly Val Thr Ser Ala Pro Asp Thr Arg Pro
305                 310                 315                 320

Ala Pro Gly Ala Thr Ala Pro Pro Ala His Gly Val Thr Ser Ala Pro
                325                 330                 335

Asp Thr Arg Pro Ala Pro Gly Ala Thr Ala Pro Pro Ala His Gly Val
            340                 345                 350

Thr Ser Ala Pro Asp Thr Arg Pro Ala Pro Gly Ala Thr Ala Pro Pro
        355                 360                 365

Ala His Gly Val Thr Ser Ala Pro Asp Thr Arg Pro Ala Pro Gly Ala
    370                 375                 380

Thr Ala Pro Pro Ala His Gly Val Thr Ser Ala Pro Asp Thr Arg Pro
385                 390                 395                 400

Ala Pro Gly Ala Thr Ala Pro Pro Ala His Gly Val Thr Ser Ala Pro
                405                 410                 415

Asp Thr Arg Pro Ala Pro Gly Ala Thr Ala Pro Pro Ala His Gly Val
            420                 425                 430

Thr Ser Ala Pro Asp Thr Arg Pro Ala Pro Gly Ala Thr Ala Pro Pro
        435                 440                 445

Ala His Gly Val Thr Ser Ala Pro Asp Thr Arg Pro Ala Pro Gly Ala
    450                 455                 460

Thr Ala Pro Pro Ala His Gly Val Thr Ser Ala Pro Asp Thr Arg Pro
465                 470                 475                 480

Ala Pro Gly Ala Thr Ala Pro Pro Ala His Gly Val Thr Ser Ala Pro
                485                 490                 495

Asp Thr Arg Pro Ala Pro Gly Ala Thr Ala Pro Pro Ala His Gly Val
            500                 505                 510

Thr Ser Ala Pro Asp Thr Arg Pro Ala Pro Gly Ala Thr Ala Pro Pro
        515                 520                 525

Ala His Gly Val Thr Ser Ala Ala Ser Gly Ser Ala Ser Gly Ser Ala
    530                 535                 540

Met Val Ser Lys Gly Glu Glu Leu Phe Thr Gly Val Val Pro Ile Leu
545                 550                 555                 560

Val Glu Leu Asp Gly Asp Val Asn Gly His Lys Phe Ser Val Arg Gly
                565                 570                 575

Glu Gly Glu Gly Asp Ala Thr Asn Gly Lys Leu Thr Leu Lys Phe Ile
            580                 585                 590

Ser Thr Thr Gly Lys Leu Pro Val Pro Trp Pro Thr Leu Val Thr Thr
        595                 600                 605
```

```
Leu Thr Tyr Gly Val Gln Ser Phe Ser Arg Tyr Pro Asp His Met Lys
    610                 615                 620

Arg His Asp Phe Phe Lys Ser Ala Met Pro Glu Gly Tyr Val Gln Glu
625                 630                 635                 640

Arg Thr Ile Ser Phe Lys Asp Asp Gly Thr Tyr Lys Thr Arg Ala Glu
                645                 650                 655

Val Lys Phe Glu Gly Asp Thr Leu Val Asn Arg Ile Glu Leu Lys Gly
            660                 665                 670

Ile Asp Phe Lys Glu Asp Gly Asn Ile Leu Gly His Lys Leu Glu Tyr
        675                 680                 685

Asn Phe Asn Ser His Asn Val Tyr Ile Thr Ala Asp Lys Gln Lys Asn
    690                 695                 700

Gly Ile Lys Ala Asn Phe Lys Ile Arg His Asn Val Glu Asp Gly Ser
705                 710                 715                 720

Val Gln Leu Ala Asp His Tyr Gln Gln Asn Thr Pro Ile Gly Asp Gly
                725                 730                 735

Pro Val Leu Leu Pro Asp Asn His Tyr Leu Ser Thr Gln Ser Lys Leu
            740                 745                 750

Ser Lys Asp Pro Asn Glu Lys Arg Asp His Met Val Leu Leu Glu Phe
        755                 760                 765

Val Thr Ala Ala Gly Ile Thr His Gly Met Asp Glu Leu Tyr Lys Gly
    770                 775                 780

Ser Ala Ser Thr Leu Val His Asn Gly Thr Ser Ala Arg Ala Thr Thr
785                 790                 795                 800

Thr Pro Ala Ser Lys Ser Thr Pro Phe Ser Ile Pro Ser His His Ser
                805                 810                 815

Asp Thr Pro Thr Thr Leu Ala Ser His Ser Thr Lys Thr Asp Ala Ser
            820                 825                 830

Ser Thr His His Ser Ser Val Pro Pro Leu Thr Ser Ser Asn His Ser
        835                 840                 845

Thr Ser Pro Gln Leu Ser Thr Gly Val Ser Phe Phe Phe Leu Ser Phe
    850                 855                 860

His Ile Ser Asn Leu Gln Phe Asn Ser Ser Leu Glu Asp Pro Ser Thr
865                 870                 875                 880

Asp Tyr Tyr Gln Glu Leu Gln Arg Asp Ile Ser Glu Met Phe Leu Gln
                885                 890                 895

Ile Tyr Lys Gln Gly Gly Phe Leu Gly Leu Ser Asn Ile Lys Phe Arg
            900                 905                 910

Pro Gly Ser Val Val Val Gln Leu Thr Leu Ala Phe Arg Glu Gly Thr
        915                 920                 925

Ile Asn Val His Asp Val Glu Thr Gln Phe Asn Gln Tyr Lys Thr Glu
    930                 935                 940

Ala Ala Ser Arg Tyr Asn Leu Thr Ile Ser Asp Val Ser Val Ser Asp
945                 950                 955                 960

Val Pro Phe Pro Phe Ser Ala Gln Ser Gly Ala Gly Val Pro Gly Trp
                965                 970                 975

Gly Ile Ala Leu Leu Val Leu Val Cys Val Leu Val Ala Leu Ala Ile
            980                 985                 990

Val Tyr Leu Ile Ala Leu Ala Val  Cys Gln Cys Arg Arg
        995                 1000                1005
```

<210> SEQ ID NO 40
<211> LENGTH: 1005

```
<212> TYPE: PRT
<213> ORGANISM: artificial sequence
<220> FEATURE:
<223> OTHER INFORMATION: Recombinant mucin

<400> SEQUENCE: 40

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Pro Asp Thr Arg Pro Ala Pro Gly Ala Thr Ala Pro Pro
        115                 120                 125

Ala His Gly Val Thr Ala Ala Pro Asp Thr Arg Pro Ala Pro Gly Ala
    130                 135                 140

Thr Ala Pro Pro Ala His Gly Val Thr Ala Ala Pro Asp Thr Arg Pro
145                 150                 155                 160

Ala Pro Gly Ala Thr Ala Pro Pro Ala His Gly Val Thr Ala Ala Pro
                165                 170                 175

Asp Thr Arg Pro Ala Pro Gly Ala Thr Ala Pro Pro Ala His Gly Val
            180                 185                 190

Thr Ala Ala Pro Asp Thr Arg Pro Ala Pro Gly Ala Thr Ala Pro Pro
        195                 200                 205

Ala His Gly Val Thr Ala Ala Pro Asp Thr Arg Pro Ala Pro Gly Ala
    210                 215                 220

Thr Ala Pro Pro Ala His Gly Val Thr Ala Ala Pro Asp Thr Arg Pro
225                 230                 235                 240

Ala Pro Gly Ala Thr Ala Pro Pro Ala His Gly Val Thr Ala Ala Pro
                245                 250                 255

Asp Thr Arg Pro Ala Pro Gly Ala Thr Ala Pro Pro Ala His Gly Val
            260                 265                 270

Thr Ala Ala Pro Asp Thr Arg Pro Ala Pro Gly Ala Thr Ala Pro Pro
        275                 280                 285

Ala His Gly Val Thr Ala Ala Pro Asp Thr Arg Pro Ala Pro Gly Ala
    290                 295                 300

Thr Ala Pro Pro Ala His Gly Val Thr Ala Ala Pro Asp Thr Arg Pro
305                 310                 315                 320

Ala Pro Gly Ala Thr Ala Pro Pro Ala His Gly Val Thr Ala Ala Pro
                325                 330                 335

Asp Thr Arg Pro Ala Pro Gly Ala Thr Ala Pro Pro Ala His Gly Val
            340                 345                 350

Thr Ala Ala Pro Asp Thr Arg Pro Ala Pro Gly Ala Thr Ala Pro Pro
        355                 360                 365

Ala His Gly Val Thr Ala Ala Pro Asp Thr Arg Pro Ala Pro Gly Ala
    370                 375                 380
```

-continued

```
Thr Ala Pro Pro Ala His Gly Val Thr Ala Ala Pro Asp Thr Arg Pro
385                 390                 395                 400

Ala Pro Gly Ala Thr Ala Pro Pro Ala His Gly Val Thr Ala Ala Pro
                405                 410                 415

Asp Thr Arg Pro Ala Pro Gly Ala Thr Ala Pro Pro Ala His Gly Val
            420                 425                 430

Thr Ala Ala Pro Asp Thr Arg Pro Ala Pro Gly Ala Thr Ala Pro Pro
        435                 440                 445

Ala His Gly Val Thr Ala Ala Pro Asp Thr Arg Pro Ala Pro Gly Ala
    450                 455                 460

Thr Ala Pro Pro Ala His Gly Val Thr Ala Ala Pro Asp Thr Arg Pro
465                 470                 475                 480

Ala Pro Gly Ala Thr Ala Pro Pro Ala His Gly Val Thr Ala Ala Pro
                485                 490                 495

Asp Thr Arg Pro Ala Pro Gly Ala Thr Ala Pro Pro Ala His Gly Val
            500                 505                 510

Thr Ala Ala Pro Asp Thr Arg Pro Ala Pro Gly Ala Thr Ala Pro Pro
        515                 520                 525

Ala His Gly Val Thr Ala Ala Ala Ser Gly Ser Ala Ser Gly Ser Ala
    530                 535                 540

Met Val Ser Lys Gly Glu Glu Leu Phe Thr Gly Val Val Pro Ile Leu
545                 550                 555                 560

Val Glu Leu Asp Gly Asp Val Asn Gly His Lys Phe Ser Val Arg Gly
                565                 570                 575

Glu Gly Glu Gly Asp Ala Thr Asn Gly Lys Leu Thr Leu Lys Phe Ile
            580                 585                 590

Ser Thr Thr Gly Lys Leu Pro Val Pro Trp Pro Thr Leu Val Thr Thr
        595                 600                 605

Leu Thr Tyr Gly Val Gln Ser Phe Ser Arg Tyr Pro Asp His Met Lys
    610                 615                 620

Arg His Asp Phe Phe Lys Ser Ala Met Pro Glu Gly Tyr Val Gln Glu
625                 630                 635                 640

Arg Thr Ile Ser Phe Lys Asp Asp Gly Thr Tyr Lys Thr Arg Ala Glu
                645                 650                 655

Val Lys Phe Glu Gly Asp Thr Leu Val Asn Arg Ile Glu Leu Lys Gly
            660                 665                 670

Ile Asp Phe Lys Glu Asp Gly Asn Ile Leu Gly His Lys Leu Glu Tyr
        675                 680                 685

Asn Phe Asn Ser His Asn Val Tyr Ile Thr Ala Asp Lys Gln Lys Asn
    690                 695                 700

Gly Ile Lys Ala Asn Phe Lys Ile Arg His Asn Val Glu Asp Gly Ser
705                 710                 715                 720

Val Gln Leu Ala Asp His Tyr Gln Gln Asn Thr Pro Ile Gly Asp Gly
                725                 730                 735

Pro Val Leu Leu Pro Asp Asn His Tyr Leu Ser Thr Gln Ser Lys Leu
            740                 745                 750

Ser Lys Asp Pro Asn Glu Lys Arg Asp His Met Val Leu Leu Glu Phe
        755                 760                 765

Val Thr Ala Ala Gly Ile Thr His Gly Met Asp Glu Leu Tyr Lys Gly
    770                 775                 780

Ser Ala Ser Thr Leu Val His Asn Gly Thr Ser Ala Arg Ala Thr Thr
785                 790                 795                 800

Thr Pro Ala Ser Lys Ser Thr Pro Phe Ser Ile Pro Ser His His Ser
```

-continued 805 810 815

Asp Thr Pro Thr Thr Leu Ala Ser His Ser Thr Lys Thr Asp Ala Ser
820 825 830

Ser Thr His His Ser Ser Val Pro Pro Leu Thr Ser Ser Asn His Ser
835 840 845

Thr Ser Pro Gln Leu Ser Thr Gly Val Ser Phe Phe Phe Leu Ser Phe
850 855 860

His Ile Ser Asn Leu Gln Phe Asn Ser Ser Leu Glu Asp Pro Ser Thr
865 870 875 880

Asp Tyr Tyr Gln Glu Leu Gln Arg Asp Ile Ser Glu Met Phe Leu Gln
885 890 895

Ile Tyr Lys Gln Gly Gly Phe Leu Gly Leu Ser Asn Ile Lys Phe Arg
900 905 910

Pro Gly Ser Val Val Val Gln Leu Thr Leu Ala Phe Arg Glu Gly Thr
915 920 925

Ile Asn Val His Asp Val Glu Thr Gln Phe Asn Gln Tyr Lys Thr Glu
930 935 940

Ala Ala Ser Arg Tyr Asn Leu Thr Ile Ser Asp Val Ser Val Ser Asp
945 950 955 960

Val Pro Phe Pro Phe Ser Ala Gln Ser Gly Ala Gly Val Pro Gly Trp
965 970 975

Gly Ile Ala Leu Leu Val Leu Val Cys Val Leu Val Ala Leu Ala Ile
980 985 990

Val Tyr Leu Ile Ala Leu Ala Val Cys Gln Cys Arg Arg
995 1000 1005

<210> SEQ ID NO 41
<211> LENGTH: 1006
<212> TYPE: PRT
<213> ORGANISM: artificial sequence
<220> FEATURE:
<223> OTHER INFORMATION: Recombinant mucin

<400> SEQUENCE: 41

Met Thr Pro Gly Thr Gln Ser Pro Phe Phe Leu Leu Leu Leu Leu Thr
1 5 10 15

Val Leu Thr Val Val Thr Gly Ser Gly His Ala Ser Ser Thr Pro Gly
20 25 30

Gly Glu Lys Glu Thr Ser Ala Thr Gln Arg Ser Ser Val Pro Ser Ser
35 40 45

Thr Glu Lys Asn Ala Asp Tyr Lys Asp Asp Asp Asp Leu Tyr Met Asp
50 55 60

Met Val Ala Val Ser Met Thr Ser Ser Val Leu Ser Ser His Ser Pro
65 70 75 80

Gly Ser Gly Ser Ser Thr Thr Gln Gly Gln Asp Val Thr Leu Ala Pro
85 90 95

Ala Thr Glu Pro Ala Ser Gly Ser Ala Ala Thr Trp Gly Gln Asp Val
100 105 110

Thr Ser Val Pro Asp Ala Arg Pro Ala Pro Gly Ala Thr Ala Pro Pro
115 120 125

Ala His Gly Val Thr Ala Ala Pro Asp Ala Arg Pro Ala Pro Gly Ala
130 135 140

Thr Ala Pro Pro Ala His Gly Val Thr Ala Ala Pro Asp Ala Arg Pro
145 150 155 160

Ala Pro Gly Ala Thr Ala Pro Pro Ala His Gly Val Thr Ala Ala Pro

-continued

```
                165                 170                 175

Asp Ala Arg Pro Ala Pro Gly Ala Thr Ala Pro Pro Ala His Gly Val
            180                 185                 190

Thr Ala Ala Pro Asp Ala Arg Pro Ala Pro Gly Ala Thr Ala Pro Pro
        195                 200                 205

Ala His Gly Val Thr Ala Ala Pro Asp Ala Arg Pro Ala Pro Gly Ala
    210                 215                 220

Thr Ala Pro Pro Ala His Gly Val Thr Ala Ala Pro Asp Ala Arg Pro
225                 230                 235                 240

Ala Pro Gly Ala Thr Ala Pro Pro Ala His Gly Val Thr Ala Ala Pro
                245                 250                 255

Asp Ala Arg Pro Ala Pro Gly Ala Thr Ala Pro Pro Ala His Gly Val
            260                 265                 270

Thr Ala Ala Pro Asp Ala Arg Pro Ala Pro Gly Ala Thr Ala Pro Pro
        275                 280                 285

Ala His Gly Val Thr Ala Ala Pro Asp Ala Arg Pro Ala Pro Gly Ala
    290                 295                 300

Thr Ala Pro Pro Ala His Gly Val Thr Ala Ala Pro Asp Ala Arg Pro
305                 310                 315                 320

Ala Pro Gly Ala Thr Ala Pro Pro Ala His Gly Val Thr Ala Ala Pro
                325                 330                 335

Asp Ala Arg Pro Ala Pro Gly Ala Thr Ala Pro Pro Ala His Gly Val
            340                 345                 350

Thr Ala Ala Pro Asp Ala Arg Pro Ala Pro Gly Ala Thr Ala Pro Pro
        355                 360                 365

Ala His Gly Val Thr Ala Ala Pro Asp Ala Arg Pro Ala Pro Gly Ala
    370                 375                 380

Thr Ala Pro Pro Ala His Gly Val Thr Ala Ala Pro Asp Ala Arg Pro
385                 390                 395                 400

Ala Pro Gly Ala Thr Ala Pro Pro Ala His Gly Val Thr Ala Ala Pro
                405                 410                 415

Asp Ala Arg Pro Ala Pro Gly Ala Thr Ala Pro Pro Ala His Gly Val
            420                 425                 430

Thr Ala Ala Pro Asp Ala Arg Pro Ala Pro Gly Ala Thr Ala Pro Pro
        435                 440                 445

Ala His Gly Val Thr Ala Ala Pro Asp Ala Arg Pro Ala Pro Gly Ala
    450                 455                 460

Thr Ala Pro Pro Ala His Gly Val Thr Ala Ala Pro Asp Ala Arg Pro
465                 470                 475                 480

Ala Pro Gly Ala Thr Ala Pro Pro Ala His Gly Val Thr Ala Ala Pro
                485                 490                 495

Asp Ala Arg Pro Ala Pro Gly Ala Thr Ala Pro Pro Ala His Gly Val
            500                 505                 510

Thr Ala Ala Pro Asp Ala Arg Pro Ala Pro Gly Ala Thr Ala Pro Pro
        515                 520                 525

Ala His Gly Val Thr Ala Ala Ala Ser Gly Ser Ala Ser Gly Ser Ala
    530                 535                 540

Met Val Ser Lys Gly Glu Glu Leu Phe Thr Gly Val Val Pro Ile Leu
545                 550                 555                 560

Val Glu Leu Asp Gly Asp Val Asn Gly His Lys Phe Ser Val Arg Gly
                565                 570                 575

Glu Gly Glu Gly Asp Ala Thr Asn Gly Lys Leu Thr Leu Lys Phe Ile
            580                 585                 590
```

-continued

Ser Thr Thr Gly Lys Leu Pro Val Pro Trp Pro Thr Leu Val Thr Thr
595 600 605

Leu Thr Tyr Gly Val Gln Ser Phe Ser Arg Tyr Pro Asp His Met Lys
610 615 620

Arg His Asp Phe Phe Lys Ser Ala Met Pro Glu Gly Tyr Val Gln Glu
625 630 635 640

Arg Thr Ile Ser Phe Lys Asp Asp Gly Thr Tyr Lys Thr Arg Ala Glu
645 650 655

Val Lys Phe Glu Gly Asp Thr Leu Val Asn Arg Ile Glu Leu Lys Gly
660 665 670

Ile Asp Phe Lys Glu Asp Gly Asn Ile Leu Gly His Lys Leu Glu Tyr
675 680 685

Asn Phe Asn Ser His Asn Val Tyr Ile Thr Ala Asp Lys Gln Lys Asn
690 695 700

Gly Ile Lys Ala Asn Phe Lys Ile Arg His Asn Val Glu Asp Gly Ser
705 710 715 720

Val Gln Leu Ala Asp His Tyr Gln Gln Asn Thr Pro Ile Gly Asp Gly
725 730 735

Pro Val Leu Leu Pro Asp Asn His Tyr Leu Ser Thr Gln Ser Lys Leu
740 745 750

Ser Lys Asp Pro Asn Glu Lys Arg Asp His Met Val Leu Leu Glu Phe
755 760 765

Val Thr Ala Ala Gly Ile Thr His Gly Met Asp Glu Leu Tyr Lys Gly
770 775 780

Ser Ala Ser Thr Leu Val His Asn Gly Thr Ser Ala Arg Ala Thr Thr
785 790 795 800

Thr Pro Ala Ser Lys Ser Thr Pro Phe Ser Ile Pro Ser His His Ser
805 810 815

Asp Thr Pro Thr Thr Leu Ala Ser His Ser Thr Lys Thr Asp Ala Ser
820 825 830

Ser Thr His His Ser Ser Val Pro Pro Leu Thr Ser Ser Asn His Ser
835 840 845

Thr Ser Pro Gln Leu Ser Thr Gly Val Ser Phe Phe Phe Leu Ser Phe
850 855 860

His Ile Ser Asn Leu Gln Phe Asn Ser Ser Leu Glu Asp Pro Ser Thr
865 870 875 880

Asp Tyr Tyr Gln Glu Leu Gln Arg Asp Ile Ser Glu Met Phe Leu Gln
885 890 895

Ile Tyr Lys Gln Gly Gly Phe Leu Gly Leu Ser Asn Ile Lys Phe Arg
900 905 910

Pro Gly Ser Val Val Val Gln Leu Thr Leu Ala Phe Arg Glu Gly Thr
915 920 925

Ile Asn Val His Asp Val Glu Thr Gln Phe Asn Gln Tyr Lys Thr Glu
930 935 940

Ala Ala Ser Arg Tyr Asn Leu Thr Ile Ser Asp Val Ser Val Ser Asp
945 950 955 960

Val Pro Phe Pro Phe Ser Ala Gln Ser Gly Ala Gly Val Pro Gly Trp
965 970 975

Gly Ile Ala Leu Leu Val Leu Val Cys Val Leu Val Ala Leu Ala Ile
980 985 990

Val Tyr Leu Ile Ala Leu Ala Val Cys Gln Cys Arg Arg Lys
995 1000 1005

```
<210> SEQ ID NO 42
<211> LENGTH: 746
<212> TYPE: PRT
<213> ORGANISM: artificial sequence
<220> FEATURE:
<223> OTHER INFORMATION: Recombinant lubricin

<400> SEQUENCE: 42

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Lys Glu Pro Ala Pro Thr Thr Pro Lys Glu Pro Ala Pro
        115                 120                 125

Thr Thr Pro Lys Glu Pro Ala Pro Thr Thr Pro Lys Glu Pro Ala Pro
    130                 135                 140

Thr Thr Pro Lys Glu Pro Ala Pro Thr Thr Pro Lys Glu Pro Ala Pro
145                 150                 155                 160

Thr Thr Pro Lys Glu Pro Ala Pro Thr Thr Pro Lys Glu Pro Ala Pro
                165                 170                 175

Thr Thr Pro Lys Glu Pro Ala Pro Thr Thr Pro Lys Glu Pro Ala Pro
            180                 185                 190

Thr Thr Pro Lys Glu Pro Ala Pro Thr Thr Pro Lys Glu Pro Ala Pro
        195                 200                 205

Thr Thr Pro Lys Glu Pro Ala Pro Thr Thr Pro Lys Glu Pro Ala Pro
    210                 215                 220

Thr Thr Pro Lys Glu Pro Ala Pro Thr Thr Pro Lys Glu Pro Ala Pro
225                 230                 235                 240

Thr Thr Pro Lys Glu Pro Ala Pro Thr Thr Pro Lys Glu Pro Ala Pro
                245                 250                 255

Thr Thr Pro Lys Glu Pro Ala Pro Thr Thr Pro Lys Glu Pro Ala Pro
            260                 265                 270

Thr Thr Pro Ala Ser Gly Ser Ala Ser Gly Ser Ala Met Val Ser Lys
        275                 280                 285

Gly Glu Glu Leu Phe Thr Gly Val Val Pro Ile Leu Val Glu Leu Asp
    290                 295                 300

Gly Asp Val Asn Gly His Lys Phe Ser Val Arg Gly Glu Gly Glu Gly
305                 310                 315                 320

Asp Ala Thr Asn Gly Lys Leu Thr Leu Lys Phe Ile Ser Thr Thr Gly
                325                 330                 335

Lys Leu Pro Val Pro Trp Pro Thr Leu Val Thr Thr Leu Thr Tyr Gly
            340                 345                 350

Val Gln Ser Phe Ser Arg Tyr Pro Asp His Met Lys Arg His Asp Phe
        355                 360                 365
```

```
Phe Lys Ser Ala Met Pro Glu Gly Tyr Val Gln Glu Arg Thr Ile Ser
    370                 375                 380

Phe Lys Asp Asp Gly Thr Tyr Lys Thr Arg Ala Glu Val Lys Phe Glu
385                 390                 395                 400

Gly Asp Thr Leu Val Asn Arg Ile Glu Leu Lys Gly Ile Asp Phe Lys
                405                 410                 415

Glu Asp Gly Asn Ile Leu Gly His Lys Leu Glu Tyr Asn Phe Asn Ser
            420                 425                 430

His Asn Val Tyr Ile Thr Ala Asp Lys Gln Lys Asn Gly Ile Lys Ala
        435                 440                 445

Asn Phe Lys Ile Arg His Asn Val Glu Asp Gly Ser Val Gln Leu Ala
    450                 455                 460

Asp His Tyr Gln Gln Asn Thr Pro Ile Gly Asp Gly Pro Val Leu Leu
465                 470                 475                 480

Pro Asp Asn His Tyr Leu Ser Thr Gln Ser Lys Leu Ser Lys Asp Pro
                485                 490                 495

Asn Glu Lys Arg Asp His Met Val Leu Leu Glu Phe Val Thr Ala Ala
            500                 505                 510

Gly Ile Thr His Gly Met Asp Glu Leu Tyr Lys Gly Ser Ala Ser Thr
        515                 520                 525

Leu Val His Asn Gly Thr Ser Ala Arg Ala Thr Thr Thr Pro Ala Ser
    530                 535                 540

Lys Ser Thr Pro Phe Ser Ile Pro Ser His His Ser Asp Thr Pro Thr
545                 550                 555                 560

Thr Leu Ala Ser His Ser Thr Lys Thr Asp Ala Ser Ser Thr His His
                565                 570                 575

Ser Ser Val Pro Pro Leu Thr Ser Ser Asn His Ser Thr Ser Pro Gln
            580                 585                 590

Leu Ser Thr Gly Val Ser Phe Phe Phe Leu Ser Phe His Ile Ser Asn
        595                 600                 605

Leu Gln Phe Asn Ser Ser Leu Glu Asp Pro Ser Thr Asp Tyr Tyr Gln
    610                 615                 620

Glu Leu Gln Arg Asp Ile Ser Glu Met Phe Leu Gln Ile Tyr Lys Gln
625                 630                 635                 640

Gly Gly Phe Leu Gly Leu Ser Asn Ile Lys Phe Arg Pro Gly Ser Val
                645                 650                 655

Val Val Gln Leu Thr Leu Ala Phe Arg Glu Gly Thr Ile Asn Val His
            660                 665                 670

Asp Val Glu Thr Gln Phe Asn Gln Tyr Lys Thr Glu Ala Ala Ser Arg
        675                 680                 685

Tyr Asn Leu Thr Ile Ser Asp Val Ser Val Ser Asp Val Pro Phe Pro
    690                 695                 700

Phe Ser Ala Gln Ser Gly Ala Gly Val Pro Gly Trp Gly Ile Ala Leu
705                 710                 715                 720

Leu Val Leu Val Cys Val Leu Val Ala Leu Ala Ile Val Tyr Leu Ile
                725                 730                 735

Ala Leu Ala Val Cys Gln Cys Arg Arg Lys
            740                 745
```

<210> SEQ ID NO 43
<211> LENGTH: 866
<212> TYPE: PRT
<213> ORGANISM: artificial sequence
<220> FEATURE:
<223> OTHER INFORMATION: Recombinant lubricin

<400> SEQUENCE: 43

Met Thr Pro Gly Thr Gln Ser Pro Phe Phe Leu Leu Leu Leu Leu Thr
1 5 10 15

Val Leu Thr Val Val Thr Gly Ser Gly His Ala Ser Ser Thr Pro Gly
20 25 30

Gly Glu Lys Glu Thr Ser Ala Thr Gln Arg Ser Ser Val Pro Ser Ser
35 40 45

Thr Glu Lys Asn Ala Asp Tyr Lys Asp Asp Asp Asp Leu Tyr Met Asp
50 55 60

Met Val Ala Val Ser Met Thr Ser Ser Val Leu Ser Ser His Ser Pro
65 70 75 80

Gly Ser Gly Ser Ser Thr Thr Gln Gly Gln Asp Val Thr Leu Ala Pro
85 90 95

Ala Thr Glu Pro Ala Ser Gly Ser Ala Ala Thr Trp Gly Gln Asp Val
100 105 110

Thr Ser Val Asp Ala Ala Thr Pro Ala Pro Asp Ala Ala Thr Pro Ala
115 120 125

Pro Asp Ala Ala Thr Pro Ala Pro Asp Ala Ala Thr Pro Ala Pro Asp
130 135 140

Ala Ala Thr Pro Ala Pro Asp Ala Ala Thr Pro Ala Pro Asp Ala Ala
145 150 155 160

Thr Pro Ala Pro Asp Ala Ala Thr Pro Ala Pro Asp Ala Ala Thr Pro
165 170 175

Ala Pro Asp Ala Ala Thr Pro Ala Pro Asp Ala Ala Thr Pro Ala Pro
180 185 190

Asp Ala Ala Thr Pro Ala Pro Asp Ala Ala Thr Pro Ala Pro Asp Ala
195 200 205

Ala Thr Pro Ala Pro Asp Ala Ala Thr Pro Ala Pro Asp Ala Ala Thr
210 215 220

Pro Ala Pro Asp Ala Ala Thr Pro Ala Pro Asp Ala Ala Thr Pro Ala
225 230 235 240

Pro Asp Ala Ala Thr Pro Ala Pro Asp Ala Ala Thr Pro Ala Pro Asp
245 250 255

Ala Ala Thr Pro Ala Pro Asp Ala Ala Thr Pro Ala Pro Asp Ala Ala
260 265 270

Thr Pro Ala Pro Asp Ala Ala Thr Pro Ala Pro Asp Ala Ala Thr Pro
275 280 285

Ala Pro Asp Ala Ala Thr Pro Ala Pro Asp Ala Ala Thr Pro Ala Pro
290 295 300

Asp Ala Ala Thr Pro Ala Pro Asp Ala Ala Thr Pro Ala Pro Asp Ala
305 310 315 320

Ala Thr Pro Ala Pro Asp Ala Ala Thr Pro Ala Pro Asp Ala Ala Thr
325 330 335

Pro Ala Pro Asp Ala Ala Thr Pro Ala Pro Asp Ala Ala Thr Pro Ala
340 345 350

Pro Asp Ala Ala Thr Pro Ala Pro Asp Ala Ala Thr Pro Ala Pro Asp
355 360 365

Ala Ala Thr Pro Ala Pro Asp Ala Ala Thr Pro Ala Pro Asp Ala Ala
370 375 380

Thr Pro Ala Pro Asp Ala Ala Thr Pro Ala Pro Ala Ser Gly Ser Ala
385 390 395 400

Ser Gly Ser Ala Met Val Ser Lys Gly Glu Glu Leu Phe Thr Gly Val

```
                405                 410                 415

Val Pro Ile Leu Val Glu Leu Asp Gly Asp Val Asn Gly His Lys Phe
            420                 425                 430

Ser Val Arg Gly Glu Gly Glu Gly Asp Ala Thr Asn Gly Lys Leu Thr
        435                 440                 445

Leu Lys Phe Ile Ser Thr Thr Gly Lys Leu Pro Val Pro Trp Pro Thr
    450                 455                 460

Leu Val Thr Thr Leu Thr Tyr Gly Val Gln Ser Phe Ser Arg Tyr Pro
465                 470                 475                 480

Asp His Met Lys Arg His Asp Phe Phe Lys Ser Ala Met Pro Glu Gly
                485                 490                 495

Tyr Val Gln Glu Arg Thr Ile Ser Phe Lys Asp Asp Gly Thr Tyr Lys
            500                 505                 510

Thr Arg Ala Glu Val Lys Phe Glu Gly Asp Thr Leu Val Asn Arg Ile
        515                 520                 525

Glu Leu Lys Gly Ile Asp Phe Lys Glu Asp Gly Asn Ile Leu Gly His
    530                 535                 540

Lys Leu Glu Tyr Asn Phe Asn Ser His Asn Val Tyr Ile Thr Ala Asp
545                 550                 555                 560

Lys Gln Lys Asn Gly Ile Lys Ala Asn Phe Lys Ile Arg His Asn Val
                565                 570                 575

Glu Asp Gly Ser Val Gln Leu Ala Asp His Tyr Gln Gln Asn Thr Pro
            580                 585                 590

Ile Gly Asp Gly Pro Val Leu Leu Pro Asp Asn His Tyr Leu Ser Thr
        595                 600                 605

Gln Ser Lys Leu Ser Lys Asp Pro Asn Glu Lys Arg Asp His Met Val
    610                 615                 620

Leu Leu Glu Phe Val Thr Ala Ala Gly Ile Thr His Gly Met Asp Glu
625                 630                 635                 640

Leu Tyr Lys Gly Ser Ala Ser Thr Leu Val His Asn Gly Thr Ser Ala
                645                 650                 655

Arg Ala Thr Thr Thr Pro Ala Ser Lys Ser Thr Pro Phe Ser Ile Pro
            660                 665                 670

Ser His His Ser Asp Thr Pro Thr Thr Leu Ala Ser His Ser Thr Lys
        675                 680                 685

Thr Asp Ala Ser Ser Thr His His Ser Ser Val Pro Pro Leu Thr Ser
    690                 695                 700

Ser Asn His Ser Thr Ser Pro Gln Leu Ser Thr Gly Val Ser Phe Phe
705                 710                 715                 720

Phe Leu Ser Phe His Ile Ser Asn Leu Gln Phe Asn Ser Ser Leu Glu
                725                 730                 735

Asp Pro Ser Thr Asp Tyr Tyr Gln Glu Leu Gln Arg Asp Ile Ser Glu
            740                 745                 750

Met Phe Leu Gln Ile Tyr Lys Gln Gly Gly Phe Leu Gly Leu Ser Asn
        755                 760                 765

Ile Lys Phe Arg Pro Gly Ser Val Val Val Gln Leu Thr Leu Ala Phe
    770                 775                 780

Arg Glu Gly Thr Ile Asn Val His Asp Val Glu Thr Gln Phe Asn Gln
785                 790                 795                 800

Tyr Lys Thr Glu Ala Ala Ser Arg Tyr Asn Leu Thr Ile Ser Asp Val
                805                 810                 815

Ser Val Ser Asp Val Pro Phe Pro Phe Ser Ala Gln Ser Gly Ala Gly
            820                 825                 830
```

```
Val Pro Gly Trp Gly Ile Ala Leu Leu Val Leu Val Cys Val Leu Val
        835                 840                 845

Ala Leu Ala Ile Val Tyr Leu Ile Ala Leu Ala Val Cys Gln Cys Arg
    850                 855                 860

Arg Lys
865


<210> SEQ ID NO 44
<211> LENGTH: 1146
<212> TYPE: PRT
<213> ORGANISM: artificial sequence
<220> FEATURE:
<223> OTHER INFORMATION: Recombinant mucin

<400> SEQUENCE: 44

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Asp Ala Ala Thr Pro Ala Pro Asp Ala Ala Thr Pro Ala
        115                 120                 125

Pro Asp Ala Ala Thr Pro Ala Pro Asp Ala Ala Thr Pro Ala Pro Asp
    130                 135                 140

Ala Ala Thr Pro Ala Pro Asp Ala Ala Thr Pro Ala Pro Asp Ala Ala
145                 150                 155                 160

Thr Pro Ala Pro Asp Ala Ala Thr Pro Ala Pro Asp Ala Ala Thr Pro
                165                 170                 175

Ala Pro Asp Ala Ala Thr Pro Ala Pro Asp Ala Ala Thr Pro Ala Pro
            180                 185                 190

Asp Ala Ala Thr Pro Ala Pro Asp Ala Ala Thr Pro Ala Pro Asp Ala
        195                 200                 205

Ala Thr Pro Ala Pro Asp Ala Ala Thr Pro Ala Pro Asp Ala Ala Thr
    210                 215                 220

Pro Ala Pro Asp Ala Ala Thr Pro Ala Pro Asp Ala Ala Thr Pro Ala
225                 230                 235                 240

Pro Asp Ala Ala Thr Pro Ala Pro Asp Ala Ala Thr Pro Ala Pro Asp
                245                 250                 255

Ala Ala Thr Pro Ala Pro Asp Ala Ala Thr Pro Ala Pro Asp Ala Ala
            260                 265                 270

Thr Pro Ala Pro Asp Ala Ala Thr Pro Ala Pro Asp Ala Ala Thr Pro
        275                 280                 285

Ala Pro Asp Ala Ala Thr Pro Ala Pro Asp Ala Ala Thr Pro Ala Pro
    290                 295                 300

Asp Ala Ala Thr Pro Ala Pro Asp Ala Ala Thr Pro Ala Pro Asp Ala
305                 310                 315                 320
```

-continued

```
Ala Thr Pro Ala Pro Asp Ala Ala Thr Pro Ala Pro Asp Ala Ala Thr
                325                 330                 335

Pro Ala Pro Asp Ala Ala Thr Pro Ala Pro Asp Ala Ala Thr Pro Ala
            340                 345                 350

Pro Asp Ala Ala Thr Pro Ala Pro Asp Ala Ala Thr Pro Ala Pro Asp
        355                 360                 365

Ala Ala Thr Pro Ala Pro Asp Ala Ala Thr Pro Ala Pro Asp Ala Ala
    370                 375                 380

Thr Pro Ala Pro Asp Ala Ala Thr Pro Ala Pro Asp Ala Ala Thr Pro
385                 390                 395                 400

Ala Pro Asp Ala Ala Thr Pro Ala Pro Asp Ala Ala Thr Pro Ala Pro
                405                 410                 415

Asp Ala Ala Thr Pro Ala Pro Asp Ala Ala Thr Pro Ala Pro Asp Ala
            420                 425                 430

Ala Thr Pro Ala Pro Asp Ala Ala Thr Pro Ala Pro Asp Ala Ala Thr
        435                 440                 445

Pro Ala Pro Asp Ala Ala Thr Pro Ala Pro Asp Ala Ala Thr Pro Ala
    450                 455                 460

Pro Asp Ala Ala Thr Pro Ala Pro Asp Ala Ala Thr Pro Ala Pro Asp
465                 470                 475                 480

Ala Ala Thr Pro Ala Pro Asp Ala Ala Thr Pro Ala Pro Asp Ala Ala
                485                 490                 495

Thr Pro Ala Pro Asp Ala Ala Thr Pro Ala Pro Asp Ala Ala Thr Pro
            500                 505                 510

Ala Pro Asp Ala Ala Thr Pro Ala Pro Asp Ala Ala Thr Pro Ala Pro
        515                 520                 525

Asp Ala Ala Thr Pro Ala Pro Asp Ala Ala Thr Pro Ala Pro Asp Ala
    530                 535                 540

Ala Thr Pro Ala Pro Asp Ala Ala Thr Pro Ala Pro Asp Ala Ala Thr
545                 550                 555                 560

Pro Ala Pro Asp Ala Ala Thr Pro Ala Pro Asp Ala Ala Thr Pro Ala
                565                 570                 575

Pro Asp Ala Ala Thr Pro Ala Pro Asp Ala Ala Thr Pro Ala Pro Asp
            580                 585                 590

Ala Ala Thr Pro Ala Pro Asp Ala Ala Thr Pro Ala Pro Asp Ala Ala
        595                 600                 605

Thr Pro Ala Pro Asp Ala Ala Thr Pro Ala Pro Asp Ala Ala Thr Pro
    610                 615                 620

Ala Pro Asp Ala Ala Thr Pro Ala Pro Asp Ala Ala Thr Pro Ala Pro
625                 630                 635                 640

Asp Ala Ala Thr Pro Ala Pro Asp Ala Ala Thr Pro Ala Pro Asp Ala
                645                 650                 655

Ala Thr Pro Ala Pro Asp Ala Ala Thr Pro Ala Pro Asp Ala Ala Thr
            660                 665                 670

Pro Ala Pro Ala Ser Gly Ser Ala Ser Gly Ser Ala Met Val Ser Lys
        675                 680                 685

Gly Glu Glu Leu Phe Thr Gly Val Val Pro Ile Leu Val Glu Leu Asp
    690                 695                 700

Gly Asp Val Asn Gly His Lys Phe Ser Val Arg Gly Glu Gly Glu Gly
705                 710                 715                 720

Asp Ala Thr Asn Gly Lys Leu Thr Leu Lys Phe Ile Ser Thr Thr Gly
                725                 730                 735
```

```
Lys Leu Pro Val Pro Trp Pro Thr Leu Val Thr Thr Leu Thr Tyr Gly
            740                 745                 750

Val Gln Ser Phe Ser Arg Tyr Pro Asp His Met Lys Arg His Asp Phe
        755                 760                 765

Phe Lys Ser Ala Met Pro Glu Gly Tyr Val Gln Glu Arg Thr Ile Ser
    770                 775                 780

Phe Lys Asp Asp Gly Thr Tyr Lys Thr Arg Ala Glu Val Lys Phe Glu
785                 790                 795                 800

Gly Asp Thr Leu Val Asn Arg Ile Glu Leu Lys Gly Ile Asp Phe Lys
                805                 810                 815

Glu Asp Gly Asn Ile Leu Gly His Lys Leu Glu Tyr Asn Phe Asn Ser
            820                 825                 830

His Asn Val Tyr Ile Thr Ala Asp Lys Gln Lys Asn Gly Ile Lys Ala
        835                 840                 845

Asn Phe Lys Ile Arg His Asn Val Glu Asp Gly Ser Val Gln Leu Ala
    850                 855                 860

Asp His Tyr Gln Gln Asn Thr Pro Ile Gly Asp Gly Pro Val Leu Leu
865                 870                 875                 880

Pro Asp Asn His Tyr Leu Ser Thr Gln Ser Lys Leu Ser Lys Asp Pro
                885                 890                 895

Asn Glu Lys Arg Asp His Met Val Leu Leu Glu Phe Val Thr Ala Ala
            900                 905                 910

Gly Ile Thr His Gly Met Asp Glu Leu Tyr Lys Gly Ser Ala Ser Thr
        915                 920                 925

Leu Val His Asn Gly Thr Ser Ala Arg Ala Thr Thr Thr Pro Ala Ser
    930                 935                 940

Lys Ser Thr Pro Phe Ser Ile Pro Ser His His Ser Asp Thr Pro Thr
945                 950                 955                 960

Thr Leu Ala Ser His Ser Thr Lys Thr Asp Ala Ser Ser Thr His His
                965                 970                 975

Ser Ser Val Pro Pro Leu Thr Ser Ser Asn His Ser Thr Ser Pro Gln
            980                 985                 990

Leu Ser Thr Gly Val Ser Phe Phe  Phe Leu Ser Phe His  Ile Ser Asn
        995                 1000                1005

Leu Gln  Phe Asn Ser Ser Leu  Glu Asp Pro Ser Thr  Asp Tyr Tyr
    1010                1015                1020

Gln Glu  Leu Gln Arg Asp Ile  Ser Glu Met Phe Leu  Gln Ile Tyr
    1025                1030                1035

Lys Gln  Gly Gly Phe Leu Gly  Leu Ser Asn Ile Lys  Phe Arg Pro
    1040                1045                1050

Gly Ser  Val Val Val Gln Leu  Thr Leu Ala Phe Arg  Glu Gly Thr
    1055                1060                1065

Ile Asn  Val His Asp Val Glu  Thr Gln Phe Asn Gln  Tyr Lys Thr
    1070                1075                1080

Glu Ala  Ala Ser Arg Tyr Asn  Leu Thr Ile Ser Asp  Val Ser Val
    1085                1090                1095

Ser Asp  Val Pro Phe Pro Phe  Ser Ala Gln Ser Gly  Ala Gly Val
    1100                1105                1110

Pro Gly  Trp Gly Ile Ala Leu  Leu Val Leu Val Cys  Val Leu Val
    1115                1120                1125

Ala Leu  Ala Ile Val Tyr Leu  Ile Ala Leu Ala Val  Cys Gln Cys
    1130                1135                1140

Arg Arg  Lys
```

1145

<210> SEQ ID NO 45
<211> LENGTH: 906
<212> TYPE: PRT
<213> ORGANISM: artificial sequence
<220> FEATURE:
<223> OTHER INFORMATION: Recombinant mucin

<400> SEQUENCE: 45

Met Thr Pro Gly Thr Gln Ser Pro Phe Phe Leu Leu Leu Leu Leu Thr
1 5 10 15

Val Leu Thr Val Val Thr Gly Ser Gly His Ala Ser Ser Thr Pro Gly
20 25 30

Gly Glu Lys Glu Thr Ser Ala Thr Gln Arg Ser Ser Val Pro Ser Ser
35 40 45

Thr Glu Lys Asn Ala Asp Tyr Lys Asp Asp Asp Asp Leu Tyr Met Asp
50 55 60

Met Val Ala Val Ser Met Thr Ser Ser Val Leu Ser Ser His Ser Pro
65 70 75 80

Gly Ser Gly Ser Ser Thr Thr Gln Gly Gln Asp Val Thr Leu Ala Pro
85 90 95

Ala Thr Glu Pro Ala Ser Gly Ser Ala Ala Thr Trp Gly Gln Asp Val
100 105 110

Thr Ser Val Asp Ala Ala Thr Pro Ala Pro Pro Asp Ala Ala Thr Pro
115 120 125

Ala Pro Pro Asp Ala Ala Thr Pro Ala Pro Pro Asp Ala Ala Thr Pro
130 135 140

Ala Pro Pro Asp Ala Ala Thr Pro Ala Pro Pro Asp Ala Ala Thr Pro
145 150 155 160

Ala Pro Pro Asp Ala Ala Thr Pro Ala Pro Pro Asp Ala Ala Thr Pro
165 170 175

Ala Pro Pro Asp Ala Ala Thr Pro Ala Pro Pro Asp Ala Ala Thr Pro
180 185 190

Ala Pro Pro Asp Ala Ala Thr Pro Ala Pro Pro Asp Ala Ala Thr Pro
195 200 205

Ala Pro Pro Asp Ala Ala Thr Pro Ala Pro Pro Asp Ala Ala Thr Pro
210 215 220

Ala Pro Pro Asp Ala Ala Thr Pro Ala Pro Pro Asp Ala Ala Thr Pro
225 230 235 240

Ala Pro Pro Asp Ala Ala Thr Pro Ala Pro Pro Asp Ala Ala Thr Pro
245 250 255

Ala Pro Pro Asp Ala Ala Thr Pro Ala Pro Pro Asp Ala Ala Thr Pro
260 265 270

Ala Pro Pro Asp Ala Ala Thr Pro Ala Pro Pro Asp Ala Ala Thr Pro
275 280 285

Ala Pro Pro Asp Ala Ala Thr Pro Ala Pro Pro Asp Ala Ala Thr Pro
290 295 300

Ala Pro Pro Asp Ala Ala Thr Pro Ala Pro Pro Asp Ala Ala Thr Pro
305 310 315 320

Ala Pro Pro Asp Ala Ala Thr Pro Ala Pro Pro Asp Ala Ala Thr Pro
325 330 335

Ala Pro Pro Asp Ala Ala Thr Pro Ala Pro Pro Asp Ala Ala Thr Pro
340 345 350

Ala Pro Pro Asp Ala Ala Thr Pro Ala Pro Pro Asp Ala Ala Thr Pro

-continued

```
        355                 360                 365

Ala Pro Pro Asp Ala Ala Thr Pro Ala Pro Pro Asp Ala Ala Thr Pro
    370                 375                 380

Ala Pro Pro Asp Ala Ala Thr Pro Ala Pro Pro Asp Ala Ala Thr Pro
385                 390                 395                 400

Ala Pro Pro Asp Ala Ala Thr Pro Ala Pro Pro Asp Ala Ala Thr Pro
                405                 410                 415

Ala Pro Pro Asp Ala Ala Thr Pro Ala Pro Pro Asp Ala Ala Thr Pro
            420                 425                 430

Ala Pro Pro Ala Ser Gly Ser Ala Ser Gly Ser Ala Met Val Ser Lys
        435                 440                 445

Gly Glu Glu Leu Phe Thr Gly Val Val Pro Ile Leu Val Glu Leu Asp
    450                 455                 460

Gly Asp Val Asn Gly His Lys Phe Ser Val Arg Gly Glu Gly Glu Gly
465                 470                 475                 480

Asp Ala Thr Asn Gly Lys Leu Thr Leu Lys Phe Ile Ser Thr Thr Gly
                485                 490                 495

Lys Leu Pro Val Pro Trp Pro Thr Leu Val Thr Thr Leu Thr Tyr Gly
            500                 505                 510

Val Gln Ser Phe Ser Arg Tyr Pro Asp His Met Lys Arg His Asp Phe
        515                 520                 525

Phe Lys Ser Ala Met Pro Glu Gly Tyr Val Gln Glu Arg Thr Ile Ser
    530                 535                 540

Phe Lys Asp Asp Gly Thr Tyr Lys Thr Arg Ala Glu Val Lys Phe Glu
545                 550                 555                 560

Gly Asp Thr Leu Val Asn Arg Ile Glu Leu Lys Gly Ile Asp Phe Lys
                565                 570                 575

Glu Asp Gly Asn Ile Leu Gly His Lys Leu Glu Tyr Asn Phe Asn Ser
            580                 585                 590

His Asn Val Tyr Ile Thr Ala Asp Lys Gln Lys Asn Gly Ile Lys Ala
        595                 600                 605

Asn Phe Lys Ile Arg His Asn Val Glu Asp Gly Ser Val Gln Leu Ala
    610                 615                 620

Asp His Tyr Gln Gln Asn Thr Pro Ile Gly Asp Gly Pro Val Leu Leu
625                 630                 635                 640

Pro Asp Asn His Tyr Leu Ser Thr Gln Ser Lys Leu Ser Lys Asp Pro
                645                 650                 655

Asn Glu Lys Arg Asp His Met Val Leu Leu Glu Phe Val Thr Ala Ala
            660                 665                 670

Gly Ile Thr His Gly Met Asp Glu Leu Tyr Lys Gly Ser Ala Ser Thr
        675                 680                 685

Leu Val His Asn Gly Thr Ser Ala Arg Ala Thr Thr Thr Pro Ala Ser
    690                 695                 700

Lys Ser Thr Pro Phe Ser Ile Pro Ser His His Ser Asp Thr Pro Thr
705                 710                 715                 720

Thr Leu Ala Ser His Ser Thr Lys Thr Asp Ala Ser Ser Thr His His
                725                 730                 735

Ser Ser Val Pro Pro Leu Thr Ser Ser Asn His Ser Thr Ser Pro Gln
            740                 745                 750

Leu Ser Thr Gly Val Ser Phe Phe Phe Leu Ser Phe His Ile Ser Asn
        755                 760                 765

Leu Gln Phe Asn Ser Ser Leu Glu Asp Pro Ser Thr Asp Tyr Tyr Gln
    770                 775                 780
```

```
Glu Leu Gln Arg Asp Ile Ser Glu Met Phe Leu Gln Ile Tyr Lys Gln
785                 790                 795                 800

Gly Gly Phe Leu Gly Leu Ser Asn Ile Lys Phe Arg Pro Gly Ser Val
                805                 810                 815

Val Val Gln Leu Thr Leu Ala Phe Arg Glu Gly Thr Ile Asn Val His
            820                 825                 830

Asp Val Glu Thr Gln Phe Asn Gln Tyr Lys Thr Glu Ala Ala Ser Arg
        835                 840                 845

Tyr Asn Leu Thr Ile Ser Asp Val Ser Val Ser Asp Val Pro Phe Pro
    850                 855                 860

Phe Ser Ala Gln Ser Gly Ala Gly Val Pro Gly Trp Gly Ile Ala Leu
865                 870                 875                 880

Leu Val Leu Val Cys Val Leu Val Ala Leu Ala Ile Val Tyr Leu Ile
                885                 890                 895

Ala Leu Ala Val Cys Gln Cys Arg Arg Lys
            900                 905


<210> SEQ ID NO 46
<211> LENGTH: 1226
<212> TYPE: PRT
<213> ORGANISM: artificial sequence
<220> FEATURE:
<223> OTHER INFORMATION: Recombinant mucin

<400> SEQUENCE: 46

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Asp Ala Ala Thr Pro Ala Pro Pro Asp Ala Ala Thr Pro
        115                 120                 125

Ala Pro Pro Asp Ala Ala Thr Pro Ala Pro Pro Asp Ala Ala Thr Pro
    130                 135                 140

Ala Pro Pro Asp Ala Ala Thr Pro Ala Pro Pro Asp Ala Ala Thr Pro
145                 150                 155                 160

Ala Pro Pro Asp Ala Ala Thr Pro Ala Pro Pro Asp Ala Ala Thr Pro
                165                 170                 175

Ala Pro Pro Asp Ala Ala Thr Pro Ala Pro Pro Asp Ala Ala Thr Pro
            180                 185                 190

Ala Pro Pro Asp Ala Ala Thr Pro Ala Pro Pro Asp Ala Ala Thr Pro
        195                 200                 205

Ala Pro Pro Asp Ala Ala Thr Pro Ala Pro Pro Asp Ala Ala Thr Pro
    210                 215                 220

Ala Pro Pro Asp Ala Ala Thr Pro Ala Pro Pro Asp Ala Ala Thr Pro
225                 230                 235                 240
```

-continued

Ala Pro Pro Asp Ala Ala Thr Pro Ala Pro Pro Asp Ala Ala Thr Pro
                245                 250                 255

Ala Pro Pro Asp Ala Ala Thr Pro Ala Pro Pro Asp Ala Ala Thr Pro
            260                 265                 270

Ala Pro Pro Asp Ala Ala Thr Pro Ala Pro Pro Asp Ala Ala Thr Pro
        275                 280                 285

Ala Pro Pro Asp Ala Ala Thr Pro Ala Pro Pro Asp Ala Ala Thr Pro
    290                 295                 300

Ala Pro Pro Asp Ala Ala Thr Pro Ala Pro Pro Asp Ala Ala Thr Pro
305                 310                 315                 320

Ala Pro Pro Asp Ala Ala Thr Pro Ala Pro Pro Asp Ala Ala Thr Pro
                325                 330                 335

Ala Pro Pro Asp Ala Ala Thr Pro Ala Pro Pro Asp Ala Ala Thr Pro
            340                 345                 350

Ala Pro Pro Asp Ala Ala Thr Pro Ala Pro Pro Asp Ala Ala Thr Pro
        355                 360                 365

Ala Pro Pro Asp Ala Ala Thr Pro Ala Pro Pro Asp Ala Ala Thr Pro
    370                 375                 380

Ala Pro Pro Asp Ala Ala Thr Pro Ala Pro Pro Asp Ala Ala Thr Pro
385                 390                 395                 400

Ala Pro Pro Asp Ala Ala Thr Pro Ala Pro Pro Asp Ala Ala Thr Pro
                405                 410                 415

Ala Pro Pro Asp Ala Ala Thr Pro Ala Pro Pro Asp Ala Ala Thr Pro
            420                 425                 430

Ala Pro Pro Asp Ala Ala Thr Pro Ala Pro Pro Asp Ala Ala Thr Pro
        435                 440                 445

Ala Pro Pro Asp Ala Ala Thr Pro Ala Pro Pro Asp Ala Ala Thr Pro
    450                 455                 460

Ala Pro Pro Asp Ala Ala Thr Pro Ala Pro Pro Asp Ala Ala Thr Pro
465                 470                 475                 480

Ala Pro Pro Asp Ala Ala Thr Pro Ala Pro Pro Asp Ala Ala Thr Pro
                485                 490                 495

Ala Pro Pro Asp Ala Ala Thr Pro Ala Pro Pro Asp Ala Ala Thr Pro
            500                 505                 510

Ala Pro Pro Asp Ala Ala Thr Pro Ala Pro Pro Asp Ala Ala Thr Pro
        515                 520                 525

Ala Pro Pro Asp Ala Ala Thr Pro Ala Pro Pro Asp Ala Ala Thr Pro
    530                 535                 540

Ala Pro Pro Asp Ala Ala Thr Pro Ala Pro Pro Asp Ala Ala Thr Pro
545                 550                 555                 560

Ala Pro Pro Asp Ala Ala Thr Pro Ala Pro Pro Asp Ala Ala Thr Pro
                565                 570                 575

Ala Pro Pro Asp Ala Ala Thr Pro Ala Pro Pro Asp Ala Ala Thr Pro
            580                 585                 590

Ala Pro Pro Asp Ala Ala Thr Pro Ala Pro Pro Asp Ala Ala Thr Pro
        595                 600                 605

Ala Pro Pro Asp Ala Ala Thr Pro Ala Pro Pro Asp Ala Ala Thr Pro
    610                 615                 620

Ala Pro Pro Asp Ala Ala Thr Pro Ala Pro Pro Asp Ala Ala Thr Pro
625                 630                 635                 640

Ala Pro Pro Asp Ala Ala Thr Pro Ala Pro Pro Asp Ala Ala Thr Pro
                645                 650                 655

-continued

```
Ala Pro Pro Asp Ala Ala Thr Pro Ala Pro Pro Asp Ala Ala Thr Pro
            660                 665                 670

Ala Pro Pro Asp Ala Ala Thr Pro Ala Pro Pro Asp Ala Ala Thr Pro
        675                 680                 685

Ala Pro Pro Asp Ala Ala Thr Pro Ala Pro Pro Asp Ala Ala Thr Pro
    690                 695                 700

Ala Pro Pro Asp Ala Ala Thr Pro Ala Pro Pro Asp Ala Ala Thr Pro
705                 710                 715                 720

Ala Pro Pro Asp Ala Ala Thr Pro Ala Pro Pro Asp Ala Ala Thr Pro
                725                 730                 735

Ala Pro Pro Asp Ala Ala Thr Pro Ala Pro Pro Asp Ala Ala Thr Pro
            740                 745                 750

Ala Pro Pro Ala Ser Gly Ser Ala Ser Gly Ser Ala Met Val Ser Lys
        755                 760                 765

Gly Glu Glu Leu Phe Thr Gly Val Val Pro Ile Leu Val Glu Leu Asp
    770                 775                 780

Gly Asp Val Asn Gly His Lys Phe Ser Val Arg Gly Glu Gly Glu Gly
785                 790                 795                 800

Asp Ala Thr Asn Gly Lys Leu Thr Leu Lys Phe Ile Ser Thr Thr Gly
                805                 810                 815

Lys Leu Pro Val Pro Trp Pro Thr Leu Val Thr Thr Leu Thr Tyr Gly
            820                 825                 830

Val Gln Ser Phe Ser Arg Tyr Pro Asp His Met Lys Arg His Asp Phe
        835                 840                 845

Phe Lys Ser Ala Met Pro Glu Gly Tyr Val Gln Glu Arg Thr Ile Ser
    850                 855                 860

Phe Lys Asp Asp Gly Thr Tyr Lys Thr Arg Ala Glu Val Lys Phe Glu
865                 870                 875                 880

Gly Asp Thr Leu Val Asn Arg Ile Glu Leu Lys Gly Ile Asp Phe Lys
                885                 890                 895

Glu Asp Gly Asn Ile Leu Gly His Lys Leu Glu Tyr Asn Phe Asn Ser
            900                 905                 910

His Asn Val Tyr Ile Thr Ala Asp Lys Gln Lys Asn Gly Ile Lys Ala
        915                 920                 925

Asn Phe Lys Ile Arg His Asn Val Glu Asp Gly Ser Val Gln Leu Ala
    930                 935                 940

Asp His Tyr Gln Gln Asn Thr Pro Ile Gly Asp Gly Pro Val Leu Leu
945                 950                 955                 960

Pro Asp Asn His Tyr Leu Ser Thr Gln Ser Lys Leu Ser Lys Asp Pro
                965                 970                 975

Asn Glu Lys Arg Asp His Met Val Leu Leu Glu Phe Val Thr Ala Ala
            980                 985                 990

Gly Ile Thr His Gly Met Asp Glu  Leu Tyr Lys Gly Ser  Ala Ser Thr
        995                 1000                1005

Leu Val  His Asn Gly Thr Ser  Ala Arg Ala Thr Thr  Thr Pro Ala
    1010                1015                1020

Ser Lys  Ser Thr Pro Phe Ser  Ile Pro Ser His His  Ser Asp Thr
    1025                1030                1035

Pro Thr  Thr Leu Ala Ser His  Ser Thr Lys Thr Asp  Ala Ser Ser
    1040                1045                1050

Thr His  His Ser Ser Val Pro  Pro Leu Thr Ser Ser  Asn His Ser
    1055                1060                1065

Thr Ser  Pro Gln Leu Ser Thr  Gly Val Ser Phe Phe  Phe Leu Ser
```

```
    1070                1075                1080

Phe His  Ile Ser Asn Leu Gln  Phe Asn Ser Ser Leu  Glu Asp Pro
    1085                1090                1095

Ser Thr  Asp Tyr Tyr Gln Glu  Leu Gln Arg Asp Ile  Ser Glu Met
    1100                1105                1110

Phe Leu  Gln Ile Tyr Lys Gln  Gly Gly Phe Leu Gly  Leu Ser Asn
    1115                1120                1125

Ile Lys  Phe Arg Pro Gly Ser  Val Val Val Gln Leu  Thr Leu Ala
    1130                1135                1140

Phe Arg  Glu Gly Thr Ile Asn  Val His Asp Val Glu  Thr Gln Phe
    1145                1150                1155

Asn Gln  Tyr Lys Thr Glu Ala  Ala Ser Arg Tyr Asn  Leu Thr Ile
    1160                1165                1170

Ser Asp  Val Ser Val Ser Asp  Val Pro Phe Pro Phe  Ser Ala Gln
    1175                1180                1185

Ser Gly  Ala Gly Val Pro Gly  Trp Gly Ile Ala Leu  Leu Val Leu
    1190                1195                1200

Val Cys  Val Leu Val Ala Leu  Ala Ile Val Tyr Leu  Ile Ala Leu
    1205                1210                1215

Ala Val  Cys Gln Cys Arg Arg  Lys
    1220                1225


<210> SEQ ID NO 47
<211> LENGTH: 946
<212> TYPE: PRT
<213> ORGANISM: artificial sequence
<220> FEATURE:
<223> OTHER INFORMATION: Recombinant mucin

<400> SEQUENCE: 47

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Pro Pro Ala Ser Thr Ser Ala Pro Gly Pro Pro Ala Ser
        115                 120                 125

Thr Ser Ala Pro Gly Pro Pro Ala Ser Thr Ser Ala Pro Gly Pro Pro
    130                 135                 140

Ala Ser Thr Ser Ala Pro Gly Pro Pro Ala Ser Thr Ser Ala Pro Gly
145                 150                 155                 160

Pro Pro Ala Ser Thr Ser Ala Pro Gly Pro Pro Ala Ser Thr Ser Ala
                165                 170                 175

Pro Gly Pro Pro Ala Ser Thr Ser Ala Pro Gly Pro Pro Ala Ser Thr
            180                 185                 190

Ser Ala Pro Gly Pro Pro Ala Ser Thr Ser Ala Pro Gly Pro Pro Ala
```

-continued

```
        195                 200                 205

Ser Thr Ser Ala Pro Gly Pro Pro Ala Ser Thr Ser Ala Pro Gly Pro
    210                 215                 220

Pro Ala Ser Thr Ser Ala Pro Gly Pro Pro Ala Ser Thr Ser Ala Pro
225                 230                 235                 240

Gly Pro Pro Ala Ser Thr Ser Ala Pro Gly Pro Pro Ala Ser Thr Ser
                245                 250                 255

Ala Pro Gly Pro Pro Ala Ser Thr Ser Ala Pro Gly Pro Pro Ala Ser
            260                 265                 270

Thr Ser Ala Pro Gly Pro Pro Ala Ser Thr Ser Ala Pro Gly Pro Pro
        275                 280                 285

Ala Ser Thr Ser Ala Pro Gly Pro Pro Ala Ser Thr Ser Ala Pro Gly
    290                 295                 300

Pro Pro Ala Ser Thr Ser Ala Pro Gly Pro Pro Ala Ser Thr Ser Ala
305                 310                 315                 320

Pro Gly Pro Pro Ala Ser Thr Ser Ala Pro Gly Pro Pro Ala Ser Thr
                325                 330                 335

Ser Ala Pro Gly Pro Pro Ala Ser Thr Ser Ala Pro Gly Pro Pro Ala
            340                 345                 350

Ser Thr Ser Ala Pro Gly Pro Pro Ala Ser Thr Ser Ala Pro Gly Pro
        355                 360                 365

Pro Ala Ser Thr Ser Ala Pro Gly Pro Pro Ala Ser Thr Ser Ala Pro
    370                 375                 380

Gly Pro Pro Ala Ser Thr Ser Ala Pro Gly Pro Pro Ala Ser Thr Ser
385                 390                 395                 400

Ala Pro Gly Pro Pro Ala Ser Thr Ser Ala Pro Gly Pro Pro Ala Ser
                405                 410                 415

Thr Ser Ala Pro Gly Pro Pro Ala Ser Thr Ser Ala Pro Gly Pro Pro
            420                 425                 430

Ala Ser Thr Ser Ala Pro Gly Pro Pro Ala Ser Thr Ser Ala Pro Gly
        435                 440                 445

Pro Pro Ala Ser Thr Ser Ala Pro Gly Pro Pro Ala Ser Thr Ser Ala
    450                 455                 460

Pro Gly Pro Pro Ala Ser Thr Ser Ala Pro Gly Ala Ser Gly Ser Ala
465                 470                 475                 480

Ser Gly Ser Ala Met Val Ser Lys Gly Glu Glu Leu Phe Thr Gly Val
                485                 490                 495

Val Pro Ile Leu Val Glu Leu Asp Gly Asp Val Asn Gly His Lys Phe
            500                 505                 510

Ser Val Arg Gly Glu Gly Glu Gly Asp Ala Thr Asn Gly Lys Leu Thr
        515                 520                 525

Leu Lys Phe Ile Ser Thr Thr Gly Lys Leu Pro Val Pro Trp Pro Thr
    530                 535                 540

Leu Val Thr Thr Leu Thr Tyr Gly Val Gln Ser Phe Ser Arg Tyr Pro
545                 550                 555                 560

Asp His Met Lys Arg His Asp Phe Phe Lys Ser Ala Met Pro Glu Gly
                565                 570                 575

Tyr Val Gln Glu Arg Thr Ile Ser Phe Lys Asp Asp Gly Thr Tyr Lys
            580                 585                 590

Thr Arg Ala Glu Val Lys Phe Glu Gly Asp Thr Leu Val Asn Arg Ile
        595                 600                 605

Glu Leu Lys Gly Ile Asp Phe Lys Glu Asp Gly Asn Ile Leu Gly His
    610                 615                 620
```

Lys Leu Glu Tyr Asn Phe Asn Ser His Asn Val Tyr Ile Thr Ala Asp
625 630 635 640

Lys Gln Lys Asn Gly Ile Lys Ala Asn Phe Lys Ile Arg His Asn Val
645 650 655

Glu Asp Gly Ser Val Gln Leu Ala Asp His Tyr Gln Gln Asn Thr Pro
660 665 670

Ile Gly Asp Gly Pro Val Leu Leu Pro Asp Asn His Tyr Leu Ser Thr
675 680 685

Gln Ser Lys Leu Ser Lys Asp Pro Asn Glu Lys Arg Asp His Met Val
690 695 700

Leu Leu Glu Phe Val Thr Ala Ala Gly Ile Thr His Gly Met Asp Glu
705 710 715 720

Leu Tyr Lys Gly Ser Ala Ser Thr Leu Val His Asn Gly Thr Ser Ala
725 730 735

Arg Ala Thr Thr Thr Pro Ala Ser Lys Ser Thr Pro Phe Ser Ile Pro
740 745 750

Ser His His Ser Asp Thr Pro Thr Thr Leu Ala Ser His Ser Thr Lys
755 760 765

Thr Asp Ala Ser Ser Thr His His Ser Ser Val Pro Pro Leu Thr Ser
770 775 780

Ser Asn His Ser Thr Ser Pro Gln Leu Ser Thr Gly Val Ser Phe Phe
785 790 795 800

Phe Leu Ser Phe His Ile Ser Asn Leu Gln Phe Asn Ser Ser Leu Glu
805 810 815

Asp Pro Ser Thr Asp Tyr Tyr Gln Glu Leu Gln Arg Asp Ile Ser Glu
820 825 830

Met Phe Leu Gln Ile Tyr Lys Gln Gly Gly Phe Leu Gly Leu Ser Asn
835 840 845

Ile Lys Phe Arg Pro Gly Ser Val Val Val Gln Leu Thr Leu Ala Phe
850 855 860

Arg Glu Gly Thr Ile Asn Val His Asp Val Glu Thr Gln Phe Asn Gln
865 870 875 880

Tyr Lys Thr Glu Ala Ala Ser Arg Tyr Asn Leu Thr Ile Ser Asp Val
885 890 895

Ser Val Ser Asp Val Pro Phe Pro Phe Ser Ala Gln Ser Gly Ala Gly
900 905 910

Val Pro Gly Trp Gly Ile Ala Leu Leu Val Leu Val Cys Val Leu Val
915 920 925

Ala Leu Ala Ile Val Tyr Leu Ile Ala Leu Ala Val Cys Gln Cys Arg
930 935 940

Arg Lys
945

<210> SEQ ID NO 48
<211> LENGTH: 1306
<212> TYPE: PRT
<213> ORGANISM: artificial sequence
<220> FEATURE:
<223> OTHER INFORMATION: Recombinant mucin

<400> SEQUENCE: 48

Met Thr Pro Gly Thr Gln Ser Pro Phe Phe Leu Leu Leu Leu Leu Thr
1 5 10 15

Val Leu Thr Val Val Thr Gly Ser Gly His Ala Ser Ser Thr Pro Gly
20 25 30

-continued

```
Gly Glu Lys Glu Thr Ser Ala Thr Gln Arg Ser Ser Val Pro Ser Ser
        35                  40                  45

Thr Glu Lys Asn Ala Asp Tyr Lys Asp Asp Asp Asp Leu Tyr Met Asp
    50                  55                  60

Met Val Ala Val Ser Met Thr Ser Ser Val Leu Ser Ser His Ser Pro
65                  70                  75                  80

Gly Ser Gly Ser Ser Thr Thr Gln Gly Gln Asp Val Thr Leu Ala Pro
                85                  90                  95

Ala Thr Glu Pro Ala Ser Gly Ser Ala Ala Thr Trp Gly Gln Asp Val
            100                 105                 110

Thr Ser Val Pro Pro Ala Ser Thr Ser Ala Pro Gly Pro Pro Ala Ser
        115                 120                 125

Thr Ser Ala Pro Gly Pro Pro Ala Ser Thr Ser Ala Pro Gly Pro Pro
    130                 135                 140

Ala Ser Thr Ser Ala Pro Gly Pro Pro Ala Ser Thr Ser Ala Pro Gly
145                 150                 155                 160

Pro Pro Ala Ser Thr Ser Ala Pro Gly Pro Pro Ala Ser Thr Ser Ala
                165                 170                 175

Pro Gly Pro Pro Ala Ser Thr Ser Ala Pro Gly Pro Pro Ala Ser Thr
            180                 185                 190

Ser Ala Pro Gly Pro Pro Ala Ser Thr Ser Ala Pro Gly Pro Pro Ala
        195                 200                 205

Ser Thr Ser Ala Pro Gly Pro Pro Ala Ser Thr Ser Ala Pro Gly Pro
    210                 215                 220

Pro Ala Ser Thr Ser Ala Pro Gly Pro Pro Ala Ser Thr Ser Ala Pro
225                 230                 235                 240

Gly Pro Pro Ala Ser Thr Ser Ala Pro Gly Pro Pro Ala Ser Thr Ser
                245                 250                 255

Ala Pro Gly Pro Pro Ala Ser Thr Ser Ala Pro Gly Pro Pro Ala Ser
            260                 265                 270

Thr Ser Ala Pro Gly Pro Pro Ala Ser Thr Ser Ala Pro Gly Pro Pro
        275                 280                 285

Ala Ser Thr Ser Ala Pro Gly Pro Pro Ala Ser Thr Ser Ala Pro Gly
    290                 295                 300

Pro Pro Ala Ser Thr Ser Ala Pro Gly Pro Pro Ala Ser Thr Ser Ala
305                 310                 315                 320

Pro Gly Pro Pro Ala Ser Thr Ser Ala Pro Gly Pro Pro Ala Ser Thr
                325                 330                 335

Ser Ala Pro Gly Pro Pro Ala Ser Thr Ser Ala Pro Gly Pro Pro Ala
            340                 345                 350

Ser Thr Ser Ala Pro Gly Pro Pro Ala Ser Thr Ser Ala Pro Gly Pro
        355                 360                 365

Pro Ala Ser Thr Ser Ala Pro Gly Pro Pro Ala Ser Thr Ser Ala Pro
    370                 375                 380

Gly Pro Pro Ala Ser Thr Ser Ala Pro Gly Pro Pro Ala Ser Thr Ser
385                 390                 395                 400

Ala Pro Gly Pro Pro Ala Ser Thr Ser Ala Pro Gly Pro Pro Ala Ser
                405                 410                 415

Thr Ser Ala Pro Gly Pro Pro Ala Ser Thr Ser Ala Pro Gly Pro Pro
            420                 425                 430

Ala Ser Thr Ser Ala Pro Gly Pro Pro Ala Ser Thr Ser Ala Pro Gly
        435                 440                 445
```

```
Pro Pro Ala Ser Thr Ser Ala Pro Gly Pro Pro Ala Ser Thr Ser Ala
    450                 455                 460

Pro Gly Pro Pro Ala Ser Thr Ser Ala Pro Gly Pro Pro Ala Ser Thr
465                 470                 475                 480

Ser Ala Pro Gly Pro Pro Ala Ser Thr Ser Ala Pro Gly Pro Pro Ala
                485                 490                 495

Ser Thr Ser Ala Pro Gly Pro Pro Ala Ser Thr Ser Ala Pro Gly Pro
            500                 505                 510

Pro Ala Ser Thr Ser Ala Pro Gly Pro Pro Ala Ser Thr Ser Ala Pro
        515                 520                 525

Gly Pro Pro Ala Ser Thr Ser Ala Pro Gly Pro Pro Ala Ser Thr Ser
    530                 535                 540

Ala Pro Gly Pro Pro Ala Ser Thr Ser Ala Pro Gly Pro Pro Ala Ser
545                 550                 555                 560

Thr Ser Ala Pro Gly Pro Pro Ala Ser Thr Ser Ala Pro Gly Pro Pro
                565                 570                 575

Ala Ser Thr Ser Ala Pro Gly Pro Pro Ala Ser Thr Ser Ala Pro Gly
            580                 585                 590

Pro Pro Ala Ser Thr Ser Ala Pro Gly Pro Pro Ala Ser Thr Ser Ala
        595                 600                 605

Pro Gly Pro Pro Ala Ser Thr Ser Ala Pro Gly Pro Pro Ala Ser Thr
    610                 615                 620

Ser Ala Pro Gly Pro Pro Ala Ser Thr Ser Ala Pro Gly Pro Pro Ala
625                 630                 635                 640

Ser Thr Ser Ala Pro Gly Pro Pro Ala Ser Thr Ser Ala Pro Gly Pro
                645                 650                 655

Pro Ala Ser Thr Ser Ala Pro Gly Pro Pro Ala Ser Thr Ser Ala Pro
            660                 665                 670

Gly Pro Pro Ala Ser Thr Ser Ala Pro Gly Pro Pro Ala Ser Thr Ser
        675                 680                 685

Ala Pro Gly Pro Pro Ala Ser Thr Ser Ala Pro Gly Pro Pro Ala Ser
    690                 695                 700

Thr Ser Ala Pro Gly Pro Pro Ala Ser Thr Ser Ala Pro Gly Pro Pro
705                 710                 715                 720

Ala Ser Thr Ser Ala Pro Gly Pro Pro Ala Ser Thr Ser Ala Pro Gly
                725                 730                 735

Pro Pro Ala Ser Thr Ser Ala Pro Gly Pro Pro Ala Ser Thr Ser Ala
            740                 745                 750

Pro Gly Pro Pro Ala Ser Thr Ser Ala Pro Gly Pro Pro Ala Ser Thr
        755                 760                 765

Ser Ala Pro Gly Pro Pro Ala Ser Thr Ser Ala Pro Gly Pro Pro Ala
    770                 775                 780

Ser Thr Ser Ala Pro Gly Pro Pro Ala Ser Thr Ser Ala Pro Gly Pro
785                 790                 795                 800

Pro Ala Ser Thr Ser Ala Pro Gly Pro Pro Ala Ser Thr Ser Ala Pro
                805                 810                 815

Gly Pro Pro Ala Ser Thr Ser Ala Pro Gly Pro Pro Ala Ser Thr Ser
            820                 825                 830

Ala Pro Gly Ala Ser Gly Ser Ala Ser Gly Ser Ala Met Val Ser Lys
        835                 840                 845

Gly Glu Glu Leu Phe Thr Gly Val Val Pro Ile Leu Val Glu Leu Asp
    850                 855                 860

Gly Asp Val Asn Gly His Lys Phe Ser Val Arg Gly Glu Gly Glu Gly
```

-continued

```
865                 870                 875                 880

Asp Ala Thr Asn Gly Lys Leu Thr Leu Lys Phe Ile Ser Thr Thr Gly
                885                 890                 895

Lys Leu Pro Val Pro Trp Pro Thr Leu Val Thr Thr Leu Thr Tyr Gly
            900                 905                 910

Val Gln Ser Phe Ser Arg Tyr Pro Asp His Met Lys Arg His Asp Phe
        915                 920                 925

Phe Lys Ser Ala Met Pro Glu Gly Tyr Val Gln Glu Arg Thr Ile Ser
    930                 935                 940

Phe Lys Asp Asp Gly Thr Tyr Lys Thr Arg Ala Glu Val Lys Phe Glu
945                 950                 955                 960

Gly Asp Thr Leu Val Asn Arg Ile Glu Leu Lys Gly Ile Asp Phe Lys
                965                 970                 975

Glu Asp Gly Asn Ile Leu Gly His Lys Leu Glu Tyr Asn Phe Asn Ser
            980                 985                 990

His Asn Val Tyr Ile Thr Ala Asp  Lys Gln Lys Asn Gly  Ile Lys Ala
        995                 1000                1005

Asn Phe  Lys Ile Arg His Asn  Val Glu Asp Gly Ser  Val Gln Leu
    1010                1015                1020

Ala Asp  His Tyr Gln Gln Asn  Thr Pro Ile Gly Asp  Gly Pro Val
    1025                1030                1035

Leu Leu  Pro Asp Asn His Tyr  Leu Ser Thr Gln Ser  Lys Leu Ser
    1040                1045                1050

Lys Asp  Pro Asn Glu Lys Arg  Asp His Met Val Leu  Leu Glu Phe
    1055                1060                1065

Val Thr  Ala Ala Gly Ile Thr  His Gly Met Asp Glu  Leu Tyr Lys
    1070                1075                1080

Gly Ser  Ala Ser Thr Leu Val  His Asn Gly Thr Ser  Ala Arg Ala
    1085                1090                1095

Thr Thr  Thr Pro Ala Ser Lys  Ser Thr Pro Phe Ser  Ile Pro Ser
    1100                1105                1110

His His  Ser Asp Thr Pro Thr  Thr Leu Ala Ser His  Ser Thr Lys
    1115                1120                1125

Thr Asp  Ala Ser Ser Thr His  His Ser Ser Val Pro  Pro Leu Thr
    1130                1135                1140

Ser Ser  Asn His Ser Thr Ser  Pro Gln Leu Ser Thr  Gly Val Ser
    1145                1150                1155

Phe Phe  Phe Leu Ser Phe His  Ile Ser Asn Leu Gln  Phe Asn Ser
    1160                1165                1170

Ser Leu  Glu Asp Pro Ser Thr  Asp Tyr Tyr Gln Glu  Leu Gln Arg
    1175                1180                1185

Asp Ile  Ser Glu Met Phe Leu  Gln Ile Tyr Lys Gln  Gly Gly Phe
    1190                1195                1200

Leu Gly  Leu Ser Asn Ile Lys  Phe Arg Pro Gly Ser  Val Val Val
    1205                1210                1215

Gln Leu  Thr Leu Ala Phe Arg  Glu Gly Thr Ile Asn  Val His Asp
    1220                1225                1230

Val Glu  Thr Gln Phe Asn Gln  Tyr Lys Thr Glu Ala  Ala Ser Arg
    1235                1240                1245

Tyr Asn  Leu Thr Ile Ser Asp  Val Ser Val Ser Asp  Val Pro Phe
    1250                1255                1260

Pro Phe  Ser Ala Gln Ser Gly  Ala Gly Val Pro Gly  Trp Gly Ile
    1265                1270                1275
```

Ala Leu Leu Val Leu Val Cys Val Leu Val Ala Leu Ala Ile Val
1280 1285 1290

Tyr Leu Ile Ala Leu Ala Val Cys Gln Cys Arg Arg Lys
1295 1300 1305

<210> SEQ ID NO 49
<211> LENGTH: 42
<212> TYPE: PRT
<213> ORGANISM: artificial sequence
<220> FEATURE:
<223> OTHER INFORMATION: Synthetic transmembrane domain

<400> SEQUENCE: 49

Ala Ser Gly Ile Leu Tyr Trp Arg Asn Pro Thr Glu Ser Asp Ser Ile
1 5 10 15

Val Leu Ala Ile Ile Val Pro Ser Leu Leu Leu Leu Cys Leu Ala
20 25 30

Leu Leu Trp Tyr Met Arg Arg Arg Ser Met
35 40

<210> SEQ ID NO 50
<211> LENGTH: 2692
<212> TYPE: DNA
<213> ORGANISM: artificial sequence
<220> FEATURE:
<223> OTHER INFORMATION: cDNA

<400> SEQUENCE: 50
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcccggat acgcgacccg 180
ccccagggtc aacagcgccc ccagcccacg gcgttacatc tgcacctgac actagacctg 240
cgccaggatc aacagctcca ccggctcacg gggtcaccag tgcccccgac actcgaccag 300
ctccggggtc taccgctccc ccggctcatg gtgtcactag cgcgcctgac acacgcccgg 360
caccagggag tacggcccct cctgcgcacg gcgtaacttc agccccagat actcgacctg 420
ctccgggctc aacagccccg cctgcacatg gagttacatc agcccctgat actagaccgg 480
ctccaggttc aactgctccg ccagcacatg gtgtaacgtc tgcgcccgat actcgcccag 540
cacctgggtc cacagctccc cctgcgcatg gagtaacatc agcacctgat accagacctg 600
ccccgggcag cactgcaccc ccagcacatg gcgtaacatc agcaccagat actcgccccg 660
ctcctggttc cacggctccc cccgcgcatg gcgttacttc agctccagat acacggccgg 720
cacccggcag tacggctcca cccgcacatg gagtaacgag tgctccggac actcggcctg 780
ctccaggaag taccgcacct ccggcccatg gcgtgacaag tgctcccgac accagaccag 840
cgcctggttc aacagcaccg ccagctcatg gtgtaacctc agctcccgat actagacccg 900
cgccaggttc caccgctcca cctgcacacg gggtgacgag cgcacctgat acgcgcccgg 960
caccgggaag cacagcgcct cccgctcacg gagtcactag cgccccggat acaagacccg 1020
cacctggatc tacagctcct ccagctcacg gcgtcacgag tgcacccgat acacgaccgg 1080
ccccaggctc tacagcccca ccagcacatg gagtcacgag tgcacctgat actaggcccg 1140
ctccgggttc cacagcacct cctgcacatg gtgttacatc cgctcctgat acgagacccg 1200
ctccaggctc tactgcccca ccggcacacg gcgtgaccag tgctccagat acccggccag 1260
ctcctgggag tactgcgcct ccagctcatg gcgtcactag tgcacctgat acaagaccag 1320

```
cccccggttc cactgctcca ccagcccatg gtgtaacaag tgcaccggac acaaggccag   1380

cccctggtag tactgctcct cctgctcacg gtgttactag tgctcctgac accagacctg   1440

cccctggaag tactgcaccg cctgctcatg gagtcacatc agctccggat actcggccgg   1500

ctccgggatc aaccgctcct ccggctcatg gagtaacctc cgcaccggat actaggcctg   1560

caccggggag tacagcacca cctgctcatg gtgtgactag cgctcctgac actcgccccg   1620

ctcccggtag cactgccccc cctgcacatg gggtgacttc agctcctgat actcggcctg   1680

cacccggaag cacagccccc ccagctcatg gggtcacaag cgctccagat actaggccag   1740

cgccgggaag tacagcccct ccagcgcacg gtgtaacttc cgcgccagac acacgccctg   1800

ctcccggatc aacggcacct ccagcacacg gtgtgacgtc cgcacccgac acaagaccgg   1860

cacctggttc tactgcacct cccgcgcacg gagttacttc agcaccagat acaagacctg   1920

ctcctggctc aactgcccct ccggcgcatg gtgtaactag tgcgcctgat acacgcccag   1980

caccgggtag tacggcacca ccagctcatg gagttacgtc agctccagat acgcgccctg   2040

caccaggcag tacagctccg ccggcccacg gagtaactag cgcaccagat accaggccag   2100

cacccggtag taccgcgcct cctgcccatg gagtaacttc cgcccccgat acccgacctg   2160

cacctggcag taccgcccct cccgcccacg gggtaaccag tgcaccagac acgcggcccg   2220

caccaggatc tactgctccc ccagcgcatg gggtaacttc tgcaccagat acgaggcctg   2280

ccccaggtag tacagcgcca cctgcccacg gtgtcacctc cgctcctgat acaaggcctg   2340

cgcctggatc aactgcacca ccggcgcacg gggttacaag tgcccctgac acgagaccag   2400

caccaggttc tacggcgcct ccggcacatg gagtgactag tgccccagac actaggccgg   2460

ctcctggatc aaccgcacca cccgctcatg gagtgacatc agcgccagat actagaccag   2520

ctcccgggtc aactgcgccg cccgcccatg gggttacttc tgctccagac actcgcccag   2580

ccccaggatc aacggctcct cccgcacacg gagtgacctc tgctcctgat accaggccag   2640

ctccagggtc tacagcaccc cctgctcatg gggtaacatc tgccgcctca gg           2692
```

```
<210> SEQ ID NO 51
<211> LENGTH: 1432
<212> TYPE: DNA
<213> ORGANISM: artificial sequence
<220> FEATURE:
<223> OTHER INFORMATION: cDNA

<400> SEQUENCE: 51

tgtacatgga catggtcgct gtgagtatga ccagcagcgt actctccagc cacagccccg     60

gttcaggctc ctccaccact cagggacagg atgtcactct ggccccggcc acggaaccag    120

cttcaggttc agctgccacc tggggacagg atgtcacctc ggtcccagac actcggcctg    180

caccgggatc aaccgcccca ccggctcatg gtgtaactag tgcgcctgat accagaccag    240

caccagggag tactgcacct cctgctcatg gggttactag tgccccccgat acgcgacctg    300

ctcctggaag cacagcaccg ccggctcacg gcgtaacgag tgctcctgac acaaggcccg    360

ctccagggtc aactgcacca cctgcacacg gagtgacatc agcgccagat acgagacctg    420

caccaggaag tacagcgccg ccagcccacg gagtaacttc agccccggac actaggccag    480

cacctggttc aacggcgcct ccagcccatg gagtaacatc cgctcccgat actcgtcctg    540

ctccgggttc cacagctcct cccgcacatg gggtgactag tgctccagat actcgcccag    600

cacccggtag taccgctcct cctgcacatg gcgtcactag tgcaccagac acgcgtccgg    660
```

-continued

```
ctcctgggtc tacagctcca ccagctcacg gagttaccag tgcacctgac actagacctg    720

cgcccggttc gacggctccg cccgcccatg gggtaacgtc tgcgccggat acacgccctg    780

cacctggatc taccgcacct ccggcccatg gtgtcacgag cgcacctgat acgaggcctg    840

ctccaggtag tactgctccc cccgctcatg gagttactag cgctcctgat actcgaccgg    900

cacctggcag cactgctcct ccagcacatg gtgttacatc ggctccagac acacgtcccg    960

cgccaggatc gactgctcca cccgctcacg gggtcacatc tgcacccgat acacggccag   1020

ctcccggttc cactgccccg cctgcccatg gcgttacttc ggcaccagat acccgacccg   1080

caccaggcag tacagcacct ccagcgcatg gtgtgacaag cgcccctgat acacgaccag   1140

ctccaggctc aacagcacca ccagcacacg gtgtaacctc agctccggat acccgtccag   1200

ctcctggtag tacagcccct cctgcgcacg gagtcacaag tgctcccgac acaagaccag   1260

ccccaggttc tactgcgcca cctgctcacg gtgttacctc tgccccagat acaagacctg   1320

cccctggctc tacggcaccc ccggcacatg gagtcacttc cgcaccggat actagaccag   1380

cgcctgggag tacggccccc ccagctcatg gcgtgacttc tgctgcctca gg           1432
```

```
<210> SEQ ID NO 52
<211> LENGTH: 772
<212> TYPE: DNA
<213> ORGANISM: artificial sequence
<220> FEATURE:
<223> OTHER INFORMATION: cDNA

<400> SEQUENCE: 52

tgtacatgga catggtcgct gtgagtatga ccagcagcgt actctccagc cacagccccg     60

gttcaggctc ctccaccact cagggacagg atgtcactct ggccccggcc acggaaccag    120

cttcaggttc agctgccacc tggggacagg atgtcacctc ggtcccagat acaagaccgg    180

ccccaggatc tacggctcct ccggctcatg gagtcacttc tgctccagac acaaggcccg    240

cgccgggttc tacagcaccg cctgctcatg gtgttactag cgcacccgat acgagacctg    300

ctccgggatc aacggcacct cctgcccacg gggtaacatc tgcaccggac actcgccctg    360

cgcccggttc aaccgctcca cccgcacacg gagtgacaag cgctcctgac actagaccag    420

caccaggttc tacagcccca ccagcccatg gagttaccag tgcaccagat actaggccag    480

ctccaggtag tactgcaccc ccagctcatg ggttacatc agctcccgac acgcgaccag     540

ctcctggaag cactgcccct ccagctcacg gtgtgacctc agcacctgat acacgccctg    600

cacctggctc tactgctccc cccgctcatg gcgtaactag tgccccggat actcgacccg    660

cccctggttc cacagctccg ccagcacatg gtgtaacaag tgctcctgat acccgaccag    720

cgcctggaag taccgcacca cctgcacatg gagtaacttc agccgcctca gg            772
```

```
<210> SEQ ID NO 53
<211> LENGTH: 1432
<212> TYPE: DNA
<213> ORGANISM: artificial sequence
<220> FEATURE:
<223> OTHER INFORMATION: cDNA

<400> SEQUENCE: 53

tgtacatgga catggtcgct gtgagtatga ccagcagcgt actctccagc cacagccccg     60

gttcaggctc ctccaccact cagggacagg atgtcactct ggccccggcc acggaaccag    120

cttcaggttc agctgccacc tggggacagg atgtcacctc ggtcccagat accagacctg    180

cgcctggagc cacagctcct cctgcccatg gcgtcacaag tgcccctgac acacgcccag    240
```

ctcccggggc tacagcccca cctgcacatg gtgttactag tgcaccagac accagaccgg 300
ctccgggagc cacggcaccc cccgctcatg gtgtcacttc cgcaccggat acgaggccag 360
cacctggggc cactgcgccg ccggcacatg ggtgactag tgcgccagat actcgccctg 420
ctccaggggc tactgcccct ccagctcatg gcgtaacctc agcgcctgat acccgaccag 480
cgccaggtgc cactgcaccg ccagcccatg ggtcactag tgctcctgac actagacctg 540
cacctggagc tacagcacct ccagcgcatg gtgtgacaag cgccccagac acgagaccag 600
cccccggtgc caccgctcct cccgcacatg gagttactag cgctccggac acaagaccgg 660
caccaggtgc gactgcacca ccggctcatg gagtaacttc agcaccagat acacggcctg 720
ctcccggcgc tacagctcca ccagcacatg gcgttacctc cgcacctgac acgaggcccg 780
ctccaggagc cactgctccc cctgcacacg gtgttacgtc agctccagat acgcggccag 840
ctccgggcgc aacagctccc ccggctcacg gtgtaaccag tgctcccgac acaaggcctg 900
cacccggagc aaccgcacct ccggcccatg gtgtaacaag tgcacctgat actaggcccg 960
cgcctggtgc tactgctcca cctgctcacg gcgtgacatc agcccctgat acgagacctg 1020
ccccaggggc aactgcacct cctgctcatg gggtaactag tgcccccgat acaagaccag 1080
caccgggagc gaccgccccc ccagcacacg gagtaacgag cgcacccgat actcgacctg 1140
caccaggagc gacggctcca cccgctcacg gagtcacgag tgctccagac actcgacctg 1200
ctcctggcgc gacagcacca ccagctcacg gggttactag tgctcctgat acacgacccg 1260
caccaggggc gactgctcct ccagcccacg gagttacatc tgccccggat acaaggccag 1320
cacccggtgc aactgctccg cccgcccatg gagtcacaag tgctccggat actagaccag 1380
ctcctggggc tacggcgcct cctgcgcacg gagtgacttc tgctgcctca gg 1432

<210> SEQ ID NO 54
<211> LENGTH: 1432
<212> TYPE: DNA
<213> ORGANISM: artificial sequence
<220> FEATURE:
<223> OTHER INFORMATION: cDNA

<400> SEQUENCE: 54
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcccagat gcaaggcctg 180
ccccgggagc gacagcacca ccagcacatg gagtgacggc cgccccagac gctcgaccgg 240
caccaggagc aactgctcct cccgcacatg gggtcactgc ggcccctgat gcgaggccgg 300
cacctggagc tactgctcca ccggcccatg gtgtcactgc agccccggat gctagaccgg 360
ctccgggcgc aactgcgccg ccagcccatg gagttactgc tgcgccagat gcgcggcctg 420
ccccaggtgc tacagccccc cctgcccatg gcgtaacagc tgcccccgat gctcgccctg 480
caccgggagc aacggcgcct ccagcgcacg gagtaacggc agcaccagat gctcggccag 540
caccgggggc tacagctcca cctgctcacg gtgtaactgc agcgcctgat gcacgaccag 600
cccctggagc aacagctccg cctgcacacg gagtgactgc tgcacctgat gctaggccag 660
ccccaggggc gactgcacct ccagcacacg gtgttacagc tgctccagac gcacgcccag 720
cacccggtgc cacagctcct cctgcgcatg gtgtgacagc tgcaccagac gcccgacccg 780
cgccaggagc cacggctcca ccagctcacg gcgtgaccgc ggctcctgac gctaggccag 840
ctcctggagc caccgctcct ccagctcatg gcgttacagc agctcccgac gcaagacccg 900
ctcctggggc cactgctccc cccgctcacg gggtaacagc cgctccggat gcaagacctg 960
cccctggtgc tactgcacca cccgcccatg gggttactgc agctccggac gctagacctg 1020
ctccgggagc tacagcgccc ccagcccacg gagtcacagc agcacctgac gcgagaccag 1080
cgccaggtgc aactgcccct cctgcacatg gtgttactgc cgcaccggat gccagacctg 1140
cacccggagc tacggccccg ccggctcatg gggtaactgc tgctcctgat gcccgacccg 1200
ctccaggcgc gaccgcacct cctgctcatg gagtaacagc ggcacccgat gcacggccgg 1260
ctcccggcgc tacagcacct ccggcacatg gcgtcaccgc agctccagat gccaggcccg 1320
caccaggtgc gacggcaccg cccgctcatg gtgtaaccgc tgctcccgat gcgagacctg 1380
cgcctggtgc aacagcaccc ccggctcacg gagttacggc tgctgcctca gg 1432

<210> SEQ ID NO 55
<211> LENGTH: 652
<212> TYPE: DNA
<213> ORGANISM: artificial sequence
<220> FEATURE:
<223> OTHER INFORMATION: Recounted mucin consensus

<400> SEQUENCE: 55
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcaaggaa cctgcaccta 180
caaccccgaa ggagcccgca ccgaccaccc caaaagaacc tgcgccgaca actccaaagg 240
agccagctcc aacgacgcca aaggaaccag cacctacgac ccccaaggaa cccgccccga 300
cgactccgaa ggagcctgca ccaacaactc ctaaagaacc agcgcctact acgcctaaag 360
aacctgctcc tactacacca aaagagccag cacccacgac accgaaagaa cctgccccta 420
ctacccctaa agaacccgct cctaccacac caaaggaacc ggctcccact actcccaaag 480
aaccagcccc aactacacct aaagaaccgg cccccaccac tcctaaagag ccggcgccaa 540
ctactccaaa agaaccagct cctacaactc ccaaggagcc ggcacctact actccgaaag 600
agcccgcgcc cacaacaccc aaagagcctg ctccgactac tcctgcctca gg 652

<210> SEQ ID NO 56
<211> LENGTH: 1012
<212> TYPE: DNA
<213> ORGANISM: artificial sequence
<220> FEATURE:
<223> OTHER INFORMATION: Recombinant lubricin sequence

<400> SEQUENCE: 56
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcgatgca gctactccag 180
ctccggacgc cgcaacaccc gctccagacg ccgccacccc agctccagat gctgctacac 240
ctgcacctga tgccgcaact cccgcgccgg atgccgcgac tccagcaccg gacgctgcga 300
cgccagcccc tgatgctgca acaccggctc ctgatgctgc gactcctgcg ccagatgcag 360
ctacaccagc cccggatgct gcaacgcctg ctcctgacgc agctactccg gcccccgacg 420
ctgctacccc ggcgcctgat gctgctactc ccgctcctga tgcggccact ccagccccag 480
acgcagcaac cccagccccc gatgctgcta cgcctgcacc cgacgcggcc acacctgcgc 540

```
cggacgcagc gacacctgcc cctgacgctg ccacgcccgc acctgatgca gctacgccag    600

ctcccgatgc ggcaacacct gctccagatg ccgccactcc tgctccggat gcggcgacac    660

cagcgcctga cgccgctacg ccggcacctg atgctgccac tccggctcca gatgcagcga    720

ccccagcgcc agacgcggca actccagcgc ccgatgcagc taccccagca ccagatgctg    780

caacccctgc accggatgca gcaacgccag cacctgacgc ggctactcct gcaccagatg    840

cagcaactcc tgccccggac gcggcgactc ccgcaccaga cgctgcaact ccggcaccag    900

atgcggctac ccccgctccc gacgcagcca ctcccgcccc agatgcagcc acaccagctc    960

ctgatgcagc aacaccagca cccgatgccg ctacccctgc tcccgcctca gg           1012
```

```
<210> SEQ ID NO 57
<211> LENGTH: 1852
<212> TYPE: DNA
<213> ORGANISM: artificial sequence
<220> FEATURE:
<223> OTHER INFORMATION: Recombinant lubricin sequence

<400> SEQUENCE: 57

tgtacatgga catggtcgct gtgagtatga ccagcagcgt actctccagc cacagccccg     60

gttcaggctc ctccaccact cagggacagg atgtcactct ggccccggcc acggaaccag    120

cttcaggttc agctgccacc tggggacagg atgtcacctc ggtcgatgca gctactccag    180

ctccggacgc cgcaacaccc gctccagacg ccgccacccc agctccagat gctgctacac    240

ctgcacctga tgccgcaact cccgcgccgg atgccgcgac tccagcaccg gacgctgcga    300

cgccagcccc tgatgctgca acaccggctc ctgatgctgc gactcctgcg ccagatgcag    360

ctacaccagc ccggatgct gcaacgcctg ctcctgacgc agctactccg gcccccgacg    420

ctgctacccc ggcgcctgat gctgctactc ccgctcctga tgcggccact ccagccccag    480

acgcagcaac cccagccccc gatgctgcta cgcctgcacc cgacgcggcc acacctgcgc    540

cggacgcagc gacacctgcc cctgacgctg ccacgcccgc acctgatgca gctacgccag    600

ctcccgatgc ggcaacacct gctccagatg ccgccactcc tgctccggat gcggcgacac    660

cagcgcctga cgccgctacg ccggcacctg atgctgccac tccggctcca gatgcagcga    720

ccccagcgcc agacgcggca actccagcgc ccgatgcagc taccccagca ccagatgctg    780

caacccctgc accggatgca gcaacgccag cacctgacgc ggctactcct gcaccagatg    840

cagcaactcc tgccccggac gcggcgactc ccgcaccaga cgctgcaact ccggcaccag    900

atgcggctac ccccgctccc gacgcagcca ctcccgcccc agatgcagcc acaccagctc    960

ctgatgcagc aacaccagca cccgatgccg ctacccctgc tcccgatgca gctactccag   1020

ctccggacgc cgcaacaccc gctccagacg ccgccacccc agctccagat gctgctacac   1080

ctgcacctga tgccgcaact cccgcgccgg atgccgcgac tccagcaccg gacgctgcga   1140

cgccagcccc tgatgctgca acaccggctc ctgatgctgc gactcctgcg ccagatgcag   1200

ctacaccagc ccggatgct gcaacgcctg ctcctgacgc agctactccg gcccccgacg   1260

ctgctacccc ggcgcctgat gctgctactc ccgctcctga tgcggccact ccagccccag   1320

acgcagcaac cccagccccc gatgctgcta cgcctgcacc cgacgcggcc acacctgcgc   1380

cggacgcagc gacacctgcc cctgacgctg ccacgcccgc acctgatgca gctacgccag   1440

ctcccgatgc ggcaacacct gctccagatg ccgccactcc tgctccggat gcggcgacac   1500

cagcgcctga cgccgctacg ccggcacctg atgctgccac tccggctcca gatgcagcga   1560
```

ccccagcgcc agacgcggca actccagcgc ccgatgcagc taccccagca ccagatgctg 1620
caacccctgc accggatgca gcaacgccag cacctgacgc ggctactcct gcaccagatg 1680
cagcaactcc tgccccggac gcggcgactc ccgcaccaga cgctgcaact ccggcaccag 1740
atgcggctac cccgctccc gacgcagcca ctcccgcccc agatgcagcc acaccagctc 1800
ctgatgcagc aacaccagca cccgatgccg ctacccctgc tcccgcctca gg 1852

<210> SEQ ID NO 58
<211> LENGTH: 1132
<212> TYPE: DNA
<213> ORGANISM: artificial sequence
<220> FEATURE:
<223> OTHER INFORMATION: Recombinant lubricin sequence

<400> SEQUENCE: 58
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcgatgca gctaccccgg 180
ctccacccga tgcggcaaca ccagcccctc ccgatgcagc aacacctgct ccccccgatg 240
ctgctacccc tgctccgcct gatgctgcaa ctccagctcc gcccgatgcc gctacacctg 300
ccccccctga cgccgccacg cccgctcctc cggatgctgc aaccccagca cccccagacg 360
ccgctacccc agctccacca gatgctgcta cacccgcacc acctgatgcc gcaacaccgg 420
cgcctcctga tgctgctact ccagccccac ctgatgcagc aactcctgcg ccaccagacg 480
ctgccacacc tgcaccacca gatgcagcca caccagcacc gccagacgca gcaacgccgg 540
ctccgccaga tgcagcgaca ccagcgccac ctgacgcagc gactccagca ccaccggatg 600
cggctacccc cgctccgccg gacgcggcga ctcctgcccc tcctgacgcg gcaactccgg 660
cccctccaga tgcggcgacc ccagccccgc cggatgccgc gactccggct cccccggacg 720
ctgcaacacc cgctccacct gatgctgcca ctcccgcgcc tccagatgct gcaacgccag 780
ctccccctga tgctgcgacg cctgctcctc cagatgcagc tacaccggct cctcctgatg 840
cagctacgcc tgcaccgcct gacgctgcta cgccagcacc tcccgacgca gccactcctg 900
cacctcctga tgcggccact ccagcgcccc cggatgcagc tactcctgct ccaccggacg 960
ccgcaactcc cgcccctccg gacgcagcta ctcccgctcc cccagatgca gcaacccctg 1020
caccccccga cgcggccacc cctgccccac cagatgccgc cactccggca ccacccgacg 1080
ctgcgactcc cgcacctcca gacgcggcta caccagctcc tcccgcctca gg 1132

<210> SEQ ID NO 59
<211> LENGTH: 2092
<212> TYPE: DNA
<213> ORGANISM: artificial sequence
<220> FEATURE:
<223> OTHER INFORMATION: Recombinant lubricin sequence

<400> SEQUENCE: 59
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcgatgca gctaccccgg 180
ctccacccga tgcggcaaca ccagcccctc ccgatgcagc aacacctgct ccccccgatg 240
ctgctacccc tgctccgcct gatgctgcaa ctccagctcc gcccgatgcc gctacacctg 300
ccccccctga cgccgccacg cccgctcctc cggatgctgc aaccccagca cccccagacg 360
ccgctacccc agctccacca gatgctgcta cacccgcacc acctgatgcc gcaacaccgg 420
cgcctcctga tgctgctact ccagccccac ctgatgcagc aactcctgcg ccaccagacg 480
ctgccacacc tgcaccacca gatgcagcca caccagcacc gccagacgca gcaacgccgg 540
ctccgccaga tgcagcgaca ccagcgccac ctgacgcagc gactccagca ccaccggatg 600
cggctacccc cgctccgccg gacgcggcga ctcctgcccc tcctgacgcg gcaactccgg 660
cccctccaga tgcggcgacc ccagccccgc cggatgccgc gactccggct cccccggacg 720
ctgcaacacc cgctccacct gatgctgcca ctcccgcgcc tccagatgct gcaacgccag 780
ctccccctga tgctgcgacg cctgctcctc cagatgcagc tacaccggct cctcctgatg 840
cagctacgcc tgcaccgcct gacgctgcta cgccagcacc tcccgacgca gccactcctg 900
cacctcctga tgcggccact ccagcgcccc cggatgcagc tactcctgct ccaccggacg 960
ccgcaactcc cgcccctccg gacgcagcta ctcccgctcc cccagatgca gcaacccctg 1020
caccccccga cgcggccacc cctgccccac cagatgccgc cactccggca ccacccgacg 1080
ctgcgactcc cgcacctcca gacgcggcta caccagctcc tcccgatgca gctaccccgg 1140
ctccacccga tgcggcaaca ccagcccctc ccgatgcagc aacacctgct ccccccgatg 1200
ctgctacccc tgctccgcct gatgctgcaa ctccagctcc gcccgatgcc gctacacctg 1260
ccccccctga cgccgccacg cccgctcctc cggatgctgc aaccccagca cccccagacg 1320
ccgctacccc agctccacca gatgctgcta cacccgcacc acctgatgcc gcaacaccgg 1380
cgcctcctga tgctgctact ccagccccac ctgatgcagc aactcctgcg ccaccagacg 1440
ctgccacacc tgcaccacca gatgcagcca caccagcacc gccagacgca gcaacgccgg 1500
ctccgccaga tgcagcgaca ccagcgccac ctgacgcagc gactccagca ccaccggatg 1560
cggctacccc cgctccgccg gacgcggcga ctcctgcccc tcctgacgcg gcaactccgg 1620
cccctccaga tgcggcgacc ccagccccgc cggatgccgc gactccggct cccccggacg 1680
ctgcaacacc cgctccacct gatgctgcca ctcccgcgcc tccagatgct gcaacgccag 1740
ctccccctga tgctgcgacg cctgctcctc cagatgcagc tacaccggct cctcctgatg 1800
cagctacgcc tgcaccgcct gacgctgcta cgccagcacc tcccgacgca gccactcctg 1860
cacctcctga tgcggccact ccagcgcccc cggatgcagc tactcctgct ccaccggacg 1920
ccgcaactcc cgcccctccg gacgcagcta ctcccgctcc cccagatgca gcaacccctg 1980
caccccccga cgcggccacc cctgccccac cagatgccgc cactccggca ccacccgacg 2040
ctgcgactcc cgcacctcca gacgcggcta caccagctcc tcccgcctca gg 2092

<210> SEQ ID NO 60
<211> LENGTH: 1252
<212> TYPE: DNA
<213> ORGANISM: artificial sequence
<220> FEATURE:
<223> OTHER INFORMATION: Recombinant mucin sequence

<400> SEQUENCE: 60
tgtacatgga catggtcgct gtgagtatga ccagcagcgt actctccagc cacagccccg 60
gttcaggctc ctccaccact cagggacagg atgtcactct ggccccggcc acggaaccag 120
cttcaggttc agctgccacc tggggacagg atgtcacctc ggtcccacct gcatctacca 180
gtgccccggg tccacctgcc tctactagcg ccccaggacc tccggcaagt acatcagcgc 240
caggaccccc tgcttccact agtgcacccg gtcccccggc atctacgtct gcccctggcc 300

-continued

```
cacctgcttc aacttcagca ccaggaccac ccgcaagcac atcagcccca ggccctcccg    360

cctctacaag cgctccgggg cctccggcct ctacctcagc tccaggccca ccagccagca    420

cttcagcccc tggtccaccc gcttcaacct cagcacccgg acctcctgcc tcaacttccg    480

ctcccggtcc accagctagt acctctgctc cgggccctcc ggcgagcacg tcagcaccgg    540

gaccacctgc gagtacaagt gcacctggcc cgcccgctag cacaagtgcc cccggtcctc    600

cagcatccac tagtgcacca gggcctccag ccagcactag tgcgccgggt ccccccgcga    660

gtacgtcagc tccgggacct ccagcttcta catctgctcc tgggccccct gcatcaacta    720

gtgcccctgg accaccggct agtacgtcag ctcctggtcc ccctgccagt actagcgctc    780

cagggccacc agcaagtacg agcgcaccag gccccccagc ctctacgagt gcaccgggtc    840

ctcctgcaag tacctccgct ccaggtcctc cggcttcaac gtccgcacct ggacctcccg    900

cgtccacatc agctcccggc cctccagcga gtacttctgc tcccggacca ccagcgtcca    960

catctgcgcc tggtcctccc gctagtacct ctgcacctgg tccgccggcc agtacaagtg   1020

ctcccgggcc tcccgcatca acatctgcac caggtccacc ggcgtctact agtgccccag   1080

gtcccccagc ttcaacatca gcacctgggc cgcctgctag tacatccgct cctggacccc   1140

cagcaagtac ttccgcccct gggcctcctg cttctacttc agctcctggc cctcctgcgt   1200

caactagtgc tccaggaccg ccagctagta cttccgcgcc cggtgcctca gg           1252
```

```
<210> SEQ ID NO 61
<211> LENGTH: 751
<212> TYPE: DNA
<213> ORGANISM: artificial sequence
<220> FEATURE:
<223> OTHER INFORMATION: cDNA

<400> SEQUENCE: 61

cctcaggctc tgcatcaggc tcagctatgg tgtccaaggg cgaggagctg ttcaccgggg     60

tggtgcccat cctggtcgag ctggacggcg acgtaaacgg ccacaagttc tccgtgcggg    120

gcgagggcga gggcgatgcc accaacggca agctgaccct gaagttcatc agcaccaccg    180

gcaagctgcc cgtgccctgg cccaccctcg tgaccaccct gacctacggc gtgcagagct    240

tctcccgcta ccccgaccac atgaagcgcc acgacttctt caagagcgcc atgcccgaag    300

gctacgtcca ggagcgcacc atctccttca aggacgacgg cacctacaag acccgcgccg    360

aggtgaagtt cgagggcgac accctggtga accgcatcga gctgaagggc atcgacttca    420

aggaggacgg caacatcctg gggcacaagc tggagtacaa cttcaactcc cacaacgtct    480

atatcaccgc cgacaagcag aagaacggca tcaaggccaa cttcaagatc cgccacaacg    540

tggaggacgg ctccgtgcag ctcgccgacc actaccagca gaacaccccc atcggcgacg    600

gccccgtgct gctgcccgac aaccactacc tgtccaccca gtccaagctg tccaaagacc    660

ccaacgagaa gcgcgatcac atggtccttc tggaattcgt gaccgccgcc gggatcactc    720

acggcatgga cgagctgtat aagggctcag c                                   751


<210> SEQ ID NO 62
<211> LENGTH: 678
<212> TYPE: DNA
<213> ORGANISM: artificial sequence
<220> FEATURE:
<223> OTHER INFORMATION: Recombinant membrane anchor cDNA

<400> SEQUENCE: 62

gctcagcttc tactctggtg cacaacggca cctctgccag ggctaccaca accccagcca     60
```

gcaagagcac tccattctca attcccagcc accactctga tactcctacc acccttgcca 120
gccatagcac caagactgat gccagtagca ctcaccatag ctcggtacct cctctcacct 180
cctccaatca cagcacttct ccccagttgt ctactggggt ctctttcttt ttcctgtctt 240
ttcacatttc aaacctccag tttaattcct ctctggaaga tcccagcacc gactactacc 300
aagagctgca gagagacatt tctgaaatgt ttttgcagat ttataaacaa gggggttttc 360
tgggcctctc caatattaag ttcaggccag gatctgtggt ggtacaattg actctggcct 420
tccgagaagg taccatcaat gtccacgacg tggagacaca gttcaatcag tataaaacgg 480
aagcagcctc tcgatataac ctgacgatct cagacgtcag cgtgagtgat gtgccatttc 540
ctttctctgc ccagtctggg gctggggtgc caggctgggg catcgcgctg ctggtgctgg 600
tctgtgttct ggttgcgctg gccattgtct atctcattgc cttggctgtc tgtcagtgcc 660
gccgaaagta gggaattc 678

<210> SEQ ID NO 63
<211> LENGTH: 134
<212> TYPE: DNA
<213> ORGANISM: artificial sequence
<220> FEATURE:
<223> OTHER INFORMATION: Transmembrane cDNA

<400> SEQUENCE: 63
cctcaggcat actttattgg cgaaacccaa cggaaagtga tagcatcgtt ttggcaatta 60
tcgtccccag tctgctcctc ttgctctgcc tggctttgtt gtggtacatg cgccgacgaa 120
gtatgtagga attc 134

<210> SEQ ID NO 64
<211> LENGTH: 231
<212> TYPE: DNA
<213> ORGANISM: artificial sequence
<220> FEATURE:
<223> OTHER INFORMATION: Cytoplasmic motif cDNA

<400> SEQUENCE: 64
tctagatgtc agtgccgccg aaagaactac gggcagctgg acatctttcc agcccgggat 60
acctaccatc ctatgagcga gtaccccacc taccacaccc atgggcgcta tgtgccccct 120
agcagtaccg atcgtagccc ctatgagaag gtttctgcag gtaatggtgg cagcagcctc 180
tcttacacaa acccagcagt ggcagccgct tctgccaact tgtaggaatt c 231

<210> SEQ ID NO 65
<211> LENGTH: 33
<212> TYPE: DNA
<213> ORGANISM: artificial sequence
<220> FEATURE:
<223> OTHER INFORMATION: Cytoplasmic motif cDNA

<400> SEQUENCE: 65
tctagatgtc agtgccgccg aaagtaggaa ttc 33

<210> SEQ ID NO 66
<211> LENGTH: 1404
<212> TYPE: PRT
<213> ORGANISM: Homo sapiens

<400> SEQUENCE: 66

Met Ala Trp Lys Thr Leu Pro Ile Tyr Leu Leu Leu Leu Leu Ser Val
1               5                   10                  15

-continued

```
Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
            100                 105                 110

Pro Pro Ser Ser Lys Lys Ala Pro Pro Pro Ser Gly Ala Ser Gln Thr
        115                 120                 125

Ile Lys Ser Thr Thr Lys Arg Ser Pro Lys Pro Pro Asn Lys Lys Lys
    130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
            180                 185                 190

Glu Leu Gln Lys Lys Leu Lys Val Lys Asp Asn Lys Lys Asn Arg Thr
        195                 200                 205

Lys Lys Lys Pro Thr Pro Lys Pro Pro Val Val Asp Glu Ala Gly Ser
    210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
            260                 265                 270

Glu Thr Ser Leu Thr Val Asn Lys Glu Thr Thr Val Glu Thr Lys Glu
        275                 280                 285

Thr Thr Thr Thr Asn Lys Gln Thr Ser Thr Asp Gly Lys Glu Lys Thr
    290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
        355                 360                 365

Thr Thr Ile Lys Ser Ala Pro Thr Thr Pro Lys Glu Pro Ala Pro Thr
    370                 375                 380

Thr Thr Lys Ser Ala Pro Thr Thr Pro Lys Glu Pro Ala Pro Thr Thr
385                 390                 395                 400

Thr Lys Glu Pro Ala Pro Thr Thr Pro Lys Glu Pro Ala Pro Thr Thr
                405                 410                 415

Thr Lys Glu Pro Ala Pro Thr Thr Thr Lys Ser Ala Pro Thr Thr Pro
            420                 425                 430
```

```
Lys Glu Pro Ala Pro Thr Thr Pro Lys Lys Pro Ala Pro Thr Thr Pro
        435                 440                 445

Lys Glu Pro Ala Pro Thr Thr Pro Lys Glu Pro Thr Pro Thr Thr Pro
    450                 455                 460

Lys Glu Pro Ala Pro Thr Thr Lys Glu Pro Ala Pro Thr Thr Pro Lys
465                 470                 475                 480

Glu Pro Ala Pro Thr Ala Pro Lys Lys Pro Ala Pro Thr Thr Pro Lys
                485                 490                 495

Glu Pro Ala Pro Thr Thr Pro Lys Glu Pro Ala Pro Thr Thr Thr Lys
            500                 505                 510

Glu Pro Ser Pro Thr Thr Pro Lys Glu Pro Ala Pro Thr Thr Thr Lys
        515                 520                 525

Ser Ala Pro Thr Thr Thr Lys Glu Pro Ala Pro Thr Thr Thr Lys Ser
    530                 535                 540

Ala Pro Thr Thr Pro Lys Glu Pro Ser Pro Thr Thr Thr Lys Glu Pro
545                 550                 555                 560

Ala Pro Thr Thr Pro Lys Glu Pro Ala Pro Thr Thr Pro Lys Lys Pro
                565                 570                 575

Ala Pro Thr Thr Pro Lys Glu Pro Ala Pro Thr Thr Pro Lys Glu Pro
            580                 585                 590

Ala Pro Thr Thr Thr Lys Lys Pro Ala Pro Thr Thr Pro Lys Glu Pro
        595                 600                 605

Ala Pro Thr Thr Pro Lys Glu Thr Ala Pro Thr Thr Pro Lys Lys Leu
    610                 615                 620

Thr Pro Thr Thr Pro Glu Lys Leu Ala Pro Thr Thr Pro Glu Lys Pro
625                 630                 635                 640

Ala Pro Thr Thr Pro Glu Glu Leu Ala Pro Thr Thr Pro Glu Glu Pro
                645                 650                 655

Thr Pro Thr Thr Pro Glu Glu Pro Ala Pro Thr Thr Pro Lys Ala Ala
            660                 665                 670

Ala Pro Asn Thr Pro Lys Glu Pro Ala Pro Thr Thr Pro Lys Glu Pro
        675                 680                 685

Ala Pro Thr Thr Pro Lys Glu Pro Ala Pro Thr Thr Pro Lys Glu Thr
    690                 695                 700

Ala Pro Thr Thr Pro Lys Gly Thr Ala Pro Thr Thr Leu Lys Glu Pro
705                 710                 715                 720

Ala Pro Thr Thr Pro Lys Lys Pro Ala Pro Lys Glu Leu Ala Pro Thr
                725                 730                 735

Thr Thr Lys Glu Pro Thr Ser Thr Thr Ser Asp Lys Pro Ala Pro Thr
            740                 745                 750

Thr Pro Lys Gly Thr Ala Pro Thr Thr Pro Lys Glu Pro Ala Pro Thr
        755                 760                 765

Thr Pro Lys Glu Pro Ala Pro Thr Thr Pro Lys Gly Thr Ala Pro Thr
    770                 775                 780

Thr Leu Lys Glu Pro Ala Pro Thr Thr Pro Lys Lys Pro Ala Pro Lys
785                 790                 795                 800

Glu Leu Ala Pro Thr Thr Thr Lys Gly Pro Thr Ser Thr Thr Ser Asp
                805                 810                 815

Lys Pro Ala Pro Thr Thr Pro Lys Glu Thr Ala Pro Thr Thr Pro Lys
            820                 825                 830

Glu Pro Ala Pro Thr Thr Pro Lys Lys Pro Ala Pro Thr Thr Pro Glu
        835                 840                 845

Thr Pro Pro Pro Thr Thr Ser Glu Val Ser Thr Pro Thr Thr Thr Lys
```

```
    850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
            900                 905                 910

Thr Thr Ala Lys Asp Lys Thr Thr Glu Arg Asp Leu Arg Thr Thr Pro
        915                 920                 925

Glu Thr Thr Thr Ala Ala Pro Lys Met Thr Lys Glu Thr Ala Thr Thr
    930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
            980                 985                 990

Thr Thr Thr Glu Ile Met Asn Lys  Pro Glu Glu Thr Ala  Lys Pro Lys
        995                 1000                1005

Asp Arg  Ala Thr Asn Ser Lys  Ala Thr Thr Pro Lys  Pro Gln Lys
    1010                 1015                1020

Pro Thr  Lys Ala Pro Lys Lys  Pro Thr Ser Thr Lys  Lys Pro Lys
    1025                 1030                1035

Thr Met  Pro Arg Val Arg Lys  Pro Lys Thr Thr Pro  Thr Pro Arg
    1040                 1045                1050

Lys Met  Thr Ser Thr Met Pro  Glu Leu Asn Pro Thr  Ser Arg Ile
    1055                 1060                1065

Ala Glu  Ala Met Leu Gln Thr  Thr Thr Arg Pro Asn  Gln Thr Pro
    1070                 1075                1080

Asn Ser  Lys Leu Val Glu Val  Asn Pro Lys Ser Glu  Asp Ala Gly
    1085                 1090                1095

Gly Ala  Glu Gly Glu Thr Pro  His Met Leu Leu Arg  Pro His Val
    1100                 1105                1110

Phe Met  Pro Glu Val Thr Pro  Asp Met Asp Tyr Leu  Pro Arg Val
    1115                 1120                1125

Pro Asn  Gln Gly Ile Ile Ile  Asn Pro Met Leu Ser  Asp Glu Thr
    1130                 1135                1140

Asn Ile  Cys Asn Gly Lys Pro  Val Asp Gly Leu Thr  Thr Leu Arg
    1145                 1150                1155

Asn Gly  Thr Leu Val Ala Phe  Arg Gly His Tyr Phe  Trp Met Leu
    1160                 1165                1170

Ser Pro  Phe Ser Pro Pro Ser  Pro Ala Arg Arg Ile  Thr Glu Val
    1175                 1180                1185

Trp Gly  Ile Pro Ser Pro Ile  Asp Thr Val Phe Thr  Arg Cys Asn
    1190                 1195                1200

Cys Glu  Gly Lys Thr Phe Phe  Phe Lys Asp Ser Gln  Tyr Trp Arg
    1205                 1210                1215

Phe Thr  Asn Asp Ile Lys Asp  Ala Gly Tyr Pro Lys  Pro Ile Phe
    1220                 1225                1230

Lys Gly  Phe Gly Gly Leu Thr  Gly Gln Ile Val Ala  Ala Leu Ser
    1235                 1240                1245

Thr Ala  Lys Tyr Lys Asn Trp  Pro Glu Ser Val Tyr  Phe Phe Lys
    1250                 1255                1260
```

```
Arg Gly Gly Ser Ile Gln Gln Tyr Ile Tyr Lys Gln Glu Pro Val
    1265                1270                1275

Gln Lys Cys Pro Gly Arg Arg Pro Ala Leu Asn Tyr Pro Val Tyr
    1280                1285                1290

Gly Glu Thr Thr Gln Val Arg Arg Arg Arg Phe Glu Arg Ala Ile
    1295                1300                1305

Gly Pro Ser Gln Thr His Thr Ile Arg Ile Gln Tyr Ser Pro Ala
    1310                1315                1320

Arg Leu Ala Tyr Gln Asp Lys Gly Val Leu His Asn Glu Val Lys
    1325                1330                1335

Val Ser Ile Leu Trp Arg Gly Leu Pro Asn Val Val Thr Ser Ala
    1340                1345                1350

Ile Ser Leu Pro Asn Ile Arg Lys Pro Asp Gly Tyr Asp Tyr Tyr
    1355                1360                1365

Ala Phe Ser Lys Asp Gln Tyr Tyr Asn Ile Asp Val Pro Ser Arg
    1370                1375                1380

Thr Ala Arg Ala Ile Thr Thr Arg Ser Gly Gln Thr Leu Ser Lys
    1385                1390                1395

Val Trp Tyr Asn Cys Pro
    1400
```

<210> SEQ ID NO 67
<211> LENGTH: 4107
<212> TYPE: DNA
<213> ORGANISM: artificial sequence
<220> FEATURE:
<223> OTHER INFORMATION: cDNA

<400> SEQUENCE: 67

```
atggagacag acacactcct gctatgggta ctgctgctct gggttccagg ttccactggt      60

gacggctccc aggacctgtc tagctgtgcc ggaagatgtg gcgagggcta cagcagagat     120

gccacctgta actgcgacta caactgccag cactacatgg aatgctgccc cgacttcaag     180

agagtgtgca cagccgagct gagctgcaag ggcagatgct tcgagtcctt cgagaggggc     240

agagagtgcg attgcgacgc ccagtgcaag aaatacgaca agtgctgccc tgactacgag     300

agcttctgtg ccgaggtgca caaccccaca tctccaccta gcagcaagaa ggcccctcca     360

ccttctggcg cctctcagac aatcaagagc accaccaagc ggagccccaa gcctcctaac     420

aagaaaaaga ccaagaaagt gatcgagagc gaggaaatca ccgaggaaca cagcgtgtcc     480

gagaatcaag agagcagctc cagcagcagc tcctccagct ctagctccac catccggaag     540

atcaagtcca gcaagaacag cgccgccaac agagagctgc agaaaaagct gaaagtgaag     600

gacaacaaga agaaccggac caagaagaag cccacaccta agcctccagt ggtggatgag     660

gctggcagcg gactggacaa cggcgacttc aaagtgacca cacctgacac cagcaccaca     720

cagcacaaca aggtgtccac ctctcctaag atcaccaccg ccaagcctat caaccccaga     780

cctagcctgc ctccaaacag cgacacctcc aaagaaacca gcctgaccgt gaacaaagag     840

acaaccgtcg agacaaaaga gactaccacc accaacaagc agactagtac cgacggcaaa     900

gagaaaacca ccagcgccaa agagactcag agcatcgaaa agacctccgc caaggatctg     960

gcccctacct ctaaggtgct ggccaagcca acaccaaagg ccgagacaac cacaaagggc    1020

cctgctctga caacccctaa ggagccagca cccacaacgc cgaaggaacc agcgcccacg    1080

acccctaaag aaccagctcc tacaacgccc aaggaaccgg cgccaacaac gcctaaggaa    1140
```

-continued

```
ccggcaccaa caacacccaa agagcccgcc cccactactc ctaaagaacc ggctccaact   1200
acaccgaagg aacctgcccc gacaacccca aaggaaccag cccctacaac ccctaaagag   1260
ccagcgccaa ccacgcccaa agaacctgcg ccgactaccc cgaaagagcc ggcacccact   1320
acgcccaaag agccggcccc cacaaccccg aaggaaccgg ctccgacgac accaaaggag   1380
cctgcgccca ctacacccaa ggagcctgca ccaaccactc ccaaggagcc agctcccaca   1440
acaccaaagg aacccgcgcc caccacgcca aaagagccag cacctacaac acctaaggaa   1500
cctgctccaa ccaccccaaa ggagcccgca cctacgactc ccaaggaacc cgctccaacg   1560
acgcctaagg agccggcacc taccactcca aaggagccag ccccgactac tccgaaggag   1620
cctgccccaa ctactcccaa agagccagcc cccacgactc ctaaggaacc agcaccaacg   1680
acaccgaaag aacccgctcc cacgacgccg aaagaacctg cccctacgac acccaaagaa   1740
ccagccccaa caactcctaa agagccggct cccactaccc ctaaggagcc agcgcctacg   1800
accccaaaag agcctgcacc gacaacgcca aaggaacctg cacccaccac ccctaaggaa   1860
cccgcaccaa ctaccccaaa agaacctgca cctactactc caaaggaacc ggcccctacc   1920
acccccaagg aacctgcgcc aactacgccg aaagagcccg cgccaacgac tccgaaagaa   1980
ccagcgccga caactccaaa agagcccgct ccgaccacac cgaaagagcc tgctcccacc   2040
acaccaaaag aaccagcacc gaccactcct aaggagcctg ctcctactac gcctaaagaa   2100
cctgctccga ctacacctaa agaacccgcg cctaccacgc ctaaagagcc tgcgcctaca   2160
actcccaaag aacccgcacc gactacgcca aaagaaccgg ccccaacgac cccgaaagaa   2220
ccggcaccga cgactccaaa agaacccgcc ccaaccacac ctaaagagcc cgcacccacg   2280
acacctaagg agcccgctcc taccacaccc aaggaaccag ctccaacaac ccccaaagag   2340
cctgccccca ccactccgaa ggaacccgcc cctactacac caaaagagcc ggcgcctact   2400
acccccaaag aaccggcgcc cacaactccg aaagagccag ctccgacaac accgagcgaa   2460
gtgtctaccc ctacaaccac caaagagcca accaccatcc acaagagccc cgacgagtct   2520
acacctgagc tgtctgccga gcctactcct aaggctctgg aaaacagccc caaagaaccc   2580
ggggtgccca ccacaaaaac accagccgcc acaaagcccg agatgaccac cacagccaag   2640
gacaagacca ccgagcggga cctgagaaca acccctgaaa ccacaaccgc cgctccaaag   2700
atgacaaaag aaaccgccac aaccaccgag aaaacaaccg agagcaagat caccgccacc   2760
acaacacaag tgacctccac caccactcag gacaccacac ctttcaagat cacaaccctc   2820
aagaccacta cactggcccc aaaagtgacg accacaaaga aaaccatcac cacgaccgag   2880
atcatgaaca agcccgagga aaccgctaag cccaaggaca gggccaccaa cagcaaggcc   2940
accacaccaa agccacagaa gcctacaaag gcccctaaga agccaaccag cacaaaaaag   3000
cccaagacca tgcctagagt gcggaagcct aagacaaccc caacacctcg gaagatgacc   3060
agcactatgc ccgagctgaa ccccacctct agaatcgccg aagccatgct gcagaccacc   3120
actagaccca atcagacccc taacagcaag ctggtggaag tgaaccccaa gtccgaagat   3180
gccggcggag ctgaaggcga gacacctcat atgctgctga ggccccacgt gttcatgccc   3240
gaagtgaccc ctgacatgga ctacctgcca agagtgccca accagggcat catcatcaac   3300
cctatgctga gcgacgagac aaacatctgc aacggcaagc ccgtggacgg cctgaccaca   3360
ctgagaaatg gaaccctggt ggctttccgg ggccactact tttggatgct gagccctttc   3420
agccctccat ctcctgccag acggatcaca gaagtgtggg gcatcccttc tccaatcgac   3480
accgtgttca cccggtgcaa ctgcgagggc aagacattct tcttcaagga cagccagtat   3540
```

```
tggcggttca ccaacgacat caaggacgcc ggctatccca agccaatctt caaaggcttc   3600

ggaggcctga ccggccagat tgtggctgct ctgtctaccg ccaagtacaa gaactggccc   3660

gagagcgtgt acttctttaa gagaggcggc tccatccagc agtacatcta caagcaagag   3720

cccgtgcaga agtgccccgg aagaaggcca gctctgaatt accccgtgta cggcgagact   3780

acccaagtgc ggagaagaag attcgagaga gccatcggac ccagccagac acacaccatc   3840

agaatccagt acagccccgc cagactggcc taccaggata agggcgtgct gcacaacgaa   3900

gtgaaagtgt ccatcctgtg gcggggactg cccaatgtgg tcacaagcgc catcagcctg   3960

cctaacatca gaaagcccga cggctacgac tactacgcct ttagcaagga ccagtactac   4020

aacatcgacg tgcccagcag aaccgccaga gccatcacaa caagatccgg ccagacactg   4080

agcaaagtgt ggtacaactg tccttga                                       4107
```

<210> SEQ ID NO 68
<211> LENGTH: 1368
<212> TYPE: PRT
<213> ORGANISM: artificial sequence
<220> FEATURE:
<223> OTHER INFORMATION: Recombinant protein

<400> SEQUENCE: 68

```
Met Glu Thr Asp Thr Leu Leu Leu Trp Val Leu Leu Leu Trp Val Pro
1               5                   10                  15

Gly Ser Thr Gly Asp Gly Ser Gln Asp Leu Ser Ser Cys Ala Gly Arg
            20                  25                  30

Cys Gly Glu Gly Tyr Ser Arg Asp Ala Thr Cys Asn Cys Asp Tyr Asn
        35                  40                  45

Cys Gln His Tyr Met Glu Cys Cys Pro Asp Phe Lys Arg Val Cys Thr
    50                  55                  60

Ala Glu Leu Ser Cys Lys Gly Arg Cys Phe Glu Ser Phe Glu Arg Gly
65                  70                  75                  80

Arg Glu Cys Asp Cys Asp Ala Gln Cys Lys Lys Tyr Asp Lys Cys Cys
                85                  90                  95

Pro Asp Tyr Glu Ser Phe Cys Ala Glu Val His Asn Pro Thr Ser Pro
            100                 105                 110

Pro Ser Ser Lys Lys Ala Pro Pro Pro Ser Gly Ala Ser Gln Thr Ile
        115                 120                 125

Lys Ser Thr Thr Lys Arg Ser Pro Lys Pro Pro Asn Lys Lys Lys Thr
    130                 135                 140

Lys Lys Val Ile Glu Ser Glu Glu Ile Thr Glu Glu His Ser Val Ser
145                 150                 155                 160

Glu Asn Gln Glu Ser Ser Ser Ser Ser Ser Ser Ser Ser Ser Ser Ser
                165                 170                 175

Thr Ile Arg Lys Ile Lys Ser Ser Lys Asn Ser Ala Ala Asn Arg Glu
            180                 185                 190

Leu Gln Lys Lys Leu Lys Val Lys Asp Asn Lys Lys Asn Arg Thr Lys
        195                 200                 205

Lys Lys Pro Thr Pro Lys Pro Pro Val Val Asp Glu Ala Gly Ser Gly
    210                 215                 220

Leu Asp Asn Gly Asp Phe Lys Val Thr Thr Pro Asp Thr Ser Thr Thr
225                 230                 235                 240

Gln His Asn Lys Val Ser Thr Ser Pro Lys Ile Thr Thr Ala Lys Pro
                245                 250                 255
```

```
Ile Asn Pro Arg Pro Ser Leu Pro Pro Asn Ser Asp Thr Ser Lys Glu
            260                 265                 270

Thr Ser Leu Thr Val Asn Lys Glu Thr Thr Val Glu Thr Lys Glu Thr
        275                 280                 285

Thr Thr Thr Asn Lys Gln Thr Ser Thr Asp Gly Lys Glu Lys Thr Thr
    290                 295                 300

Ser Ala Lys Glu Thr Gln Ser Ile Glu Lys Thr Ser Ala Lys Asp Leu
305                 310                 315                 320

Ala Pro Thr Ser Lys Val Leu Ala Lys Pro Thr Pro Lys Ala Glu Thr
                325                 330                 335

Thr Thr Lys Gly Pro Ala Leu Thr Thr Pro Lys Glu Pro Ala Pro Thr
            340                 345                 350

Thr Pro Lys Glu Pro Ala Pro Thr Thr Pro Lys Glu Pro Ala Pro Thr
        355                 360                 365

Thr Pro Lys Glu Pro Ala Pro Thr Thr Pro Lys Glu Pro Ala Pro Thr
    370                 375                 380

Thr Pro Lys Glu Pro Ala Pro Thr Thr Pro Lys Glu Pro Ala Pro Thr
385                 390                 395                 400

Thr Pro Lys Glu Pro Ala Pro Thr Thr Pro Lys Glu Pro Ala Pro Thr
                405                 410                 415

Thr Pro Lys Glu Pro Ala Pro Thr Thr Pro Lys Glu Pro Ala Pro Thr
            420                 425                 430

Thr Pro Lys Glu Pro Ala Pro Thr Thr Pro Lys Glu Pro Ala Pro Thr
        435                 440                 445

Thr Pro Lys Glu Pro Ala Pro Thr Thr Pro Lys Glu Pro Ala Pro Thr
    450                 455                 460

Thr Pro Lys Glu Pro Ala Pro Thr Thr Pro Lys Glu Pro Ala Pro Thr
465                 470                 475                 480

Thr Pro Lys Glu Pro Ala Pro Thr Thr Pro Lys Glu Pro Ala Pro Thr
                485                 490                 495

Thr Pro Lys Glu Pro Ala Pro Thr Thr Pro Lys Glu Pro Ala Pro Thr
            500                 505                 510

Thr Pro Lys Glu Pro Ala Pro Thr Thr Pro Lys Glu Pro Ala Pro Thr
        515                 520                 525

Thr Pro Lys Glu Pro Ala Pro Thr Thr Pro Lys Glu Pro Ala Pro Thr
    530                 535                 540

Thr Pro Lys Glu Pro Ala Pro Thr Thr Pro Lys Glu Pro Ala Pro Thr
545                 550                 555                 560

Thr Pro Lys Glu Pro Ala Pro Thr Thr Pro Lys Glu Pro Ala Pro Thr
                565                 570                 575

Thr Pro Lys Glu Pro Ala Pro Thr Thr Pro Lys Glu Pro Ala Pro Thr
            580                 585                 590

Thr Pro Lys Glu Pro Ala Pro Thr Thr Pro Lys Glu Pro Ala Pro Thr
        595                 600                 605

Thr Pro Lys Glu Pro Ala Pro Thr Thr Pro Lys Glu Pro Ala Pro Thr
    610                 615                 620

Thr Pro Lys Glu Pro Ala Pro Thr Thr Pro Lys Glu Pro Ala Pro Thr
625                 630                 635                 640

Thr Pro Lys Glu Pro Ala Pro Thr Thr Pro Lys Glu Pro Ala Pro Thr
                645                 650                 655

Thr Pro Lys Glu Pro Ala Pro Thr Thr Pro Lys Glu Pro Ala Pro Thr
            660                 665                 670

Thr Pro Lys Glu Pro Ala Pro Thr Thr Pro Lys Glu Pro Ala Pro Thr
```

-continued

```
        675                 680                 685

Thr Pro Lys Glu Pro Ala Pro Thr Thr Pro Lys Glu Pro Ala Pro Thr
    690                 695                 700

Thr Pro Lys Glu Pro Ala Pro Thr Thr Pro Lys Glu Pro Ala Pro Thr
705                 710                 715                 720

Thr Pro Lys Glu Pro Ala Pro Thr Thr Pro Lys Glu Pro Ala Pro Thr
                725                 730                 735

Thr Pro Lys Glu Pro Ala Pro Thr Thr Pro Lys Glu Pro Ala Pro Thr
            740                 745                 750

Thr Pro Lys Glu Pro Ala Pro Thr Thr Pro Lys Glu Pro Ala Pro Thr
        755                 760                 765

Thr Pro Lys Glu Pro Ala Pro Thr Thr Pro Lys Glu Pro Ala Pro Thr
    770                 775                 780

Thr Pro Lys Glu Pro Ala Pro Thr Thr Pro Lys Glu Pro Ala Pro Thr
785                 790                 795                 800

Thr Pro Lys Glu Pro Ala Pro Thr Thr Pro Lys Glu Pro Ala Pro Thr
                805                 810                 815

Thr Pro Ser Glu Val Ser Thr Pro Thr Thr Thr Lys Glu Pro Thr Thr
            820                 825                 830

Ile His Lys Ser Pro Asp Glu Ser Thr Pro Glu Leu Ser Ala Glu Pro
        835                 840                 845

Thr Pro Lys Ala Leu Glu Asn Ser Pro Lys Glu Pro Gly Val Pro Thr
    850                 855                 860

Thr Lys Thr Pro Ala Ala Thr Lys Pro Glu Met Thr Thr Thr Ala Lys
865                 870                 875                 880

Asp Lys Thr Thr Glu Arg Asp Leu Arg Thr Thr Pro Glu Thr Thr Thr
                885                 890                 895

Ala Ala Pro Lys Met Thr Lys Glu Thr Ala Thr Thr Thr Glu Lys Thr
            900                 905                 910

Thr Glu Ser Lys Ile Thr Ala Thr Thr Thr Gln Val Thr Ser Thr Thr
        915                 920                 925

Thr Gln Asp Thr Thr Pro Phe Lys Ile Thr Thr Leu Lys Thr Thr Thr
    930                 935                 940

Leu Ala Pro Lys Val Thr Thr Thr Lys Lys Thr Ile Thr Thr Thr Glu
945                 950                 955                 960

Ile Met Asn Lys Pro Glu Glu Thr Ala Lys Pro Lys Asp Arg Ala Thr
                965                 970                 975

Asn Ser Lys Ala Thr Thr Pro Lys Pro Gln Lys Pro Thr Lys Ala Pro
            980                 985                 990

Lys Lys Pro Thr Ser Thr Lys Lys  Pro Lys Thr Met Pro  Arg Val Arg
        995                 1000                1005

Lys Pro  Lys Thr Thr Pro Thr  Pro Arg Lys Met Thr  Ser Thr Met
    1010                 1015                 1020

Pro Glu  Leu Asn Pro Thr Ser  Arg Ile Ala Glu Ala  Met Leu Gln
    1025                 1030                 1035

Thr Thr  Thr Arg Pro Asn Gln  Thr Pro Asn Ser Lys  Leu Val Glu
    1040                 1045                 1050

Val Asn  Pro Lys Ser Glu Asp  Ala Gly Gly Ala Glu  Gly Glu Thr
    1055                 1060                 1065

Pro His  Met Leu Leu Arg Pro  His Val Phe Met Pro  Glu Val Thr
    1070                 1075                 1080

Pro Asp  Met Asp Tyr Leu Pro  Arg Val Pro Asn Gln  Gly Ile Ile
    1085                 1090                 1095
```

```
Ile Asn  Pro Met Leu Ser Asp  Glu Thr Asn Ile Cys  Asn Gly Lys
    1100                 1105                 1110

Pro Val  Asp Gly Leu Thr Thr  Leu Arg Asn Gly Thr  Leu Val Ala
    1115                 1120                 1125

Phe Arg  Gly His Tyr Phe Trp  Met Leu Ser Pro Phe  Ser Pro Pro
    1130                 1135                 1140

Ser Pro  Ala Arg Arg Ile Thr  Glu Val Trp Gly Ile  Pro Ser Pro
    1145                 1150                 1155

Ile Asp  Thr Val Phe Thr Arg  Cys Asn Cys Glu Gly  Lys Thr Phe
    1160                 1165                 1170

Phe Phe  Lys Asp Ser Gln Tyr  Trp Arg Phe Thr Asn  Asp Ile Lys
    1175                 1180                 1185

Asp Ala  Gly Tyr Pro Lys Pro  Ile Phe Lys Gly Phe  Gly Gly Leu
    1190                 1195                 1200

Thr Gly  Gln Ile Val Ala Ala  Leu Ser Thr Ala Lys  Tyr Lys Asn
    1205                 1210                 1215

Trp Pro  Glu Ser Val Tyr Phe  Phe Lys Arg Gly Gly  Ser Ile Gln
    1220                 1225                 1230

Gln Tyr  Ile Tyr Lys Gln Glu  Pro Val Gln Lys Cys  Pro Gly Arg
    1235                 1240                 1245

Arg Pro  Ala Leu Asn Tyr Pro  Val Tyr Gly Glu Thr  Thr Gln Val
    1250                 1255                 1260

Arg Arg  Arg Arg Phe Glu Arg  Ala Ile Gly Pro Ser  Gln Thr His
    1265                 1270                 1275

Thr Ile  Arg Ile Gln Tyr Ser  Pro Ala Arg Leu Ala  Tyr Gln Asp
    1280                 1285                 1290

Lys Gly  Val Leu His Asn Glu  Val Lys Val Ser Ile  Leu Trp Arg
    1295                 1300                 1305

Gly Leu  Pro Asn Val Val Thr  Ser Ala Ile Ser Leu  Pro Asn Ile
    1310                 1315                 1320

Arg Lys  Pro Asp Gly Tyr Asp  Tyr Tyr Ala Phe Ser  Lys Asp Gln
    1325                 1330                 1335

Tyr Tyr  Asn Ile Asp Val Pro  Ser Arg Thr Ala Arg  Ala Ile Thr
    1340                 1345                 1350

Thr Arg  Ser Gly Gln Thr Leu  Ser Lys Val Trp Tyr  Asn Cys Pro
    1355                 1360                 1365
```

<210> SEQ ID NO 69
<211> LENGTH: 3921
<212> TYPE: DNA
<213> ORGANISM: artificial sequence
<220> FEATURE:
<223> OTHER INFORMATION: cDNA

<400> SEQUENCE: 69

```
atgcaatgga agattctccc catatacttg ttgctgctca gtgtattcct catccaacaa     60

gtaagtagtc aagatctccc ttcttgtgca ggcaggtgtg gagaaggcta tagtcgggat    120

gcgatttgta attgtgatta taactgccaa cattacatgg agtgctgtcc ggactttaag    180

aaagcatgta cggtcgagct cagttgtaaa gggcgctgtt tcgaatcttt cgctagaggc    240

cgagaatgtg actgcgacag tgactgcaaa aagtacggaa agtgttgccc agattacgag    300

gacttttgcg ggagagtaca caaccctact tcaccacctt cttccaaaac tgcaccacct    360

tccccggggg cctctcagac aattaagtca acggccaaac gctcacccaa ggctccgaac    420
```

-continued

```
aaaaaaaaga ctaagaaggt aatagagagt gaggaaatca ccgaggagca ctctgtgtca    480
gaaaaccaag aaagttcttc atcatcaagc tcttcttcat ccactattcg caaaataaag    540
tcatctaaga actctgcggc gaataaagag cttaaaaaga agccaaaagt aaaggataat    600
aaaaaggagc gaacaccgaa gaaaaagcca ccacctgaac cccccgtagt tgatgaggcg    660
gggtcaggct tggacaatgg agacattaaa ttgacaccca cgcctgacat tcctacgact    720
caacgaaata aggttactac aagtcccaaa ttcaccacag gtaagcccat caacccaaaa    780
cctagtctcc caccgaacac cgatacgtca aaggagacgt catccactcc caacaaggaa    840
acaactgtca aaagtaaaga gacacttgct aacaaggaaa ccagcagtaa agcgaaggag    900
aaaattacgt ctgctaaaga gactcggtct gcggagaaga ccccagcgaa ggactttgtg    960
cctacgacga aagcccctgt caaatctact ccgaaggcgg aaagcactac taagggccct   1020
gctctgacaa cccctaagga gccagcaccc acaacgccga aggaaccagc gcccacgacc   1080
cctaaagaac cagctcctac aacgcccaag gaaccggcgc caacaacgcc taaggaaccg   1140
gcaccaacaa cacccaaaga gcccgccccc actactccta aagaaccggc tccaactaca   1200
ccgaaggaac ctgccccgac aaccccaaag gaaccagccc ctacaacccc taaagagcca   1260
gcgccaacca cgcccaaaga acctgcgccg actaccccga aagagccggc acccactacg   1320
cccaaagagc cggcccccac aaccccgaag gaaccggctc cgacgacacc aaaggagcct   1380
gcgcccacta cacccaagga gcctgcacca accactccca aggagccagc tcccacaaca   1440
ccaaaggaac ccgcgcccac cacgccaaaa gagccagcac ctacaacacc taaggaacct   1500
gctccaacca ccccaaagga gcccgcacct acgactccca aggaacccgc tccaacgacg   1560
cctaaggagc cggcacctac cactccaaag gagccagccc cgactactcc gaaggagcct   1620
gccccaacta ctcccaaaga gccagccccc acgactccta aggaaccagc accaacgaca   1680
ccgaaagaac ccgctcccac gacgccgaaa gaacctgccc ctacgacacc caaagaacca   1740
gccccaacaa ctcctaaaga gccggctccc actaccccta aggagccagc gcctacgacc   1800
ccaaaagagc ctgcaccgac aacgccaaag gaacctgcac ccaccacccc taaggaaccc   1860
gcaccaacta ccccaaaaga acctgcacct actactccaa aggaaccggc ccctaccacc   1920
cccaaggaac ctgcgccaac tacgccgaaa gagcccgcgc caacgactcc gaaagaacca   1980
gcgccgacaa ctccaaaaga gcccgctccg accacaccga aagagcctgc tcccaccaca   2040
ccaaaagaac cagcaccgac cactcctaag gagcctgctc ctactacgcc taaagaacct   2100
gctccgacta cacctaaaga acccgcgcct accacgccta aagagcctgc gcctacaact   2160
cccaaagaac ccgcaccgac tacgccaaaa gaaccggccc caacgacccc gaaagaaccg   2220
gcaccgacga ctccaaaaga acccgcccca accacaccta aagagcccgc acccacgaca   2280
cctaaggagc ccgctcctac cacacccaag gaaccagctc caacaacccc caaagagcct   2340
gcccccacca ctccgaagga acccgcccct actacaccaa aagagccggc gcctactacc   2400
cccaaagaac cggcgcccac aactccgaaa gagccagctc cgacaacacc gagcgaagtg   2460
acaacgacgg ctaaagataa aacgaccgag aaagacataa ttccagagat taccactgct   2520
gttcccaaga tcacaactca agaaactgct acgccaaccg aggagacgac tacggaatct   2580
aagacctcaa ctacgaccca agtcacttct actactagta gcaaaaacac tccaaaagcc   2640
acgaccctcg cgcccaaggt gatgacagca acacaaaaaa ccacgactac tgaagagacc   2700
atgaacaagc ccgaagagac gacggcagtg cctaaagata ctgcaacatc aacgaaggta   2760
agcaccccgc gaccccgaaa gccaaccaaa gcaccaaaga aacccgcaag tacaaagaaa   2820
```

```
cccaacacga tccctaaacg aaaaaaacca aaaactacac ctaccccgcc aaagatgact   2880
acgagcacta tgcctaaact ccatcctacc tcctccgttg aggcaatgct gcaaactaca   2940
acgtccccca atcaacgacc taattctgag atagtagagg tcaaccccaa cgaggatacg   3000
gacgcggctg gaaagaaacc ccatatgttc ccgcgacctc ctgttttgac cccatattt    3060
atccctggaa ccgacattct tgtgcggggg tccaatcaag atattgccat aaatcccatg   3120
ctttccgacg agacaaatct ctgtaatgga aaacctgtcg acggattgac aaccctccga   3180
aatggtacta tggtggcgtt ccgcggccat tatttctgga tgttgagtcc ttccaaaccc   3240
ccgagtcctc cccggaagat tacagaggtt tggggcatcc cctctcccat agataccgtt   3300
tttacgcgat gcaattgtga gggtaaaaca ttcttcttca agggcagtca gtactggcga   3360
ttcactaacg acatcaagga cgcaggctac cccaaacaga tcgtcaaggg tttcggaggc   3420
ttgaatggtc gaattgtcgc tgccctgtct atagctaagt acaaggaccg gccagagtct   3480
gtctattttt tcaagcgcgg cggctcagtg caacaatata cttacaagca agagccgata   3540
aaaaaatgta cagggcgccg gccggcgatt aactaccctg tatatggtga gactacacaa   3600
gtgaggcgga gacgctttga gagggcgata ggcccttctc agacgcatac catccggata   3660
cactactccc ctattcgggt tagctaccag gacaagggtt tcttgcacaa tgaagtaaaa   3720
atgtccagtc aatggagagg tttcccgaac gttgttacct cagcaattgc gctgcctaac   3780
atcaggaagc ctgatggtta cgactattac gcgttttctc gcaatcaata ttataacatt   3840
gatgttccct cccgcactgc cagagttgtg actacaagat ttggacgaac cctctccaat   3900
atatggtaca attgccccta g                                             3921
```

<210> SEQ ID NO 70
<211> LENGTH: 1306
<212> TYPE: PRT
<213> ORGANISM: artificial sequence
<220> FEATURE:
<223> OTHER INFORMATION: Recombinant protein

<400> SEQUENCE: 70

```
Met Gln Trp Lys Ile Leu Pro Ile Tyr Leu Leu Leu Leu Ser Val Phe
1               5                   10                  15

Leu Ile Gln Gln Val Ser Ser Gln Asp Leu Pro Ser Cys Ala Gly Arg
            20                  25                  30

Cys Gly Glu Gly Tyr Ser Arg Asp Ala Ile Cys Asn Cys Asp Tyr Asn
        35                  40                  45

Cys Gln His Tyr Met Glu Cys Cys Pro Asp Phe Lys Lys Ala Cys Thr
    50                  55                  60

Val Glu Leu Ser Cys Lys Gly Arg Cys Phe Glu Ser Phe Ala Arg Gly
65                  70                  75                  80

Arg Glu Cys Asp Cys Asp Ser Asp Cys Lys Lys Tyr Gly Lys Cys Cys
                85                  90                  95

Pro Asp Tyr Glu Asp Phe Cys Gly Arg Val His Asn Pro Thr Ser Pro
            100                 105                 110

Pro Ser Ser Lys Thr Ala Pro Pro Ser Pro Gly Ala Ser Gln Thr Ile
        115                 120                 125

Lys Ser Thr Ala Lys Arg Ser Pro Lys Ala Pro Asn Lys Lys Lys Thr
    130                 135                 140

Lys Lys Val Ile Glu Ser Glu Glu Ile Thr Glu Glu His Ser Val Ser
145                 150                 155                 160
```

```
Glu Asn Gln Glu Ser Ser Ser Ser Ser Ser Ser Ser Ser Ser Thr Ile
                165                 170                 175

Arg Lys Ile Lys Ser Ser Lys Asn Ser Ala Ala Asn Lys Glu Leu Lys
            180                 185                 190

Lys Lys Pro Lys Val Lys Asp Asn Lys Lys Glu Arg Thr Pro Lys Lys
        195                 200                 205

Lys Pro Pro Pro Glu Pro Pro Val Val Asp Glu Ala Gly Ser Gly Leu
    210                 215                 220

Asp Asn Gly Asp Ile Lys Leu Thr Pro Thr Pro Asp Ile Pro Thr Thr
225                 230                 235                 240

Gln Arg Asn Lys Val Thr Thr Ser Pro Lys Phe Thr Thr Gly Lys Pro
                245                 250                 255

Ile Asn Pro Lys Pro Ser Leu Pro Pro Asn Thr Asp Thr Ser Lys Glu
            260                 265                 270

Thr Ser Ser Thr Pro Asn Lys Glu Thr Thr Val Lys Ser Lys Glu Thr
        275                 280                 285

Leu Ala Asn Lys Glu Thr Ser Ser Lys Ala Lys Glu Lys Ile Thr Ser
    290                 295                 300

Ala Lys Glu Thr Arg Ser Ala Glu Lys Thr Pro Ala Lys Asp Phe Val
305                 310                 315                 320

Pro Thr Thr Lys Ala Pro Val Lys Ser Thr Pro Lys Ala Glu Ser Thr
                325                 330                 335

Thr Lys Gly Pro Ala Leu Thr Thr Pro Lys Glu Pro Ala Pro Thr Thr
            340                 345                 350

Pro Lys Glu Pro Ala Pro Thr Thr Pro Lys Glu Pro Ala Pro Thr Thr
        355                 360                 365

Pro Lys Glu Pro Ala Pro Thr Thr Pro Lys Glu Pro Ala Pro Thr Thr
    370                 375                 380

Pro Lys Glu Pro Ala Pro Thr Thr Pro Lys Glu Pro Ala Pro Thr Thr
385                 390                 395                 400

Pro Lys Glu Pro Ala Pro Thr Thr Pro Lys Glu Pro Ala Pro Thr Thr
                405                 410                 415

Pro Lys Glu Pro Ala Pro Thr Thr Pro Lys Glu Pro Ala Pro Thr Thr
            420                 425                 430

Pro Lys Glu Pro Ala Pro Thr Thr Pro Lys Glu Pro Ala Pro Thr Thr
        435                 440                 445

Pro Lys Glu Pro Ala Pro Thr Thr Pro Lys Glu Pro Ala Pro Thr Thr
    450                 455                 460

Pro Lys Glu Pro Ala Pro Thr Thr Pro Lys Glu Pro Ala Pro Thr Thr
465                 470                 475                 480

Pro Lys Glu Pro Ala Pro Thr Thr Pro Lys Glu Pro Ala Pro Thr Thr
                485                 490                 495

Pro Lys Glu Pro Ala Pro Thr Thr Pro Lys Glu Pro Ala Pro Thr Thr
            500                 505                 510

Pro Lys Glu Pro Ala Pro Thr Thr Pro Lys Glu Pro Ala Pro Thr Thr
        515                 520                 525

Pro Lys Glu Pro Ala Pro Thr Thr Pro Lys Glu Pro Ala Pro Thr Thr
    530                 535                 540

Pro Lys Glu Pro Ala Pro Thr Thr Pro Lys Glu Pro Ala Pro Thr Thr
545                 550                 555                 560

Pro Lys Glu Pro Ala Pro Thr Thr Pro Lys Glu Pro Ala Pro Thr Thr
                565                 570                 575

Pro Lys Glu Pro Ala Pro Thr Thr Pro Lys Glu Pro Ala Pro Thr Thr
```

-continued

```
            580                 585                 590

Pro Lys Glu Pro Ala Pro Thr Thr Pro Lys Glu Pro Ala Pro Thr Thr
        595                 600                 605

Pro Lys Glu Pro Ala Pro Thr Thr Pro Lys Glu Pro Ala Pro Thr Thr
    610                 615                 620

Pro Lys Glu Pro Ala Pro Thr Thr Pro Lys Glu Pro Ala Pro Thr Thr
625                 630                 635                 640

Pro Lys Glu Pro Ala Pro Thr Thr Pro Lys Glu Pro Ala Pro Thr Thr
                645                 650                 655

Pro Lys Glu Pro Ala Pro Thr Thr Pro Lys Glu Pro Ala Pro Thr Thr
            660                 665                 670

Pro Lys Glu Pro Ala Pro Thr Thr Pro Lys Glu Pro Ala Pro Thr Thr
        675                 680                 685

Pro Lys Glu Pro Ala Pro Thr Thr Pro Lys Glu Pro Ala Pro Thr Thr
    690                 695                 700

Pro Lys Glu Pro Ala Pro Thr Thr Pro Lys Glu Pro Ala Pro Thr Thr
705                 710                 715                 720

Pro Lys Glu Pro Ala Pro Thr Thr Pro Lys Glu Pro Ala Pro Thr Thr
                725                 730                 735

Pro Lys Glu Pro Ala Pro Thr Thr Pro Lys Glu Pro Ala Pro Thr Thr
            740                 745                 750

Pro Lys Glu Pro Ala Pro Thr Thr Pro Lys Glu Pro Ala Pro Thr Thr
        755                 760                 765

Pro Lys Glu Pro Ala Pro Thr Thr Pro Lys Glu Pro Ala Pro Thr Thr
    770                 775                 780

Pro Lys Glu Pro Ala Pro Thr Thr Pro Lys Glu Pro Ala Pro Thr Thr
785                 790                 795                 800

Pro Lys Glu Pro Ala Pro Thr Thr Pro Lys Glu Pro Ala Pro Thr Thr
                805                 810                 815

Pro Ser Glu Val Thr Thr Thr Ala Lys Asp Lys Thr Thr Glu Lys Asp
            820                 825                 830

Ile Ile Pro Glu Ile Thr Thr Ala Val Pro Lys Ile Thr Thr Gln Glu
        835                 840                 845

Thr Ala Thr Pro Thr Glu Glu Thr Thr Thr Glu Ser Lys Thr Ser Thr
    850                 855                 860

Thr Thr Gln Val Thr Ser Thr Thr Ser Ser Lys Asn Thr Pro Lys Ala
865                 870                 875                 880

Thr Thr Leu Ala Pro Lys Val Met Thr Ala Thr Gln Lys Thr Thr Thr
                885                 890                 895

Thr Glu Glu Thr Met Asn Lys Pro Glu Glu Thr Thr Ala Val Pro Lys
            900                 905                 910

Asp Thr Ala Thr Ser Thr Lys Val Ser Thr Pro Arg Pro Arg Lys Pro
        915                 920                 925

Thr Lys Ala Pro Lys Lys Pro Ala Ser Thr Lys Lys Pro Asn Thr Ile
    930                 935                 940

Pro Lys Arg Lys Lys Pro Lys Thr Thr Pro Thr Pro Pro Lys Met Thr
945                 950                 955                 960

Thr Ser Thr Met Pro Lys Leu His Pro Thr Ser Ser Val Glu Ala Met
                965                 970                 975

Leu Gln Thr Thr Thr Ser Pro Asn Gln Arg Pro Asn Ser Glu Ile Val
            980                 985                 990

Glu Val Asn Pro Asn Glu Asp Thr  Asp Ala Ala Gly Lys  Lys Pro His
        995                 1000                 1005
```

```
Met Phe  Pro Arg Pro Pro Val  Leu Thr Pro Ile Phe  Ile Pro Gly
    1010                 1015                 1020

Thr Asp  Ile Leu Val Arg Gly  Ser Asn Gln Asp Ile  Ala Ile Asn
    1025                 1030                 1035

Pro Met  Leu Ser Asp Glu Thr  Asn Leu Cys Asn Gly  Lys Pro Val
    1040                 1045                 1050

Asp Gly  Leu Thr Thr Leu Arg  Asn Gly Thr Met Val  Ala Phe Arg
    1055                 1060                 1065

Gly His  Tyr Phe Trp Met Leu  Ser Pro Ser Lys Pro  Pro Ser Pro
    1070                 1075                 1080

Pro Arg  Lys Ile Thr Glu Val  Trp Gly Ile Pro Ser  Pro Ile Asp
    1085                 1090                 1095

Thr Val  Phe Thr Arg Cys Asn  Cys Glu Gly Lys Thr  Phe Phe Phe
    1100                 1105                 1110

Lys Gly  Ser Gln Tyr Trp Arg  Phe Thr Asn Asp Ile  Lys Asp Ala
    1115                 1120                 1125

Gly Tyr  Pro Lys Gln Ile Val  Lys Gly Phe Gly Gly  Leu Asn Gly
    1130                 1135                 1140

Arg Ile  Val Ala Ala Leu Ser  Ile Ala Lys Tyr Lys  Asp Arg Pro
    1145                 1150                 1155

Glu Ser  Val Tyr Phe Phe Lys  Arg Gly Gly Ser Val  Gln Gln Tyr
    1160                 1165                 1170

Thr Tyr  Lys Gln Glu Pro Ile  Lys Lys Cys Thr Gly  Arg Arg Pro
    1175                 1180                 1185

Ala Ile  Asn Tyr Pro Val Tyr  Gly Glu Thr Thr Gln  Val Arg Arg
    1190                 1195                 1200

Arg Arg  Phe Glu Arg Ala Ile  Gly Pro Ser Gln Thr  His Thr Ile
    1205                 1210                 1215

Arg Ile  His Tyr Ser Pro Ile  Arg Val Ser Tyr Gln  Asp Lys Gly
    1220                 1225                 1230

Phe Leu  His Asn Glu Val Lys  Met Ser Ser Gln Trp  Arg Gly Phe
    1235                 1240                 1245

Pro Asn  Val Val Thr Ser Ala  Ile Ala Leu Pro Asn  Ile Arg Lys
    1250                 1255                 1260

Pro Asp  Gly Tyr Asp Tyr Tyr  Ala Phe Ser Arg Asn  Gln Tyr Tyr
    1265                 1270                 1275

Asn Ile  Asp Val Pro Ser Arg  Thr Ala Arg Val Val  Thr Thr Arg
    1280                 1285                 1290

Phe Gly  Arg Thr Leu Ser Asn  Ile Trp Tyr Asn Cys  Pro
    1295                 1300                 1305
```

<210> SEQ ID NO 71
<211> LENGTH: 4113
<212> TYPE: DNA
<213> ORGANISM: artificial sequence
<220> FEATURE:
<223> OTHER INFORMATION: cDNA

<400> SEQUENCE: 71

```
atggagtgga aaatcctgcc tatttacctt ctcctgttgc tgagtatatt ctccatccag      60

gaggtttcaa gccaagacct ttctagttgc gctggtcggt gtggggaggg atactctcgg     120

gatgcgactt gcaactgcga ttttaattgt caatactaca tggaatgttg tccggacttt     180

aagaaagtct gtacatctga attgtcttgt aaaggccgct gtttcgagag tttcgaaagg     240
```

-continued

```
gggcgagaat gcgattgcga tgctgactgt aagaaatacg gtaagtgttg ttcagattat    300
gaaagcttct gcgaggaagt ccataatcct acgtctccgc cgagttccaa gacagctccc    360
ccgcctccag gggccagcca gactatcaag agtacagcta aacggtcacc aaagtcaaat    420
aagaaaaaaa ctaaaaaagt tatcgagagt gaagagatca tagaagaaca cagtgtgtcc    480
gagaatcagg agtcatcttc cagctctagc tcaagttcat ctaccatccg caaggttaag    540
tctagcaaaa actcagcagc gaacagagaa ctcaaaaaga agcctaaggt caaggattct    600
aaaaaaaaac gaaccccgaa aaaaaaaccg acgcctgagc caccagtcat agacgaggcc    660
gggagtggtt tggataacgg agacttcatg ttgattccca ccccgaaaat tccaaccacg    720
caaagaaata aggtgacgac atcaccaaag attacaacgg taaaaccaat taaccccaag    780
ccttcccttc ctcccaattc cgacacgtca aaagagacca ctagcacacc taataaagaa    840
actacggtcg agaccaagga gaccgagatc acaaacaagg agacttctac aagcgccaat    900
gaaaagacta cgagcgccag gaagagtaca gagaaaacat ccgacaaaga ttttgctccg    960
gccagcgaag tacctgcaaa aagtacccct aaggctgaaa ccaccacaaa gggccctgct   1020
ctgacaaccc ctaaggagcc agcacccaca acgccgaagg aaccagcgcc cacgacccct   1080
aaagaaccag ctcctacaac gcccaaggaa ccggcgccaa caacgcctaa ggaaccggca   1140
ccaacaacac ccaaagagcc cgcccccact actcctaaag aaccggctcc aactacaccg   1200
aaggaacctg ccccgacaac cccaaaggaa ccagccccta caacccctaa agagccagcg   1260
ccaaccacgc ccaaagaacc tgcgccgact accccgaaag agccggcacc cactacgccc   1320
aaagagccgg cccccacaac cccgaaggaa ccggctccga cgacaccaaa ggagcctgcg   1380
cccactacac ccaaggagcc tgcaccaacc actcccaagg agccagctcc cacaacacca   1440
aaggaacccg cgcccaccac gccaaaagag ccagcaccta caacacctaa ggaacctgct   1500
ccaaccaccc caaaggagcc cgcacctacg actcccaagg aacccgctcc aacgacgcct   1560
aaggagccgg cacctaccac tccaaaggag ccagccccga ctactccgaa ggagcctgcc   1620
ccaactactc ccaaagagcc agcccccacg actcctaagg aaccagcacc aacgacaccg   1680
aaagaacccg ctcccacgac gccgaaagaa cctgccccta cgacacccaa agaaccagcc   1740
ccaacaactc ctaaagagcc ggctcccact acccctaagg agccagcgcc tacgacccca   1800
aaagagcctg caccgacaac gccaaaggaa cctgcaccca ccacccctaa ggaacccgca   1860
ccaactaccc caaaagaacc tgcacctact actccaaagg aaccggcccc taccaccccc   1920
aaggaacctg cgccaactac gccgaaagag cccgcgccaa cgactccgaa agaaccagcg   1980
ccgacaactc caaaagagcc cgctccgacc acaccgaaag agcctgctcc caccacacca   2040
aaagaaccag caccgaccac tcctaaggag cctgctccta ctacgcctaa agaacctgct   2100
ccgactacac ctaaagaacc cgcgcctacc acgcctaaag agcctgcgcc tacaactccc   2160
aaagaacccg caccgactac gccaaaagaa ccggccccaa cgaccccgaa agaaccggca   2220
ccgacgactc caaaagaacc cgccccaacc acacctaaag agcccgcacc cacgacacct   2280
aaggagcccg ctcctaccac acccaaggaa ccagctccaa caacccccaa agagcctgcc   2340
cccaccactc cgaaggaacc cgcccctact acaccaaaag agccggcgcc tactaccccc   2400
aaagaaccgg cgcccacaac tccgaaagag ccagctccga caacaccgag cgaagtgtct   2460
accacgacga ctaccatgaa acctccgacg acacccaaaa atcttgctga aagcacccca   2520
gagttcccag cggagccaac acccaaagca ctggagaact cacccaaaga accggctgta   2580
ccgactacga aggcccctga agtaaccaaa ccagaagtca caacaaccgc taaagacaag   2640
```

```
gttacgggaa aggatattca cacgattccc gagataacta cagcggcacc taagataacg   2700

accgaaacgg ccacgacaac tgaagagaaa acaacggaaa gtaaggtgac ctctactata   2760

atgcaagtga cctccacgac cgaggatacg acgacaagct ccaagataac gcctaaagca   2820

acgacattgg caccgaaagt gatgaccgca acaaaaacta ccacaacaca ggaaacgata   2880

aacaagctgg aggagacgac ggctattcct aaggatacgg cgacgcacag caaagtgact   2940

acgccaaagc cgaagaagcc gaccaaagcg cctcgaaagc cgacatccac aaagaaaccg   3000

aaaacgccgc gcaagcgcaa accaaagaca acaccgattc ccccgaaaat caccaccccg   3060

accactccta aaagtaaccc tacgactttg gcggaagcca tgcttcagac tacaacttca   3120

cctaaccaga ctccaaattc cgctatgata gaggtcaacc cgaaaaacga ggacgcggac   3180

gctgcggaag gggaaaagcc gctcgtgata cttcgaccac acgtccttac tccaatcgtc   3240

ataccgggtc cggactttct tgtccgcggt ccaaacttgg gaatcggaat taaccccatg   3300

cttagcgacg agacgaactt gtgtaacggt aaaccagtgg acggactcac caccctgaga   3360

aatggaactc tcgtggcttt caggggccac tatttctgga tgctccgacc atttagtccc   3420

ccgagtccgc cgaggagaat caccgaggta tgggggattc cctctcctat tgataccgtc   3480

ttcactcgct gcaactgcga gggaaagaca tttttcttca aggactcaca gtattggcga   3540

ttcaccaacg acataaagga tgctggatac cctaaattga ttagcaaggg ctttgggggg   3600

cttagtggca aaatcgtggc cgctctttca atagcaacgt acaagaacag gccagagagc   3660

gtttattttt ttaagcgagg ggggcgaata cagcaataca tctacaagca agaacccata   3720

agaaagtgtc caggacgccg accagctata cattattcag tttacggaga ggctcctcag   3780

attcggagga gaaggttcga acgggccata ggcccgtctc agacgcacac catccgcatt   3840

cactactccc ccgtacgcgt atcataccaa gacaaagtgc cgtccactga ctttctccac   3900

aacgaggtca aagtaagcac cctgtggcgc ggacttccag acaccgttac atccgccatt   3960

tcccttccta acttgcggaa accagacgga tacgactatt atgctttttc aaaagaccaa   4020

tattataata ttgacgtccc gagccgaact gctcgcgcaa taactacccg aagtggccag   4080

acattgagta aggtctggta taactgtccc tag                                4113
```

<210> SEQ ID NO 72
<211> LENGTH: 24
<212> TYPE: PRT
<213> ORGANISM: Homo sapiens

<400> SEQUENCE: 72

```
Met Ala Trp Lys Thr Leu Pro Ile Tyr Leu Leu Leu Leu Leu Ser Val
1               5                   10                  15

Phe Val Ile Gln Gln Val Ser Ser
            20
```

<210> SEQ ID NO 73
<211> LENGTH: 22
<212> TYPE: PRT
<213> ORGANISM: Canis lupus familiaris

<400> SEQUENCE: 73

```
Met Gln Trp Lys Ile Leu Pro Ile Tyr Leu Leu Leu Leu Ser Val Phe
1               5                   10                  15

Leu Ile Gln Gln Val Ser
            20
```

-continued

<210> SEQ ID NO 74
<211> LENGTH: 24
<212> TYPE: PRT
<213> ORGANISM: Equus ferus caballus

<400> SEQUENCE: 74

Met Glu Trp Lys Ile Leu Pro Ile Tyr Leu Leu Leu Leu Leu Ser Ile
1 5 10 15

Phe Ser Ile Gln Glu Val Ser Ser
20

<210> SEQ ID NO 75
<211> LENGTH: 323
<212> TYPE: PRT
<213> ORGANISM: Homo sapiens

<400> SEQUENCE: 75

Gln Asp Leu Ser Ser Cys Ala Gly Arg Cys Gly Glu Gly Tyr Ser Arg
1 5 10 15

Asp Ala Thr Cys Asn Cys Asp Tyr Asn Cys Gln His Tyr Met Glu Cys
20 25 30

Cys Pro Asp Phe Lys Arg Val Cys Thr Ala Glu Leu Ser Cys Lys Gly
35 40 45

Arg Cys Phe Glu Ser Phe Glu Arg Gly Arg Glu Cys Asp Cys Asp Ala
50 55 60

Gln Cys Lys Lys Tyr Asp Lys Cys Cys Pro Asp Tyr Glu Ser Phe Cys
65 70 75 80

Ala Glu Val His Asn Pro Thr Ser Pro Pro Ser Ser Lys Lys Ala Pro
85 90 95

Pro Pro Ser Gly Ala Ser Gln Thr Ile Lys Ser Thr Thr Lys Arg Ser
100 105 110

Pro Lys Pro Pro Asn Lys Lys Lys Thr Lys Lys Val Ile Glu Ser Glu
115 120 125

Glu Ile Thr Glu Glu His Ser Val Ser Glu Asn Gln Glu Ser Ser Ser
130 135 140

Ser Ser Ser Ser Ser Ser Ser Ser Ser Thr Ile Arg Lys Ile Lys Ser
145 150 155 160

Ser Lys Asn Ser Ala Ala Asn Arg Glu Leu Gln Lys Lys Leu Lys Val
165 170 175

Lys Asp Asn Lys Lys Asn Arg Thr Lys Lys Lys Pro Thr Pro Lys Pro
180 185 190

Pro Val Val Asp Glu Ala Gly Ser Gly Leu Asp Asn Gly Asp Phe Lys
195 200 205

Val Thr Thr Pro Asp Thr Ser Thr Thr Gln His Asn Lys Val Ser Thr
210 215 220

Ser Pro Lys Ile Thr Thr Ala Lys Pro Ile Asn Pro Arg Pro Ser Leu
225 230 235 240

Pro Pro Asn Ser Asp Thr Ser Lys Glu Thr Ser Leu Thr Val Asn Lys
245 250 255

Glu Thr Thr Val Glu Thr Lys Glu Thr Thr Thr Thr Asn Lys Gln Thr
260 265 270

Ser Thr Asp Gly Lys Glu Lys Thr Thr Ser Ala Lys Glu Thr Gln Ser
275 280 285

Ile Glu Lys Thr Ser Ala Lys Asp Leu Ala Pro Thr Ser Lys Val Leu
290 295 300

-continued

```
Ala Lys Pro Thr Pro Lys Ala Glu Thr Thr Thr Lys Gly Pro Ala Leu
305                 310                 315                 320

Thr Thr Pro


<210> SEQ ID NO 76
<211> LENGTH: 550
<212> TYPE: PRT
<213> ORGANISM: Homo sapiens

<400> SEQUENCE: 76

Ser Glu Val Ser Thr Pro Thr Thr Thr Lys Glu Pro Thr Thr Ile His
1               5                   10                  15

Lys Ser Pro Asp Glu Ser Thr Pro Glu Leu Ser Ala Glu Pro Thr Pro
            20                  25                  30

Lys Ala Leu Glu Asn Ser Pro Lys Glu Pro Gly Val Pro Thr Thr Lys
        35                  40                  45

Thr Pro Ala Ala Thr Lys Pro Glu Met Thr Thr Thr Ala Lys Asp Lys
    50                  55                  60

Thr Thr Glu Arg Asp Leu Arg Thr Thr Pro Glu Thr Thr Thr Ala Ala
65                  70                  75                  80

Pro Lys Met Thr Lys Glu Thr Ala Thr Thr Thr Glu Lys Thr Thr Glu
                85                  90                  95

Ser Lys Ile Thr Ala Thr Thr Thr Gln Val Thr Ser Thr Thr Thr Gln
            100                 105                 110

Asp Thr Thr Pro Phe Lys Ile Thr Thr Leu Lys Thr Thr Thr Leu Ala
        115                 120                 125

Pro Lys Val Thr Thr Thr Lys Lys Thr Ile Thr Thr Thr Glu Ile Met
    130                 135                 140

Asn Lys Pro Glu Glu Thr Ala Lys Pro Lys Asp Arg Ala Thr Asn Ser
145                 150                 155                 160

Lys Ala Thr Thr Pro Lys Pro Gln Lys Pro Thr Lys Ala Pro Lys Lys
                165                 170                 175

Pro Thr Ser Thr Lys Lys Pro Lys Thr Met Pro Arg Val Arg Lys Pro
            180                 185                 190

Lys Thr Thr Pro Thr Pro Arg Lys Met Thr Ser Thr Met Pro Glu Leu
        195                 200                 205

Asn Pro Thr Ser Arg Ile Ala Glu Ala Met Leu Gln Thr Thr Thr Arg
    210                 215                 220

Pro Asn Gln Thr Pro Asn Ser Lys Leu Val Glu Val Asn Pro Lys Ser
225                 230                 235                 240

Glu Asp Ala Gly Gly Ala Glu Gly Glu Thr Pro His Met Leu Leu Arg
                245                 250                 255

Pro His Val Phe Met Pro Glu Val Thr Pro Asp Met Asp Tyr Leu Pro
            260                 265                 270

Arg Val Pro Asn Gln Gly Ile Ile Ile Asn Pro Met Leu Ser Asp Glu
        275                 280                 285

Thr Asn Ile Cys Asn Gly Lys Pro Val Asp Gly Leu Thr Thr Leu Arg
    290                 295                 300

Asn Gly Thr Leu Val Ala Phe Arg Gly His Tyr Phe Trp Met Leu Ser
305                 310                 315                 320

Pro Phe Ser Pro Pro Ser Pro Ala Arg Arg Ile Thr Glu Val Trp Gly
                325                 330                 335

Ile Pro Ser Pro Ile Asp Thr Val Phe Thr Arg Cys Asn Cys Glu Gly
            340                 345                 350
```

```
Lys Thr Phe Phe Phe Lys Asp Ser Gln Tyr Trp Arg Phe Thr Asn Asp
        355                 360                 365

Ile Lys Asp Ala Gly Tyr Pro Lys Pro Ile Phe Lys Gly Phe Gly Gly
    370                 375                 380

Leu Thr Gly Gln Ile Val Ala Ala Leu Ser Thr Ala Lys Tyr Lys Asn
385                 390                 395                 400

Trp Pro Glu Ser Val Tyr Phe Phe Lys Arg Gly Gly Ser Ile Gln Gln
                405                 410                 415

Tyr Ile Tyr Lys Gln Glu Pro Val Gln Lys Cys Pro Gly Arg Arg Pro
            420                 425                 430

Ala Leu Asn Tyr Pro Val Tyr Gly Glu Thr Thr Gln Val Arg Arg Arg
        435                 440                 445

Arg Phe Glu Arg Ala Ile Gly Pro Ser Gln Thr His Thr Ile Arg Ile
    450                 455                 460

Gln Tyr Ser Pro Ala Arg Leu Ala Tyr Gln Asp Lys Gly Val Leu His
465                 470                 475                 480

Asn Glu Val Lys Val Ser Ile Leu Trp Arg Gly Leu Pro Asn Val Val
                485                 490                 495

Thr Ser Ala Ile Ser Leu Pro Asn Ile Arg Lys Pro Asp Gly Tyr Asp
            500                 505                 510

Tyr Tyr Ala Phe Ser Lys Asp Gln Tyr Tyr Asn Ile Asp Val Pro Ser
        515                 520                 525

Arg Thr Ala Arg Ala Ile Thr Thr Arg Ser Gly Gln Thr Leu Ser Lys
    530                 535                 540

Val Trp Tyr Asn Cys Pro
545                 550


<210> SEQ ID NO 77
<211> LENGTH: 322
<212> TYPE: PRT
<213> ORGANISM: Canis lupus familiaris

<400> SEQUENCE: 77

Gln Asp Leu Pro Ser Cys Ala Gly Arg Cys Gly Glu Gly Tyr Ser Arg
1               5                   10                  15

Asp Ala Ile Cys Asn Cys Asp Tyr Asn Cys Gln His Tyr Met Glu Cys
            20                  25                  30

Cys Pro Asp Phe Lys Lys Ala Cys Thr Val Glu Leu Ser Cys Lys Gly
        35                  40                  45

Arg Cys Phe Glu Ser Phe Ala Arg Gly Arg Glu Cys Asp Cys Asp Ser
    50                  55                  60

Asp Cys Lys Lys Tyr Gly Lys Cys Cys Pro Asp Tyr Glu Asp Phe Cys
65                  70                  75                  80

Gly Arg Val His Asn Pro Thr Ser Pro Pro Ser Ser Lys Thr Ala Pro
                85                  90                  95

Pro Ser Pro Gly Ala Ser Gln Thr Ile Lys Ser Thr Ala Lys Arg Ser
            100                 105                 110

Pro Lys Ala Pro Asn Lys Lys Lys Thr Lys Lys Val Ile Glu Ser Glu
        115                 120                 125

Glu Ile Thr Glu Glu His Ser Val Ser Glu Asn Gln Glu Ser Ser Ser
    130                 135                 140

Ser Ser Ser Ser Ser Ser Ser Thr Ile Arg Lys Ile Lys Ser Ser Lys
145                 150                 155                 160

Asn Ser Ala Ala Asn Lys Glu Leu Lys Lys Lys Pro Lys Val Lys Asp
                165                 170                 175
```

```
Asn Lys Lys Glu Arg Thr Pro Lys Lys Lys Pro Pro Pro Glu Pro Pro
            180                 185                 190

Val Val Asp Glu Ala Gly Ser Gly Leu Asp Asn Gly Asp Ile Lys Leu
        195                 200                 205

Thr Pro Thr Pro Asp Ile Pro Thr Thr Gln Arg Asn Lys Val Thr Thr
    210                 215                 220

Ser Pro Lys Phe Thr Thr Gly Lys Pro Ile Asn Pro Lys Pro Ser Leu
225                 230                 235                 240

Pro Pro Asn Thr Asp Thr Ser Lys Glu Thr Ser Ser Thr Pro Asn Lys
                245                 250                 255

Glu Thr Thr Val Lys Ser Lys Glu Thr Leu Ala Asn Lys Glu Thr Ser
            260                 265                 270

Ser Lys Ala Lys Glu Lys Ile Thr Ser Ala Lys Glu Thr Arg Ser Ala
        275                 280                 285

Glu Lys Thr Pro Ala Lys Asp Phe Val Pro Thr Thr Lys Ala Pro Val
    290                 295                 300

Lys Ser Thr Pro Lys Ala Glu Ser Thr Thr Lys Gly Pro Ala Leu Thr
305                 310                 315                 320

Thr Pro


<210> SEQ ID NO 78
<211> LENGTH: 488
<212> TYPE: PRT
<213> ORGANISM: Canis lupus familiaris

<400> SEQUENCE: 78

Ser Glu Val Thr Thr Thr Ala Lys Asp Lys Thr Thr Glu Lys Asp Ile
1               5                   10                  15

Ile Pro Glu Ile Thr Thr Ala Val Pro Lys Ile Thr Thr Gln Glu Thr
            20                  25                  30

Ala Thr Pro Thr Glu Glu Thr Thr Thr Glu Ser Lys Thr Ser Thr Thr
        35                  40                  45

Thr Gln Val Thr Ser Thr Thr Ser Ser Lys Asn Thr Pro Lys Ala Thr
    50                  55                  60

Thr Leu Ala Pro Lys Val Met Thr Ala Thr Gln Lys Thr Thr Thr Thr
65                  70                  75                  80

Glu Glu Thr Met Asn Lys Pro Glu Glu Thr Thr Ala Val Pro Lys Asp
                85                  90                  95

Thr Ala Thr Ser Thr Lys Val Ser Thr Pro Arg Pro Arg Lys Pro Thr
            100                 105                 110

Lys Ala Pro Lys Lys Pro Ala Ser Thr Lys Lys Pro Asn Thr Ile Pro
        115                 120                 125

Lys Arg Lys Lys Pro Lys Thr Thr Pro Thr Pro Pro Lys Met Thr Thr
    130                 135                 140

Ser Thr Met Pro Lys Leu His Pro Thr Ser Ser Val Glu Ala Met Leu
145                 150                 155                 160

Gln Thr Thr Thr Ser Pro Asn Gln Arg Pro Asn Ser Glu Ile Val Glu
                165                 170                 175

Val Asn Pro Asn Glu Asp Thr Asp Ala Ala Gly Lys Lys Pro His Met
            180                 185                 190

Phe Pro Arg Pro Pro Val Leu Thr Pro Ile Phe Ile Pro Gly Thr Asp
        195                 200                 205

Ile Leu Val Arg Gly Ser Asn Gln Asp Ile Ala Ile Asn Pro Met Leu
    210                 215                 220
```

```
Ser Asp Glu Thr Asn Leu Cys Asn Gly Lys Pro Val Asp Gly Leu Thr
225                 230                 235                 240

Thr Leu Arg Asn Gly Thr Met Val Ala Phe Arg Gly His Tyr Phe Trp
                245                 250                 255

Met Leu Ser Pro Ser Lys Pro Pro Ser Pro Pro Arg Lys Ile Thr Glu
            260                 265                 270

Val Trp Gly Ile Pro Ser Pro Ile Asp Thr Val Phe Thr Arg Cys Asn
        275                 280                 285

Cys Glu Gly Lys Thr Phe Phe Phe Lys Gly Ser Gln Tyr Trp Arg Phe
    290                 295                 300

Thr Asn Asp Ile Lys Asp Ala Gly Tyr Pro Lys Gln Ile Val Lys Gly
305                 310                 315                 320

Phe Gly Gly Leu Asn Gly Arg Ile Val Ala Ala Leu Ser Ile Ala Lys
                325                 330                 335

Tyr Lys Asp Arg Pro Glu Ser Val Tyr Phe Phe Lys Arg Gly Gly Ser
            340                 345                 350

Val Gln Gln Tyr Thr Tyr Lys Gln Glu Pro Ile Lys Lys Cys Thr Gly
        355                 360                 365

Arg Arg Pro Ala Ile Asn Tyr Pro Val Tyr Gly Glu Thr Thr Gln Val
    370                 375                 380

Arg Arg Arg Arg Phe Glu Arg Ala Ile Gly Pro Ser Gln Thr His Thr
385                 390                 395                 400

Ile Arg Ile His Tyr Ser Pro Ile Arg Val Ser Tyr Gln Asp Lys Gly
                405                 410                 415

Phe Leu His Asn Glu Val Lys Met Ser Ser Gln Trp Arg Gly Phe Pro
            420                 425                 430

Asn Val Val Thr Ser Ala Ile Ala Leu Pro Asn Ile Arg Lys Pro Asp
        435                 440                 445

Gly Tyr Asp Tyr Tyr Ala Phe Ser Arg Asn Gln Tyr Tyr Asn Ile Asp
    450                 455                 460

Val Pro Ser Arg Thr Ala Arg Val Val Thr Thr Arg Phe Gly Arg Thr
465                 470                 475                 480

Leu Ser Asn Ile Trp Tyr Asn Cys
                485
```

<210> SEQ ID NO 79
<211> LENGTH: 320
<212> TYPE: PRT
<213> ORGANISM: Equus ferus caballus

<400> SEQUENCE: 79

```
Gln Asp Leu Ser Ser Cys Ala Gly Arg Cys Gly Glu Gly Tyr Ser Arg
1               5                   10                  15

Asp Ala Thr Cys Asn Cys Asp Phe Asn Cys Gln Tyr Tyr Met Glu Cys
            20                  25                  30

Cys Pro Asp Phe Lys Lys Val Cys Thr Ser Glu Leu Ser Cys Lys Gly
        35                  40                  45

Arg Cys Phe Glu Ser Phe Glu Arg Gly Arg Glu Cys Asp Cys Asp Ala
    50                  55                  60

Asp Cys Lys Lys Tyr Gly Lys Cys Cys Ser Asp Tyr Glu Ser Phe Cys
65                  70                  75                  80

Glu Glu Val His Asn Pro Thr Ser Pro Pro Ser Ser Lys Thr Ala Pro
                85                  90                  95

Pro Pro Pro Gly Ala Ser Gln Thr Ile Lys Ser Thr Ala Lys Arg Ser
```

```
            100                 105                 110

Pro Lys Ser Asn Lys Lys Lys Thr Lys Lys Val Ile Glu Ser Glu Glu
        115                 120                 125

Ile Ile Glu Glu His Ser Val Ser Glu Asn Gln Glu Ser Ser Ser Ser
    130                 135                 140

Ser Ser Ser Ser Ser Ser Thr Ile Arg Lys Val Lys Ser Ser Lys Asn
145                 150                 155                 160

Ser Ala Ala Asn Arg Glu Leu Lys Lys Lys Pro Lys Val Lys Asp Ser
                165                 170                 175

Lys Lys Lys Arg Thr Pro Lys Lys Lys Pro Thr Pro Glu Pro Pro Val
            180                 185                 190

Ile Asp Glu Ala Gly Ser Gly Leu Asp Asn Gly Asp Phe Met Leu Ile
        195                 200                 205

Pro Thr Pro Lys Ile Pro Thr Thr Gln Arg Asn Lys Val Thr Thr Ser
    210                 215                 220

Pro Lys Ile Thr Thr Val Lys Pro Ile Asn Pro Lys Pro Ser Leu Pro
225                 230                 235                 240

Pro Asn Ser Asp Thr Ser Lys Glu Thr Thr Ser Thr Pro Asn Lys Glu
                245                 250                 255

Thr Thr Val Glu Thr Lys Glu Thr Glu Ile Thr Asn Lys Glu Thr Ser
            260                 265                 270

Thr Ser Ala Asn Glu Lys Thr Thr Ser Ala Arg Lys Ser Thr Glu Lys
        275                 280                 285

Thr Ser Asp Lys Asp Phe Ala Pro Ala Ser Glu Val Pro Ala Lys Ser
    290                 295                 300

Thr Pro Lys Ala Glu Thr Thr Thr Lys Gly Pro Ala Leu Thr Thr Pro
305                 310                 315                 320


<210> SEQ ID NO 80
<211> LENGTH: 554
<212> TYPE: PRT
<213> ORGANISM: Equus ferus caballus

<400> SEQUENCE: 80

Ser Glu Val Ser Thr Thr Thr Thr Thr Met Lys Pro Pro Thr Thr Pro
1               5                   10                  15

Lys Asn Leu Ala Glu Ser Thr Pro Glu Phe Pro Ala Glu Pro Thr Pro
            20                  25                  30

Lys Ala Leu Glu Asn Ser Pro Lys Glu Pro Ala Val Pro Thr Thr Lys
        35                  40                  45

Ala Pro Glu Val Thr Lys Pro Glu Val Thr Thr Thr Ala Lys Asp Lys
    50                  55                  60

Val Thr Gly Lys Asp Ile His Thr Ile Pro Glu Ile Thr Thr Ala Ala
65                  70                  75                  80

Pro Lys Ile Thr Thr Glu Thr Ala Thr Thr Thr Glu Glu Lys Thr Thr
                85                  90                  95

Glu Ser Lys Val Thr Ser Thr Ile Met Gln Val Thr Ser Thr Thr Glu
            100                 105                 110

Asp Thr Thr Thr Ser Ser Lys Ile Thr Pro Lys Ala Thr Thr Leu Ala
        115                 120                 125

Pro Lys Val Met Thr Ala Thr Lys Thr Thr Thr Thr Gln Glu Thr Ile
    130                 135                 140

Asn Lys Leu Glu Glu Thr Thr Ala Ile Pro Lys Asp Thr Ala Thr His
145                 150                 155                 160
```

```
Ser Lys Val Thr Thr Pro Lys Pro Lys Lys Pro Thr Lys Ala Pro Arg
                165                 170                 175

Lys Pro Thr Ser Thr Lys Lys Pro Lys Thr Pro Arg Lys Arg Lys Pro
            180                 185                 190

Lys Thr Thr Pro Ile Pro Pro Lys Ile Thr Thr Pro Thr Thr Pro Lys
        195                 200                 205

Ser Asn Pro Thr Thr Leu Ala Glu Ala Met Leu Gln Thr Thr Thr Ser
    210                 215                 220

Pro Asn Gln Thr Pro Asn Ser Ala Met Ile Glu Val Asn Pro Lys Asn
225                 230                 235                 240

Glu Asp Ala Asp Ala Ala Glu Gly Glu Lys Pro Leu Val Ile Leu Arg
                245                 250                 255

Pro His Val Leu Thr Pro Ile Val Ile Pro Gly Pro Asp Phe Leu Val
            260                 265                 270

Arg Gly Pro Asn Leu Gly Ile Gly Ile Asn Pro Met Leu Ser Asp Glu
        275                 280                 285

Thr Asn Leu Cys Asn Gly Lys Pro Val Asp Gly Leu Thr Thr Leu Arg
    290                 295                 300

Asn Gly Thr Leu Val Ala Phe Arg Gly His Tyr Phe Trp Met Leu Arg
305                 310                 315                 320

Pro Phe Ser Pro Pro Ser Pro Pro Arg Arg Ile Thr Glu Val Trp Gly
                325                 330                 335

Ile Pro Ser Pro Ile Asp Thr Val Phe Thr Arg Cys Asn Cys Glu Gly
            340                 345                 350

Lys Thr Phe Phe Phe Lys Asp Ser Gln Tyr Trp Arg Phe Thr Asn Asp
        355                 360                 365

Ile Lys Asp Ala Gly Tyr Pro Lys Leu Ile Ser Lys Gly Phe Gly Gly
    370                 375                 380

Leu Ser Gly Lys Ile Val Ala Ala Leu Ser Ile Ala Thr Tyr Lys Asn
385                 390                 395                 400

Arg Pro Glu Ser Val Tyr Phe Phe Lys Arg Gly Gly Arg Ile Gln Gln
                405                 410                 415

Tyr Ile Tyr Lys Gln Glu Pro Ile Arg Lys Cys Pro Gly Arg Arg Pro
            420                 425                 430

Ala Ile His Tyr Ser Val Tyr Gly Glu Ala Pro Gln Ile Arg Arg Arg
        435                 440                 445

Arg Phe Glu Arg Ala Ile Gly Pro Ser Gln Thr His Thr Ile Arg Ile
    450                 455                 460

His Tyr Ser Pro Val Arg Val Ser Tyr Gln Asp Lys Val Pro Ser Thr
465                 470                 475                 480

Asp Phe Leu His Asn Glu Val Lys Val Ser Thr Leu Trp Arg Gly Leu
                485                 490                 495

Pro Asp Thr Val Thr Ser Ala Ile Ser Leu Pro Asn Leu Arg Lys Pro
            500                 505                 510

Asp Gly Tyr Asp Tyr Tyr Ala Phe Ser Lys Asp Gln Tyr Tyr Asn Ile
        515                 520                 525

Asp Val Pro Ser Arg Thr Ala Arg Ala Ile Thr Thr Arg Ser Gly Gln
    530                 535                 540

Thr Leu Ser Lys Val Trp Tyr Asn Cys Pro
545                 550
```

<210> SEQ ID NO 81
<211> LENGTH: 21
<212> TYPE: PRT

<213> ORGANISM: artificial sequence
<220> FEATURE:
<223> OTHER INFORMATION: Recombinant secretory signal

<400> SEQUENCE: 81

Met Glu Thr Asp Thr Leu Leu Leu Trp Val Leu Leu Leu Trp Val Pro
1 5 10 15

Gly Ser Thr Gly Asp
20

<210> SEQ ID NO 82
<211> LENGTH: 23
<212> TYPE: PRT
<213> ORGANISM: artificial sequence
<220> FEATURE:
<223> OTHER INFORMATION: Recombinant secretory signal

<400> SEQUENCE: 82

Met Gln Trp Lys Ile Leu Pro Ile Tyr Leu Leu Leu Leu Ser Val Phe
1 5 10 15

Leu Ile Gln Gln Val Ser Ser
20

<210> SEQ ID NO 83
<211> LENGTH: 7
<212> TYPE: PRT
<213> ORGANISM: artificial sequence
<220> FEATURE:
<223> OTHER INFORMATION: Altered canine sequence

<400> SEQUENCE: 83

Ser Pro Ala Pro Thr Thr Pro
1 5

<210> SEQ ID NO 84
<211> LENGTH: 6
<212> TYPE: PRT
<213> ORGANISM: artificial sequence
<220> FEATURE:
<223> OTHER INFORMATION: Modified equine sequence

<400> SEQUENCE: 84

Ser Pro Ser Leu Thr Thr
1 5

<210> SEQ ID NO 85
<211> LENGTH: 20
<212> TYPE: DNA
<213> ORGANISM: artificial sequence
<220> FEATURE:
<223> OTHER INFORMATION: Primer

<400> SEQUENCE: 85
atgacaccgg gcacccagtc 20

<210> SEQ ID NO 86
<211> LENGTH: 25
<212> TYPE: DNA
<213> ORGANISM: artificial sequence
<220> FEATURE:
<223> OTHER INFORMATION: Primer

<400> SEQUENCE: 86
ctacatactt cgtcggcgca tgtac 25

-continued

```
<210> SEQ ID NO 87
<211> LENGTH: 8
<212> TYPE: PRT
<213> ORGANISM: artificial sequence
<220> FEATURE:
<223> OTHER INFORMATION: Consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 87

Lys Xaa Pro Xaa Pro Thr Thr Xaa
1               5


<210> SEQ ID NO 88
<211> LENGTH: 33
<212> TYPE: DNA
<213> ORGANISM: artificial sequence
<220> FEATURE:
<223> OTHER INFORMATION: Primer

<400> SEQUENCE: 88

ggcacctcga ggatgccggt gcagctgacg aca                                  33


<210> SEQ ID NO 89
<211> LENGTH: 34
<212> TYPE: DNA
<213> ORGANISM: artificial sequence
<220> FEATURE:
<223> OTHER INFORMATION: Primer

<400> SEQUENCE: 89

ggcagaattc ttacacctca gcaaaagcca agct                                 34


<210> SEQ ID NO 90
<211> LENGTH: 37
<212> TYPE: DNA
<213> ORGANISM: artificial sequence
<220> FEATURE:
<223> OTHER INFORMATION: Primer

<400> SEQUENCE: 90

ggcagctcag ctatggtgtc caagggcgag gagctgt                              37


<210> SEQ ID NO 91
<211> LENGTH: 39
<212> TYPE: DNA
<213> ORGANISM: artificial sequence
<220> FEATURE:
<223> OTHER INFORMATION: Primer

<400> SEQUENCE: 91

ggcagctgag cccttataca gctcgtccat gccgtgagt                            39


<210> SEQ ID NO 92
<211> LENGTH: 27
<212> TYPE: DNA
<213> ORGANISM: artificial sequence
<220> FEATURE:
<223> OTHER INFORMATION: Primer
```

<400> SEQUENCE: 92
tggaggagcc tcaggcatac tttattg 27

<210> SEQ ID NO 93
<211> LENGTH: 26
<212> TYPE: DNA
<213> ORGANISM: artificial sequence
<220> FEATURE:
<223> OTHER INFORMATION: Primer

<400> SEQUENCE: 93
ccaccgccga ccgaggtgac atcctg 26

<210> SEQ ID NO 94
<211> LENGTH: 37
<212> TYPE: DNA
<213> ORGANISM: artificial sequence
<220> FEATURE:
<223> OTHER INFORMATION: Primer

<400> SEQUENCE: 94
gttgcgactg cttaacggac agatctcgat ggtgagc 37

<210> SEQ ID NO 95
<211> LENGTH: 39
<212> TYPE: DNA
<213> ORGANISM: artificial sequence
<220> FEATURE:
<223> OTHER INFORMATION: Primer

<400> SEQUENCE: 95
agccagctca gggaatcccc agcattcttc tcagtagag 39

<210> SEQ ID NO 96
<211> LENGTH: 41
<212> TYPE: DNA
<213> ORGANISM: artificial sequence
<220> FEATURE:
<223> OTHER INFORMATION: Primer

<400> SEQUENCE: 96
tcaggccacc accaccatca ccatcatcac caccattagg g 41

<210> SEQ ID NO 97
<211> LENGTH: 42
<212> TYPE: DNA
<213> ORGANISM: artificial sequence
<220> FEATURE:
<223> OTHER INFORMATION: Primer

<400> SEQUENCE: 97
ccggtggtgg tggtagtggt agtagtggtg gtaatccctt aa 42

<210> SEQ ID NO 98
<211> LENGTH: 1369
<212> TYPE: PRT
<213> ORGANISM: artificial sequence
<220> FEATURE:
<223> OTHER INFORMATION: Recombinant equine SynLubricin

<400> SEQUENCE: 98

Glu Trp Lys Ile Leu Pro Ile Tyr Leu Leu Leu Leu Ser Ile Phe
1 5 10 15

Ser Ile Gln Glu Val Ser Ser Gln Asp Leu Ser Ser Cys Ala Gly Arg

-continued

```
            20                  25                  30

Cys Gly Glu Gly Tyr Ser Arg Asp Ala Thr Cys Asn Cys Asp Phe Asn
        35                  40                  45

Cys Gln Tyr Tyr Met Glu Cys Cys Pro Asp Phe Lys Lys Val Cys Thr
    50                  55                  60

Ser Glu Leu Ser Cys Lys Gly Arg Cys Phe Glu Ser Phe Glu Arg Gly
65                  70                  75                  80

Arg Glu Cys Asp Cys Asp Ala Asp Cys Lys Lys Tyr Gly Lys Cys Cys
                85                  90                  95

Ser Asp Tyr Glu Ser Phe Cys Glu Glu Val His Asn Pro Thr Ser Pro
            100                 105                 110

Pro Ser Ser Lys Thr Ala Pro Pro Pro Pro Gly Ala Ser Gln Thr Ile
        115                 120                 125

Lys Ser Thr Ala Lys Arg Ser Pro Lys Ser Asn Lys Lys Lys Thr Lys
    130                 135                 140

Lys Val Ile Glu Ser Glu Glu Ile Ile Glu Glu His Ser Val Ser Glu
145                 150                 155                 160

Asn Gln Glu Ser Ser Ser Ser Ser Ser Ser Ser Ser Ser Thr Ile Arg
                165                 170                 175

Lys Val Lys Ser Ser Lys Asn Ser Ala Ala Asn Arg Glu Leu Lys Lys
            180                 185                 190

Lys Pro Lys Val Lys Asp Ser Lys Lys Lys Arg Thr Pro Lys Lys Lys
        195                 200                 205

Pro Thr Pro Glu Pro Pro Val Ile Asp Glu Ala Gly Ser Gly Leu Asp
    210                 215                 220

Asn Gly Asp Phe Met Leu Ile Pro Thr Pro Lys Ile Pro Thr Thr Gln
225                 230                 235                 240

Arg Asn Lys Val Thr Thr Ser Pro Lys Ile Thr Thr Val Lys Pro Ile
                245                 250                 255

Asn Pro Lys Pro Ser Leu Pro Pro Asn Ser Asp Thr Ser Lys Glu Thr
            260                 265                 270

Thr Ser Thr Pro Asn Lys Glu Thr Thr Val Glu Thr Lys Glu Thr Glu
        275                 280                 285

Ile Thr Asn Lys Glu Thr Ser Thr Ser Ala Asn Glu Lys Thr Thr Ser
    290                 295                 300

Ala Arg Lys Ser Thr Glu Lys Thr Ser Asp Lys Asp Phe Ala Pro Ala
305                 310                 315                 320

Ser Glu Val Pro Ala Lys Ser Thr Pro Lys Ala Glu Thr Thr Thr Lys
                325                 330                 335

Gly Pro Ala Leu Thr Thr Pro Lys Glu Pro Ala Pro Thr Thr Pro Lys
            340                 345                 350

Glu Pro Ala Pro Thr Thr Pro Lys Glu Pro Ala Pro Thr Thr Pro Lys
        355                 360                 365

Glu Pro Ala Pro Thr Thr Pro Lys Glu Pro Ala Pro Thr Thr Pro Lys
    370                 375                 380

Glu Pro Ala Pro Thr Thr Pro Lys Glu Pro Ala Pro Thr Thr Pro Lys
385                 390                 395                 400

Glu Pro Ala Pro Thr Thr Pro Lys Glu Pro Ala Pro Thr Thr Pro Lys
                405                 410                 415

Glu Pro Ala Pro Thr Thr Pro Lys Glu Pro Ala Pro Thr Thr Pro Lys
            420                 425                 430

Glu Pro Ala Pro Thr Thr Pro Lys Glu Pro Ala Pro Thr Thr Pro Lys
        435                 440                 445
```

-continued

```
Glu Pro Ala Pro Thr Thr Pro Lys Glu Pro Ala Pro Thr Thr Pro Lys
    450                 455                 460

Glu Pro Ala Pro Thr Thr Pro Lys Glu Pro Ala Pro Thr Thr Pro Lys
465                 470                 475                 480

Glu Pro Ala Pro Thr Thr Pro Lys Glu Pro Ala Pro Thr Thr Pro Lys
                485                 490                 495

Glu Pro Ala Pro Thr Thr Pro Lys Glu Pro Ala Pro Thr Thr Pro Lys
            500                 505                 510

Glu Pro Ala Pro Thr Thr Pro Lys Glu Pro Ala Pro Thr Thr Pro Lys
        515                 520                 525

Glu Pro Ala Pro Thr Thr Pro Lys Glu Pro Ala Pro Thr Thr Pro Lys
    530                 535                 540

Glu Pro Ala Pro Thr Thr Pro Lys Glu Pro Ala Pro Thr Thr Pro Lys
545                 550                 555                 560

Glu Pro Ala Pro Thr Thr Pro Lys Glu Pro Ala Pro Thr Thr Pro Lys
                565                 570                 575

Glu Pro Ala Pro Thr Thr Pro Lys Glu Pro Ala Pro Thr Thr Pro Lys
            580                 585                 590

Glu Pro Ala Pro Thr Thr Pro Lys Glu Pro Ala Pro Thr Thr Pro Lys
        595                 600                 605

Glu Pro Ala Pro Thr Thr Pro Lys Glu Pro Ala Pro Thr Thr Pro Lys
    610                 615                 620

Glu Pro Ala Pro Thr Thr Pro Lys Glu Pro Ala Pro Thr Thr Pro Lys
625                 630                 635                 640

Glu Pro Ala Pro Thr Thr Pro Lys Glu Pro Ala Pro Thr Thr Pro Lys
                645                 650                 655

Glu Pro Ala Pro Thr Thr Pro Lys Glu Pro Ala Pro Thr Thr Pro Lys
            660                 665                 670

Glu Pro Ala Pro Thr Thr Pro Lys Glu Pro Ala Pro Thr Thr Pro Lys
        675                 680                 685

Glu Pro Ala Pro Thr Thr Pro Lys Glu Pro Ala Pro Thr Thr Pro Lys
    690                 695                 700

Glu Pro Ala Pro Thr Thr Pro Lys Glu Pro Ala Pro Thr Thr Pro Lys
705                 710                 715                 720

Glu Pro Ala Pro Thr Thr Pro Lys Glu Pro Ala Pro Thr Thr Pro Lys
                725                 730                 735

Glu Pro Ala Pro Thr Thr Pro Lys Glu Pro Ala Pro Thr Thr Pro Lys
            740                 745                 750

Glu Pro Ala Pro Thr Thr Pro Lys Glu Pro Ala Pro Thr Thr Pro Lys
        755                 760                 765

Glu Pro Ala Pro Thr Thr Pro Lys Glu Pro Ala Pro Thr Thr Pro Lys
    770                 775                 780

Glu Pro Ala Pro Thr Thr Pro Lys Glu Pro Ala Pro Thr Thr Pro Lys
785                 790                 795                 800

Glu Pro Ala Pro Thr Thr Pro Lys Glu Pro Ala Pro Thr Thr Pro Ser
                805                 810                 815

Glu Val Ser Thr Thr Thr Thr Thr Met Lys Pro Pro Thr Thr Pro Lys
            820                 825                 830

Asn Leu Ala Glu Ser Thr Pro Glu Phe Pro Ala Glu Pro Thr Pro Lys
        835                 840                 845

Ala Leu Glu Asn Ser Pro Lys Glu Pro Ala Val Pro Thr Thr Lys Ala
    850                 855                 860
```

-continued

Pro Glu Val Thr Lys Pro Glu Val Thr Thr Thr Ala Lys Asp Lys Val
865 870 875 880

Thr Gly Lys Asp Ile His Thr Ile Pro Glu Ile Thr Thr Ala Ala Pro
885 890 895

Lys Ile Thr Thr Glu Thr Ala Thr Thr Thr Glu Glu Lys Thr Thr Glu
900 905 910

Ser Lys Val Thr Ser Thr Ile Met Gln Val Thr Ser Thr Thr Glu Asp
915 920 925

Thr Thr Thr Ser Ser Lys Ile Thr Pro Lys Ala Thr Thr Leu Ala Pro
930 935 940

Lys Val Met Thr Ala Thr Lys Thr Thr Thr Thr Gln Glu Thr Ile Asn
945 950 955 960

Lys Leu Glu Glu Thr Thr Ala Ile Pro Lys Asp Thr Ala Thr His Ser
965 970 975

Lys Val Thr Thr Pro Lys Pro Lys Lys Pro Thr Lys Ala Pro Arg Lys
980 985 990

Pro Thr Ser Thr Lys Lys Pro Lys Thr Pro Arg Lys Arg Lys Pro Lys
995 1000 1005

Thr Thr Pro Ile Pro Pro Lys Ile Thr Thr Pro Thr Thr Pro Lys
1010 1015 1020

Ser Asn Pro Thr Thr Leu Ala Glu Ala Met Leu Gln Thr Thr Thr
1025 1030 1035

Ser Pro Asn Gln Thr Pro Asn Ser Ala Met Ile Glu Val Asn Pro
1040 1045 1050

Lys Asn Glu Asp Ala Asp Ala Ala Glu Gly Glu Lys Pro Leu Val
1055 1060 1065

Ile Leu Arg Pro His Val Leu Thr Pro Ile Val Ile Pro Gly Pro
1070 1075 1080

Asp Phe Leu Val Arg Gly Pro Asn Leu Gly Ile Gly Ile Asn Pro
1085 1090 1095

Met Leu Ser Asp Glu Thr Asn Leu Cys Asn Gly Lys Pro Val Asp
1100 1105 1110

Gly Leu Thr Thr Leu Arg Asn Gly Thr Leu Val Ala Phe Arg Gly
1115 1120 1125

His Tyr Phe Trp Met Leu Arg Pro Phe Ser Pro Pro Ser Pro Pro
1130 1135 1140

Arg Arg Ile Thr Glu Val Trp Gly Ile Pro Ser Pro Ile Asp Thr
1145 1150 1155

Val Phe Thr Arg Cys Asn Cys Glu Gly Lys Thr Phe Phe Phe Lys
1160 1165 1170

Asp Ser Gln Tyr Trp Arg Phe Thr Asn Asp Ile Lys Asp Ala Gly
1175 1180 1185

Tyr Pro Lys Leu Ile Ser Lys Gly Phe Gly Gly Leu Ser Gly Lys
1190 1195 1200

Ile Val Ala Ala Leu Ser Ile Ala Thr Tyr Lys Asn Arg Pro Glu
1205 1210 1215

Ser Val Tyr Phe Phe Lys Arg Gly Gly Arg Ile Gln Gln Tyr Ile
1220 1225 1230

Tyr Lys Gln Glu Pro Ile Arg Lys Cys Pro Gly Arg Arg Pro Ala
1235 1240 1245

Ile His Tyr Ser Val Tyr Gly Glu Ala Pro Gln Ile Arg Arg Arg
1250 1255 1260

Arg Phe Glu Arg Ala Ile Gly Pro Ser Gln Thr His Thr Ile Arg

-continued

```
    1265                1270                1275

Ile His  Tyr Ser Pro Val Arg  Val Ser Tyr Gln Asp  Lys Val Pro
    1280                1285                1290

Ser Thr  Asp Phe Leu His Asn  Glu Val Lys Val Ser  Thr Leu Trp
    1295                1300                1305

Arg Gly  Leu Pro Asp Thr Val  Thr Ser Ala Ile Ser  Leu Pro Asn
    1310                1315                1320

Leu Arg  Lys Pro Asp Gly Tyr  Asp Tyr Tyr Ala Phe  Ser Lys Asp
    1325                1330                1335

Gln Tyr  Tyr Asn Ile Asp Val  Pro Ser Arg Thr Ala  Arg Ala Ile
    1340                1345                1350

Thr Thr  Arg Ser Gly Gln Thr  Leu Ser Lys Val Trp  Tyr Asn Cys
    1355                1360                1365

Pro


<210> SEQ ID NO 99
<211> LENGTH: 187
<212> TYPE: DNA
<213> ORGANISM: artificial sequence
<220> FEATURE:
<223> OTHER INFORMATION: cDNA

<400> SEQUENCE: 99

tgtacatgga catggtcgct gtgagtatga ccagcagcgt actctccagc cacagccccg     60

gttcaggctc ctccaccact cagggacagg atgtcactct ggccccggcc acggaaccag    120

cttcaggttc agctgccacc tggggacagg atgtcacctc ggtcggcggt ggtggaggag    180

cctcagg                                                              187
```